US010485401B2

(12) United States Patent
Cruz et al.

(10) Patent No.: US 10,485,401 B2
(45) Date of Patent: Nov. 26, 2019

(54) METHOD AND APPARATUS FOR MANIPULATING THE SIDE WALL OF A BODY LUMEN OR BODY CAVITY SO AS TO PROVIDE INCREASED VISUALIZATION OF THE SAME AND/OR INCREASED ACCESS TO THE SAME, AND/OR FOR STABILIZING INSTRUMENTS RELATIVE TO THE SAME

(71) Applicant: Lumendi Ltd., Buckinghamshire (GB)

(72) Inventors: Amos Cruz, Wrentham, MA (US); Jonathan O'Keefe, North Attleboro, MA (US); Jeffrey Cerier, Franklin, MA (US); Tuan Anh Nguyen, Woburn, MA (US); Laurence Lefebvre, Westport, CT (US)

(73) Assignee: Lumendi Ltd., High Wycombe (GB)

( * ) Notice: Subject to any disclaimer, the term of this patent is extended or adjusted under 35 U.S.C. 154(b) by 0 days.

(21) Appl. No.: 15/718,910

(22) Filed: Sep. 28, 2017

(65) Prior Publication Data
US 2018/0035872 A1 Feb. 8, 2018

Related U.S. Application Data

(63) Continuation-in-part of application No. 14/619,845, filed on Feb. 11, 2015, now Pat. No. 9,986,893, which is a continuation-in-part of application No. 14/540,355, filed on Nov. 13, 2014, now Pat. No. 9,924,853, which is a continuation of application No.
(Continued)

(51) Int. Cl.
*A61B 1/00* (2006.01)
*A61B 1/31* (2006.01)
*A61M 25/10* (2013.01)

(52) U.S. Cl.
CPC ...... *A61B 1/00082* (2013.01); *A61B 1/00101* (2013.01); *A61B 1/00135* (2013.01); *A61B 1/00154* (2013.01); *A61B 1/31* (2013.01); *A61M 25/10182* (2013.11); *A61M 25/10187* (2013.11)

(58) Field of Classification Search
CPC ......... A61B 1/00154; A61B 1/04; A61B 1/12; A61B 1/00135; A61B 1/00082; A61B 17/0218; A61B 17/12; A61B 17/22; A61B 17/34; A61B 2017/00557; A61B 2017/3486; A61M 25/1011;
(Continued)

(56) References Cited

U.S. PATENT DOCUMENTS 2,473,742 A 6/1949 Auzin
4,066,071 A 1/1978 Nagel
(Continued)

FOREIGN PATENT DOCUMENTS

CA 2988249 12/2016
EP 0 402 467 12/1990
(Continued)

*Primary Examiner* — Katrina M Stransky
(74) *Attorney, Agent, or Firm* — Pandiscio & Pandiscio

(57) ABSTRACT

Apparatus comprising a sleeve adapted to be slid over the exterior of an endoscope, the sleeve having a distal end and a proximal end; an aft balloon secured to the sleeve; a fore balloon movably mounted to the sleeve so that the fore balloon may be advanced relative to the sleeve; and a locking assembly for releasably securing the distal end of the sleeve to the endoscope.

172 Claims, 120 Drawing Sheets

Related U.S. Application Data

12/969,059, filed on Dec. 15, 2010, now Pat. No. 8,979,884, application No. 15/718,910, which is a continuation-in-part of application No. 15/172,385, filed on Jun. 3, 2016, now Pat. No. 10,149,601.

(60) Provisional application No. 61/284,215, filed on Dec. 15, 2009, provisional application No. 61/938,446, filed on Feb. 11, 2014, provisional application No. 62/170,476, filed on Jun. 3, 2015, provisional application No. 62/170,497, filed on Jun. 3, 2015, provisional application No. 62/244,008, filed on Oct. 20, 2015, provisional application No. 62/244,214, filed on Oct. 21, 2015, provisional application No. 62/305,773, filed on Mar. 9, 2016, provisional application No. 62/305,797, filed on Mar. 9, 2016, provisional application No. 62/305,804, filed on Mar. 9, 2016, provisional application No. 62/400,948, filed on Sep. 28, 2016.

(58) Field of Classification Search
CPC ...... A61M 25/1018; A61M 2025/1015; A61M 25/10182; A61M 25/10187
See application file for complete search history.

(56) References Cited

U.S. PATENT DOCUMENTS

| | | |
|---|---|---|
| 4,198,981 A | 4/1980 | Sinnreich |
| 4,224,929 A | 9/1980 | Furihata |
| 4,445,892 A | 5/1984 | Hussein et al. |
| 4,862,874 A | 9/1989 | Kellner |
| 5,025,778 A | 6/1991 | Silverstein et al. |
| 5,078,731 A | 1/1992 | Hayhurst |
| 5,105,800 A | 4/1992 | Takahashi et al. |
| 5,147,382 A | 9/1992 | Gertzman et al. |
| 5,197,971 A | 3/1993 | Bonutti |
| 5,423,821 A | 6/1995 | Pasque |
| 5,662,587 A | 9/1997 | Grundfest et al. |
| 5,718,680 A | 2/1998 | Kraus et al. |
| 5,762,604 A | 6/1998 | Kieturakis |
| 5,833,650 A | 11/1998 | Imran |
| 5,938,585 A | 8/1999 | Donofrio |
| 5,954,731 A | 9/1999 | Yoon |
| 6,007,482 A | 12/1999 | Madni et al. |
| 6,007,483 A | 12/1999 | Kieturakis |
| 6,071,273 A | 6/2000 | Euteneuer et al. |
| 6,139,517 A | 10/2000 | Macoviak et al. |
| 6,234,958 B1 | 5/2001 | Snoke et al. |
| 6,277,065 B1 | 8/2001 | Donofrio |
| 6,309,346 B1 | 10/2001 | Farhadi |
| 6,375,665 B1 | 4/2002 | Nash et al. |
| 6,475,226 B1 | 11/2002 | Belef et al. |
| 6,575,932 B1 | 6/2003 | O'Brien et al. |
| 6,585,639 B1 | 7/2003 | Kotmel et al. |
| 6,741,884 B1 | 5/2004 | Freeman et al. |
| 6,764,441 B2 | 7/2004 | Chiel et al. |
| 6,790,173 B2 | 9/2004 | Saadat et al. |
| 6,793,661 B2 | 9/2004 | Hamilton et al. |
| 6,929,601 B2 | 8/2005 | Nakao |
| 6,951,554 B2 | 10/2005 | Johansen et al. |
| 6,988,986 B2 | 1/2006 | Gross |
| 7,041,051 B2 | 5/2006 | Bernstein |
| 7,410,483 B2 | 8/2008 | Danitz et al. |
| 7,510,523 B2 | 3/2009 | Sakamoto |
| 7,591,782 B2 | 9/2009 | Fujikura |
| 7,635,346 B2 | 12/2009 | Cabiri et al. |
| 7,678,044 B2 | 3/2010 | Fujikura |
| 7,699,771 B2 | 4/2010 | Wendlandt |
| 7,708,687 B2 | 5/2010 | Bern et al. |
| 7,798,992 B2 | 9/2010 | Ortiz |
| 7,833,150 B2 | 11/2010 | Yamamoto et al. |
| 7,901,347 B2 | 3/2011 | Sekiguchi et al. |
| 7,909,755 B2 | 3/2011 | Itoi |
| 7,935,047 B2 | 5/2011 | Yoshida et al. |
| 7,959,559 B2 | 6/2011 | Yamaya |
| 7,963,911 B2 | 6/2011 | Turliuc |
| 8,012,084 B2 | 9/2011 | Machida |
| 8,092,372 B2 | 1/2012 | Machida |
| 8,096,942 B2 | 1/2012 | Yoshida et al. |
| 8,109,903 B2 | 2/2012 | Terliuc et al. |
| 8,147,401 B2 | 4/2012 | Yamaya |
| 8,187,173 B2 | 5/2012 | Miyoshi |
| 8,337,395 B2 | 12/2012 | Suzuki et al. |
| 8,403,827 B2 | 3/2013 | Matsui et al. |
| 8,439,825 B2 | 5/2013 | Sekiguchi |
| 8,460,179 B2 | 6/2013 | Ikeda et al. |
| 8,506,479 B2 | 8/2013 | Piskun et al. |
| 8,523,763 B2 | 9/2013 | Sinai et al. |
| 8,679,001 B2 | 3/2014 | Sinai et al. |
| 8,932,211 B2 | 1/2015 | Piskun et al. |
| 8,979,884 B2 | 3/2015 | Milsom et al. |
| 9,125,636 B2 | 9/2015 | Piskun et al. |
| 9,161,746 B2 | 10/2015 | Piskun et al. |
| 9,186,130 B2 | 11/2015 | Piskun et al. |
| 9,186,131 B2 | 11/2015 | Piskun et al. |
| 9,554,690 B2 | 1/2017 | Piskun et al. |
| 9,565,998 B2 | 2/2017 | Piskun et al. |
| 9,655,506 B2 | 5/2017 | Piskun et al. |
| 9,713,416 B2 | 7/2017 | Piskun et al. |
| 9,737,194 B2 | 8/2017 | Piskun et al. |
| 2002/0013601 A1 | 1/2002 | Nobles et al. |
| 2003/0225433 A1 | 12/2003 | Nakao |
| 2004/0102681 A1 | 5/2004 | Gross |
| 2004/0186349 A1 | 9/2004 | Ewers et al. |
| 2004/0210116 A1 | 10/2004 | Nakao |
| 2004/0260150 A1 | 12/2004 | Bernstein |
| 2004/0260333 A1 | 12/2004 | Dubrul et al. |
| 2005/0033363 A1 | 2/2005 | Bojarski et al. |
| 2005/0033401 A1 | 2/2005 | Cunniffe et al. |
| 2005/0107664 A1 | 5/2005 | Kalloo et al. |
| 2005/0165432 A1 | 7/2005 | Heinrich |
| 2005/0215855 A1 | 9/2005 | Machida |
| 2005/0277809 A1 | 12/2005 | Takano et al. |
| 2006/0161044 A1 | 7/2006 | Oneda et al. |
| 2006/0183974 A1 | 8/2006 | Levy et al. |
| 2006/0189845 A1 | 8/2006 | Maahs et al. |
| 2006/0241345 A1 | 10/2006 | Oishi et al. |
| 2006/0258972 A1 | 11/2006 | Mangiardi et al. |
| 2007/0049797 A1 | 3/2007 | Yoshida et al. |
| 2007/0106302 A1 | 5/2007 | Ortiz |
| 2007/0142706 A1 | 6/2007 | Matsui et al. |
| 2007/0167682 A1* | 7/2007 | Goldfarb ............ A61B 1/00135 600/114 |
| 2007/0215162 A1 | 9/2007 | Glassenberg et al. |
| 2007/0244361 A1 | 10/2007 | Ikeda et al. |
| 2007/0265499 A1 | 11/2007 | Wood |
| 2007/0276181 A1 | 11/2007 | Terliuc |
| 2007/0282166 A1 | 12/2007 | Ayala et al. |
| 2008/0065116 A1 | 3/2008 | Lee et al. |
| 2008/0091063 A1 | 4/2008 | Terliuc |
| 2008/0091068 A1 | 4/2008 | Terliuc |
| 2008/0161645 A1 | 7/2008 | Goldwasser et al. |
| 2008/0200756 A1 | 8/2008 | Okada et al. |
| 2008/0249358 A1 | 10/2008 | Motai et al. |
| 2009/0156896 A1 | 6/2009 | Kura |
| 2009/0156996 A1 | 6/2009 | Milsom et al. |
| 2009/0187069 A1* | 7/2009 | Terliuc ............... A61B 1/00142 600/106 |
| 2009/0203995 A1 | 8/2009 | Matonick |
| 2009/0227835 A1 | 9/2009 | Terliuc |
| 2009/0234188 A1 | 9/2009 | Matsuura |
| 2009/0287051 A1 | 11/2009 | Itoi |
| 2009/0287058 A1 | 11/2009 | Terliuc |
| 2010/0010530 A1 | 1/2010 | Rhee |
| 2010/0049162 A1 | 2/2010 | Hameed |
| 2010/0105983 A1 | 4/2010 | Oneda et al. |
| 2010/0168510 A1 | 7/2010 | Rogers et al. |
| 2010/0217078 A1 | 8/2010 | Yamakawa et al. |
| 2010/0217185 A1 | 8/2010 | Terliuc et al. |
| 2011/0009863 A1 | 1/2011 | Marczyk et al. |
| 2011/0054253 A1 | 3/2011 | Albiñana et al. |
| 2011/0092770 A1 | 4/2011 | Matsui et al. |

(56) References Cited

U.S. PATENT DOCUMENTS

| | | |
|---|---|---|
| 2011/0092963 A1 | 4/2011 | Castro |
| 2011/0112410 A1 | 5/2011 | Hirota |
| 2011/0160536 A1 | 6/2011 | Blum |
| 2011/0172491 A1 | 7/2011 | Piskun et al. |
| 2011/0190583 A1 | 8/2011 | Ashida et al. |
| 2011/0245858 A1 | 10/2011 | Milsom et al. |
| 2011/0251555 A1 | 10/2011 | Ducharme et al. |
| 2012/0130170 A1 | 5/2012 | Terliuc |
| 2012/0136343 A1 | 5/2012 | Burnett |
| 2012/0150210 A1 | 6/2012 | Fan et al. |
| 2012/0157771 A1 | 6/2012 | Avitsian et al. |
| 2012/0178994 A1 | 7/2012 | Schembre |
| 2012/0232347 A1 | 9/2012 | Fujikura et al. |
| 2013/0116549 A1 | 5/2013 | Gunday et al. |
| 2013/0144118 A1 | 6/2013 | Piskun et al. |
| 2013/0165942 A1 | 6/2013 | Tan-Malecki et al. |
| 2013/0267936 A1 | 10/2013 | Stroup et al. |
| 2013/0345519 A1 | 12/2013 | Piskun et al. |
| 2014/0188159 A1 | 7/2014 | Steege |
| 2015/0018616 A1 | 1/2015 | Kumoyama |
| 2015/0133774 A1 | 5/2015 | Milsom et al. |
| 2015/0150436 A1 | 6/2015 | Cornhill et al. |
| 2015/0157192 A1 | 6/2015 | Piskun et al. |
| 2015/0164524 A1 | 6/2015 | Malkowski et al. |
| 2015/0209024 A1 | 7/2015 | Piskun et al. |
| 2015/0265818 A1 | 9/2015 | Piskun et al. |
| 2015/0272564 A1 | 10/2015 | Piskun et al. |
| 2015/0282800 A1 | 10/2015 | Piskun et al. |
| 2015/0297209 A1 | 10/2015 | Piskun et al. |
| 2015/0313584 A1 | 11/2015 | Piskun et al. |
| 2015/0335229 A1 | 11/2015 | Terliuc |
| 2016/0015252 A1 | 1/2016 | Piskun et al. |
| 2016/0089002 A1 | 3/2016 | Burton et al. |
| 2016/0278626 A1 | 9/2016 | Cornhill et al. |
| 2016/0278757 A1 | 9/2016 | Piskun et al. |
| 2016/0309996 A1 | 10/2016 | Piskun et al. |
| 2016/0310124 A1 | 10/2016 | Piskun et al. |
| 2016/0338572 A1 | 11/2016 | Piskun et al. |
| 2016/0374658 A1 | 12/2016 | Piskun |
| 2017/0079636 A1 | 3/2017 | Piskun et al. |
| 2017/0135567 A1 | 5/2017 | Piskun et al. |

FOREIGN PATENT DOCUMENTS

| | | |
|---|---|---|
| EP | 1 654 977 | 5/2006 |
| EP | 1 782 726 | 5/2007 |
| EP | 2 026 866 | 2/2009 |
| EP | 1 977 679 | 8/2010 |
| EP | 1 731 084 | 12/2010 |
| EP | 2 364 637 | 9/2011 |
| EP | 1 718 193 | 7/2013 |
| JP | 3-258268 | 11/1991 |
| JP | 6-113998 | 4/1994 |
| JP | 7-308388 | 11/1995 |
| JP | 2000-033071 | 2/2000 |
| JP | 2000-037347 | 2/2000 |
| JP | 2004-016728 | 1/2004 |
| JP | 2007-296054 | 11/2007 |
| JP | 2011-087647 | 5/2011 |
| JP | 2012-029886 | 2/2012 |
| WO | WO 1989/007413 | 8/1989 |
| WO | WO 2001/054568 | 8/2001 |
| WO | WO 2002/087495 | 11/2002 |
| WO | WO 2003/103517 | 12/2003 |
| WO | WO 2004/060463 | 7/2004 |
| WO | WO 2005/074377 | 8/2005 |
| WO | WO 2005/089627 | 9/2005 |
| WO | WO 2005/110204 | 11/2005 |
| WO | WO 2006/138013 | 12/2006 |
| WO | WO 2007/017854 | 2/2007 |
| WO | WO 2007/135665 | 11/2007 |
| WO | WO 2008/004228 | 1/2008 |
| WO | WO 2008/044615 | 4/2008 |
| WO | WO 2008/142685 | 11/2008 |
| WO | WO 2009/027394 | 3/2009 |
| WO | WO 2009/122395 | 10/2009 |
| WO | WO 2010/091440 | 8/2010 |
| WO | WO 2014/190026 | 11/2014 |
| WO | WO 2015/123313 | 8/2015 |
| WO | WO 2016/186876 | 11/2016 |
| WO | WO 2016/193820 | 12/2016 |

* cited by examiner

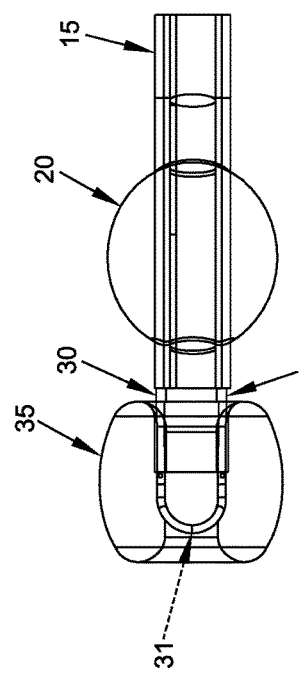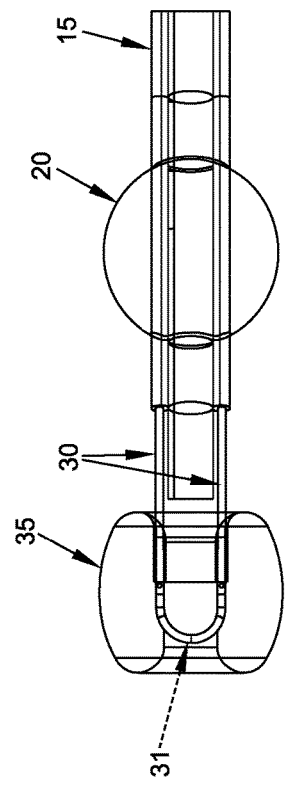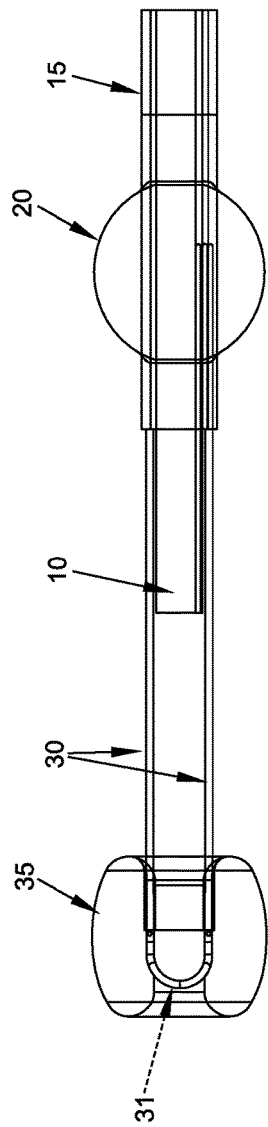

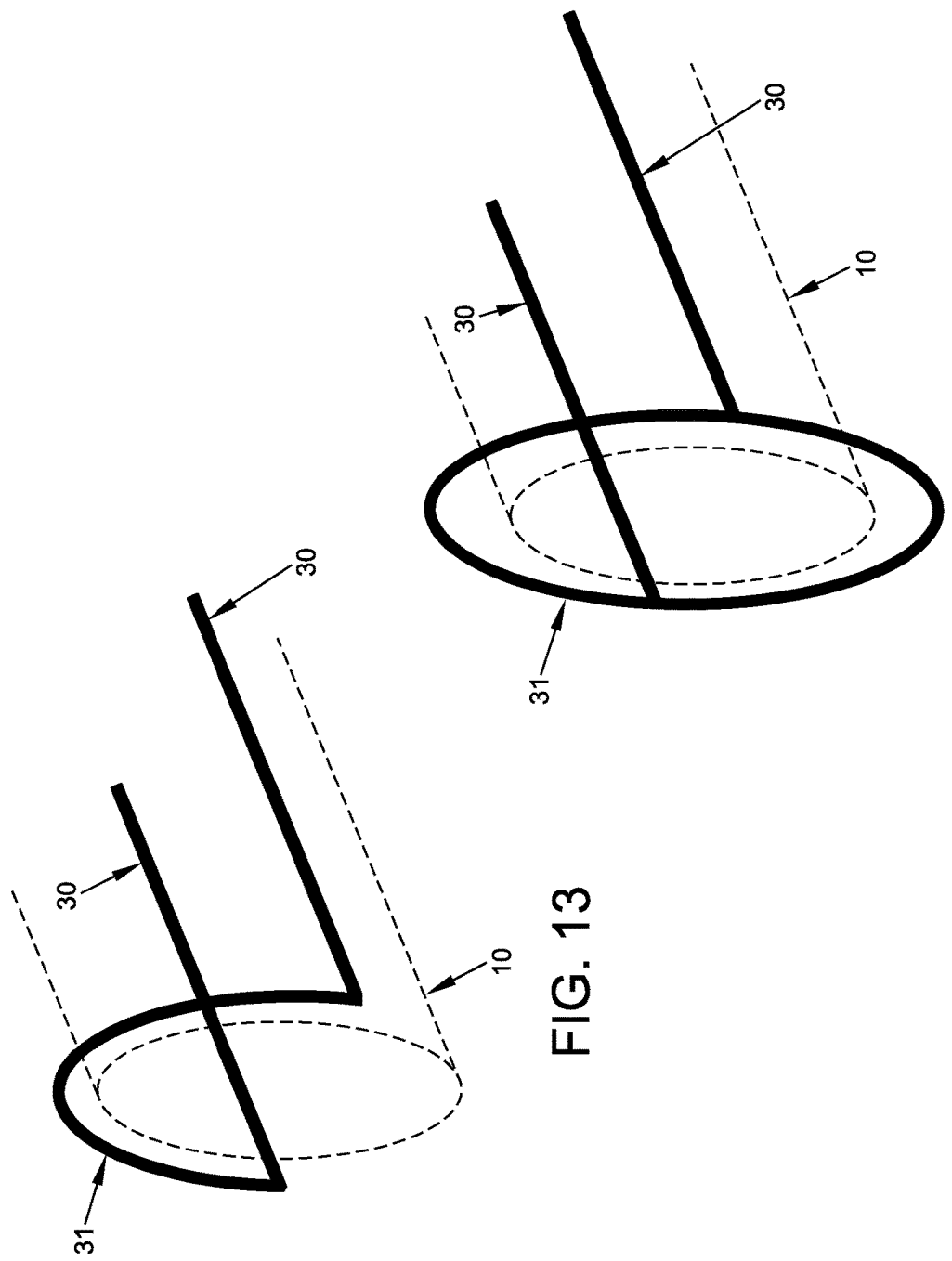

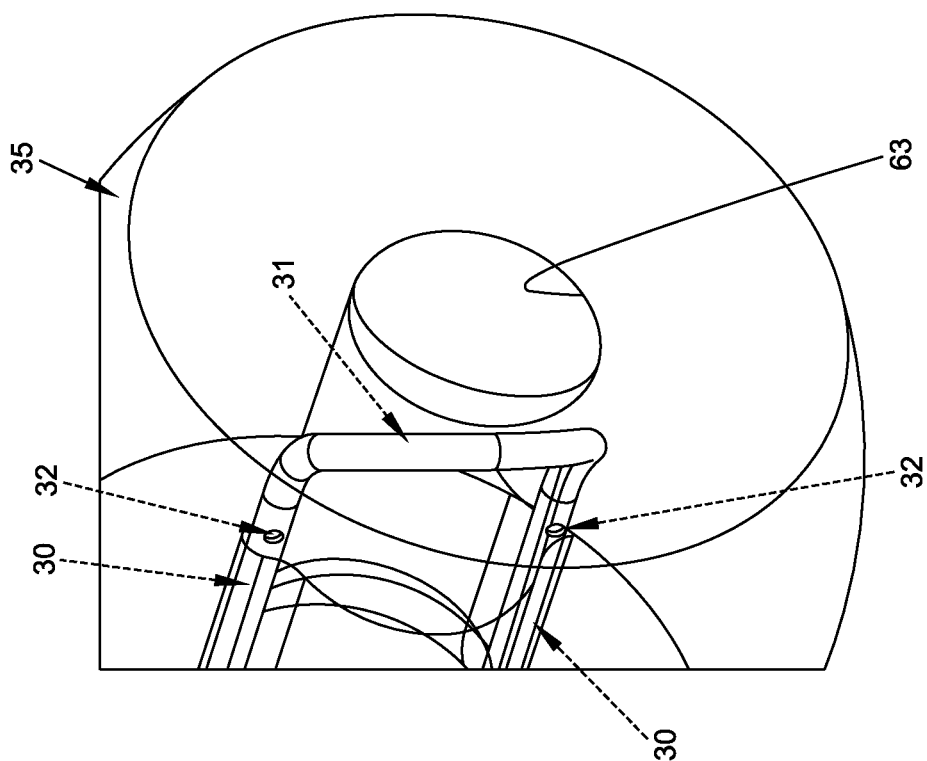
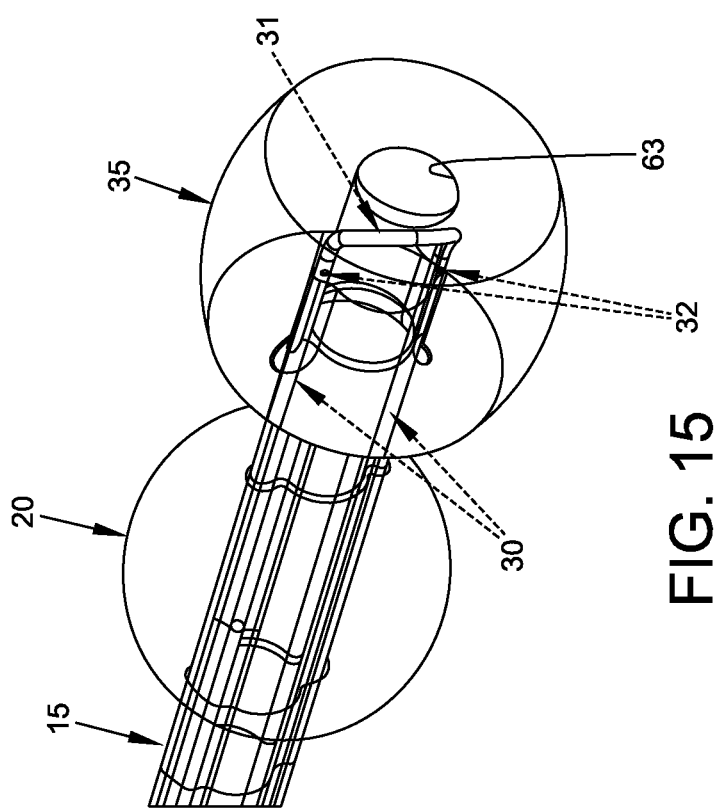

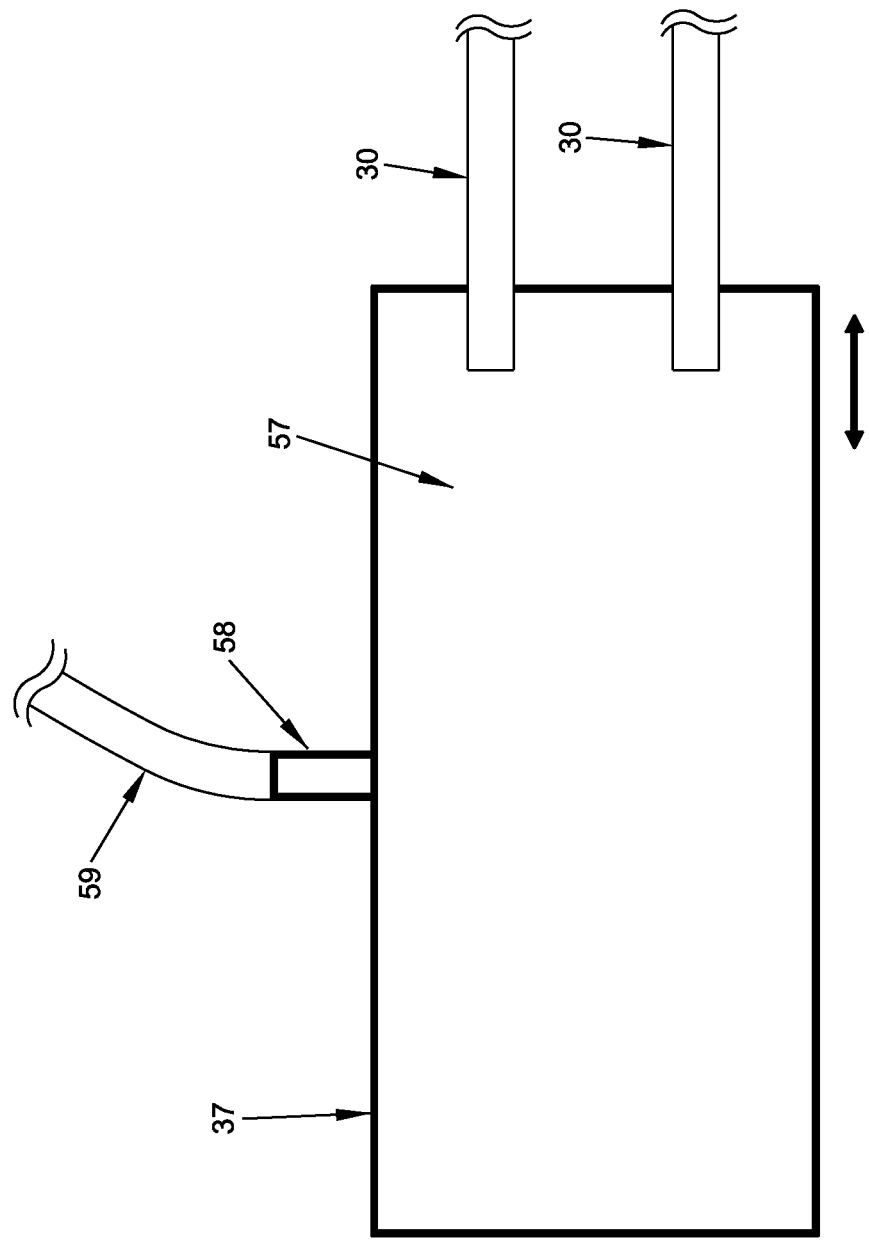

System during aft balloon inflation

System during aft balloon deflation

System during fore balloon inflation

System during fore balloon deflation

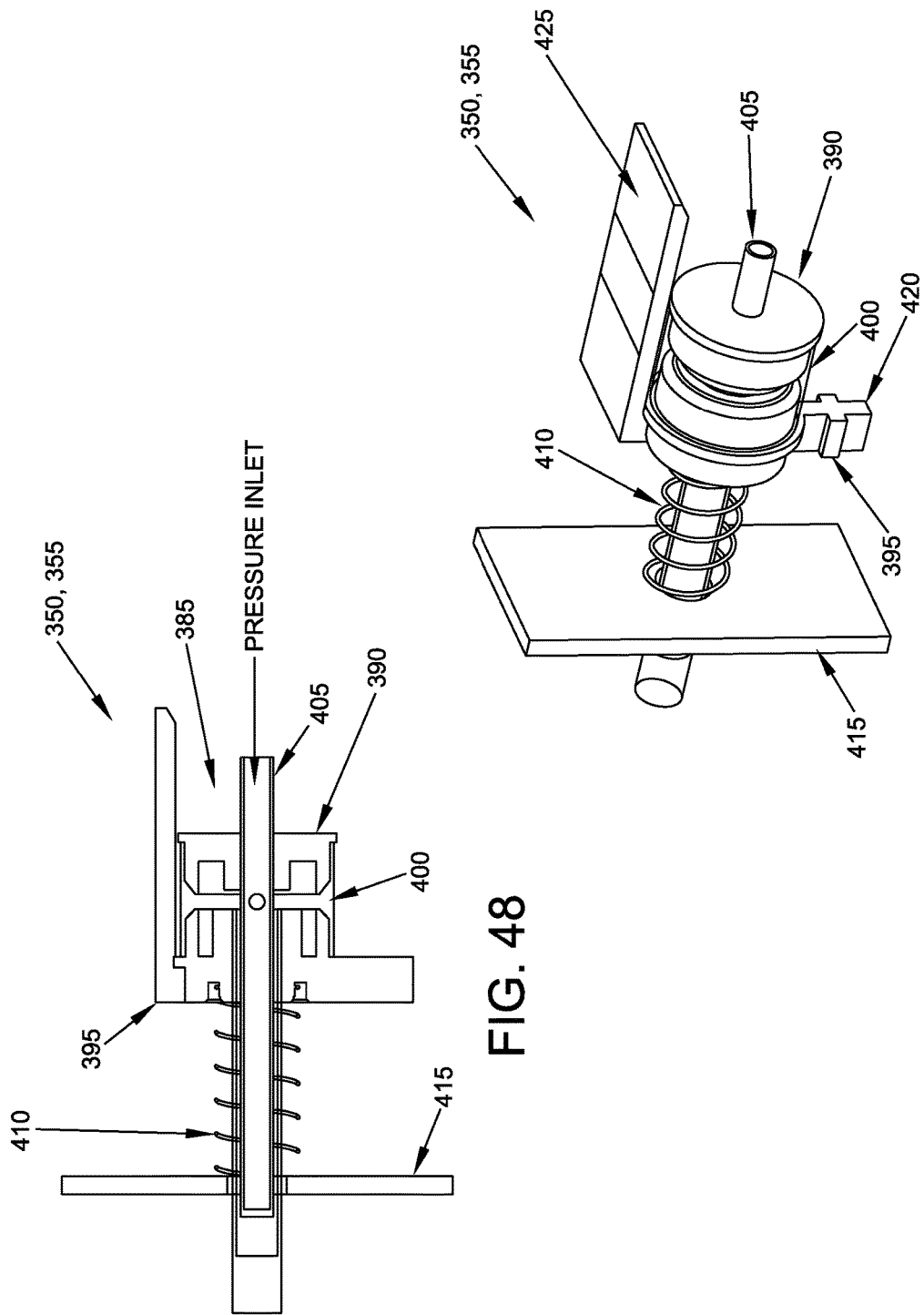

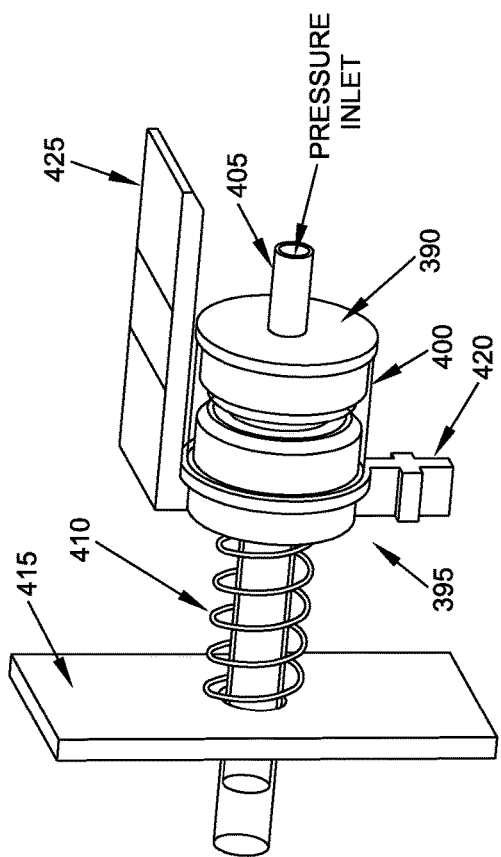
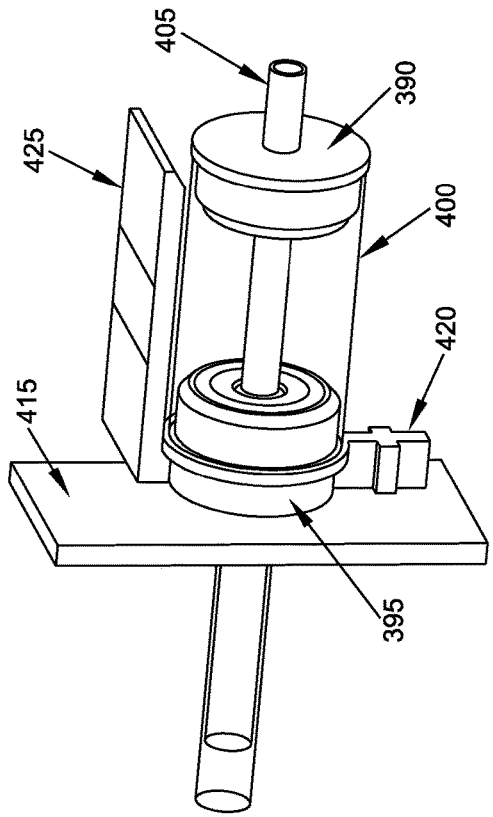
FIG. 50
FIG. 51

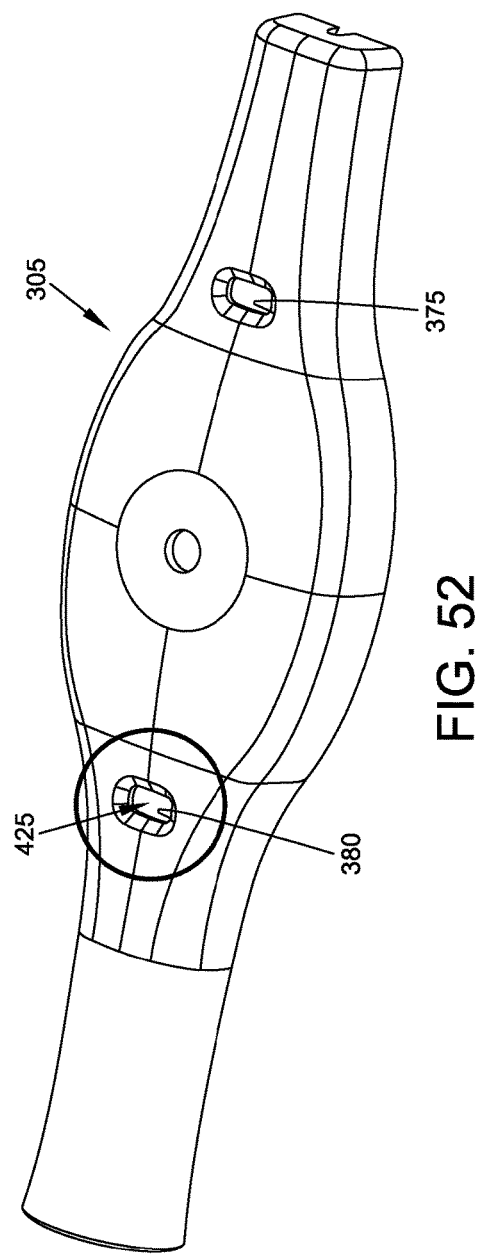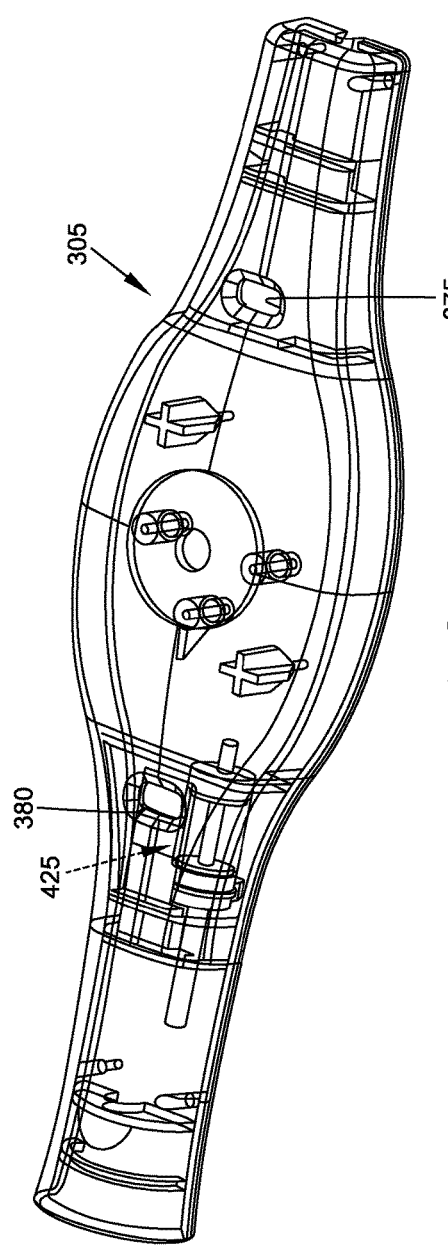

| ACTION | Ambient Out | Ambient In | Balloon 1 | | Balloon 2 | |
|---|---|---|---|---|---|---|
| | | | Line In | Line Out | Line In | Line Out |
| | Tube 1 | Tube 2 | Tube 3 | Tube 4 | Tube 5 | Tube 6 |
| Inflate Balloon 1 | O | X | O | X | X | X |
| Inflate Balloon 2 | O | X | X | X | O | X |
| Deflate Balloon 1 | X | O | X | O | X | X |
| Deflate Balloon 2 | X | O | X | X | X | O |

FIG. 82

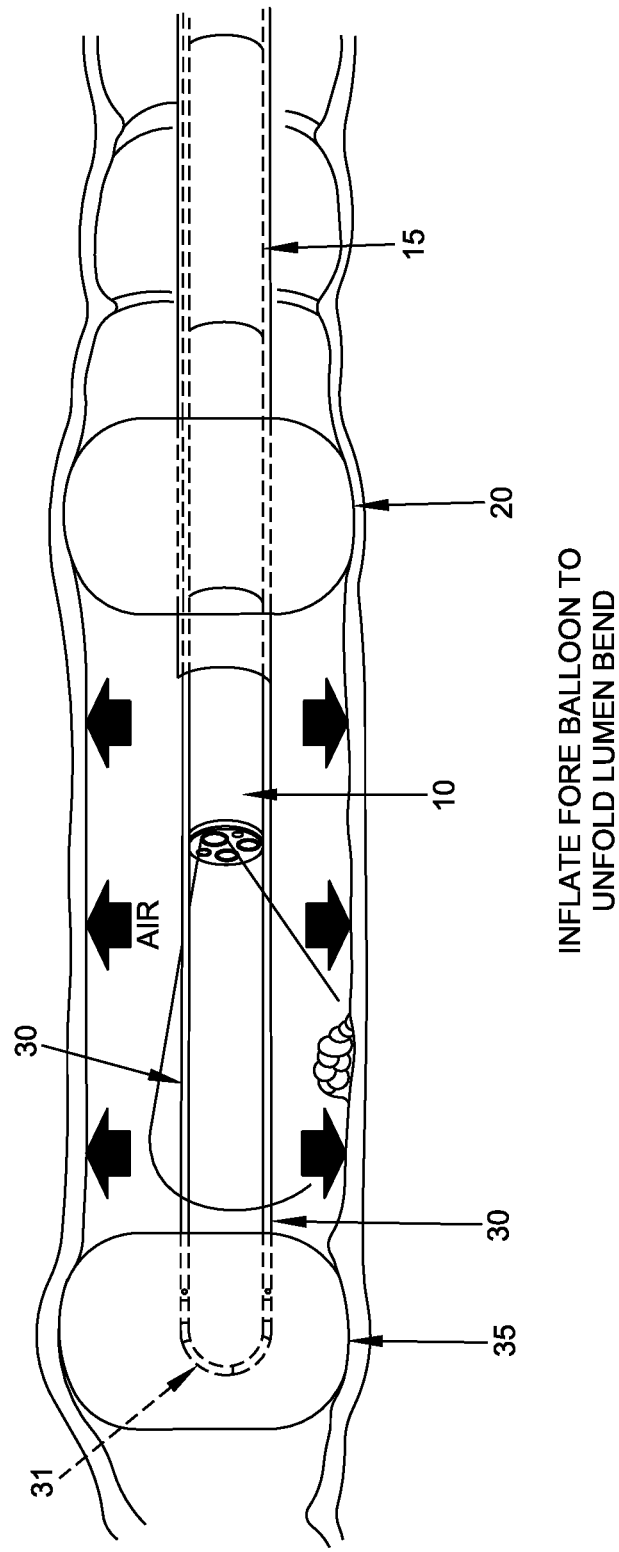

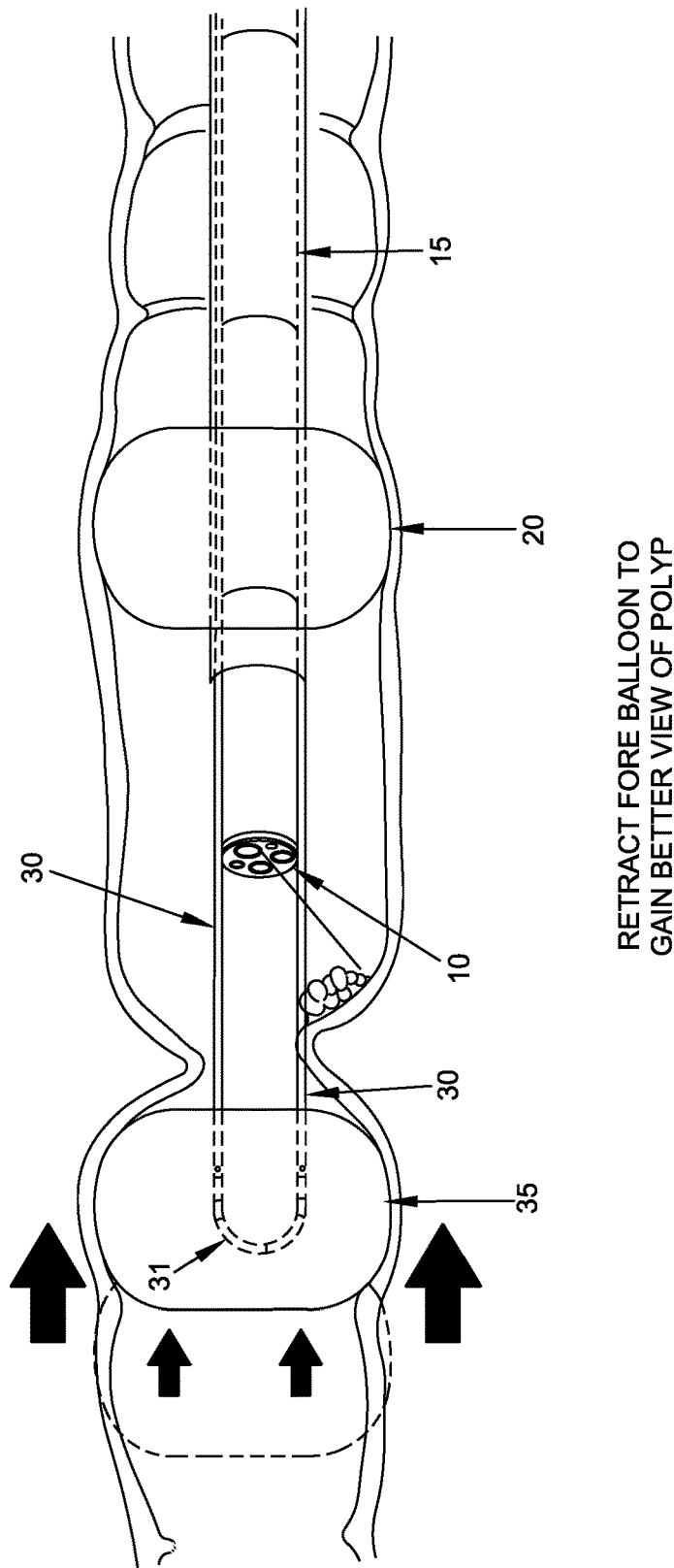

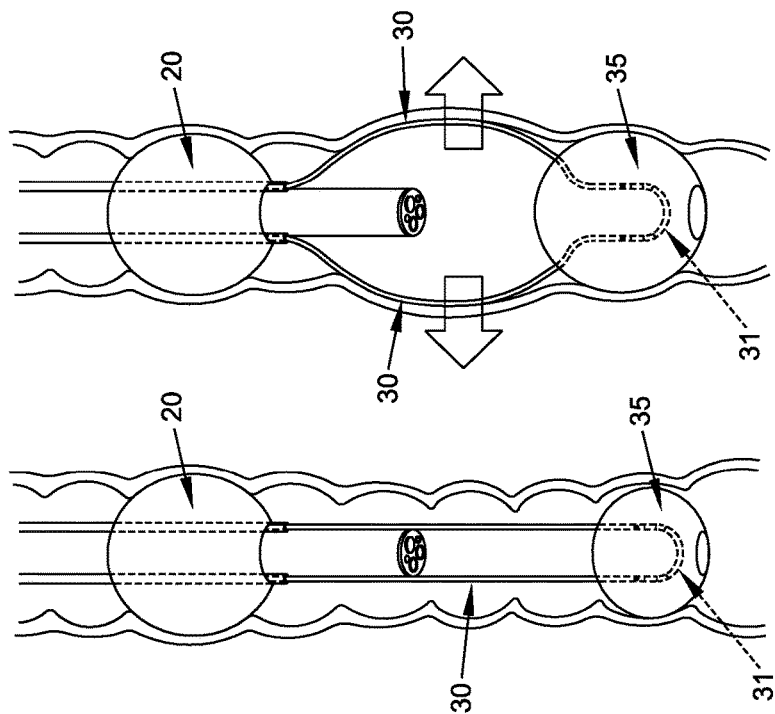
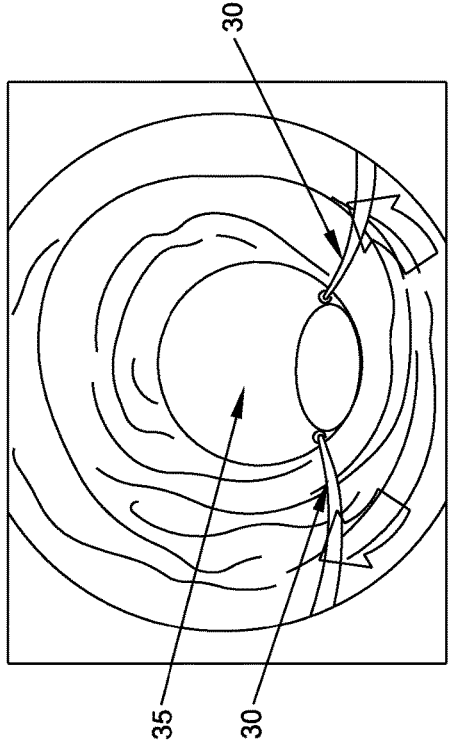 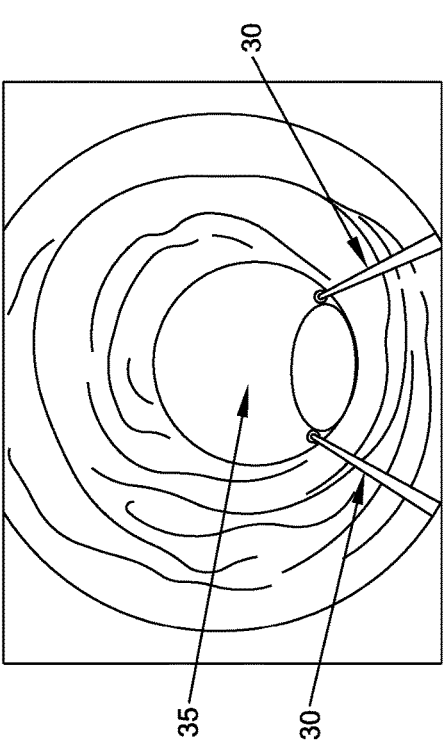

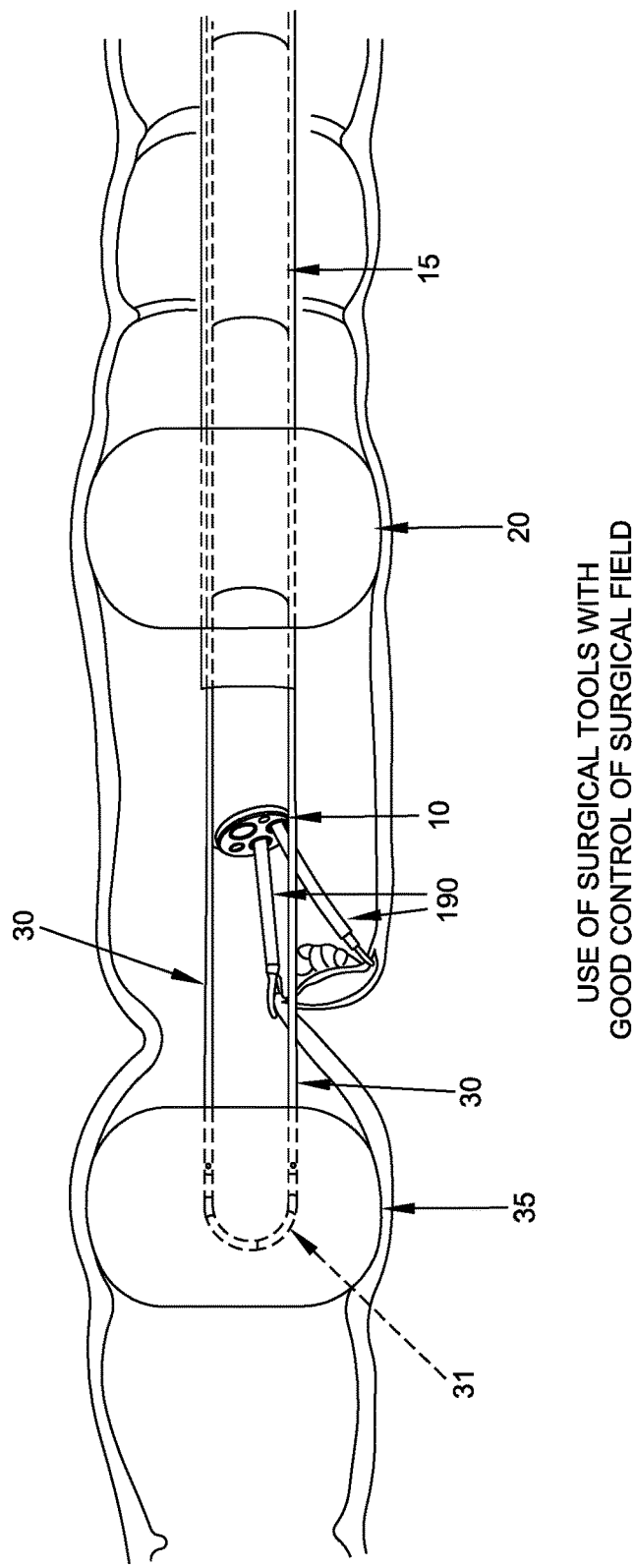
FIG. 100 USE OF SURGICAL TOOLS WITH GOOD CONTROL OF SURGICAL FIELD

ISOLATED THERAPEUTIC ZONE ENABLES RAPID FLUSHING FOR IDENTIFICATION OF BLEEDING SITES

SUCTIONING OUT FLUID FOR
FURTHER EVALUATION OF BLEEDING

FIG. 104 BLEEDING POINT CONTROLLED BY BALLOON PRESSURE

INFLATED FORE BALLOON USED AS BRAKE

SCOPE WITHDRAWAL PASSING THROUGH SECTION DEF

Figure #5: Used between the inflation and pushrod lumens

Figure #4: Shorter Length Insert - Used on the inflation lumens

Figure #3: Larger Length Insert - Used on the pushrod lumens

METHOD AND APPARATUS FOR MANIPULATING THE SIDE WALL OF A BODY LUMEN OR BODY CAVITY SO AS TO PROVIDE INCREASED VISUALIZATION OF THE SAME AND/OR INCREASED ACCESS TO THE SAME, AND/OR FOR STABILIZING INSTRUMENTS RELATIVE TO THE SAME

REFERENCE TO PENDING PRIOR PATENT APPLICATIONS

This patent application:

(1) is a continuation-in-part of pending prior U.S. patent application Ser. No. 14/619,845, filed Feb. 11, 2015 by Cornell University and John Frederick Cornhill et al. for METHOD AND APPARATUS FOR MANIPULATING THE SIDE WALL OF A BODY LUMEN OR BODY CAVITY SO AS TO PROVIDE INCREASED VISUALIZATION OF THE SAME AND/OR INCREASED ACCESS TO THE SAME, AND/OR FOR STABILIZING INSTRUMENTS RELATIVE TO THE SAME, which patent application:

(A) is a continuation-in-part of pending prior U.S. patent application Ser. No. 14/540,355, filed Nov. 13, 2014 by Cornell University and Jeffrey Milsom et al. for METHOD AND APPARATUS FOR STABILIZING, STRAIGHTENING, EXPANDING AND/OR FLATTENING THE SIDE WALL OF A BODY LUMEN AND/OR BODY CAVITY SO AS TO PROVIDE INCREASED VISUALIZATION OF THE SAME AND/OR INCREASED ACCESS TO THE SAME, AND/OR FOR STABILIZING INSTRUMENTS RELATIVE TO THE SAME, which patent application:

(i) is a continuation of prior U.S. patent application Ser. No. 12/969,059, filed Dec. 15, 2010 by Jeffrey Milsom et al. for METHOD AND APPARATUS FOR STABILIZING, STRAIGHTENING, EXPANDING AND/OR FLATTENING THE SIDE WALL OF A BODY LUMEN AND/OR BODY CAVITY SO AS TO PROVIDE INCREASED VISUALIZATION OF THE SAME AND/OR INCREASED ACCESS TO THE SAME, AND/OR FOR STABILIZING INSTRUMENTS RELATIVE TO THE SAME, which patent application:

(a) claims benefit of prior U.S. Provisional Patent Application Ser. No. 61/284,215, filed Dec. 15, 2009 by Jeffrey Milsom et al. for METHOD AND APPARATUS FOR STABILIZING, STRAIGHTENING, EXPANDING AND/OR FLATTENING THE SIDE WALL OF A BODY LUMEN OR BODY CAVITY SO AS TO PROVIDE INCREASED VISUALIZATION OF THE SIDE WALL OF THE BODY LUMEN OR BODY CAVITY, AND/OR FOR STABILIZING INSTRUMENTS RELATIVE TO THE SAME; and (B) claims benefit of prior U.S. Provisional Patent Application Ser. No. 61/938,446, filed Feb. 11, 2014 by Cornell University and John Frederick Cornhill et al. for METHOD AND APPARATUS FOR MANIPULATING THE SIDE WALL OF A BODY LUMEN OR BODY CAVITY SO AS TO PROVIDE INCREASED VISUALIZATION OF THE SAME AND/OR INCREASED ACCESS TO THE SAME, AND/OR FOR STABILIZING INSTRUMENTS RELATIVE TO THE SAME;

(2) is a continuation-in-part of pending prior U.S. patent application Ser. No. 15/172,385, filed Jun. 3, 2016 by Lumendi Ltd. and John Frederick Cornhill et al. for METHOD AND APPARATUS FOR MANIPULATING THE SIDE WALL OF A BODY LUMEN OR BODY CAVITY SO AS TO PROVIDE INCREASED VISUALIZATION OF THE SAME AND/OR INCREASED ACCESS TO THE SAME, AND/OR FOR STABILIZING INSTRUMENTS RELATIVE TO THE SAME, which patent application:

(A) claims benefit of prior U.S. Provisional Patent Application Ser. No. 62/170,476, filed Jun. 3, 2015 by Lumendi Ltd. and John Frederick Cornhill et al. for METHOD AND APPARATUS FOR MANIPULATING THE SIDE WALL OF A BODY LUMEN OR BODY CAVITY SO AS TO PROVIDE INCREASED VISUALIZATION OF THE SAME AND/OR INCREASED ACCESS TO THE SAME, AND/OR FOR STABILIZING INSTRUMENTS RELATIVE TO THE SAME;

(B) claims benefit of prior U.S. Provisional Patent Application Ser. No. 62/170,497, filed Jun. 3, 2015 by Lumendi Ltd. and Stephen Evans et al. for METHOD AND APPARATUS FOR MANIPULATING THE SIDE WALL OF A BODY LUMEN OR BODY CAVITY SO AS TO PROVIDE INCREASED VISUALIZATION OF THE SAME AND/OR INCREASED ACCESS TO THE SAME, AND/OR FOR STABILIZING INSTRUMENTS RELATIVE TO THE SAME;

(C) claims benefit of prior U.S. Provisional Patent Application Ser. No. 62/244,008, filed Oct. 20, 2015 by Lumendi Ltd. and Alan Fortunate et al. for METHOD AND APPARATUS FOR MANIPULATING THE SIDE WALL OF A BODY LUMEN OR BODY CAVITY SO AS TO PROVIDE INCREASED VISUALIZATION OF THE SAME AND/OR INCREASED ACCESS TO THE SAME, AND/OR FOR STABILIZING INSTRUMENTS RELATIVE TO THE SAME;

(D) claims benefit of prior U.S. Provisional Patent Application Ser. No. 62/244,214, filed Oct. 21, 2015 by Lumendi Ltd. and Audrey Bell et al. for METHOD AND APPARATUS FOR MANIPULATING THE SIDE WALL OF A BODY LUMEN OR BODY CAVITY SO AS TO PROVIDE INCREASED VISUALIZATION OF THE SAME AND/OR INCREASED ACCESS TO THE SAME, AND/OR FOR STABILIZING INSTRUMENTS RELATIVE TO THE SAME;

(E) claims benefit of prior U.S. Provisional Patent Application Ser. No. 62/305,773, filed Mar. 9, 2016 by Lumendi Ltd. and Alan Fortunate for METHOD AND APPARATUS FOR MANIPULATING THE SIDE WALL OF A BODY LUMEN OR BODY CAVITY SO AS TO PROVIDE INCREASED VISUALIZATION OF THE SAME AND/OR INCREASED ACCESS TO THE SAME, AND/OR FOR STABILIZING INSTRUMENTS RELATIVE TO THE SAME, INCLUDING VENTING OF BALLOONS THROUGH PACKAGING DESIGN;

(F) claims benefit of prior U.S. Provisional Patent Application Ser. No. 62/305,797, filed Mar. 9, 2016 by Lumendi Ltd. and Brian David Chouinard for METHOD AND APPARATUS FOR MANIPULATING THE SIDE WALL OF A BODY LUMEN OR BODY CAVITY SO AS TO PROVIDE INCREASED VISUALIZATION OF THE SAME AND/OR INCREASED ACCESS TO THE SAME, AND/OR FOR STABILIZING INSTRUMENTS RELATIVE TO THE SAME, INCLUDING IMPROVED AFT BALLOON THERMAL BONDING USING INSERT MATERIAL; and (G) claims benefit of prior U.S. Provisional Patent Application Ser. No. 62/305,804, filed Mar. 9, 2016 by Lumendi Ltd. and Brian David Chouinard et al. for METHOD AND APPARATUS FOR MANIPULATING THE SIDE WALL OF A BODY LUMEN OR BODY CAVITY SO AS TO PROVIDE INCREASED VISUALIZATION OF THE SAME AND/OR INCREASED ACCESS TO THE SAME, AND/OR FOR STABILIZING INSTRUMENTS RELATIVE TO THE SAME, INCLUDING IMPROVED FORE BALLOON CONSTRUCTION; and (3) claims benefit of pending prior U.S. Provisional Patent Application Ser. No. 62/400,948, filed Sep. 28, 2016 by Lumendi Ltd. and Amos Cruz et al. for METHOD AND APPARATUS FOR MANIPULATING THE SIDE WALL OF A BODY LUMEN OR BODY CAVITY SO AS TO PROVIDE INCREASED VISUALIZATION OF THE SAME AND/OR INCREASED ACCESS TO THE SAME, AND/OR FOR STABILIZING INSTRUMENTS RELATIVE TO THE SAME.

The fourteen (14) above-identified patent applications are hereby incorporated herein by reference.

FIELD OF THE INVENTION

This invention relates to surgical methods and apparatus in general, and more particularly to surgical methods and apparatus for manipulating the side wall of a body lumen and/or body cavity so as to provide increased visualization of the same and/or increased access to the same, and/or for stabilizing instruments relative to the same.

BACKGROUND OF THE INVENTION

The human body comprises many different body lumens and body cavities. By way of example but not limitation, the human body comprises body lumens such as the gastrointestinal (GI) tract, blood vessels, lymphatic vessels, the urinary tract, fallopian tubes, bronchi, bile ducts, etc. By way of further example but not limitation, the human body comprises body cavities such as the head, chest, abdomen, nasal sinuses, bladder, cavities within organs, etc.

In many cases it may be desirable to endoscopically examine and/or treat a disease process or abnormality which is located within, or on the side wall of, a body lumen and/or body cavity. By way of example but not limitation, it may be desirable to examine the side wall of the gastrointestinal tract for lesions and, if a lesion is found, to biopsy, remove and/or otherwise treat the lesion.

The endoscopic examination and/or treatment of the side wall of a body lumen and/or body cavity can be complicated by the anatomic configuration (both regional and local) of the side wall of the body lumen and/or body cavity, and/or by the consistency of the tissue making up the side wall of the body lumen and/or body cavity, and/or by the tethering of the side wall of the body lumen and/or body cavity to other anatomical structures.

By way of example but not limitation, the intestine is an elongated tubular organ having an inner lumen and is characterized by frequent turns (i.e., the regional anatomic configuration of the intestine), and comprises a side wall characterized by numerous folds (i.e., the local anatomic configuration of the intestine), with the side wall tissue having a relatively soft, pliable consistency, and with the colon in particular being tethered to the abdomen and/or other abdominal structures via soft tissue. It can be difficult to fully visualize the side wall of the intestine, and/or to treat a lesion formed on the side wall of the intestine, due to this varying side wall anatomic configuration (both regional and local), its relatively soft, pliable consistency, and its tethering to other anatomical structures via soft tissue. By way of example but not limitation, in the case of colonoscopies, it has been found that approximately 5-40% of patients have an anatomic configuration (regional and/or local) of the side wall, and/or a tissue consistency, and/or colon tethering to other anatomical structures, which makes it difficult to fully visualize the anatomy (including pathologic conditions of that anatomy, such as polyps or tumors) using conventional endoscopes, and/or to fully access the anatomy using instruments introduced through conventional endoscopes.

In addition to the foregoing, it has also been found that some body lumens and/or body cavities can spasm and/or contract. This spasming and/or contraction can occur spontaneously, but it is particularly common when an endoscope or other instrument is inserted into the body lumen and/or body cavity. This spasming and/or contraction can cause the body lumen and/or body cavity to constrict and/or otherwise move and/or change its configuration, which can further complicate and/or compromise endoscopic visualization of the anatomy, and/or further complicate and/or compromise access to the anatomy using instruments introduced through conventional, flexible endoscopes. In addition, during examination of the colon, which is typically conducted while both advancing and withdrawing the endoscope through the colon, the endoscope may grip and/or otherwise gather the colon during advancement and/or withdrawal and then suddenly slip and release the colon. This gripping and then sudden release of the colon can result in the endoscope moving quickly past significant lengths of the colon, thereby making accurate examination of the colon challenging.

It would, therefore, be highly advantageous to provide novel apparatus capable of manipulating the side wall of a body lumen and/or body cavity so as to better present the side wall tissue (including visualization of areas which may be initially hidden from view or outside the field of view) for examination and/or treatment during an endoscopic procedure.

It would also be highly advantageous to provide novel apparatus capable of steadying and/or stabilizing the distal tips and/or working ends of instruments (e.g., endoscopes, articulating and/or non-articulating devices such as graspers, cutters or dissectors, cauterizing tools, ultrasound probes, etc.) inserted into a body lumen and/or body cavity with respect to the side wall of the body lumen and/or body cavity, whereby to facilitate the precision use of those instruments.

Among other things, it would be highly advantageous to provide novel apparatus capable of steadying and/or stabilizing the distal tips and/or working ends of endoscopes (and hence also steadying and/or stabilizing the distal tips and/or working ends of other instruments inserted through the working channels of those endoscopes, such as graspers, cutters or dissectors, cauterizing tools, ultrasound probes, etc.).

And it would be highly advantageous to provide novel apparatus capable of steadying and/or stabilizing the distal tips and/or working ends of instruments (such as graspers, cutters or dissectors, cauterizing tools, ultrasound probes, etc.) advanced to the surgical site by means other than through the working channels of endoscopes.

It would also be highly advantageous to be able to straighten bends, "iron out" inner luminal surface folds and create a substantially static or stable side wall of the body lumen and/or body cavity, whereby to enable more precise visual examination (including visualization of areas which may be initially hidden from view or outside the field of view) and/or therapeutic intervention.

SUMMARY OF THE INVENTION

The present invention comprises the provision and use of novel apparatus for manipulating the side wall of a body lumen and/or body cavity so as to better present the side wall tissue (including visualization of areas which may be initially hidden from view or outside the field of view) for examination and/or treatment during an endoscopic procedure.

The present invention also comprises the provision and use of novel apparatus capable of steadying and/or stabilizing the distal tips and/or working ends of instruments (e.g., endoscopes, articulating and/or non-articulating devices such as graspers, cutters or dissectors, cauterizing tools, ultrasound probes, etc.) inserted into a body lumen and/or body cavity with respect to the side wall of the body lumen and/or body cavity, whereby to facilitate the precision use of those instruments.

Among other things, the present invention comprises the provision and use of novel apparatus capable of steadying and/or stabilizing the distal tips and/or working ends of endoscopes (and hence also steadying and/or stabilizing the distal tips and/or working ends of other instruments inserted through the working channels of those endoscopes, such as graspers, cutters or dissectors, cauterizing tools, ultrasound probes, etc.).

And the present invention comprises the provision and use of novel apparatus capable of steadying and/or stabilizing the distal tips and/or working ends of instruments (such as graspers, cutters or dissectors, cauterizing tools, ultrasound probes, etc.) advanced to the surgical site by means other than through the working channels of endoscopes.

And the present invention comprises the provision and use of novel apparatus capable of straightening bends, "ironing out" folds and creating a substantially static or stable side wall of the body lumen and/or body cavity which enables more precise visual examination (including visualization of areas which may be initially hidden from view or outside the field of view) and/or therapeutic intervention.

In one preferred form of the present invention, there is provided apparatus comprising:
  a sleeve adapted to be slid over the exterior of an endoscope, the sleeve having a distal end and a proximal end;
  an aft balloon secured to the sleeve;
  a fore balloon movably mounted to the sleeve so that the fore balloon may be advanced relative to the sleeve; and
  a locking assembly for releasably securing the distal end of the sleeve to the endoscope.

In another preferred form of the present invention, there is provided a method for performing a procedure in a body lumen and/or body cavity, said method comprising:
  providing apparatus comprising:
    a sleeve adapted to be slid over the exterior of an endoscope, the sleeve having a distal end and a proximal end;
    an aft balloon secured to the sleeve;
    a fore balloon movably mounted to the sleeve so that the fore balloon may be advanced relative to the sleeve; and
    a locking assembly for releasably securing the distal end of the sleeve to the endoscope;
  positioning the apparatus in the body lumen and/or body cavity;
  inflating the aft balloon;
  advancing the fore balloon distally;
  inflating the fore balloon; and
  performing the procedure.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein:

FIGS. 2-4 are schematic views showing various dispositions of the fore balloon relative to the aft balloon;

FIG. 13 is a schematic view showing another pair of hollow push tubes and a raised push tube bridge formed in accordance with the present invention;

FIG. 14 is a schematic view showing another pair of hollow push tubes and a raised push tube bridge formed in accordance with the present invention;

FIGS. 15 and 16 are schematic views showing further details of the fore balloon;

FIG. 17 is a schematic view showing the push tube handle;

FIGS. 39-58 are schematic views showing another form of inflation mechanism provided in accordance with the present invention;

FIGS. 61-82 are schematic views showing novel apparatus for inflating and deflating balloons;

FIGS. 89-107 are schematic views showing preferred ways of using the apparatus of FIG. 1;

DETAILED DESCRIPTION OF THE PREFERRED EMBODIMENTS

The present invention comprises the provision and use of novel apparatus for manipulating the side wall of a body lumen and/or body cavity so as to better present the side wall tissue (including visualization of areas initially hidden or outside the field of view) for examination and/or treatment during an endoscopic procedure.

(As used herein, the term "endoscopic procedure" is intended to mean substantially any minimally-invasive or limited access procedure, diagnostic and/or therapeutic and/or surgical, for accessing, endoluminally or transluminally or otherwise, the interior of a body lumen and/or body cavity for the purposes of viewing, biopsying and/or treating tissue, including removing a lesion and/or resecting tissue, etc.)

The present invention also comprises the provision and use of novel apparatus capable of steadying and/or stabilizing the distal tips and/or working ends of instruments (e.g., endoscopes, articulating and/or non-articulating devices such as graspers, cutters or dissectors, cauterizing tools, ultrasound probes, etc.) inserted into a body lumen and/or body cavity with respect to the side wall of the body lumen and/or body cavity, whereby to facilitate the precision use of those instruments.

Among other things, the present invention comprises the provision and use of novel apparatus capable of steadying and/or stabilizing the distal tips and/or working ends of endoscopes (and hence also steadying and/or stabilizing the distal tips and/or working ends of other instruments inserted through the working channels of those endoscopes, such as graspers, cutters or dissectors, cauterizing tools, ultrasound probes, etc.).

And the present invention comprises the provision and use of novel apparatus capable of steadying and/or stabilizing the distal tips and/or working ends of instruments (such as graspers, cutters or dissectors, cauterizing tools, ultrasound probes, etc.) advanced to the surgical site by means other than through the working channels of endoscopes.

And the present invention comprises the provision and use of novel apparatus capable of straightening bends, "ironing out" folds and creating a substantially static or stable side wall of the body lumen and/or body cavity which enables more precise visual examination (including visualization of areas which may be initially hidden from view or outside the field of view) and/or therapeutic intervention.

The Novel Apparatus

Figure 1:
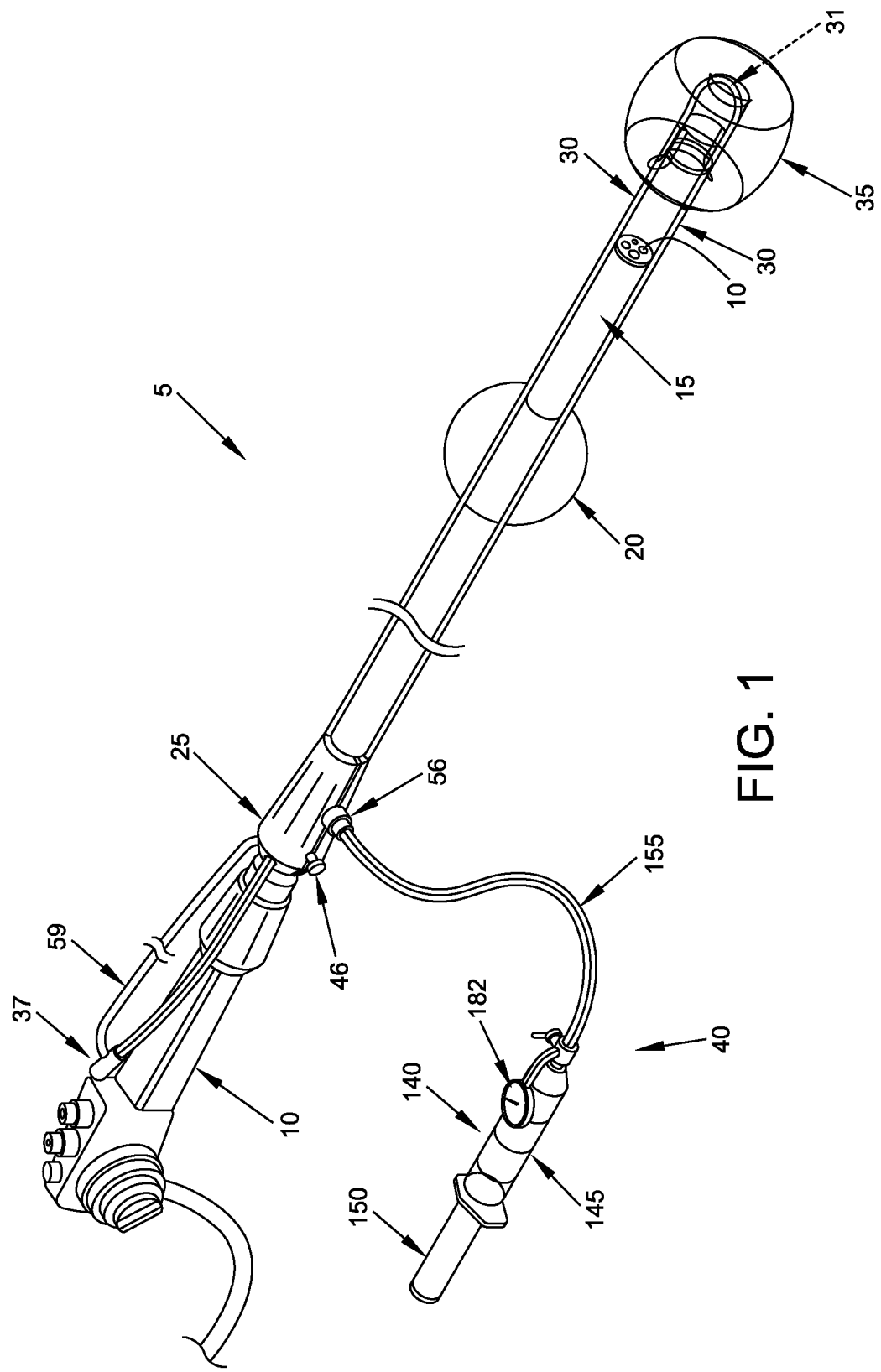
FIG. 1 is a schematic view showing novel apparatus formed in accordance with the present invention, wherein the novel apparatus comprises, among other things, a sleeve for disposition over the end of an endoscope, an aft balloon mounted to the sleeve, a pair of hollow push tubes slidably mounted to the sleeve, the pair of hollow push tubes being connected to one another at their distal ends with a raised push tube bridge, the raised push tube bridge being configured to nest an endoscope therein, a fore balloon mounted to the distal end of the hollow push tubes, and a push tube handle mounted to the proximal ends of the hollow push tubes.
Figure 5:
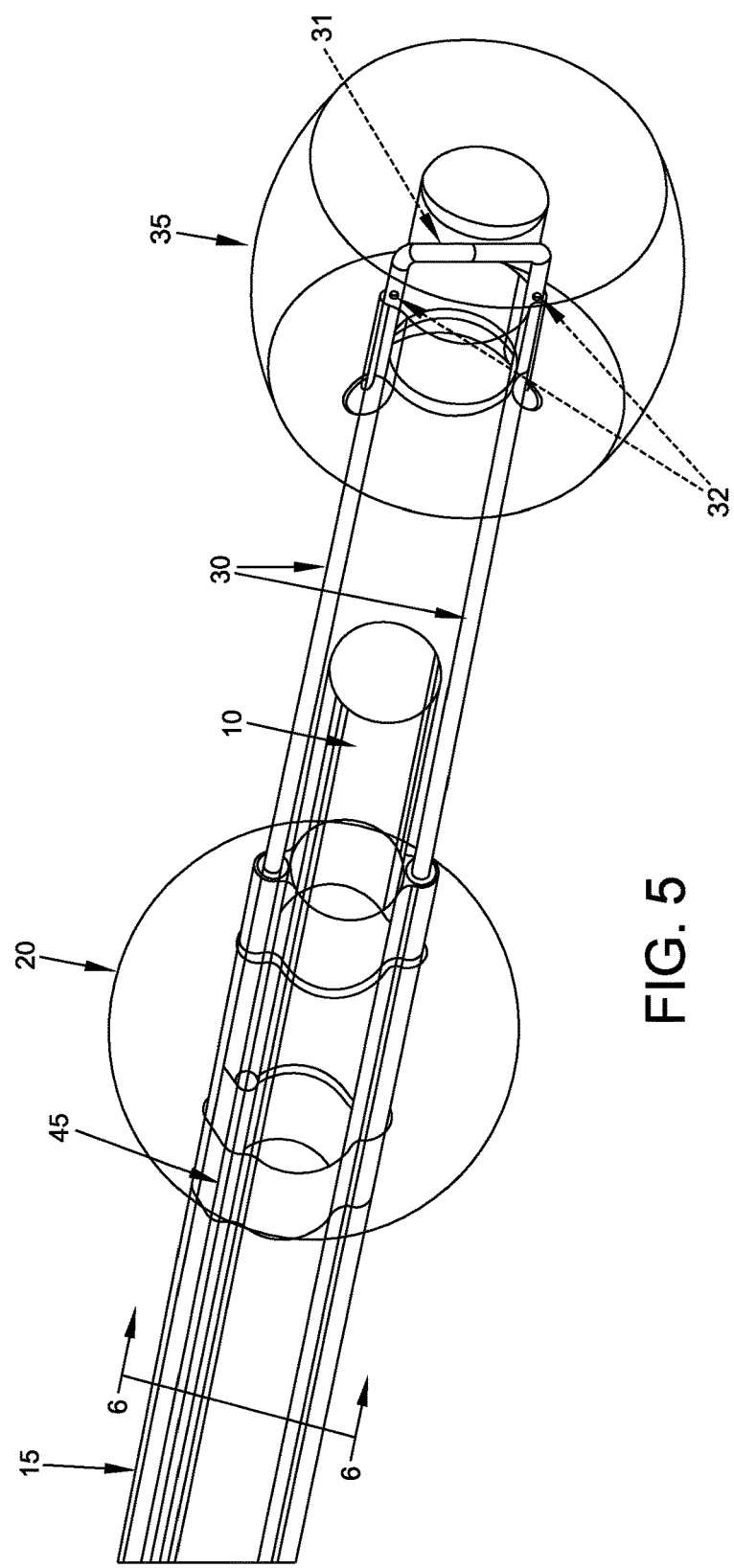
FIG. 5 is a schematic view showing further details of the distal end of the apparatus shown in FIG. 1.
Figure 6:
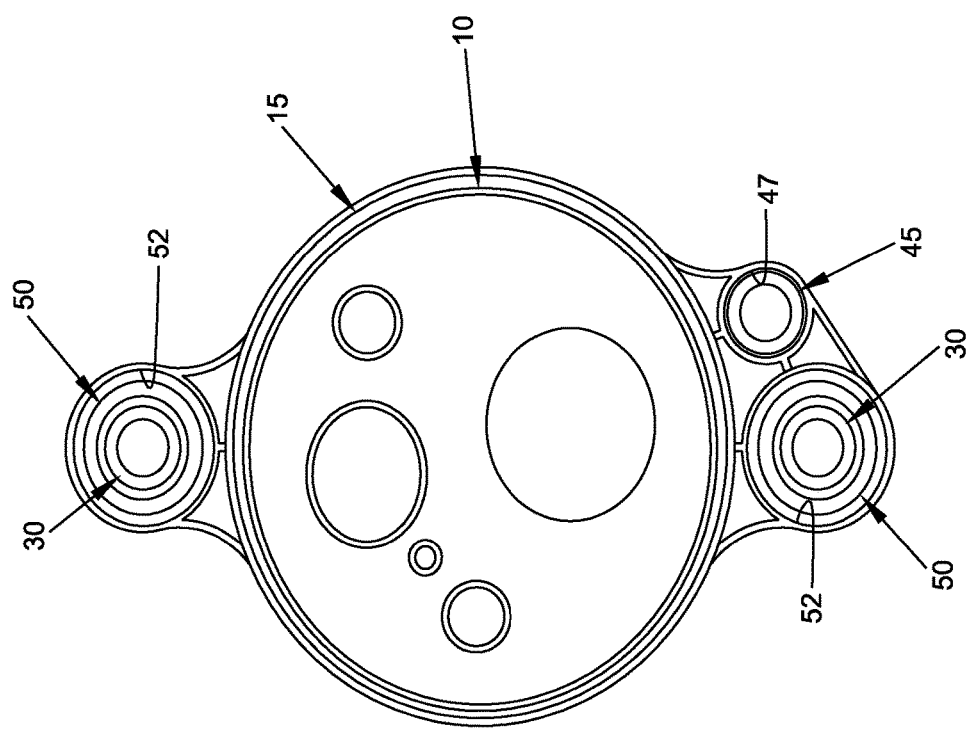
FIG. 6 is a section view taken along line 6-6 of FIG. 5.

In accordance with the present invention, and looking now at FIG. 1, there is shown novel apparatus 5 which is capable of manipulating (e.g., stabilizing, straightening, expanding and/or flattening, etc.) the side wall of a body lumen and/or body cavity so as to better present the side wall tissue (including visualization of areas which may be initially hidden from view or outside the field of view) for examination and/or treatment during an endoscopic procedure using an endoscope 10 (e.g., an articulating endoscope), and/or for stabilizing the distal end of endoscope 10 and/or the distal tips and/or working ends of other instruments (e.g., graspers, cutters or dissectors, cauterizing tools, ultrasound probes, etc., not shown in FIG. 1).

More particularly, apparatus 5 generally comprises a sleeve 15 adapted to be slid over the exterior of the shaft of endoscope 10, a proximal (or "aft") balloon 20 (the terms "proximal" and "aft" will hereinafter be used interchangeably) secured to sleeve 15 near the distal end of the sleeve, and a base 25 secured to sleeve 15 at the proximal end of the sleeve. Apparatus 5 also comprises a pair of hollow push tubes 30 slidably mounted to sleeve 15 as will hereinafter be discussed, the pair of hollow push tubes being connected to one another at their distal ends with a raised push tube bridge 31, the raised push tube bridge 31 being configured to nest an endoscope therein, and a distal (or "fore") balloon 35 (the terms "distal" and "fore" will hereinafter be used interchangeably) secured to the distal ends of hollow push tubes 30, such that the spacing between aft balloon 20 and fore balloon 35 can be adjusted by the physician (or other operator or user) by moving hollow push tubes 30 relative to sleeve 15 (e.g., by advancing the two hollow push tubes simultaneously at push tube handle 37, see below). See FIGS. 1 and 2-4. Apparatus 5 also comprises an associated inflation mechanism 40 (FIG. 1) for enabling selective inflation/deflation of one or both of aft balloon 20 and fore balloon 35 by the physician (or other operator or user).

The Sleeve

Looking now at FIGS. 1-6, sleeve 15 generally comprises an elongated, thin-walled tube configured to be slid over the exterior of the shaft of endo scope 10 (e.g., retrograde from the distal tip of the endoscope) so as to make a close fit therewith, with the sleeve being sized and constructed so that it will slide easily back over the endoscope during mounting thereon (preferably with the scope "dry") but will have sufficient residual friction (when gripped by the hand of the physician or other operator or user) with the outer surface of the endoscope such that the sleeve will remain in place to allow torqueing (i.e., rotational turning) and pushing/pulling of the endoscope during use (e.g., within the colon of a patient). In one preferred form of the invention, sleeve 15 can move circumferentially to some extent about endoscope 10 (and when gripped securely by the hand of the physician or other operator or user, can rotate in conjunction with the shaft of the endoscope); but sleeve 15 can only move nominally in an axial direction relative to endoscope 10. Sleeve 15 is sized so that when its distal end is substantially aligned with the distal end of endoscope 10, sleeve 15 (in conjunction with base 25) will substantially cover the shaft of the endoscope. In any case, sleeve 15 is sized so that when it is mounted to endoscope 10 and endoscope 10 is inserted into a patient, sleeve 15 extends out of the body of the patient. In one preferred form of the invention, apparatus 5 is provided according to the particular endoscope with which it is intended to be used, with apparatus 5 being sized so that when base 25 is in engagement with the handle of the endoscope, the distal end of sleeve 15 will be appropriately positioned at the distal end of the endoscope, i.e., substantially aligned with the distal end of the endoscope or slightly proximal to the distal end of the endoscope.

If desired, the distal end of sleeve 15 may be provided with a radially-inwardly-extending stop (not shown) to positively engage the distal end surface of endoscope 10, whereby to prevent the distal end of sleeve 15 from moving proximally beyond the distal end surface of endoscope 10. Such a radially-inwardly-extending stop can also assist in preventing "torque slip" of sleeve 15 relative to endoscope 10 during torqueing (i.e., rotational turning) of the endoscope while within the colon, and/or "thrust slip" of sleeve 15 relative to endoscope 10 during forward pushing of the endoscope while within the colon.

Sleeve 15 preferably has a smooth outer surface so as to be non-traumatic to tissue, and is preferably made of a highly flexible material such that the sleeve will not inhibit bending of the endoscope during use. In one preferred form of the invention, sleeve 15 comprises polyurethane, polyethylene, poly(vinyl chloride) (PVC), polytetrafluoroethylene (PTFE), etc., and is preferably transparent (or at least translucent) so as to allow distance markings on endoscope 10 to be visualized through sleeve 15. And in one preferred form of the invention, sleeve 15 preferably has nominal hoop strength, so that the physician (or other operator or user) can grip endoscope 10 through sleeve 15, e.g., so as to torque the scope. If desired, sleeve 15 can include a lubricious coating (e.g., a liquid such as perfluoropolyether synthetic oil, a powder, etc.) on some or all of its interior and/or exterior surfaces, so as to facilitate disposition of the sleeve over the endoscope and/or movement of apparatus 5 through a body lumen and/or body cavity. Alternatively, sleeve 15 may be formed of a material which is itself lubricious, e.g., polytetrafluoroethylene (PTFE), etc. It should be appreciated that the inside surface of sleeve 15 may include features (e.g., ribs) to prevent the sleeve from rotating relative to the endoscope during use.

If desired, a vacuum may be "pulled" between sleeve 15 and endoscope 10, whereby to secure sleeve 15 to endoscope 10 and minimize the profile of sleeve 15. By way of example but not limitation, a vacuum may be introduced at the proximal end of sleeve 15 (i.e., at base 25) or a vacuum may be introduced at a point intermediate sleeve 15. By way of further example but not limitation, it should also be appreciated that removal of sleeve 15 from endoscope 10 (e.g., at the conclusion of a procedure) may be facilitated by introducing a fluid (e.g., air or a liquid lubricant) into the space between sleeve 15 and endoscope 10, e.g., at the proximal end of sleeve 15 (i.e., at base 25) or intermediate sleeve 15.

The Aft Balloon

Still looking now at FIGS. 1-6, aft balloon 20 is secured to sleeve 15 just proximal to the articulating joint of the endoscope near to, but spaced from, the distal end of the sleeve. Aft balloon 20 is disposed concentrically about sleeve 15, and hence concentrically about an endoscope 10 disposed within sleeve 15. Thus, aft balloon 20 has a generally toroidal shape. Aft balloon 20 may be selectively inflated/deflated by means of a proximal inflation/deflation tube 45 which has its distal end in fluid communication with the interior of aft balloon 20, and which has its proximal end in fluid communication with a fitting 46 mounted to base 25. Fitting 46 is configured for connection to the aforementioned associated inflation mechanism 40. Fitting 46 is preferably a luer-activated valve, allowing inflation mechanism 40 to be disconnected from fitting 46 without losing pressure in aft balloon 20. Inflation/deflation tube 45 may be secured to the exterior surface of sleeve 15 or, more preferably, inflation/deflation tube 45 may be contained within a lumen 47 formed within sleeve 15.

Preferably aft balloon 20 is disposed a short distance back from the distal end of sleeve 15, i.e., by a distance which is approximately the same as the length of the articulating portion of a steerable endoscope 10, such that the articulating portion of the steerable endoscope will be disposed distal to aft balloon 20 when the steerable endoscope is disposed in sleeve 15. This construction allows the flexible portion of the steerable endoscope to be articulated even when aft balloon 20 has been inflated in the anatomy so as to stabilize the adjacent non-articulating portion of the endoscope relative to the anatomy, as will hereinafter be discussed in further detail. Thus, when inflated, aft balloon 20 provides a secure platform within the anatomy for maintaining endoscope 10 in a stable position within a body lumen or body cavity, with endoscope 10 centered within the body lumen or body cavity. As a result, endoscope 10 can provide improved visualization of the anatomy. Furthermore, inasmuch as endoscope 10 is securely maintained within the body lumen or body cavity by the inflated aft balloon 20, instruments advanced through the internal lumens (sometimes referred to as the "working channel" or "working channels") of endoscope 10 will also be provided with a secure platform for supporting those instruments within the body lumen or body cavity.

When aft balloon 20 is appropriately inflated, the aft balloon can atraumatically engage and form a sealing relationship with the side wall of a body lumen within which apparatus 5 is disposed.

In one preferred form of the invention, aft balloon 20 is formed out of polyurethane.

The Base

Base 25 is secured to the proximal end of sleeve 15. Base 25 engages endoscope 10 and helps secure the entire assembly (i.e., apparatus 5) to endoscope 10. Base 25 preferably comprises a substantially rigid or semi-rigid structure which may be gripped by the physician (or other operator or user) and pulled proximally, whereby to allow the physician (or other operator or user) to pull sleeve 15 over the distal end of endoscope 10 and then proximally back along the length of endoscope 10, whereby to mount sleeve 15 to the outer surface of the shaft of the endoscope. In one preferred form of the invention, base 25 is pulled proximally along the endoscope until base 25 seats against the handle of the endoscope, thereby prohibiting further proximal movement of base 25 (and hence thereby prohibiting further proximal movement of sleeve 15). In one preferred form of the invention, base 25 makes a sealing engagement with endoscope 10.

The Pair of Hollow Push Tubes and the Push Tube Handle

The pair of hollow push tubes 30 are slidably mounted to sleeve 15, whereby the distal ends of the hollow push tubes (and the raised push tube bridge 31 connecting the distal ends of the pair of hollow push tubes 30) can be extended and/or retracted relative to sleeve 15 (e.g., by advancing or withdrawing the hollow push tubes via push tube handle 37, see below), and hence extended and/or retracted relative to the distal end of endoscope 10 which is disposed in sleeve 15. Preferably, hollow push tubes 30 are slidably disposed in support tubes 50 which are secured to the outer surface of sleeve 15 or, more preferably, are contained within lumens 52 formed within sleeve 15. Support tubes 50 are preferably formed out of a low friction material (e.g., polytetrafluoroethylene, also known as "PTFE") so as to minimize resistance to movement of hollow push tubes 30 relative to support tubes 50 (and hence minimize resistance to movement of hollow push tubes 30 relative to sleeve 15). In this respect it should be appreciated that minimizing resistance to the movement of hollow push tubes 30 relative to support tubes 50 improves tactile feedback to the user when hollow push tubes 30 are being used to manipulate fore balloon 35. In one form of the invention, support tubes 50 are flexible (so as to permit endoscope 10, and particularly the articulating portion of steerable endoscope 10, to flex as needed during the procedure); however, support tubes 50 also provide some column strength. Thus, when support tubes 50 are mounted within lumens 52 formed in sleeve 15, the assembly of sleeve 15 and hollow support tubes 50 is flexible yet has a degree of column strength (whereas sleeve 15 alone is flexible but has substantially no column strength). In the event that hollow push tubes 30 are contained within lumens 52 formed in sleeve 15, and in the event that support tubes 50 are not disposed between hollow push tubes 30 and lumens 52, lumens 52 are preferably lubricated so as to minimize friction between hollow push tubes 30 and lumens 52.

Figure 8:
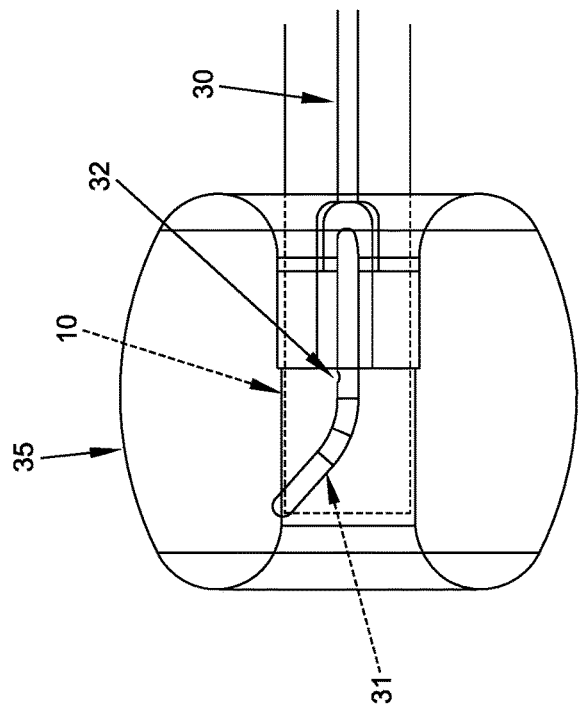
FIGS. 7 and 8 are schematic views showing a pair of hollow push tubes, a raised push tube bridge, and the fore balloon.
Figure 7:
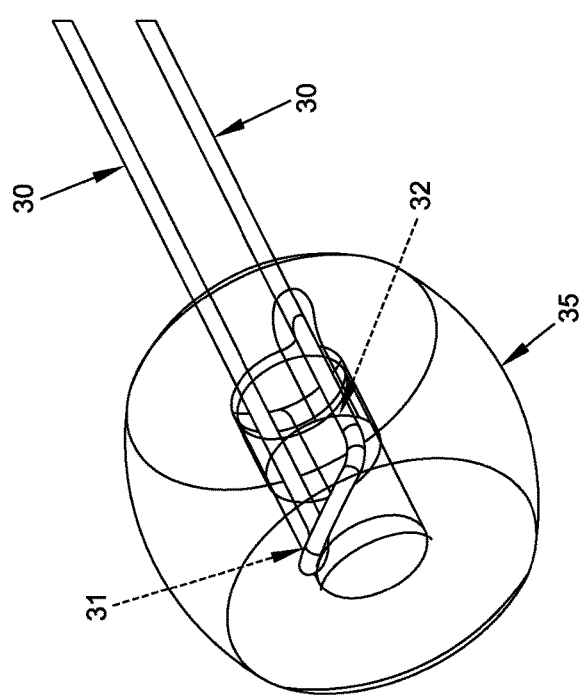

The distal ends of the pair of hollow push tubes 30 are connected together with a raised push tube bridge 31 (FIG. 7). Raised push tube bridge 31 provides a rounded structure at the distal ends of hollow push tubes 30 which simultaneously serves to (i) connect the distal ends of hollow push tubes 30 together, and (ii) eliminate abrupt ends at the distal end of hollow push tubes 30 which could cause trauma to tissue, e.g., during distal advancement of hollow push tubes 30. Raised push tube bridge 31 is configured to nest an endoscope therein (FIG. 8).

Figure 11:
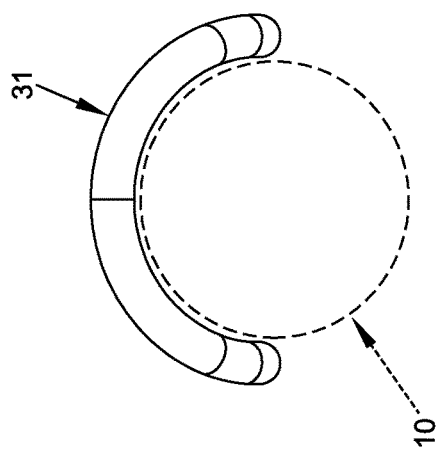
FIGS. 9-11 are schematic views showing a pair of hollow push tubes and a raised push tube bridge formed in accordance with the present invention.
Figure 10:
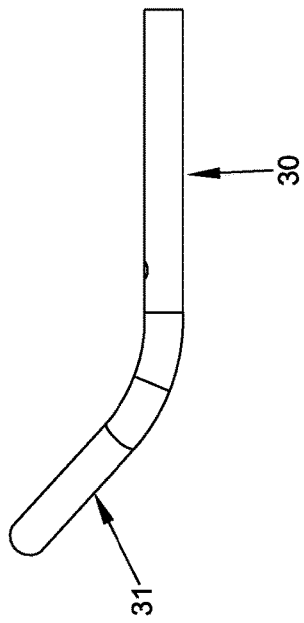
Figure 9:
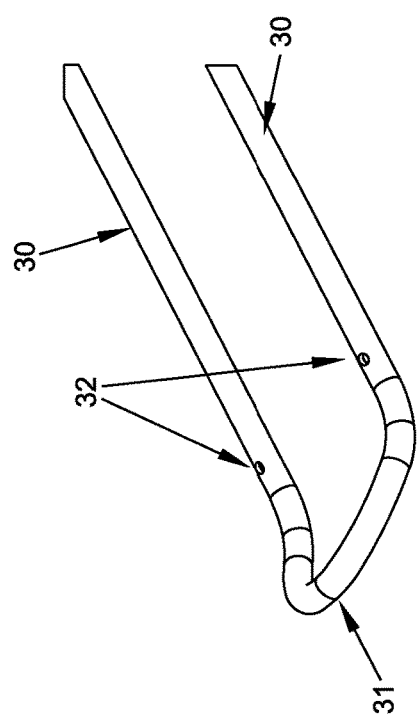
Figure 12:
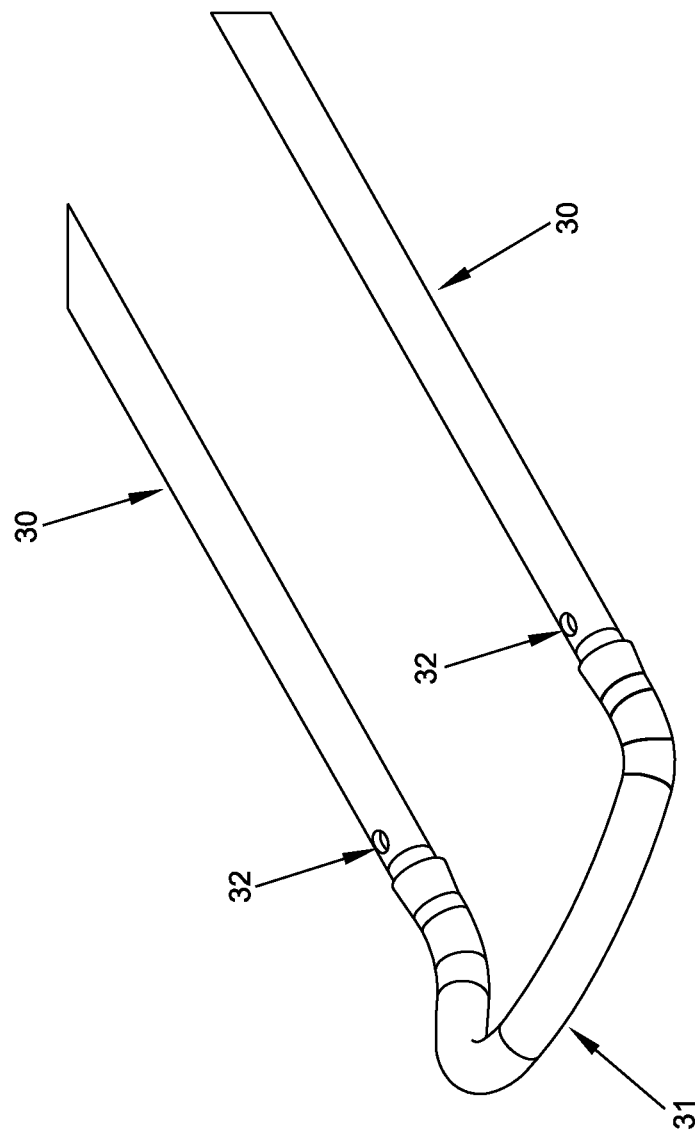
FIG. 12 is a schematic view showing another pair of hollow push tubes and a raised push tube bridge formed in accordance with the present invention.

In one preferred form of the invention, raised push tube bridge 31 is also hollow. In this form of the invention, the hollow raised push tube bridge 31 may be formed integral with hollow push tubes 30, i.e., the hollow push tubes 30 and the hollow raised push tube bridge 31 may form one continuous tube (FIGS. 9-11). Or, in this form of the invention, the hollow raised push tube bridge 31 may be formed separately from hollow push tubes 30 and the hollow raised push tube bridge 31 may be joined to hollow push tubes 30 during manufacturing (FIG. 12).

In one preferred form of the invention, raised push tube bridge 31 may be substantially solid and is connected with hollow push tubes 30 during manufacture.

If desired, raised push tube bridge 31 may be inclined distally, e.g., in the manner shown in FIGS. 7-12.

Alternatively, if desired, raised push tube bridge 31 may be set substantially perpendicular to the longitudinal axes of hollow push tubes 30, e.g., in the manner shown in FIG. 13.

Furthermore, if desired, raised push tube bridge 31 may be in the form of a ring, with endoscope 10 nesting within the interior of the ring, e.g., in the manner shown in FIG. 14.

The proximal ends of hollow push tubes 30 are connected to push tube handle 37. As a result of this construction, pushing distally on push tube handle 37 causes the distal ends of hollow push tubes 30 to move distally (at the same rate) relative to sleeve 15 (whereby to move fore balloon 35 distally relative to aft balloon 20) and pulling proximally on push tube handle 37 causes the distal ends of hollow push tubes 30 to retract proximally (at the same rate) relative to sleeve 15 (whereby to move fore balloon 35 proximally relative to aft balloon 20). Note that by moving hollow push tubes 30 distally or proximally at the same rate, the distal ends of the hollow push tubes are maintained parallel to each other. A clamp 53 (FIGS. 37 and 60) is provided at base 25 for holding hollow push tubes 30 in a selected disposition relative to base 25 (and hence in a selected disposition relative to sleeve 15).

Hollow push tubes 30 and raised push tube bridge 31 are preferably formed out of a relatively flexible material which provides good column strength, e.g., a thermoplastic polyethylene resin such as Isoplast™ (available from The Lubrizol Corporation of Wickliffe, Ohio), polyethylene, polypropylene, nylon, etc. It should be appreciated that hollow push tubes 30 and raised push tube bridge 31 can comprise a single material or a plurality of materials, and that the stiffness of hollow push tubes 30 and raised push tube bridge 31 can vary along their length. By way of example but not limitation, the distal-most portion of hollow push tubes 30 and raised push tube bridge 31 can be formed of the same material as the remainder of the hollow push tubes but have a lower modulus so as to be more flexible than the remainder of the hollow push tubes, or the distal-most portion of hollow push tubes 30 and raised push tube bridge 31 can comprise a different, more resilient flexible material. By way of example but not limitation, the distal-most portion of hollow push tubes 30 and raised push tube bridge 31 can comprise Nitinol. By way of further example but not limitation, the distal-most portion of hollow push tubes 30 and raised push tube bridge 31 can comprise a stainless steel coil covered with an outer jacket of polytetrafluoroethylene (PTFE), with the distal-most jacket/more-proximal tubing together providing a sealed lumen for inflating/deflating fore balloon 35. By forming hollow push tubes 30 and raised push tube bridge 31 with distal ends which are more flexible than the remainder of the hollow push tubes, the hollow push tubes 30, raised push tube bridge 31 and fore balloon 35 can together function as a lead (with a soft atraumatic tip) for apparatus 5 and endoscope 10, as discussed further below.

In one preferred form of the invention, hollow push tubes 30 are configured to maintain a parallel disposition when they are in an unbiased state, i.e., when no force is being applied to hollow push tubes 30. This is true regardless of the state of inflation or deflation of fore balloon 35. The provision of raised push tube bridge 31 can help maintain the parallel disposition of hollow push tubes 30.

The distal-most portion of hollow push tubes 30 can be configured to bend inwardly or outwardly if desired e.g., via their connection to raised push tube bridge 31. With such a configuration, when the distal ends of hollow push tubes 30 are held longitudinally stationary (e.g., by an inflated fore balloon, as will hereinafter be discussed) and a sufficient distally-directed force is applied to hollow push tubes 30, the middle portions of hollow push tubes 30 (i.e., the portions between the inflated fore balloon 35 and sleeve 15) can bend or bow outwardly, whereby to push outwardly on the side wall of the body lumen which apparatus 5 is disposed in, thereby providing a "tenting" effect on the side wall of the body lumen and/or body cavity in the space between aft balloon 20 and fore balloon 35. This "tenting" effect can significantly enhance visibility and/or tissue stability in the area distal to endoscope 10, by pushing outwardly on the side wall of the body lumen and/or body cavity in which apparatus 5 is disposed.

It should also be appreciated that by forming hollow push tubes 30 out of a flexible material, it is possible to manually adjust their position during use (e.g., by using a separate tool, by torqueing the apparatus, etc.) so as to prevent the hollow push tubes 30 from interfering with visualization of the patient's anatomy and/or interfering with diagnostic or therapeutic tools introduced into the space between the fore and aft balloons 35, 20. By way of example but not limitation, if apparatus 5 is disposed in the anatomy in such a way that a hollow push tube 30 blocks visual or physical access to a target region of the anatomy, the flexible hollow push tube(s) may be moved out of the way by using a separate tool or instrument, or by rotating the apparatus with a torqueing motion so as to move the flexible hollow push tube(s) out of the way, etc. By way of further example but not limitation, by constructing hollow push tubes 30 so that they are circular and flexible and of a diameter significantly smaller than the round circumference of endoscope 10, the movement of the round endoscope, when articulated, can simply push the hollow push tubes out of the way and provides a unobstructed visual path to the tissue of interest.

It should also be appreciated that, if desired, hollow push tubes 30 can be marked with an indicator including distance markers (not shown in the figures), e.g., colored indicators or radiopaque indicators, so that a physician (or other operator or user) observing the surgical site via endoscope 10 or by radiological guidance (e.g., X-ray fluoroscopy) can ascertain the relative disposition of hollow push tubes 30 at the surgical site both longitudinally and/or circumferentially with respect to the side wall of the body lumen and/or other body cavity.

Hollow push tubes 30 have their internal lumens (i) in fluid communication with the interior of fore balloon 35 (FIGS. 1-5, 15 and 16), e.g., via a plurality of openings 32, and (ii) in fluid communication with a fitting 56 mounted to base 25. Fitting 56 is configured for connection to the aforementioned associated inflation mechanism 40, in order that fore balloon 35 may be selectively inflated/deflated with air or other fluids (including liquids). Fitting 56 is preferably a luer-activated valve, allowing inflation mechanism 40 to be disconnected from fitting 56 without losing pressure in fore balloon 35.

More particularly, in one preferred form of the present invention, and looking now at FIG. 17, push tube handle 37 comprises a hollow interior 57. Hollow push tubes 30 are mounted to push tube handle 37 so that hollow push tubes 30 will move in conjunction with push tube handle 37, and so that the hollow interiors of hollow push tubes 30 are in fluid communication with the hollow interior 57 of push tube handle 37. Push tube handle 37 also comprises a fitting 58 which is in fluid communication with hollow interior 57 of push tube handle 37. A flexible tube 59 connects fitting 58 with an internal chamber (not shown) in base 25, with this internal chamber in base 25 being in fluid communication with the aforementioned fitting 56. As a result of this construction, when push tube handle 37 is moved distally, hollow push tubes 30 are moved distally, and hence fore balloon 35 is moved distally; and when push tube handle 37 is moved proximally, hollow push tubes 30 are moved proximally, and hence fore balloon 35 is moved proximally. Furthermore, when positive fluid pressure is applied to fitting 56 in base 25, positive fluid pressure is applied to the internal lumens of hollow push tubes 30, and hence to the interior of fore balloon 35 (i.e., via openings 32), whereby to inflate fore balloon 35; and when negative fluid pressure is applied to fitting 56 in base 25, negative fluid pressure is applied to the internal lumen of hollow push tubes 30, and hence to the interior of fore balloon 35 (i.e., via openings 32), whereby to deflate fore balloon 35.

It should be appreciated that the provision of a pair of hollow push tubes 30, connected together at their distal ends by a raised push tube bridge 31, provides numerous advantages. By way of example but not limitation, the provision of a pair of hollow push tubes 30, connected together at their distal ends by a raised push tube bridge 31, provides a symmetric force to fore balloon 35 when the fore balloon is advanced distally into a body lumen, as will hereinafter be discussed. Furthermore, the provision of a pair of hollow push tubes 30, connected together at their distal ends by a raised push tube bridge 31, provides equal outward forces against the adjacent anatomy when the pair of hollow push tubes are employed to straighten out the anatomy in the area proximate the distal end of endoscope 10, thereby enhancing visualization of, and/or access to, the anatomy, as will hereinafter be discussed. In addition, the provision of a pair of hollow push tubes 30, connected together at their distal ends by a raised push tube bridge 31, ensures that fore balloon 35 remains centered on endoscope 10, thereby facilitating un-docking of fore balloon 35 from endoscope 10 and re-docking of fore balloon 35 over endoscope 10, as will hereinafter be discussed. In addition, the provision of a pair of hollow push tubes 30, connected together at their distal ends by a raised push tube bridge 31, helps ensure that fore balloon 35 is stable relative to the tip of the endoscope, minimizing rotational movement of the fore balloon when inflated. Furthermore, the provision of a pair of hollow push tubes, connected together at their distal ends by a raised push tube bridge 31, provides a redundant air transfer system for inflating or deflating fore balloon 35. And the provision of a pair of hollow push tubes 30, connected together a their distal ends by a raised push tube bridge 31, presents a rounded, blunt distal end for hollow push tubes 30, thereby ensuring atraumatic advancement of fore balloon 35 within the anatomy.

The Fore Balloon

Fore balloon 35 is secured to the distal ends of hollow push tubes 30, with raised push tube bridge 31 being disposed within the interior of fore balloon 35, whereby the spacing between aft balloon 20 and fore balloon 35 can be adjusted by moving hollow push tubes 30 relative to sleeve 15, i.e., by moving push tube handle 37 relative to sleeve 15. Furthermore, hollow push tubes 30 provide a conduit between the interior of fore balloon 35 and fitting 56, whereby to permit selective inflation/deflation of fore balloon 35 via fitting 56.

Significantly, fore balloon 35 is configured so that (i) when it is deflated (or partially deflated) and it is in its "retracted" position relative to sleeve 15 (FIG. 2), fore balloon 35 provides an axial opening 63 (FIGS. 15, 16 and 19) sufficient to accommodate sleeve 15 and the shaft of endoscope 10 therein, with raised push tube bridge 31 extending concentrically about axial opening 63, whereby fore balloon 35 can be "docked" over sleeve 15 and endoscope 10, and (ii) when fore balloon 35 is in its "extended" position relative to sleeve 15 and is appropriately inflated (FIG. 4), axial opening 63 is closed down (and preferably completely closed off). At the same time, when appropriately inflated, the fore balloon can atraumatically engage and form a sealing relationship with the side wall of a body lumen and/or body cavity within which apparatus 5 is disposed. Thus, when fore balloon 35 is appropriately inflated, the fore balloon can effectively seal the body lumen and/or body cavity distal to fore balloon 35, by closing down axial opening 63 and forming a sealing relationship with the side wall of the body lumen and/or body cavity within which apparatus 5 is disposed. In this way, when hollow push tubes 30 are advanced distally so as to separate fore balloon 35 from aft balloon 20, and when fore balloon 35 and aft balloon 20 are appropriately inflated, the two balloons will create a sealed zone therebetween (sometimes hereinafter referred to as "the therapeutic zone").

It will be appreciated that, when fore balloon 35 is reconfigured from its deflated condition to its inflated condition, fore balloon 35 expands radially inwardly (so as to close down axial opening 63) as well as radially outwardly (so as to engage the surrounding tissue). Note that hollow push tubes 30 and raised push tube bridge 31 are disposed within fore balloon 35 in such a way that their presence within the fore balloon does not physically interfere with inflation or deflation of fore balloon 35.

Thus it will be seen that fore balloon 35 has a "torus" shape when deflated (to allow it to seat over the distal end of the endoscope) and a substantially "solid" shape when inflated (to allow it to close off a body lumen or body cavity).

Figure 19:
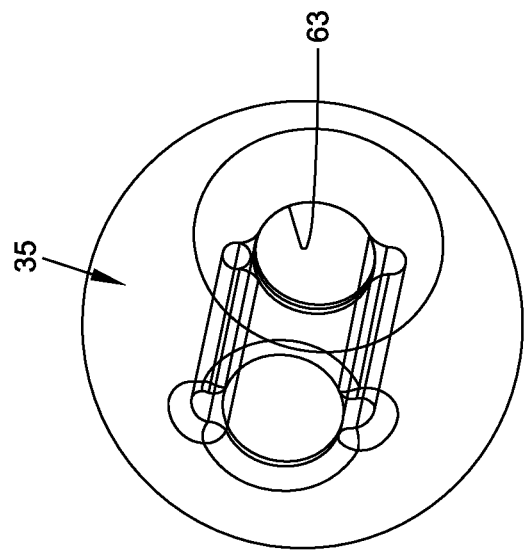
FIGS. 18 and 19 are schematic views showing construction details of the fore balloon.
Figure 18:
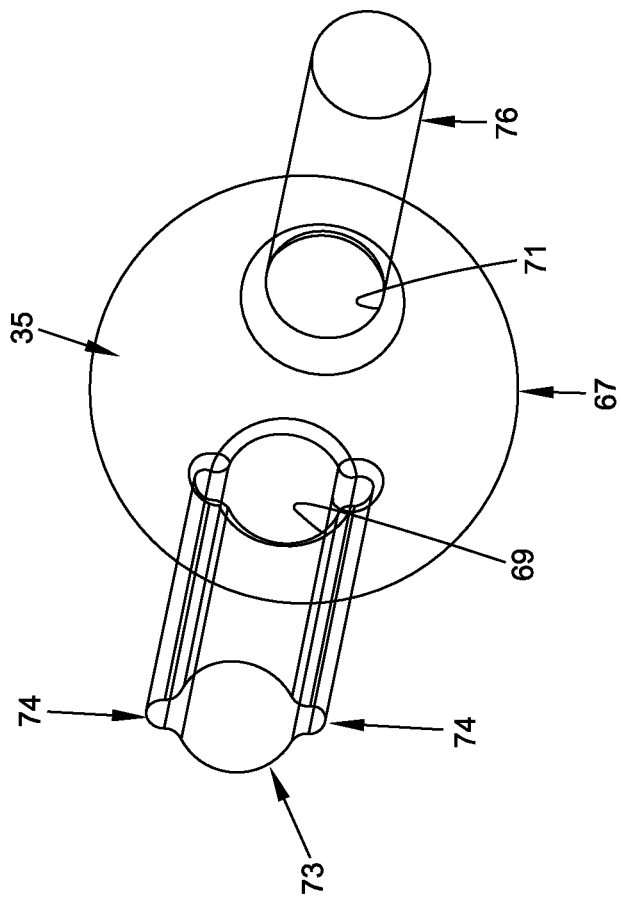
Figure 20:
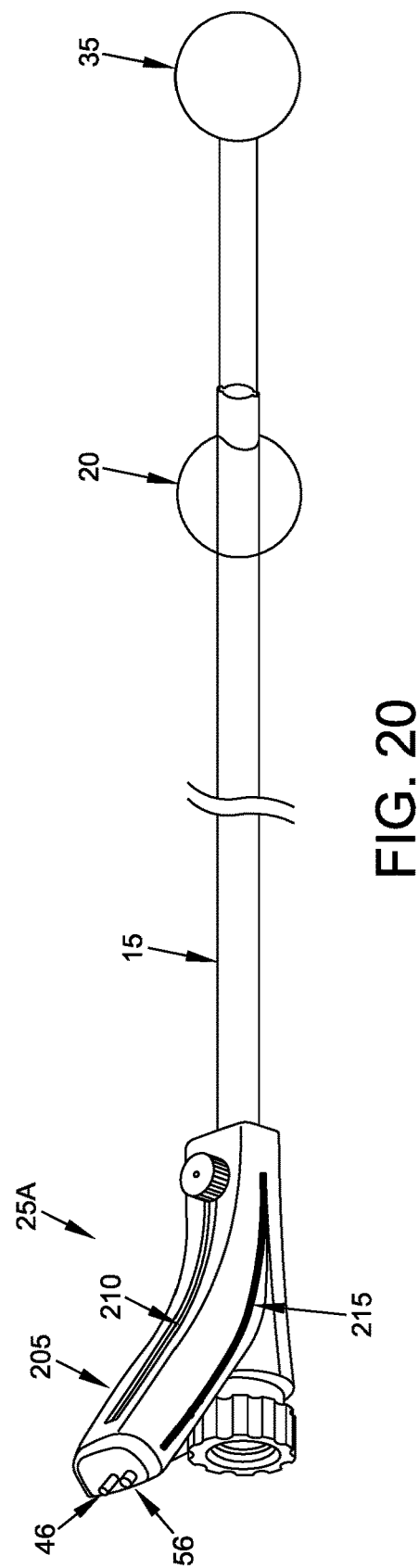
FIGS. 20-34 are schematic views showing another form of the handle mechanism for the novel apparatus of the present invention.
Figure 21:
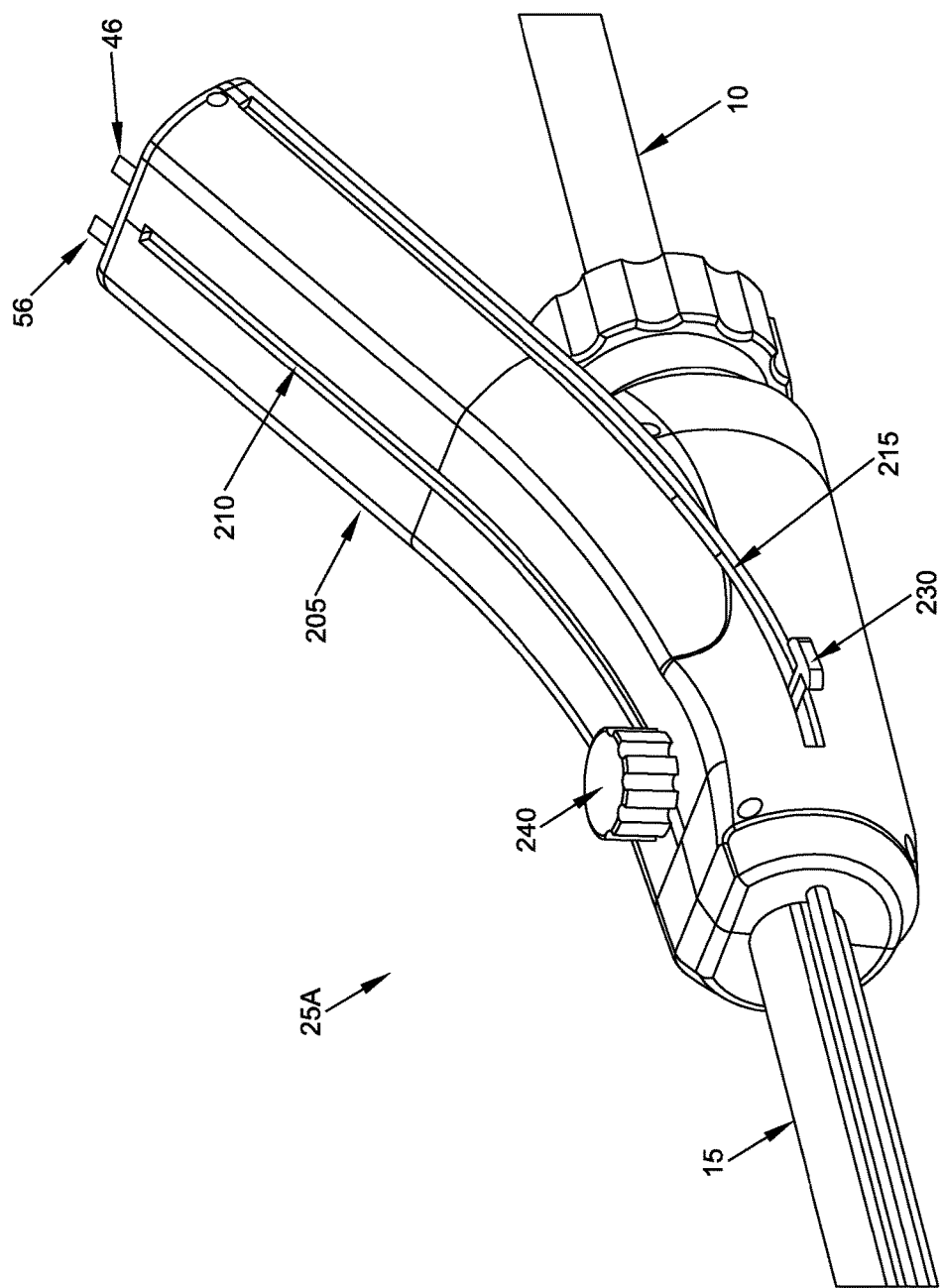
Figure 22:
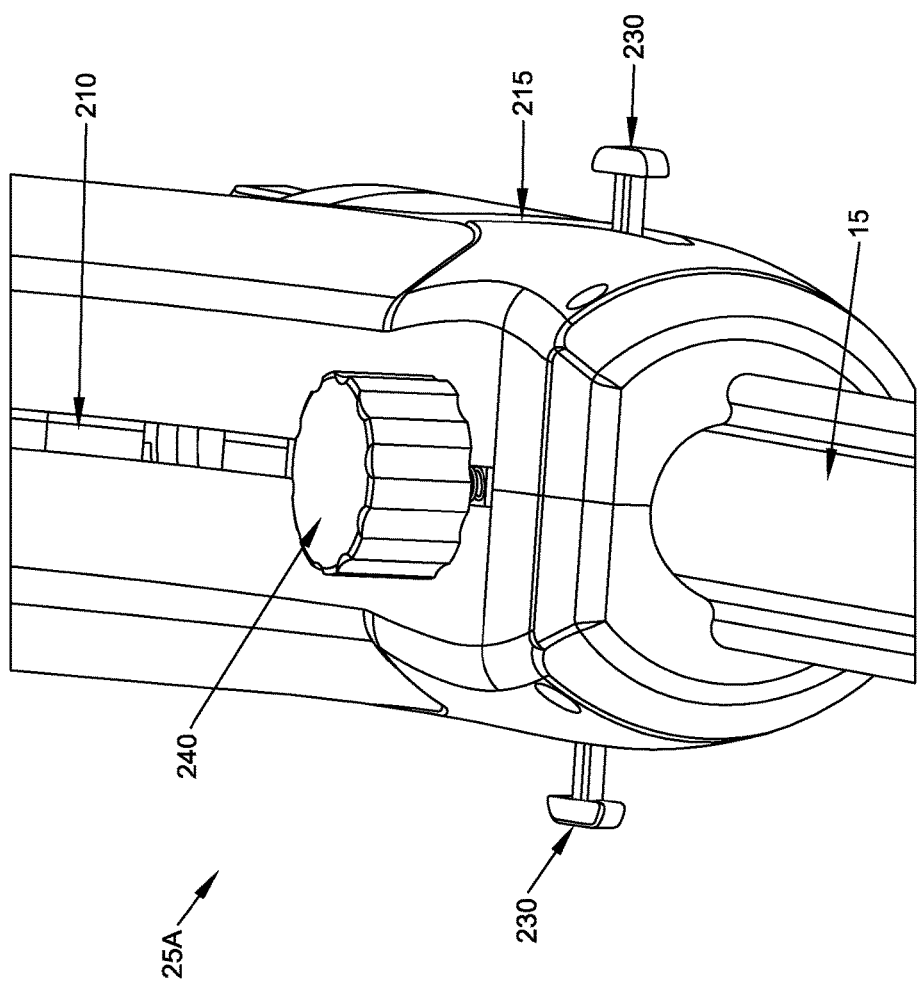
Figure 23:
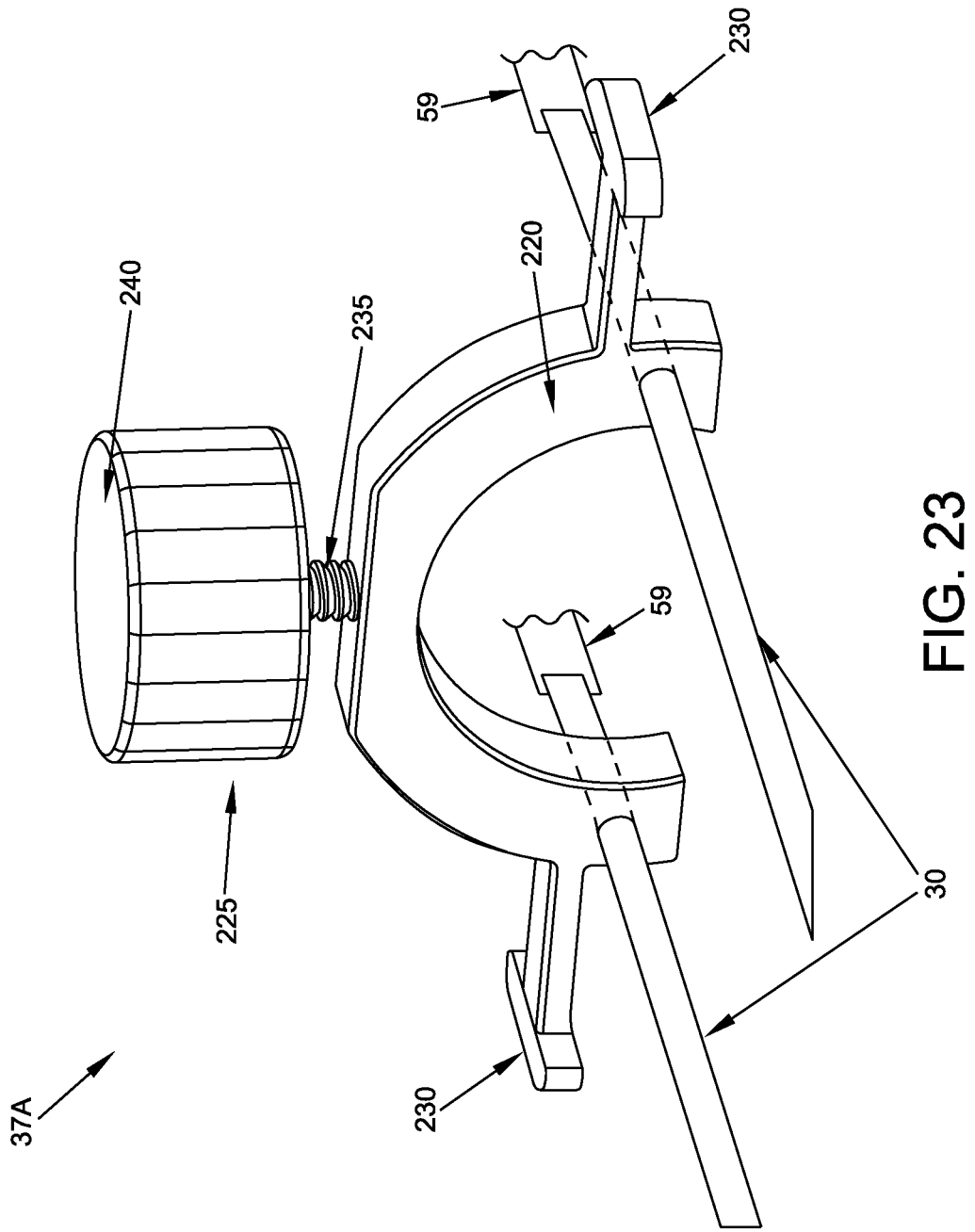
Figure 24:
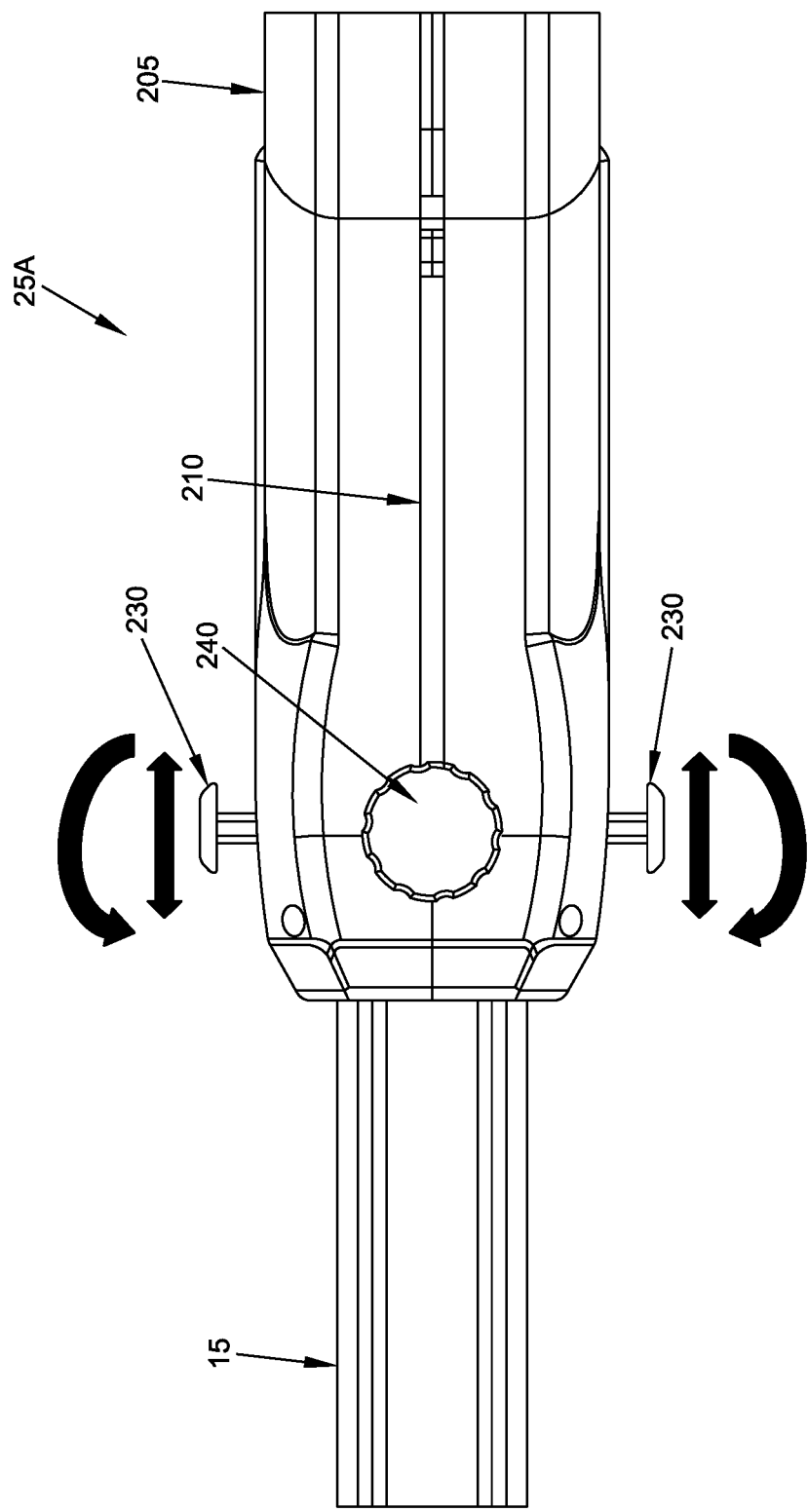
Figure 25:
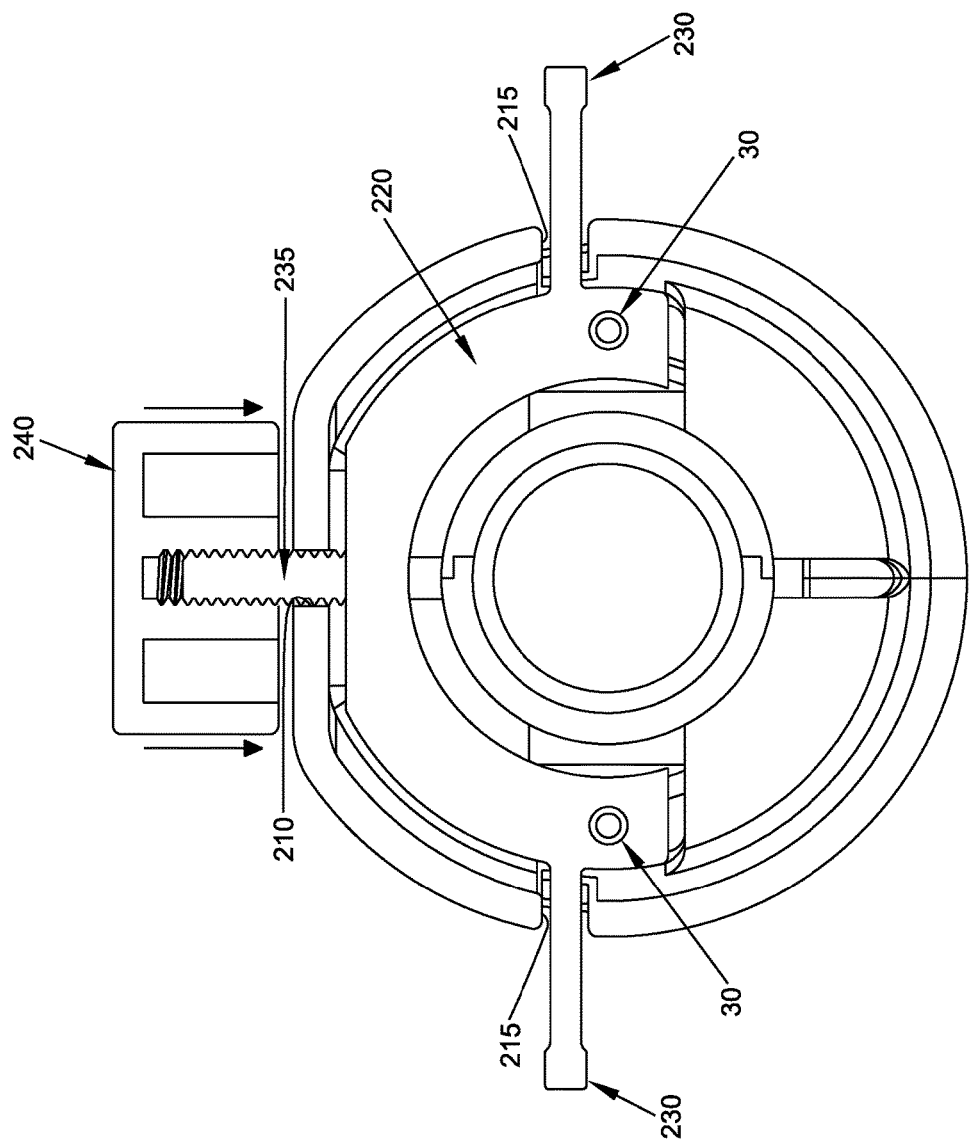
Figure 28:
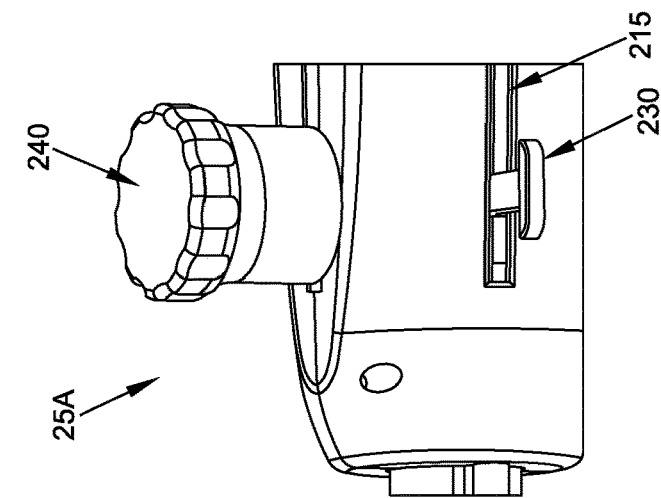
Figure 27:
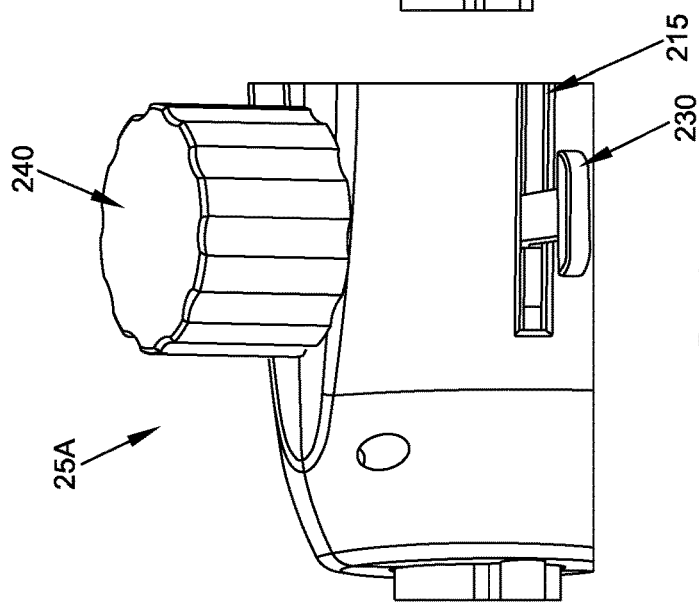
Figure 26:
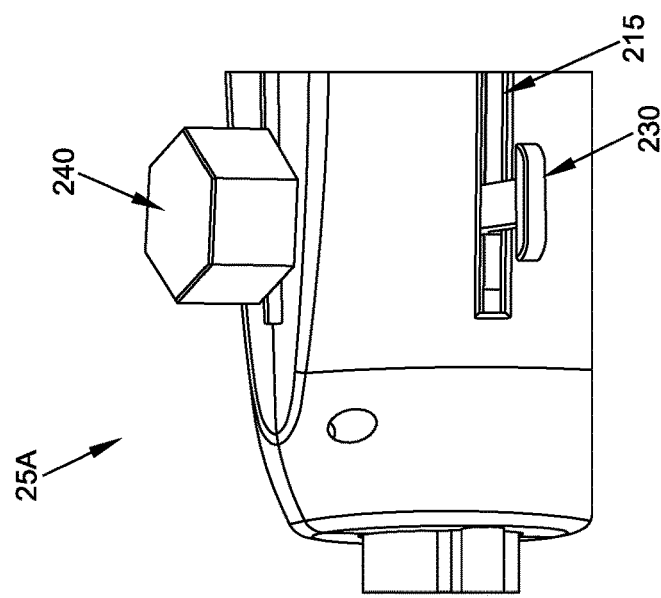
Figure 30:
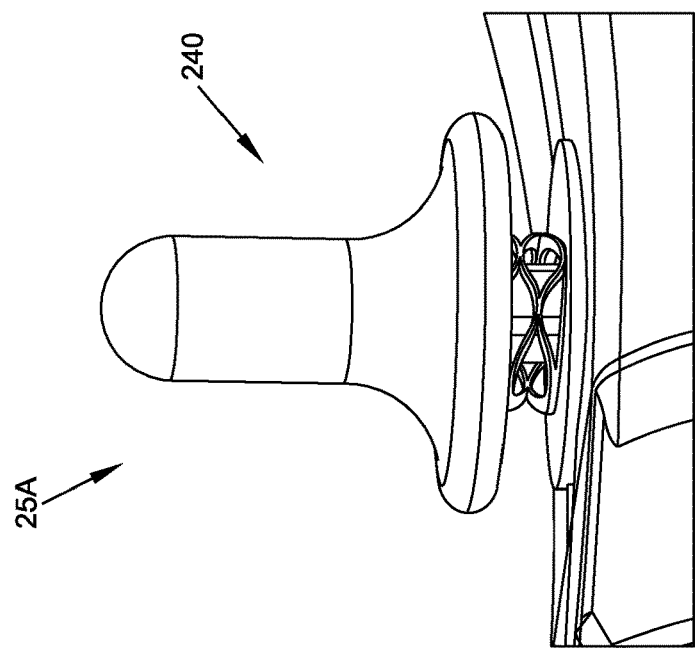
Figure 29:
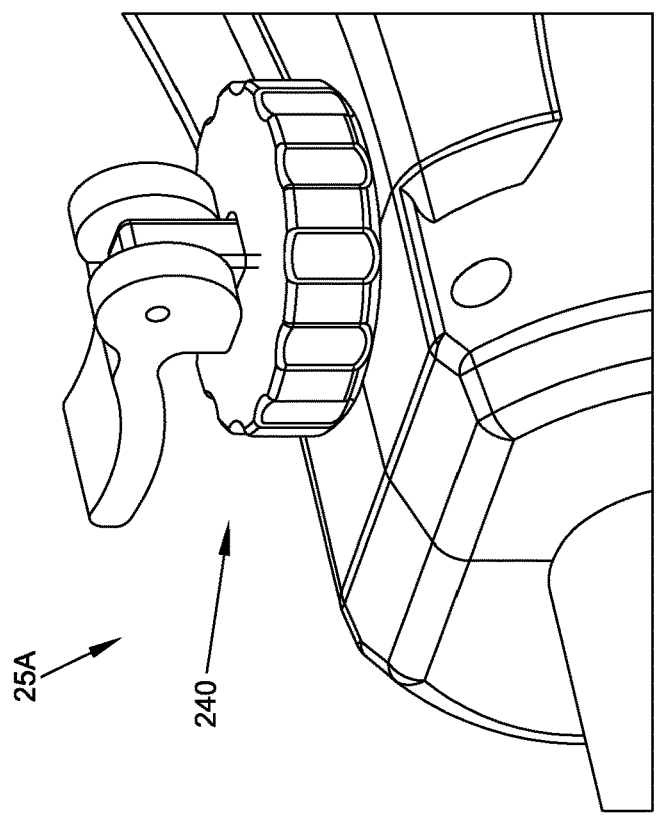

To this end, and looking now at FIGS. 18 and 19, fore balloon 35 is preferably manufactured as a single construct comprising a body 67 having a proximal opening 69 and a distal opening 71, a proximal extension 73 having a "key-shaped" cross-section comprising lobes 74, and a distal extension 76 having a circular cross-section. Note that lobes 74 are disposed on proximal extension 73 with a configuration which matches the configuration of hollow push tubes 30 (i.e., where apparatus 5 comprises two hollow push tubes 30 diametrically opposed to one another, proximal extension 73 will comprise two lobes 74 diametrically opposed to one another—for the purposes of the present invention, proximal extension 73 and lobe(s) 74 may be collectively referred to as having a "key-shaped" cross-section). During assembly, proximal extension 73 is everted into the interior of body 67, hollow push tubes 30 are seated in lobes 74 of proximal extension 73, (with the interiors of hollow push tubes 30 being in fluid communication with the interior of body 67 and with raised push tube bridge 31 disposed within the interior of body 67), and then distal extension 76 is everted into the interior of proximal extension 73, whereby to provide a fore balloon 35 having axial opening 63 extending therethrough, with hollow push tubes 30 being secured to fore balloon 35 and communicating with the interior of fore balloon 35, and with raised push tube bridge 31 being disposed concentrically about axial opening 63. Significantly, axial opening 63 is sized to receive the distal end of endoscope 10 therein, and raised push tube bridge 31 is sized to nest endoscope 10 in the area beneath the raised push tube bridge 31. Also significantly, the formation of fore balloon 35 by the aforementioned process of everting proximal extension 73 into the interior of body 67, and then everting distal extension 76 into the interior of proximal extension 73, provides multiple layers of balloon material around hollow push tubes 30, thereby providing a more robust balloon construction. Among other things, providing multiple layers of balloon material around hollow push tubes 30 adds cushioning to the distal ends of hollow push tubes 30, thereby providing an even more atraumatic distal tip to hollow push tubes 30 and further ensuring that the distal tips of hollow push tubes 30 do not damage the adjacent tissue.

In one preferred form of the invention, fore balloon 35 is formed out of polyurethane.

Figure 93:
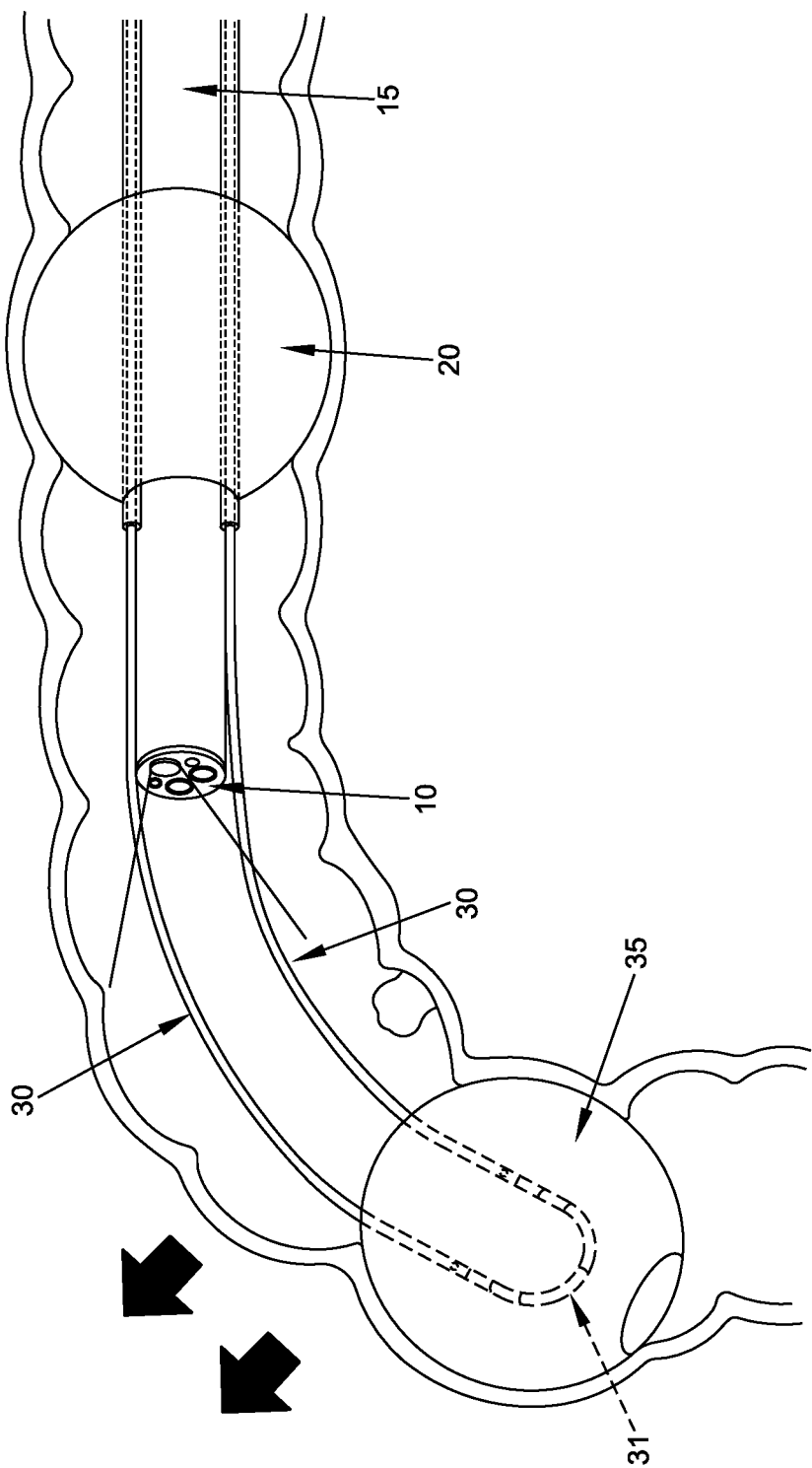

It should be appreciated that when fore balloon 35 is in its deflated condition, the material of fore balloon 35 substantially encompasses the distal ends of hollow push tubes 30 and raised push tube bridge 31 (while still allowing hollow push tubes 30 to be in fluid communication with the interior of fore balloon 35, i.e., via openings 32), thereby providing an atraumatic tip for advancing fore balloon 35 distally through a body lumen. Furthermore, hollow push tubes 30, raised push tube bridge 31 and the deflated fore balloon 35 can, together, essentially function as a soft-tipped lead for apparatus 5 and endoscope 10, as discussed further below (FIG. 93).

If desired, one or both of aft balloon 20 and fore balloon 35 can be marked with an indicator (e.g., a color indicator or a radiopaque indicator) so that a physician (or other operator or user) observing the surgical site via endoscope 10 or radiological guidance (e.g., X-ray fluoroscopy) can ascertain the disposition of one or both of the balloons at the surgical site.

Alternative Construction for the Base and the Push Tube Handle

As noted above, and as shown in FIG. 1, apparatus 5 comprises a base 25 which is secured to sleeve 15 at the proximal end of the sleeve and which carries fittings 46, 56 for inflating/deflating aft balloon 20 and/or fore balloon 35, respectively. Apparatus 5 also comprises a push tube handle 37 which has hollow push tubes 30 mounted thereto, with hollow push tubes 30 physically supporting (and providing fluid communication to) the interior of fore balloon 35. As also noted above, proximal inflation/deflation tube 45 provides fluid communication between fitting 46 of base 25 and the interior of aft balloon 20; and a flexible tube 59 provides (with other elements) fluid communication between fitting 56 of base 25 and the interior of hollow push tubes 30 (and hence the interior of fore balloon 35).

With the construction shown in FIG. 1, base 25 supports and guides hollow push tubes 30 as they are advanced distally or retracted proximally, but base 25 does not directly support and guide push tube handle 37 as it is advanced distally or retracted proximally.

To that end, if desired, and looking now at FIGS. 20-25, apparatus 5 may comprise a similar but somewhat different base (i.e., the base 25A) and a similar but somewhat different push tube handle (i.e., the push tube handle 37A). Base 25A comprises an extension 205 which has the aforementioned fittings 46, 56 mounted thereto. Extension 205 comprises a center slot 210 and a pair of side slots 215. Push tube handle 37A comprises a C-shaped body 220 having hollow push tubes 30 mounted thereto, and having a center locking element 225 and a pair of finger grips 230 mounted thereto. Locking element 225 preferably comprises a screw shaft 235 and a screw knob 240, such that screw knob 240 can be advanced towards or away from body 220 by turning the screw knob.

Push tube handle 37A is mounted within extension 205 of base 25A so that screw shaft 235 is slidably received in center slot 210 and so that finger grips 230 are slidably received in side slots 215, whereby to provide support and guidance to push tube handle 37A.

As a result of this construction, push tube handle 37A can be moved distally or proximally by moving screw shaft 235 and finger grips 230 distally or proximally, whereby to move fore balloon 35 distally or proximally; and push tube handle 37A can be locked in position relative to body 25A by turning screw knob 240 so that it securely engages the outer surface of extension 205, whereby to lock fore balloon 35 in position relative to body 25A. Note that torsion can be applied to fore balloon 35 by applying torsion to finger grips 230, e.g., by moving one side wing 230 distally while pulling the other side wing 230 proximally.

FIGS. 26-30 show different configurations for screw knob 240.

Figure 32:
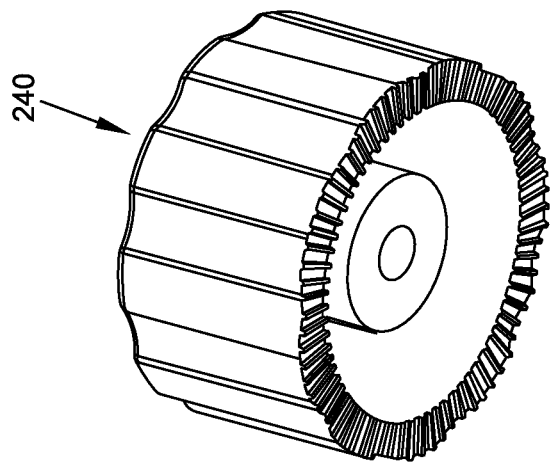
Figure 31:
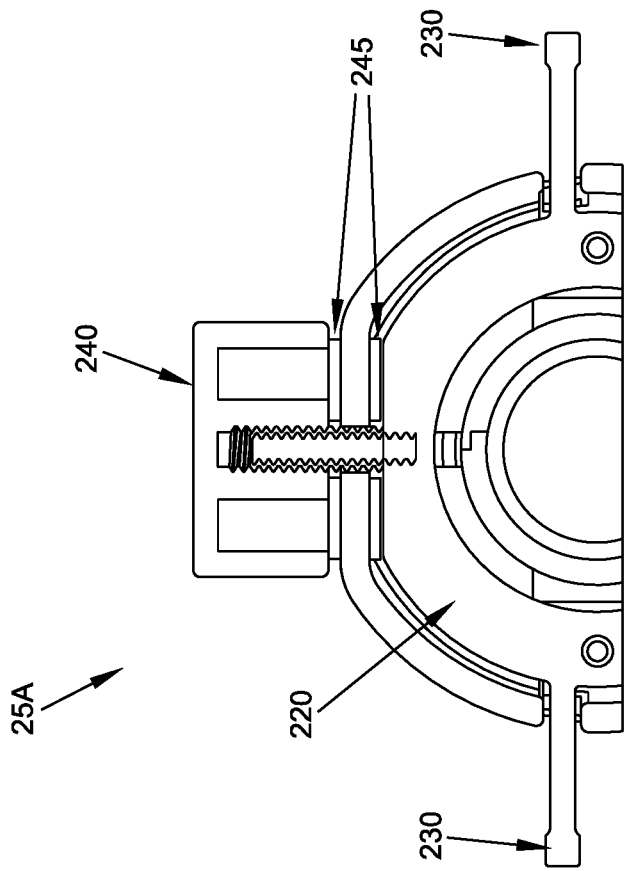
Figure 33:
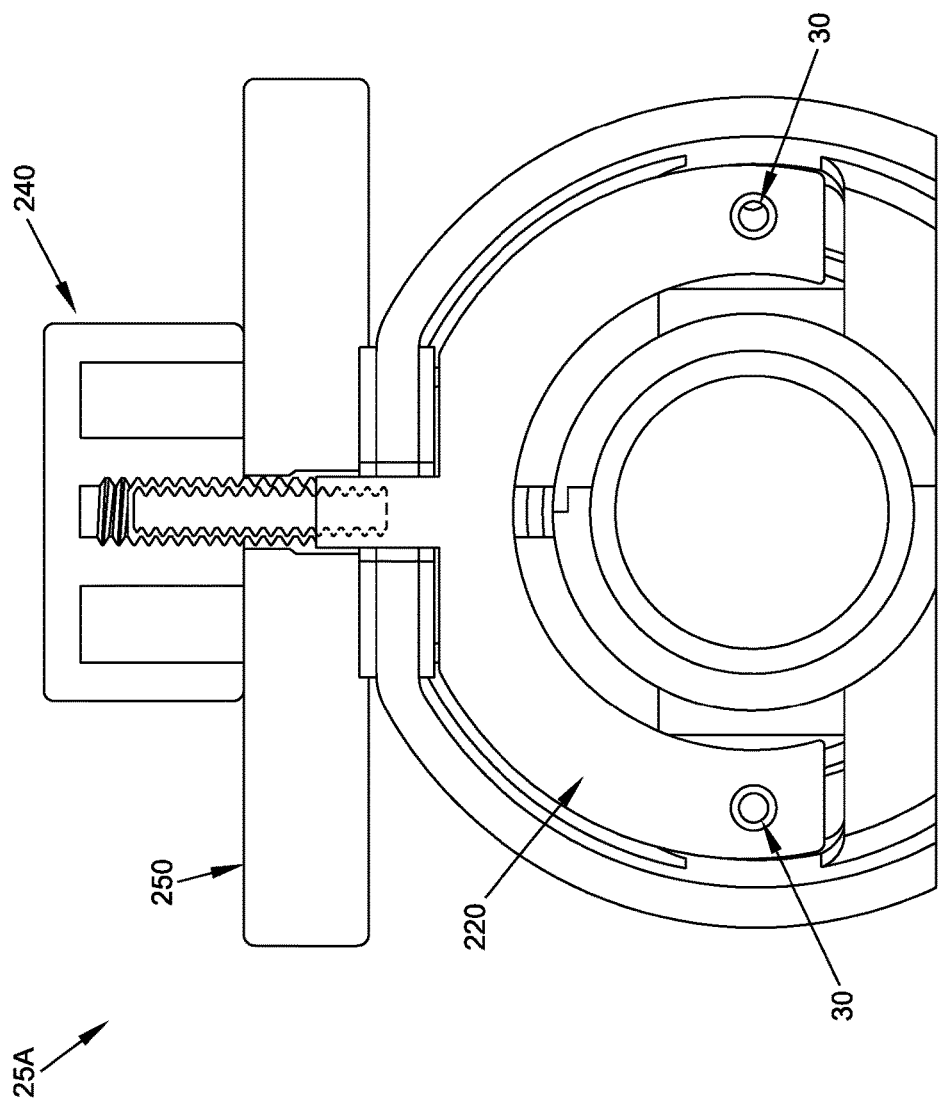

If desired, lubricious washers 245 may be added to the assembly to reduce friction (FIG. 31), or texture may be added to surfaces (e.g., the underside of screw knob 240 as shown in FIG. 32) so as to increase friction. Furthermore, finger grips 230 may be shaped differently than those illustrated in FIGS. 20-30, or moved to a different portion of the assembly. See, for example, FIG. 33, which shows finger grips 230 formed as part of a second knob 250 which keys to the slider assembly.

Figure 34:
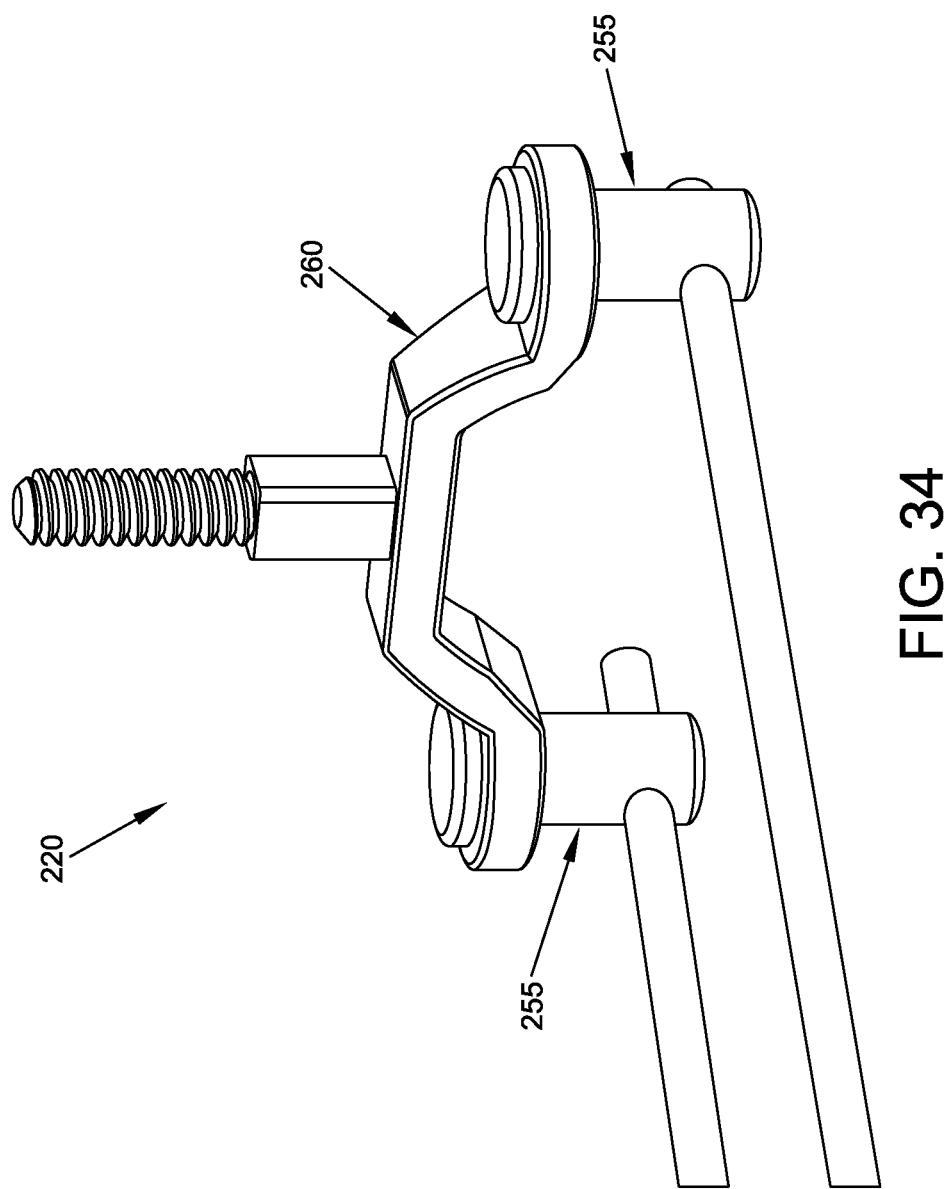

It should also be appreciated that, if desired, push tube handle 37A may comprise a generally C-shaped body having a different configuration from the C-shaped body 220 shown in FIGS. 23, 25, 31 and 33. By way of example but not limitation, and looking now at FIG. 34, C-shaped body 220 may comprise a pair of downwardly extending legs 255 connected by a linkage 260.

The Inflation Mechanism

Inflation mechanism 40 provides a means to selectively inflate aft balloon 20 and/or fore balloon 35.

Figure 35:
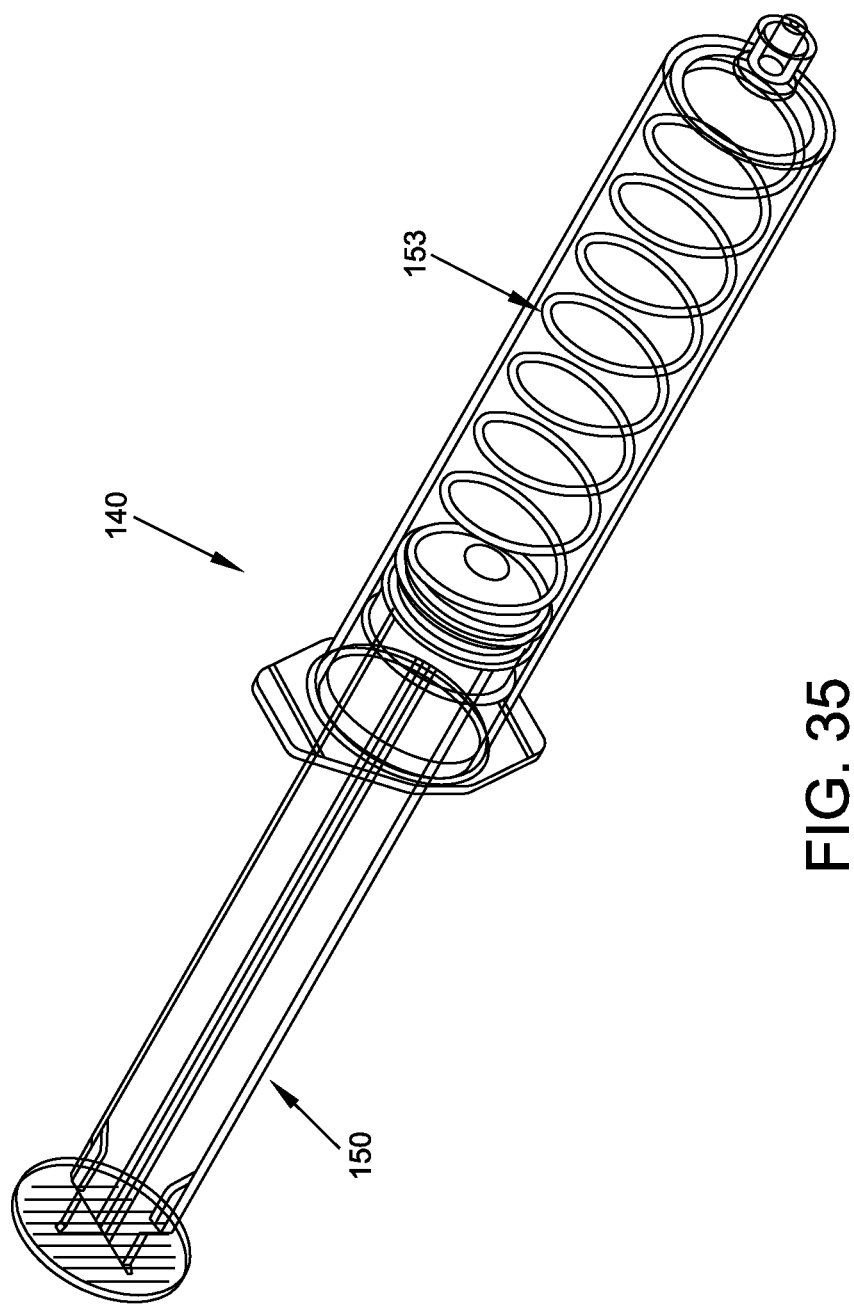
FIG. 35 is a schematic view showing one form of inflation mechanism provided in accordance with the present invention.

In one preferred form of the present invention, and looking now at FIGS. 1 and 35, inflation mechanism 40 comprises a single-line syringe inserter 140 comprising a body 145 and a plunger 150. Preferably a spring 153 is provided in body 145 to automatically return plunger 150 at the end of its stroke. Syringe inserter 140 is connected to one or the other of fittings 46, 56 via a line 155. Thus, with this construction, when single-line syringe inserter 140 is to be used to inflate aft balloon 20, syringe inserter 140 is connected to fitting 46 via line 155 so that the output of single-line syringe inserter 140 is directed to aft balloon 20 (i.e., via proximal inflation/deflation tube 45). Correspondingly, when single-line syringe inserter 140 is to be used to inflate fore balloon 35, syringe inserter 140 is connected to fitting 56 via line 155 so that the output of single-line syringe inserter 140 is directed to fore balloon 35 (i.e., via flexible tube 59 and the interiors of hollow push tubes 30 and out of openings 32).

Figure 36:
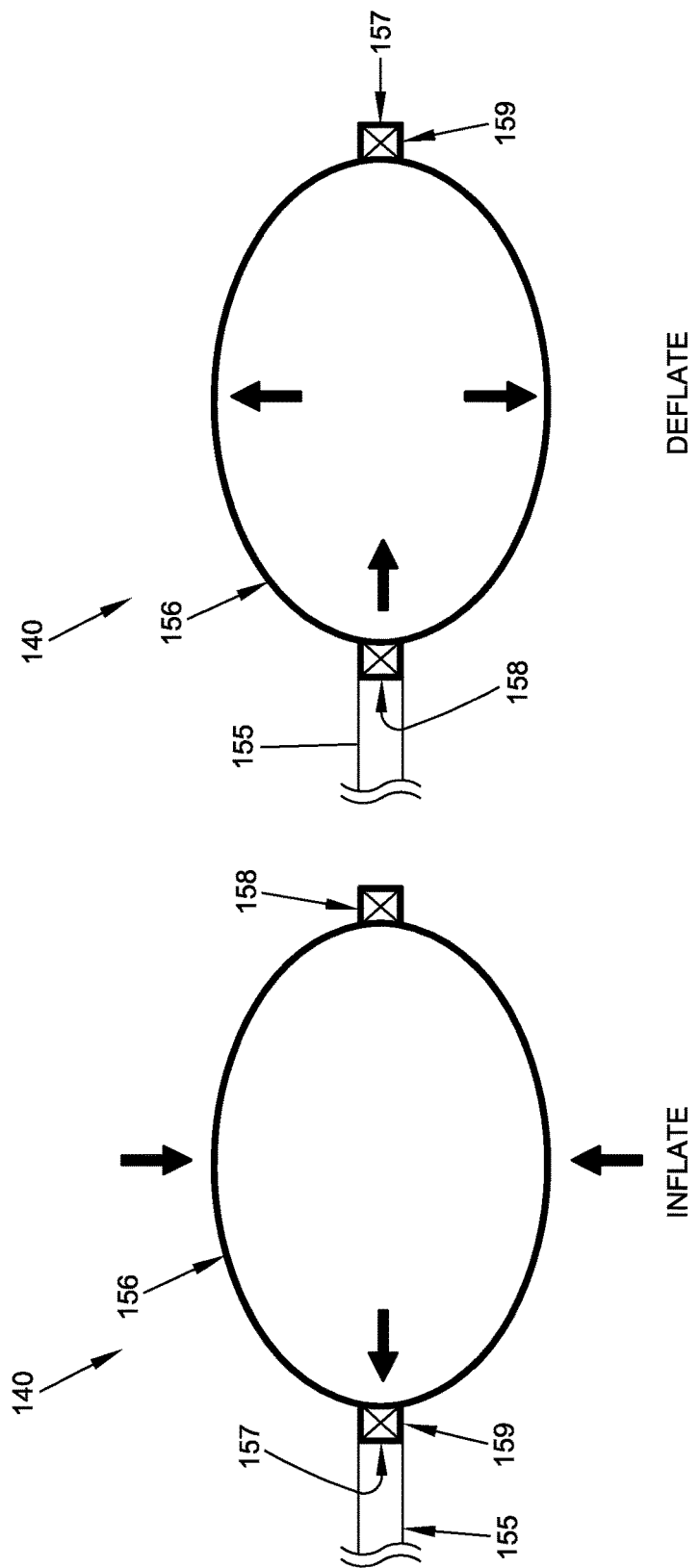
FIG. 36 is a schematic view showing another form of inflation mechanism provided in accordance with the present invention.

In another preferred form of the present invention, and looking now at FIG. 36, inflation mechanism 40 comprises an elastic bulb 156 having a first port 157 and a second port 158. A one-way valve 159 (e.g., a check valve) is disposed in first port 157 so that air can only pass through first port 157 when traveling in an outward direction. Another one-way valve 159 (e.g., a check valve) is disposed in second port 158 so that air can only pass through second port 158 when traveling in an inward direction. When elastic bulb 156 is compressed (e.g., by hand), air within the interior of elastic bulb 156 is forced out first port 157; and when elastic bulb 156 is thereafter released, air is drawn back into the interior of elastic bulb 156 through second port 158.

As a result of this construction, when elastic bulb 156 is to be used to inflate aft balloon 20, first port 157 is connected to fitting 46 via line 155 so that the positive pressure output of elastic bulb 156 is directed to aft balloon 20. Elastic bulb 156 may thereafter be used to deflate aft balloon 20, i.e., by connecting second port 158 to fitting 46 via line 155 so that the suction of elastic bulb 156 is directed to aft balloon 20. Correspondingly, when elastic bulb 156 is to be used to inflate fore balloon 35, first port 157 is connected to fitting 56 via line 155 so that the positive pressure output of elastic bulb 156 is directed to fore balloon 35. Elastic bulb 156 may thereafter be used to deflate fore balloon 35, i.e., by connecting second port 158 to fitting 56 via line 155 so that the suction of elastic bulb 156 is directed to fore balloon 35.

Figure 37:
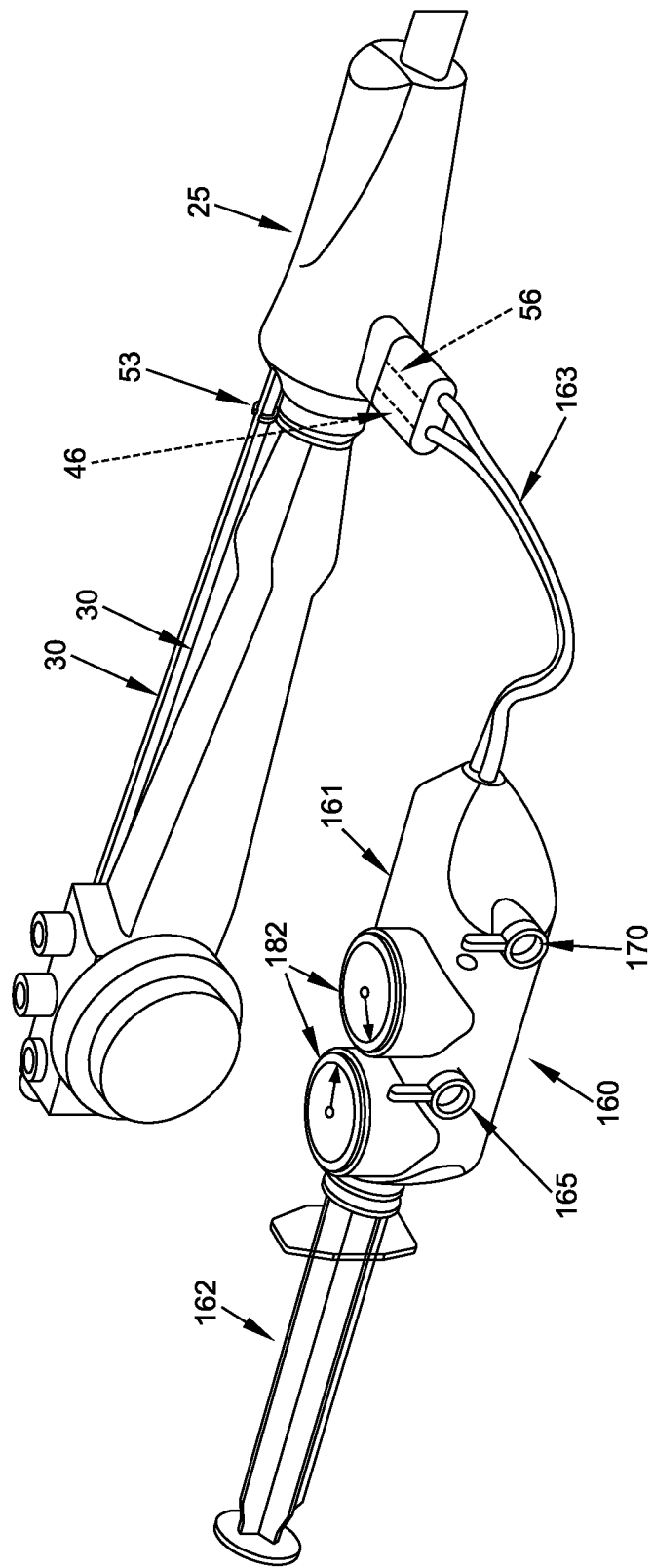
FIGS. 37 and 38 are schematic views showing another form of inflation mechanism provided in accordance with the present invention.
Figure 38:
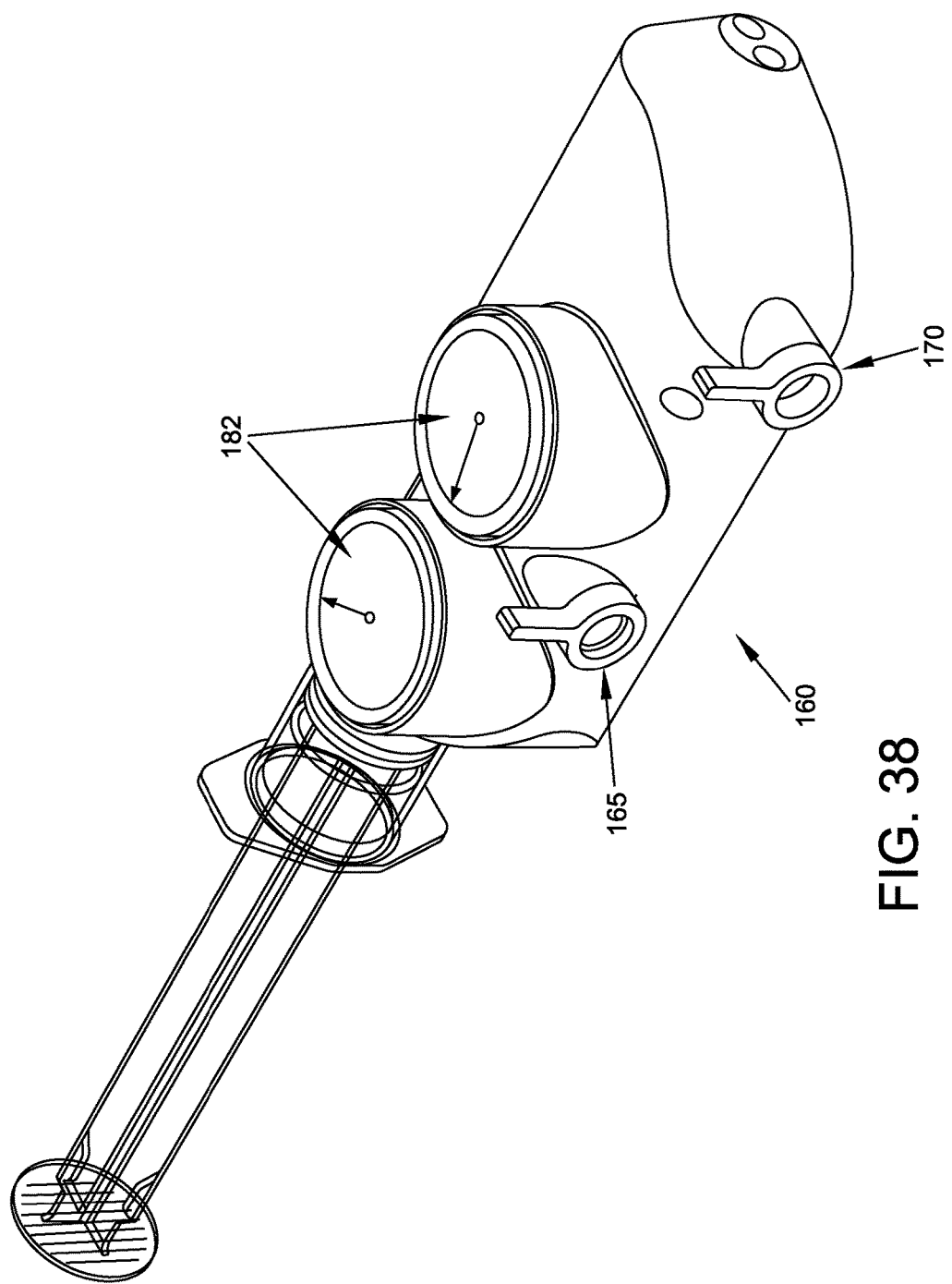
Figure 39:
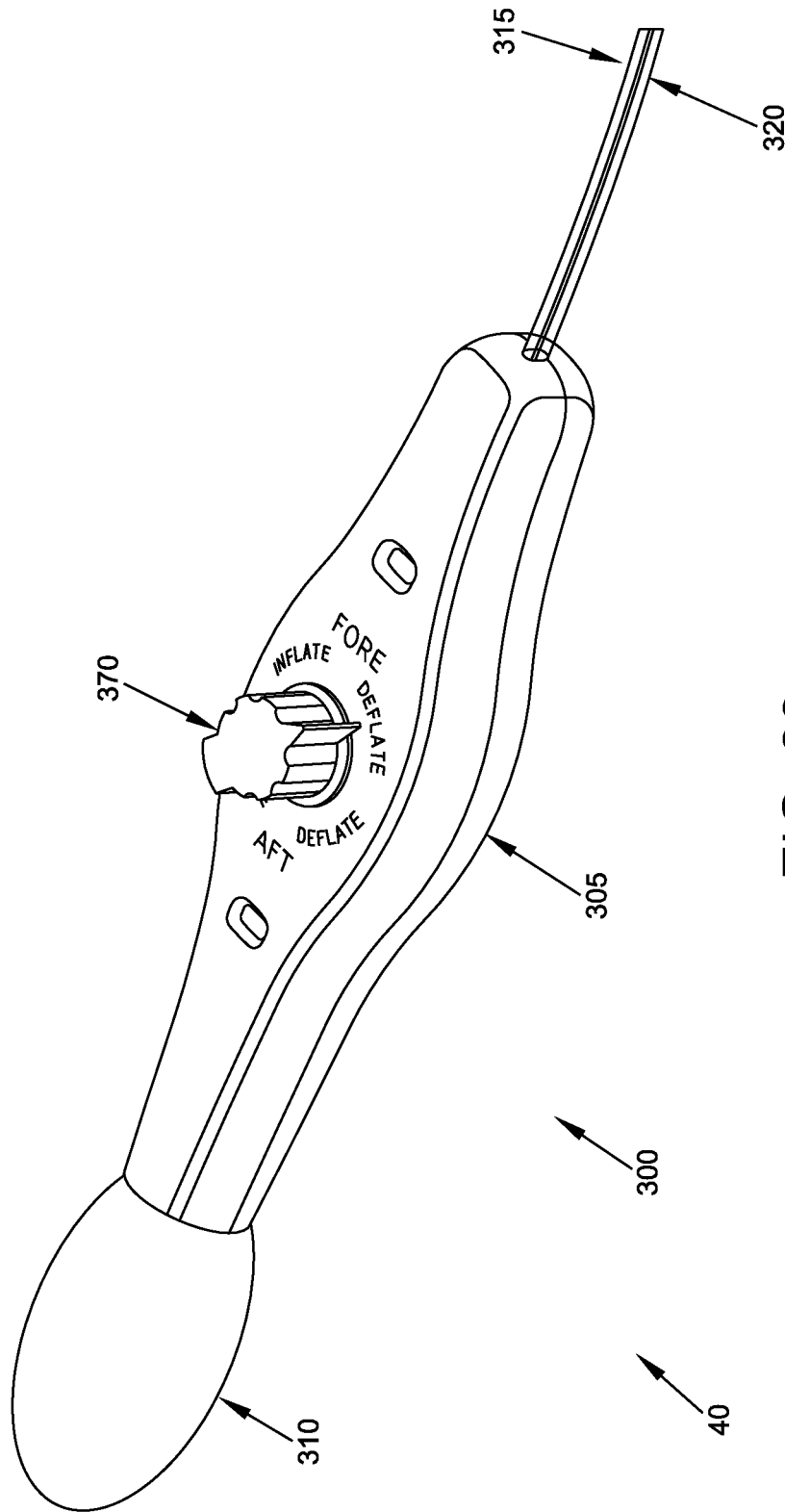
Figure 40:
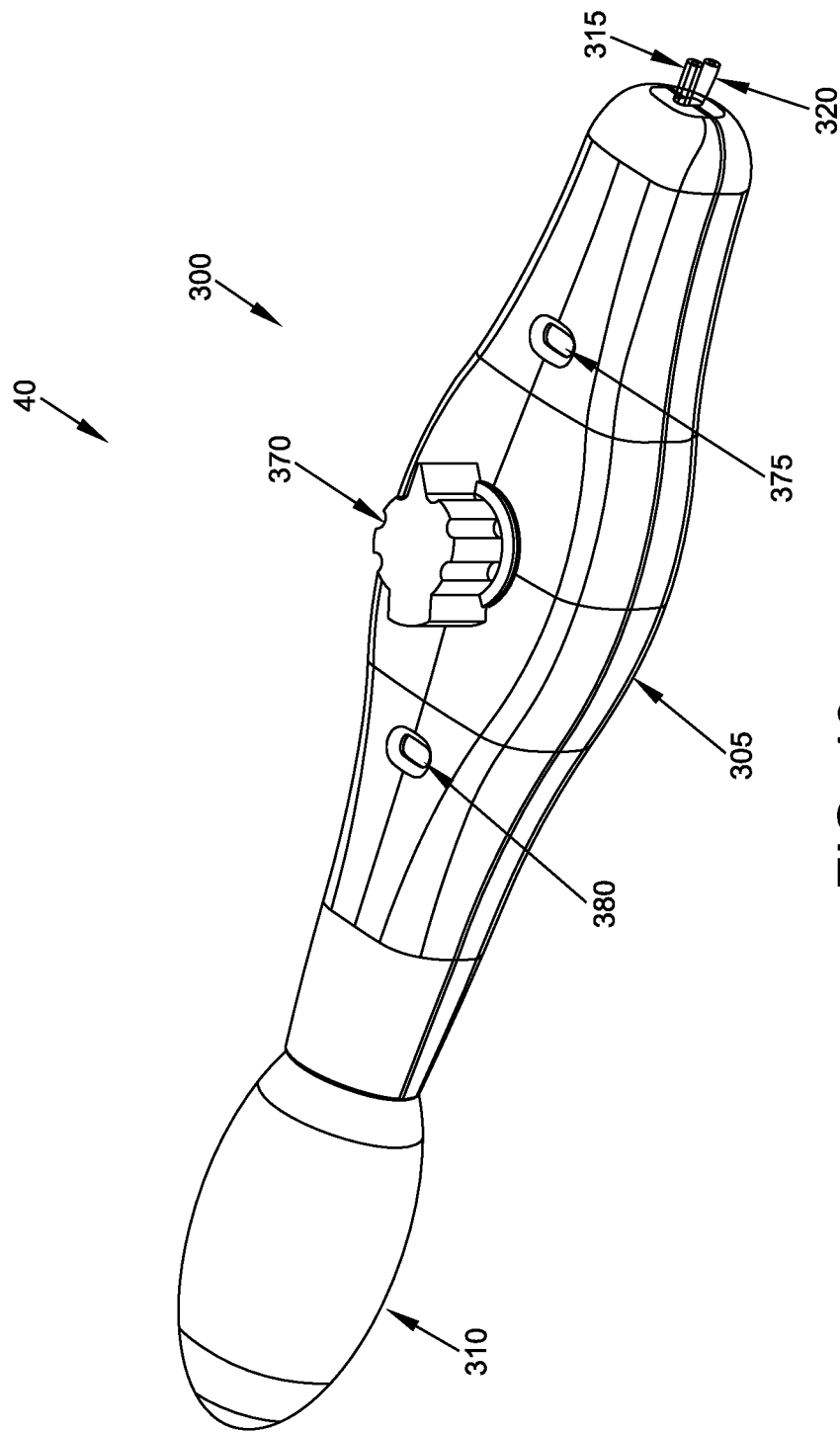
Figure 41:
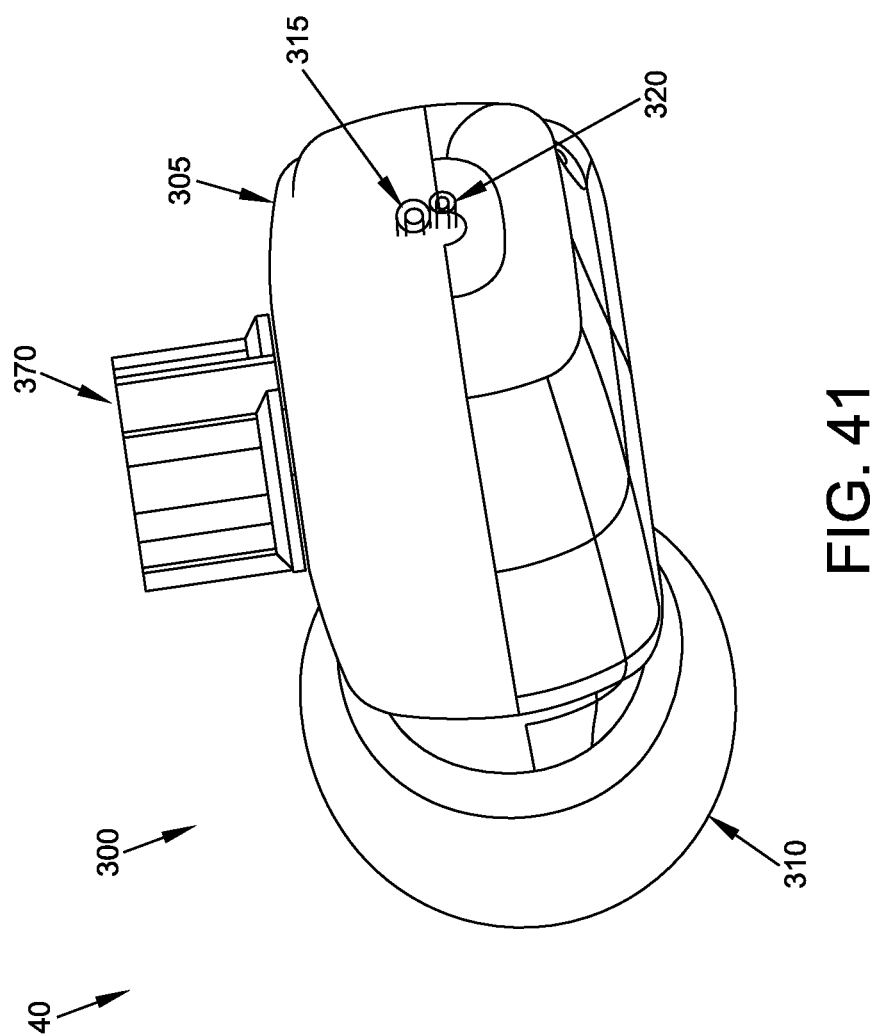

Alternatively, and looking now at FIGS. 37 and 38, a syringe 160 may be used to inflate aft balloon 20 and/or fore balloon 35. Inflation mechanism 160 comprises a body 161 and a plunger 162. Preferably a spring (not shown) is provided in body 161 to automatically return plunger 162 at the end of its power stroke. Syringe 160 is connected to fittings 46, 56 via a line 163. With this construction, syringe 160 comprises a valve 165 for connecting syringe 160 to fore balloon 35 or aft balloon 20, and a valve 170 for selecting inflation or deflation of the connected-to balloon.

Thus, with this construction, when syringe 160 is to be used to inflate aft balloon 20, valve 165 (a two-position valve that connects valve 170 to either the fore balloon or the aft balloon) is set so that the syringe 160 is connected through fitting 46 to aft balloon 20, and valve 170 (a 2-way crossover valve which allows the one-way valves to be arranged to inflate in one configuration and deflate in the other configuration) is set so that syringe 160 is providing inflation pressure. Thereafter, when aft balloon 20 is to be deflated, valve 170 is set to its deflate position.

Correspondingly, when syringe 160 is to be used to inflate fore balloon 35, valve 165 is set so that syringe 160 is connected through fitting 56 to fore balloon 35, and valve 170 is set so that syringe 160 is providing inflation pressure. Thereafter, when fore balloon 35 is to be deflated, valve 170 is set to its deflate position.

In another preferred form of the present invention, and looking now at FIGS. 39-58, inflation mechanism 40 comprises a hand inflator 300 also formed in accordance with the present invention. Hand inflator 300 generally comprises a housing 305 carrying a bulb or "pump" 310, an aft balloon inflation line 315 (for connection to fitting 46 of apparatus 5, see FIG. 1), a fore balloon inflation line 320 (for connection to fitting 56 of apparatus 5, see FIG. 1), and internal pneumatic apparatus 325 (FIG. 42) for directing air between pump 310 and aft balloon inflation line 315 and fore balloon inflation line 320 (and for venting air from aft balloon inflation line 315 and fore balloon inflation line 320), all as will hereinafter be discussed.

Figure 42:
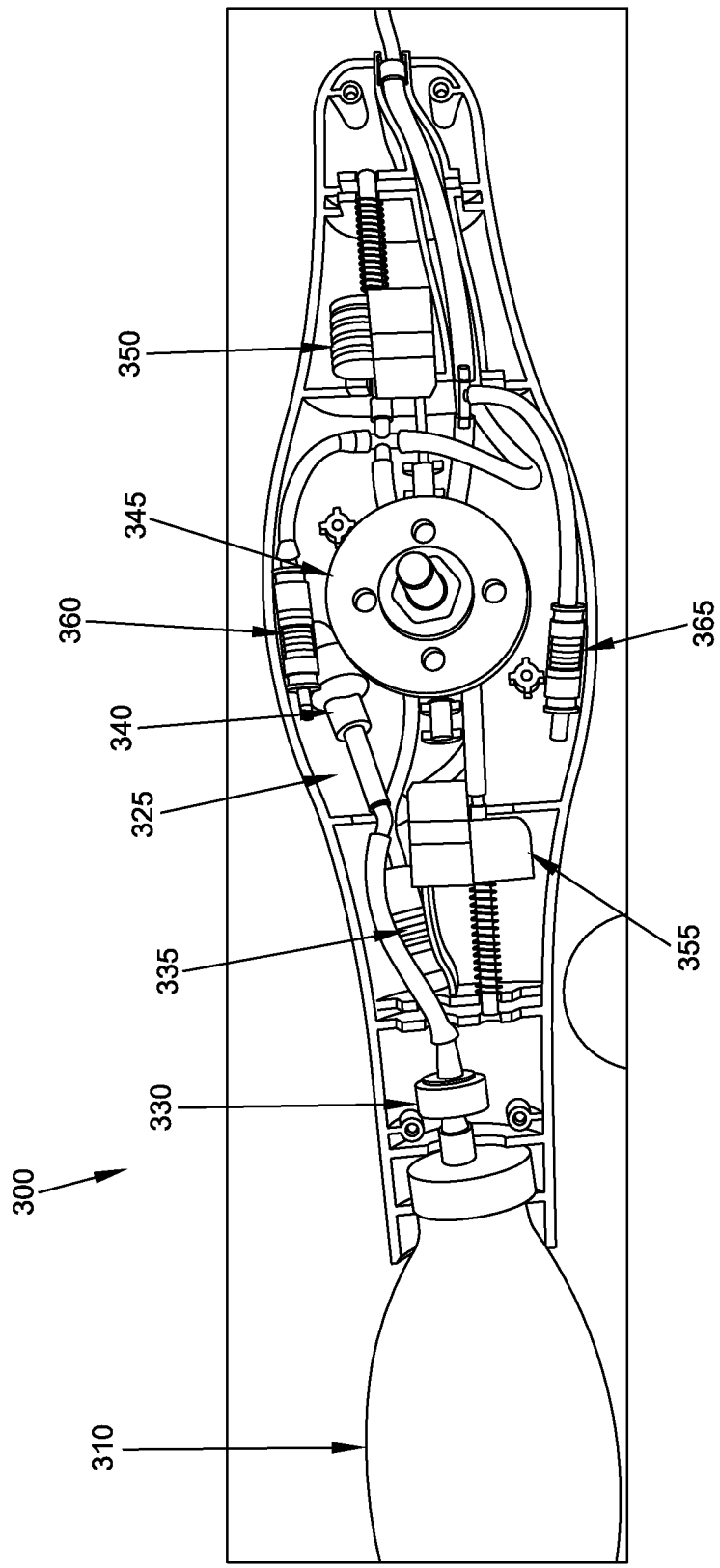
Figure 43:
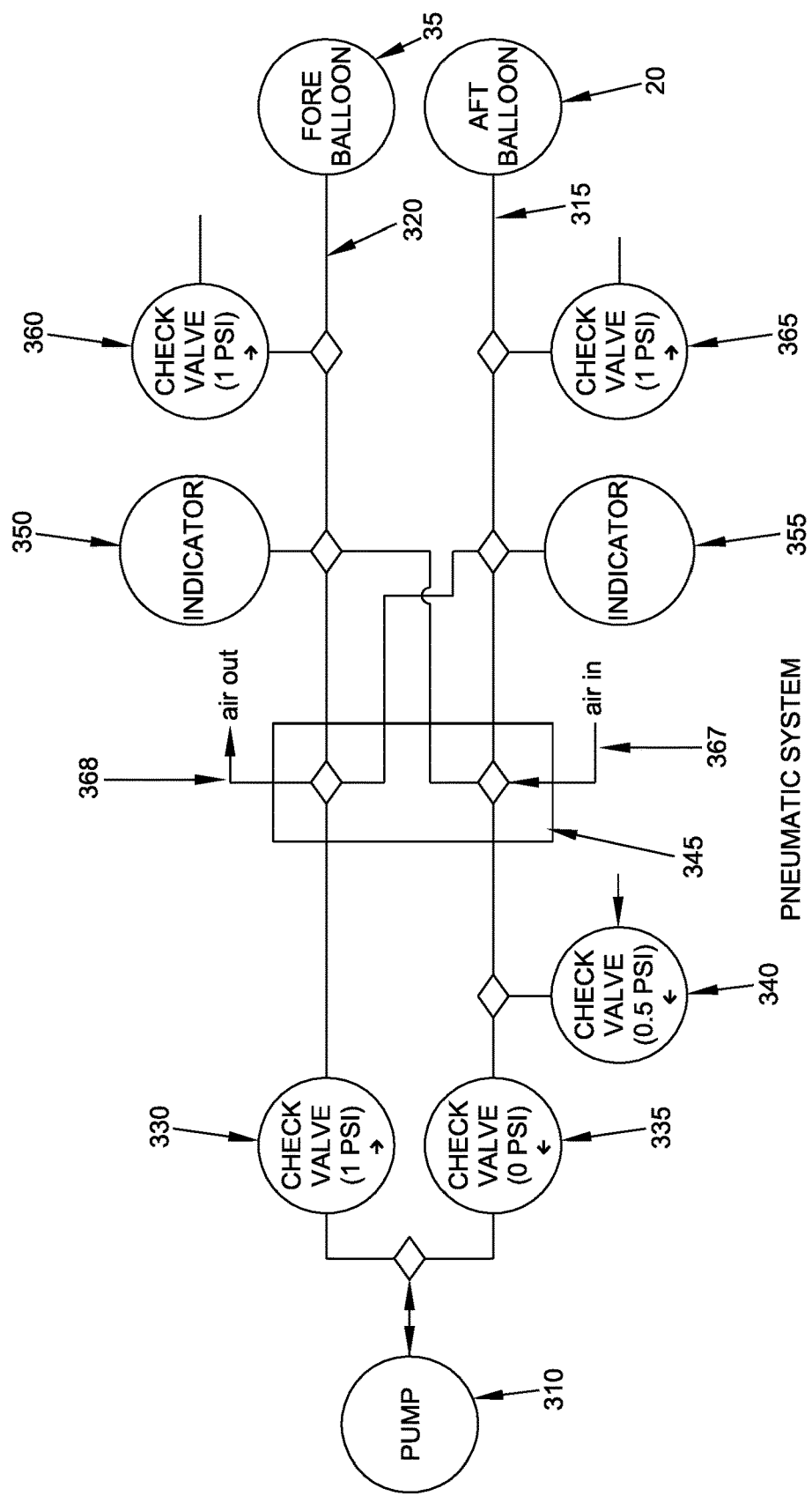

As seen in FIGS. 42 and 43, internal pneumatic apparatus 325 comprises a check valve 330, a check valve 335, a check valve 340, a multi-way valve 345, a fore balloon indicator 350, an aft balloon indicator 355, a check valve 360, a check valve 365, an "air in" port 367 and an "air out" port 368. A selector knob 370 (FIGS. 39, 40 and 41) is attached to multi-way valve 345 so as to allow the user to set multi-way valve 345 as desired, and openings 375, 380 (FIG. 40) are formed in housing 305 so as to expose fore balloon indicator 350 and aft balloon indicator 355, respectively, to the view of the user.

Looking now at FIGS. 44 through 47, internal pneumatic apparatus 325 is configured so that (i) aft balloon 20 can be selectively inflated by pump 310, (ii) aft balloon 20 can be selectively deflated by pump 310, (iii) fore balloon 35 can be selectively inflated by pump 310, and (iv) fore balloon 35 can be selectively deflated by pump 310.

Figure 44:
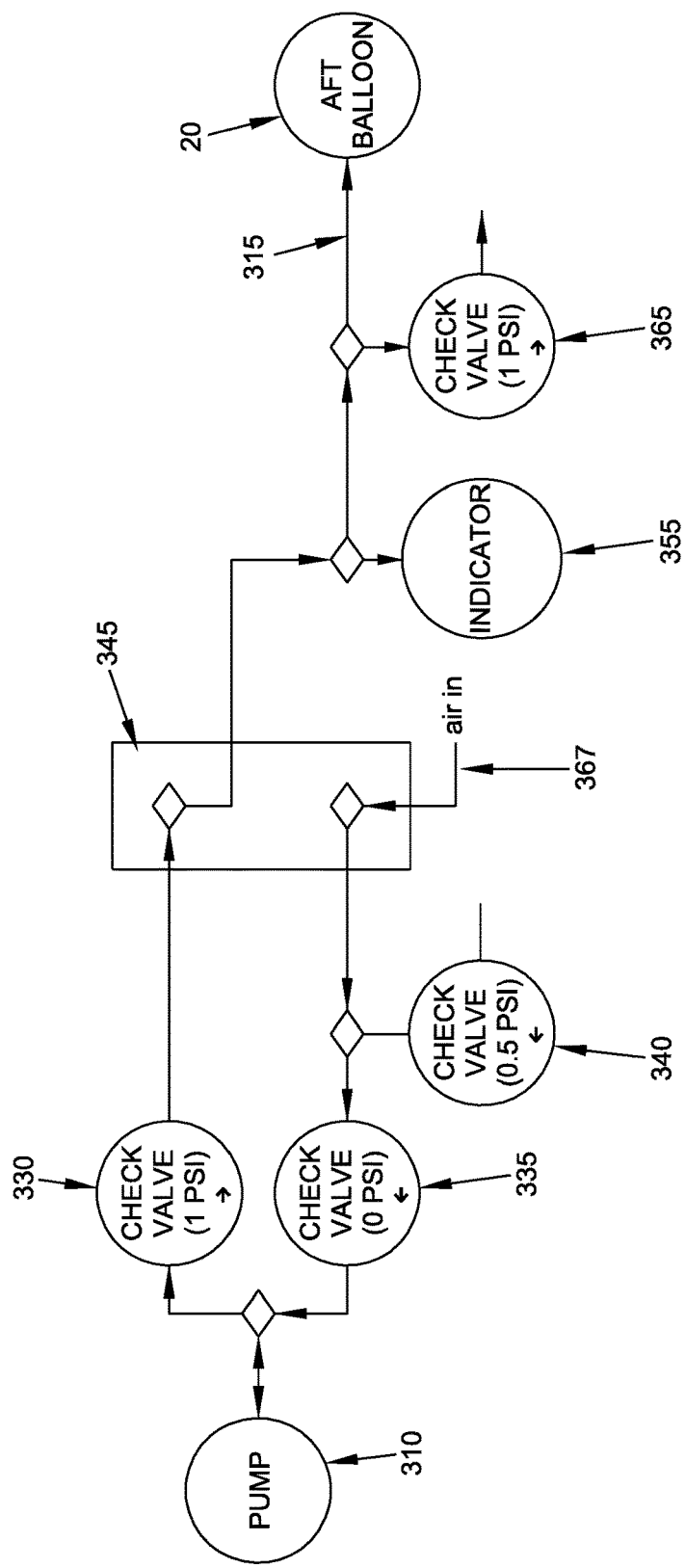

More particularly, when aft balloon 20 is to be inflated, and looking now at FIG. 44, selector knob 370 is set so that multi-way valve 345 creates a fluid line connecting "air in" port 367, check valve 340, check valve 335, pump 310, check valve 330, aft balloon indicator 355, check valve 365, aft balloon inflation line 315 and aft balloon 20, so that repeated compressions of pump 310 inflates aft balloon 20, with the pressure within aft balloon 20 being indicated by aft balloon indicator 355.

Figure 45:
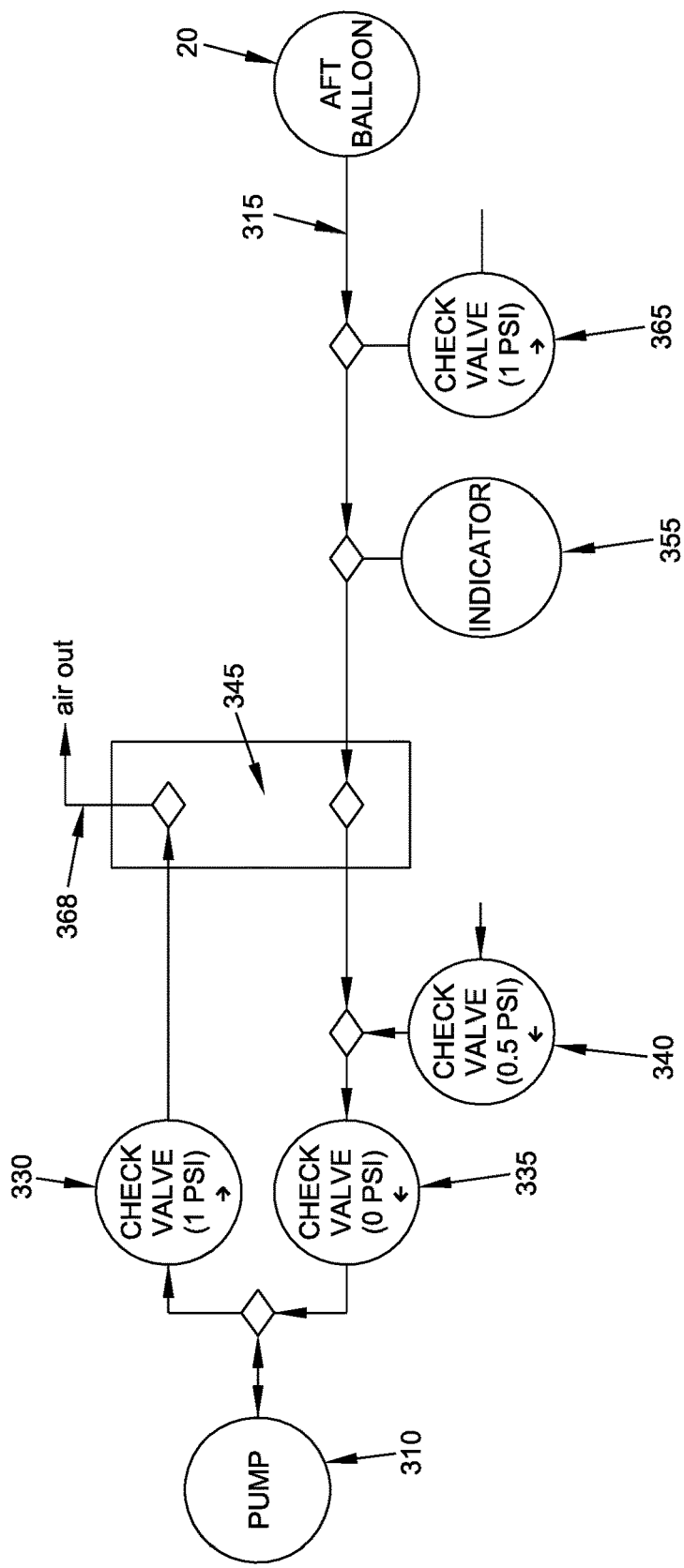

When aft balloon 20 is to be deflated, and looking now at FIG. 45, selector knob 370 is set so that multi-way valve 345 creates a fluid line connecting aft balloon 20, aft balloon inflation line 315, check valve 365, aft balloon indicator 355, check valve 340, check valve 335, pump 310, check valve 330 and "air out" port 368, so that repeated compressions of pump 310 deflates aft balloon 20, with the pressure within aft balloon 20 being indicated by aft balloon indicator 355.

Figure 46:
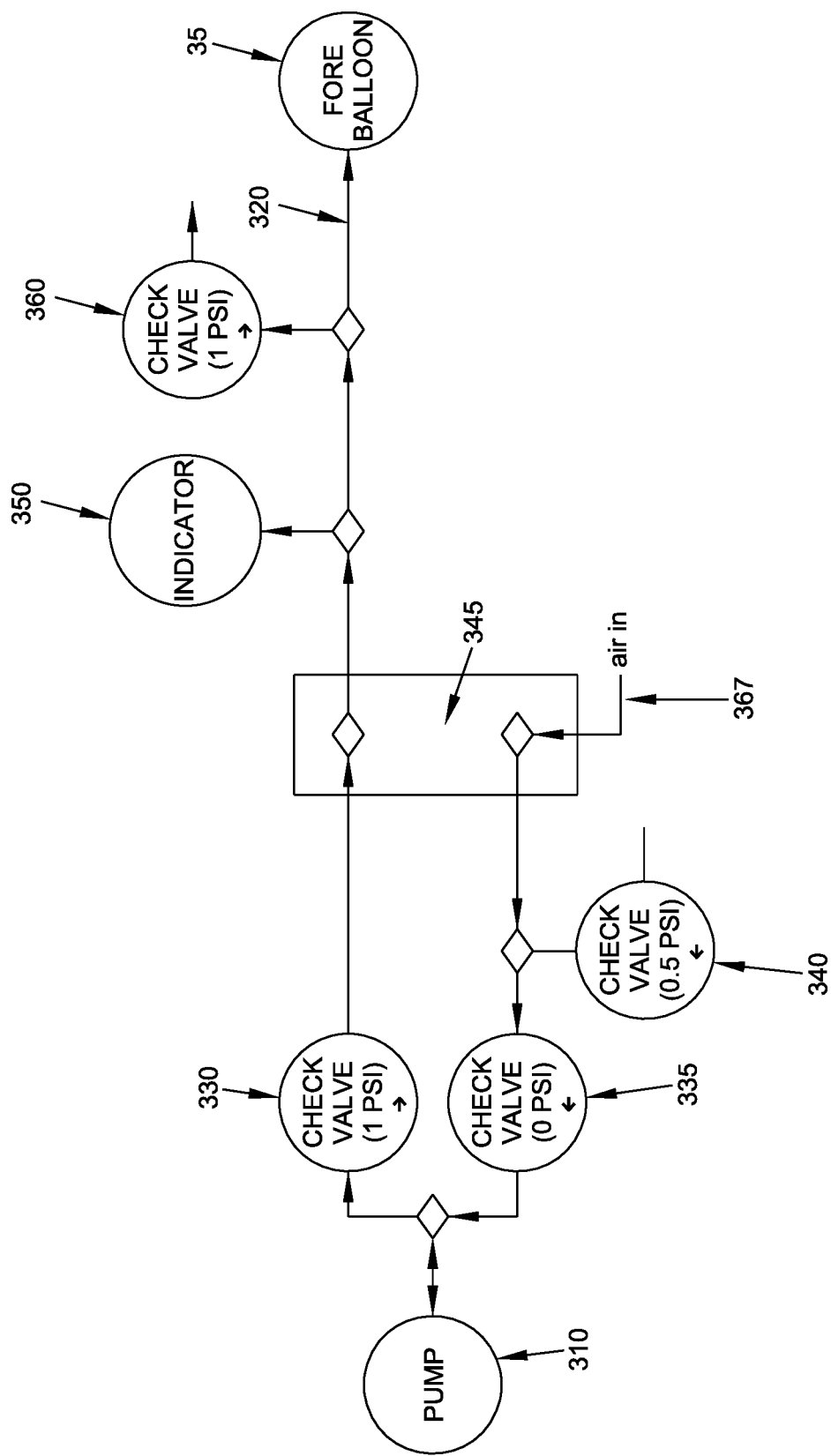

When fore balloon 35 is to be inflated, and looking now at FIG. 46, selector knob 370 is set so that multi-way valve 345 creates a fluid line connecting "air in" port 367, check valve 340, check valve 335, pump 310, check valve 330, fore balloon indicator 350, check valve 360, fore balloon inflation line 320 and fore balloon 35, so that repeated compressions of pump 310 inflates fore balloon 35, with the pressure within fore balloon 35 being indicated by fore balloon indicator 350.

Figure 47:
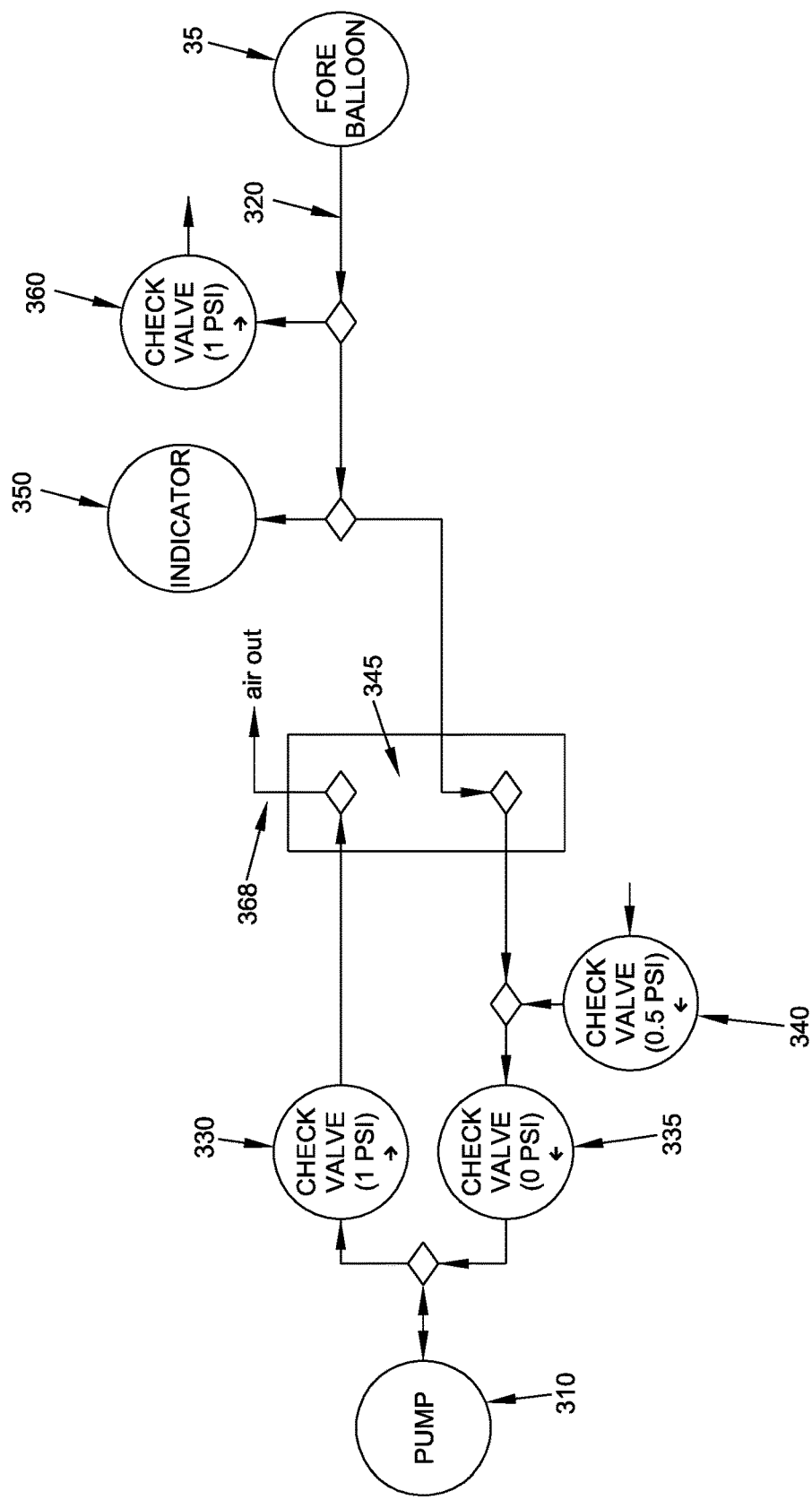

When fore balloon 35 is to be deflated, and looking now at FIG. 47, selector knob 370 is set so that multi-way valve 345 creates a fluid line connecting fore balloon 35, fore balloon inflation line 320, check valve 360, fore balloon indicator 350, check valve 340, check valve 335, pump 310, check valve 330 and "air out" port 368, so that repeated compressions of pump 310 deflates fore balloon 35, with the pressure within fore balloon 35 being indicated by fore balloon indicator 350.

In one preferred form of the invention, and looking now at FIGS. 48 and 13K, fore balloon indicator 350 and aft balloon indicator 355 each comprise a piston 385. Piston 385 is created by attaching two end caps 390, 395 together with a pliable extrusion 400. End cap 390 is securely mounted to housing 305 and is pneumatically connected by a tube 405 to the system pressure which is to be measured (i.e., to a balloon, either the fore balloon 35 or the aft balloon 20, depending on whether piston 385 is employed in fore balloon indicator 350 or aft balloon indicator 355). End cap 395 rides along tube 405 and abuts a spring 410 which engages a wall 415 of housing 305. End cap 395 includes an alignment feature 420 which is slidably disposed in a guide (not shown) in housing 305, and a color pressure indicator 425 which is visible through one or the other of the aforementioned openings 375, 380 (depending on whether piston 385 is employed in fore balloon indicator 350 or aft balloon indicator 355). End cap 395 acts as the pressure indicator, inasmuch as the longitudinal position of second end cap 395 along tube 405 (relative to wall 415) is an indicator of system pressure. In essence, the two end caps 390, 395 and extrusion 400 effectively constitute a piston (i.e., piston 385) which expands and contracts as the system pressure changes, with system pressure being reflected by the disposition of color pressure indicator 425 relative to one or the other of the aforementioned openings 375, 380.

When there is no pressure in the system (i.e., when the fore balloon or the aft balloon is entirely deflated), the indicator remains in the position shown in FIG. 50. In this position, extrusion 400 is collapsed and folded upon itself. When pressure is introduced into the system (and hence, into tube 405) and a balloon (i.e., fore balloon 35 or aft balloon 20) begins to inflate, end cap 395 begins to move relative to tube 405, compressing spring 410. The distance that end cap 395 moves depends on the pressure in the system (i.e., the pressure within tube 405), the diameter of the extrusion, and the bias force of the spring. FIG. 51 shows piston 385 and extrusion 400 fully extended (i.e., indicating maximum pressure within the system or, to put it another way, complete inflation of either fore balloon 35 or aft balloon 20). Ideally, the fully-extended position of color pressure indicator 425 relative to openings 375, 380 in housing 305 correlates to the maximum allowable pressure of fore balloon 35 or aft balloon 20.

It should be appreciated that since the position of a color pressure indicator 425 relative to an opening 375, 380 in housing 305 is reflective of the pressure within the system (i.e., the pressure within either fore balloon 35 or aft balloon 20), in one preferred form of the present invention, various colors (e.g., green, yellow and red) are used to correspond to various predetermined pressures within the system.

Thus, the design shown in FIGS. 48-53 comprises a colored indicator (i.e., color pressure indicator 425) attached to the "dynamic" (i.e., moving) end cap 395 of piston 385. The color scheme on each indicator alerts the user as to how "full" (i.e., how inflated) each of the balloons (i.e., fore balloon 35 or aft balloon 20) is. However, it should also be appreciated that, if desired, the indicator could comprise numeric pressure values instead of colors. Alternatively, the pressure level could be indicated by a strip of colors (or numbers) fixed to the housing (i.e., adjacent openings 375, 380 in housing 305). In this form of the invention, the end cap 395 comprises a pointer which extends out of opening 375 or 380 and, as the piston expands (i.e., as pliable extrusion 400 expands and end cap 395 moves toward wall 415 against the power of spring 410) and contracts (i.e., as pliable extrusion 400 contracts and end cap 395 moves away from wall 415 under the power of spring 410), the pointer points to the appropriate pressure indication mark on housing 305.

Figure 54:
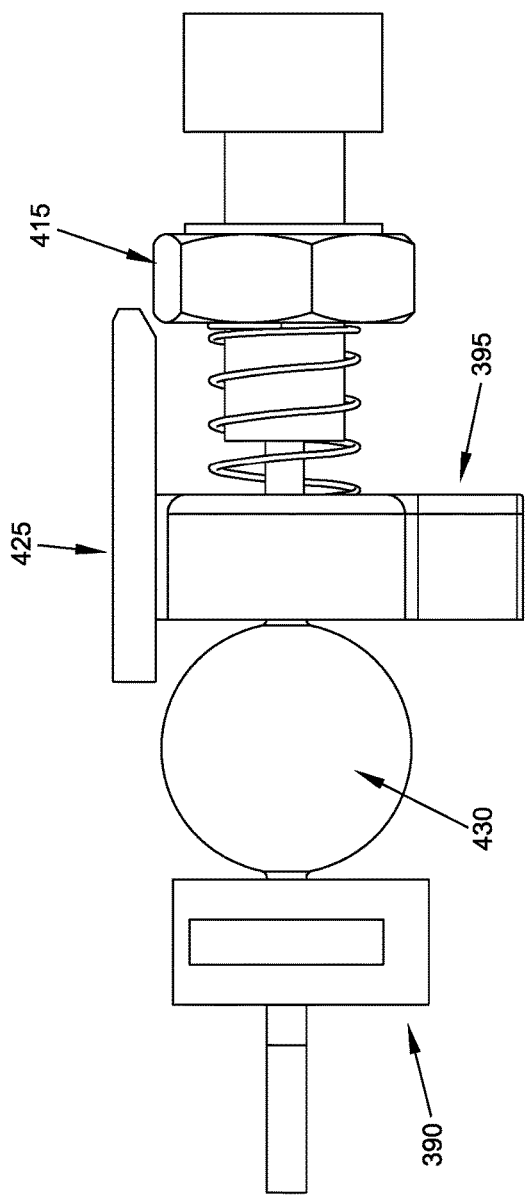
Figure 56:
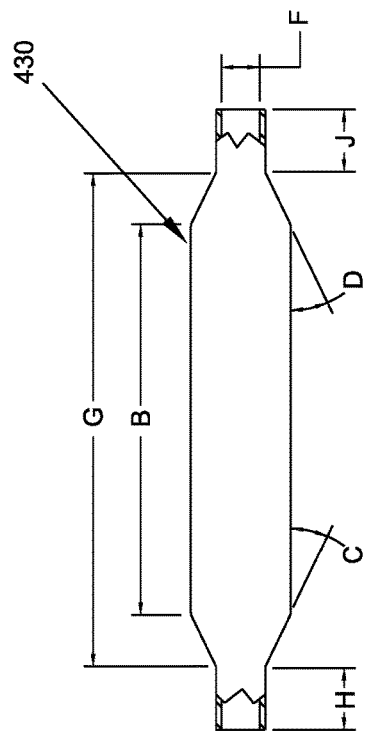
Figure 55:
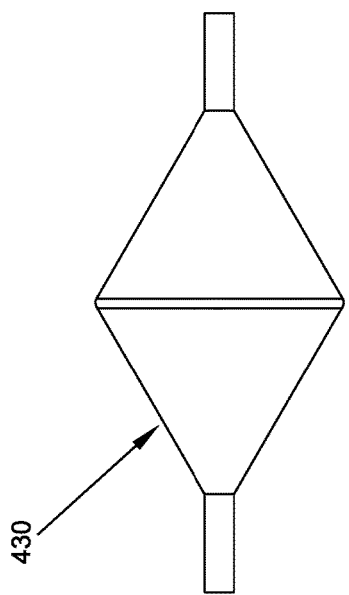
Figure 58:
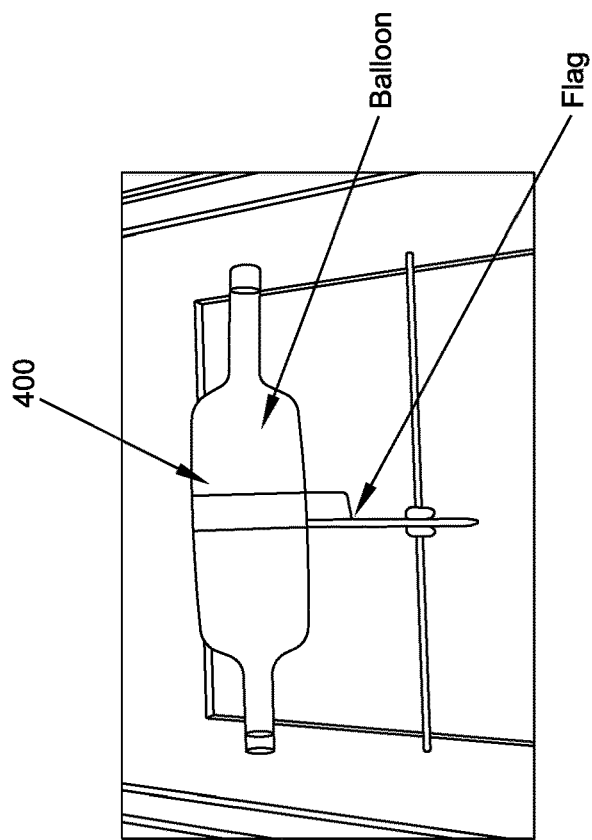
Figure 57:
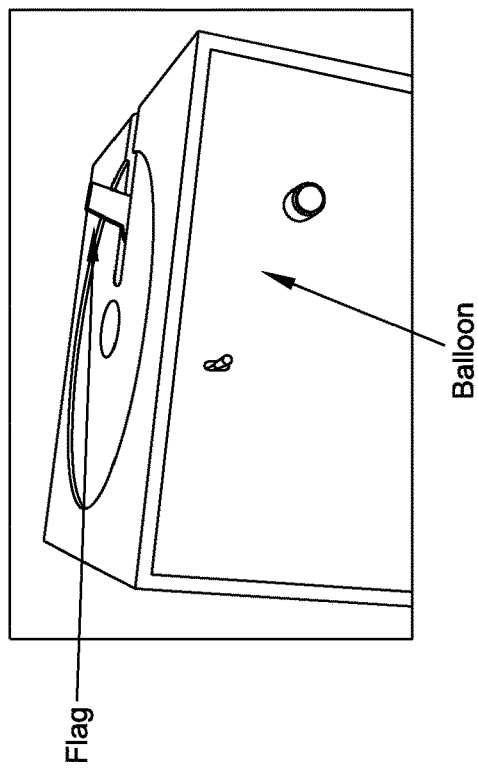

The design shown in FIGS. 48-53 illustrates the two end caps 390, 395 of piston 385 being separated by a tubular pliable extrusion 400. However, it should also be appreciated that, if desired, pliable extrusion 400 may be replaced by a balloon 430 (FIG. 54). Balloon 430 is preferably spherical (FIG. 54), although it may also comprise other shapes if desired (see, for example, FIG. 55, which shows a generally diamond-shaped balloon 430, and FIG. 56 which shows a generally tubular balloon 430). Or, if desired, balloon 430 may be used to push a flag upward, i.e., perpendicular to the axis of the balloon, instead of expanding a piston along its axis. See FIGS. 57 and 58.

In yet another form of the invention, inflation mechanism 40 may comprise an automated source of fluid pressure (either positive or negative), e.g., an electric pump.

Figure 59:
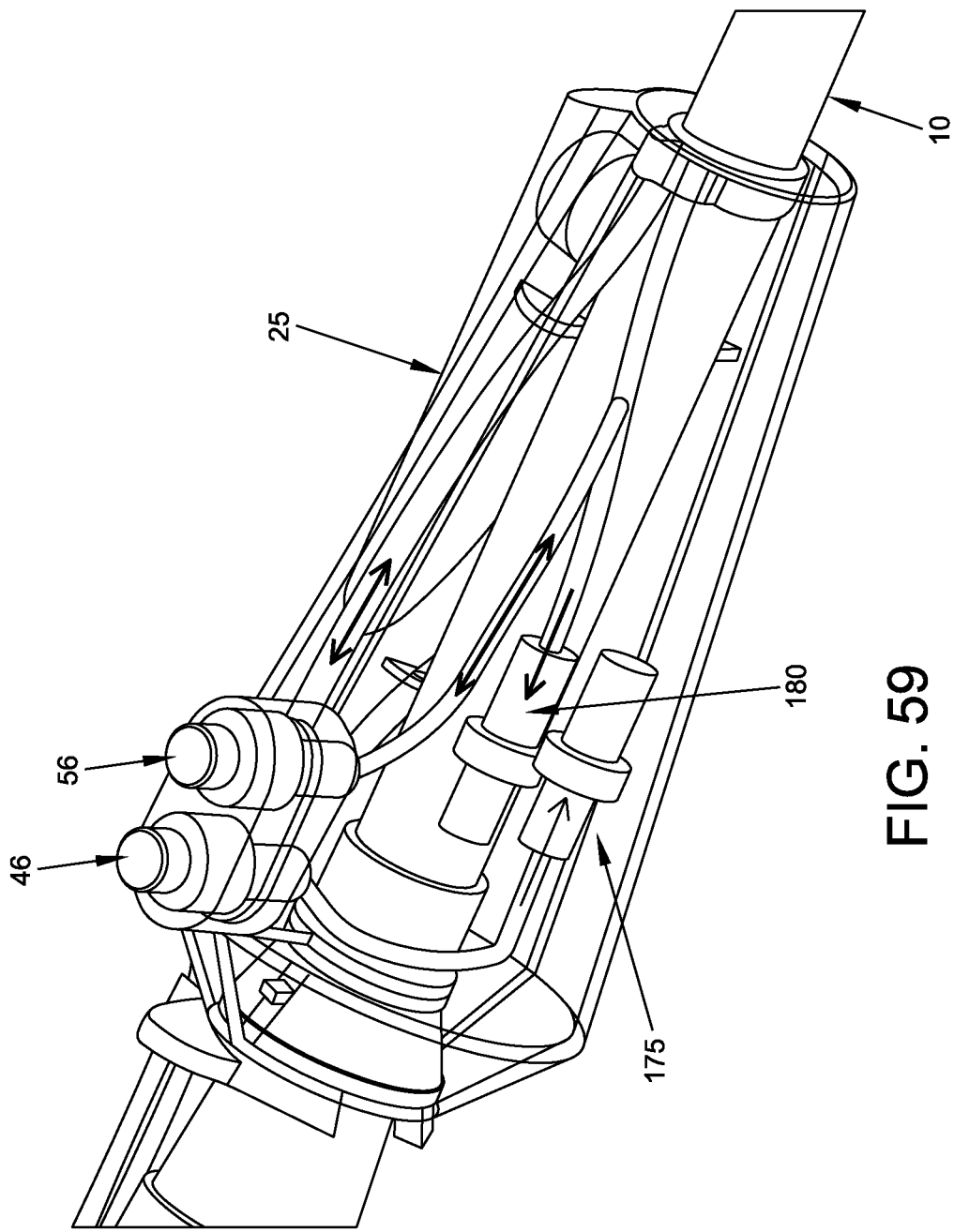
FIG. 59 is a schematic view showing relief valves which may be used to ensure that the pressure within the fore balloon and/or aft balloon does not exceed a predetermined level.

If desired, and looking now at FIG. 59, a relief valve 175 can be connected to the inflation/deflation line which connects to fore balloon 35 so as to ensure that the pressure within fore balloon 35 does not exceed a predetermined level. Similarly, and still looking now at FIG. 59, a relief valve 180 can be connected to the inflation/deflation line which connects to aft balloon 20 so as to ensure that the pressure within aft balloon 20 does not exceed a predetermined level.

Alternatively, and/or additionally, one or more pressure gauges 182 (FIG. 1 or FIG. 38) may be incorporated into the fluid line connected to aft balloon 20, and/or the fluid line connected to fore balloon 35, whereby to provide the physician (or other operator or user) with information relating to the pressure inside aft balloon 20 and/or fore balloon 35 so as to avoid over inflation and/or to help the physician (or other operator or user) ascertain the inflation state of a balloon during a procedure.

Furthermore, it will be appreciated that as fore balloon 35 moves between its "retracted" position (FIG. 2) and its "extended" position (FIG. 4), the flexible tube 59 connecting push tubes 30 to base 25 (and hence to fitting 56) may gather about base 25, potentially interfering with the physician's (or other operator's or user's) actions. Accordingly, if desired, and looking now at FIG. 60, a flexible tube retraction system 185 may be provided (e.g., within base 25) to take up slack in flexible tube 59 when fore balloon 35 is extended.

Hand Inflator Incorporating a Novel Manifold

As discussed above, in one preferred form of the invention, inflation mechanism 40 comprises a hand inflator 300 (FIGS. 39-58) for selectively inflating/deflating a selected one of fore balloon 35 and aft balloon 20. Hand inflator 300 generally comprises a manual pump (e.g., bulb 310) for providing an air pressure/suction source, and a multi-way valve 345 for directing the flow of air from/to bulb 310 to/from a selected one of fore balloon 35 and aft balloon 20.

Figure 61:
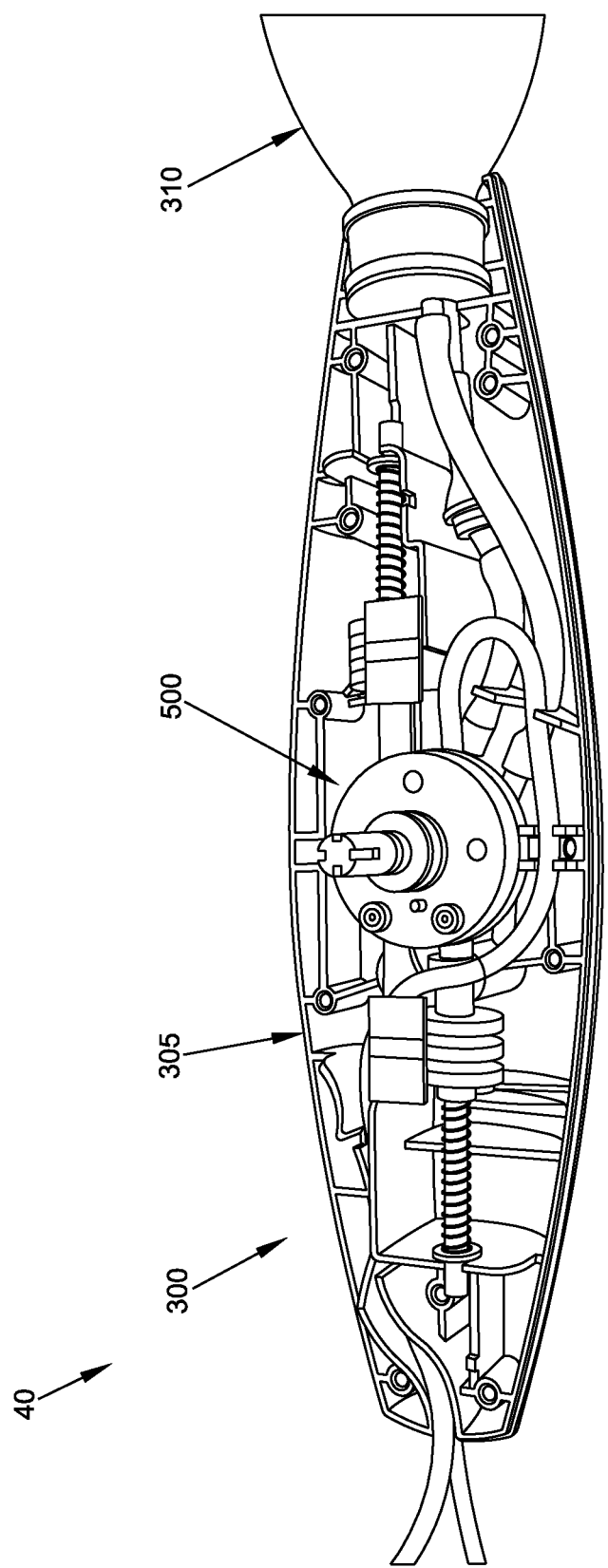
Figure 62:
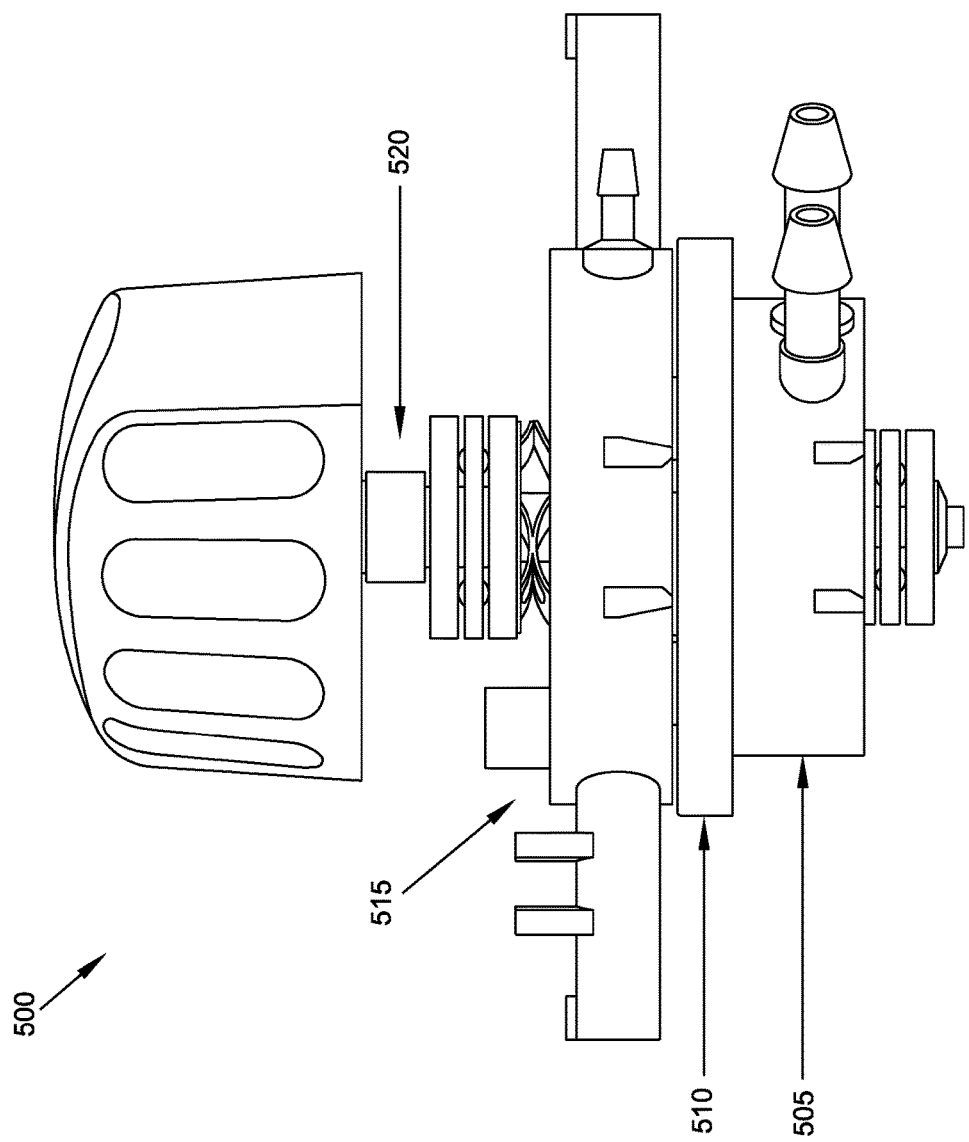

In one form of the present invention, and looking first at FIGS. 61 and 62, multi-way valve 345 preferably takes the form of a novel manifold 500 disposed within housing 305 of hand inflator 300. Manifold 500 generally comprises a bottom plate 505 fluidically connected to bulb 310, a rotatable middle plate 510, and a top plate 515 fluidically connected to fore balloon 35, aft balloon 20, fore balloon indicator 350 and aft balloon indicator 355. A shaft 520 passes through, and connects together, top plate 515, middle plate 510 and bottom plate 505, as will hereinafter be discussed in further detail.

Figure 63:
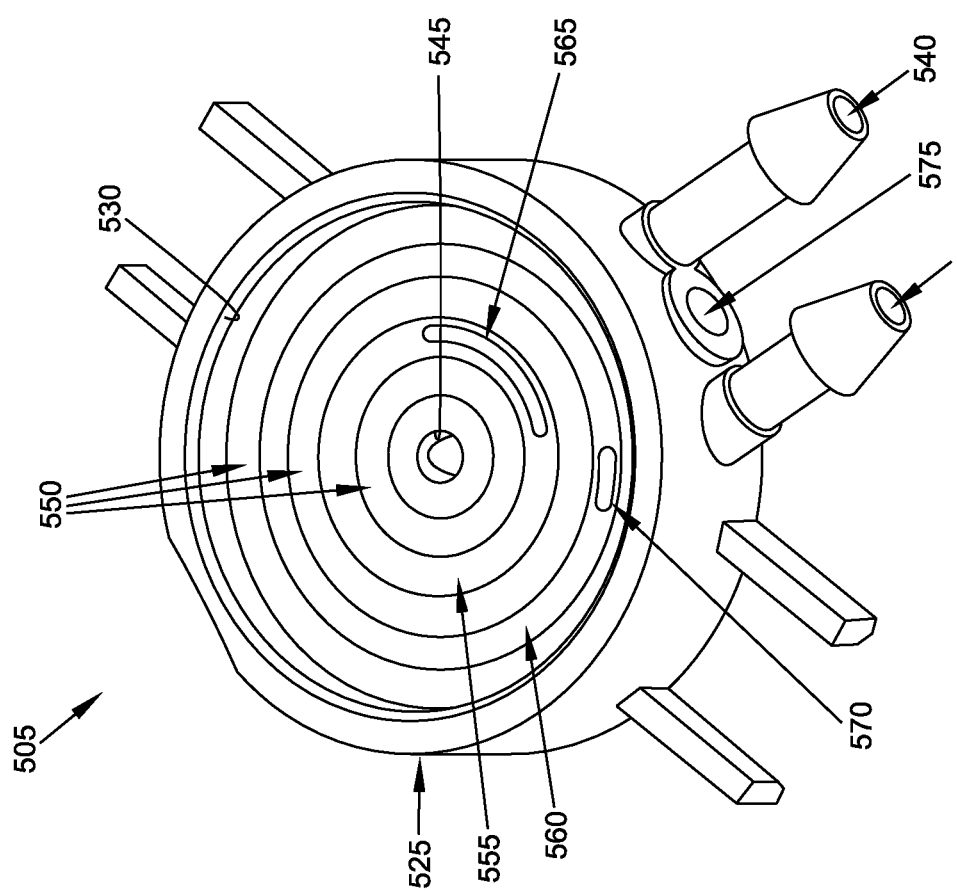

Looking next at FIG. 63, bottom plate 505 generally comprises a body 525 having a cavity 530 formed therein. Bottom plate 505 also comprises an inflation port 535 configured to be fluidically connected to an air pressure source (e.g., bulb 310) and a deflation port 540 configured to be fluidically connected to an air suction source (e.g., bulb 310). Inflation port 535 and deflation port 540 are fluidically connected to cavity 530, as will hereinafter be discussed in further detail.

Cavity 530 of bottom plate 505 comprises (i) a central opening 545 which passes through body 525 of bottom plate 505 for rotatably receiving shaft 520 therein, and (ii) a plurality of O-rings 550 which are disposed in cavity 530 and arranged concentrically about central opening 545. O-rings 550 define two ring-shaped zones which are disposed coaxially relative to one another and which can be fluidically isolated from one another (i.e., when middle plate 510 is mounted on top of bottom plate 505 and covers cavity 530, as will hereinafter be discussed). More particularly, O-rings 550 define an inner deflation zone 555 and an outer inflation zone 560 disposed coaxially about inner deflation zone 555. Inner deflation zone 555 comprises an opening 565 which is fluidically connected to deflation port 540, and outer inflation zone 560 comprises an opening 570 which is fluidically connected to inflation port 535. In one preferred form of the invention, bottom plate 505 also comprises a check valve 575 fluidically connected to deflation port 540 for allowing bulb 310 to "re-form" (i.e., draw air through check valve 575) when it is not possible to draw air from atmosphere through inner deflation zone 555 (it will be appreciated that check valve 575 is functionally equivalent to the check valve 340 shown in FIG. 65).

Figure 64:
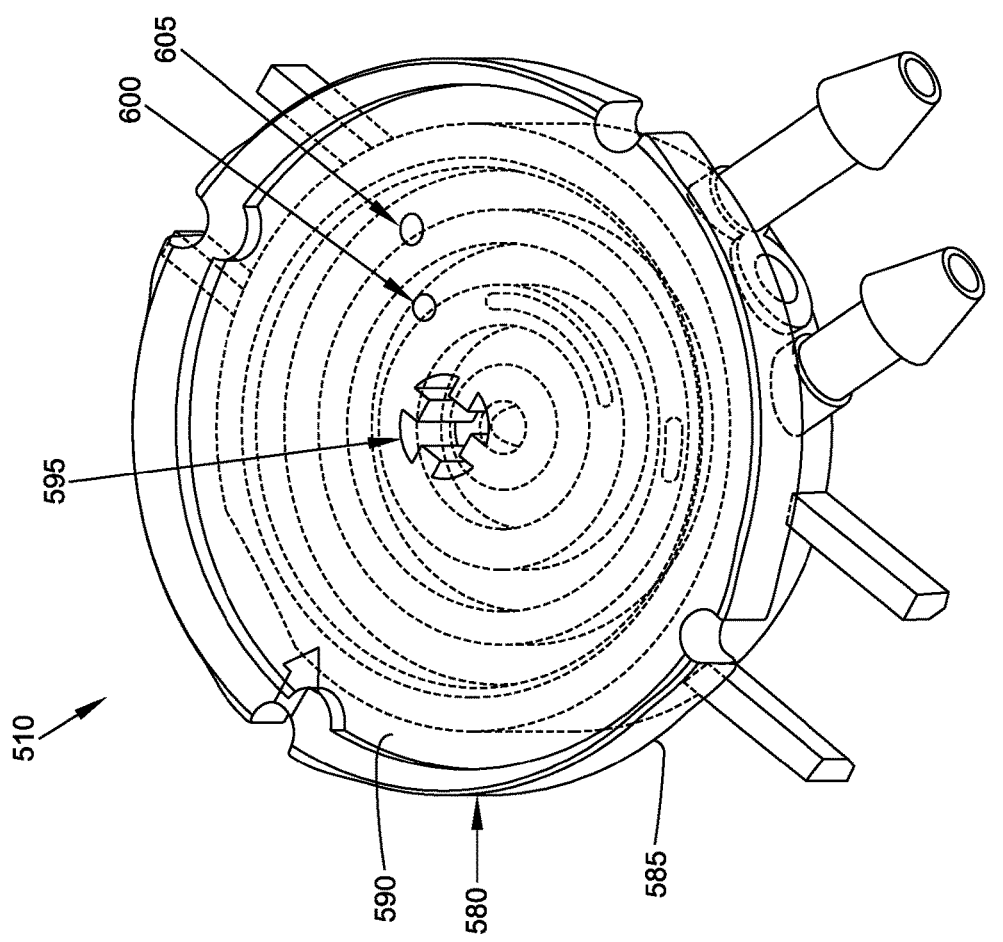

Looking next at FIG. 64, middle plate 510 comprises a body 580 having a smooth bottom surface 585 for sealingly engaging O-rings 550 disposed in cavity 530 of bottom plate 505 (whereby to fluidically seal inner deflation zone 555 and outer inflation zone 560), and a smooth top surface 590 for sealingly engaging top plate 515, as will hereinafter be discussed in further detail. Body 580 of middle plate 510 comprises a central opening 595 which passes through body 580 of middle plate 510 and is configured to engage shaft 520 (e.g., central opening 595 may comprise a non-circular cross-section which mates with a portion of shaft 520 having a corresponding non-circular cross-section) such that rotation of shaft 520 causes corresponding rotation of middle plate 510. Middle plate 510 also comprises an inner hole 600 and an outer hole 605 which are disposed on a common radius and which pass through body 580 of middle plate 510. Inner hole 600 is disposed so as to be in common orbit with, and fluidically connected to, inner deflation zone 555 of bottom plate 505 when middle plate 510 is mounted over bottom plate 505. Outer hole 605 is disposed so as to be in common orbit with, and fluidically connected to, outer inflation zone 560 of bottom plate 505 when middle plate 510 is mounted over bottom plate 505.

Figure 65:
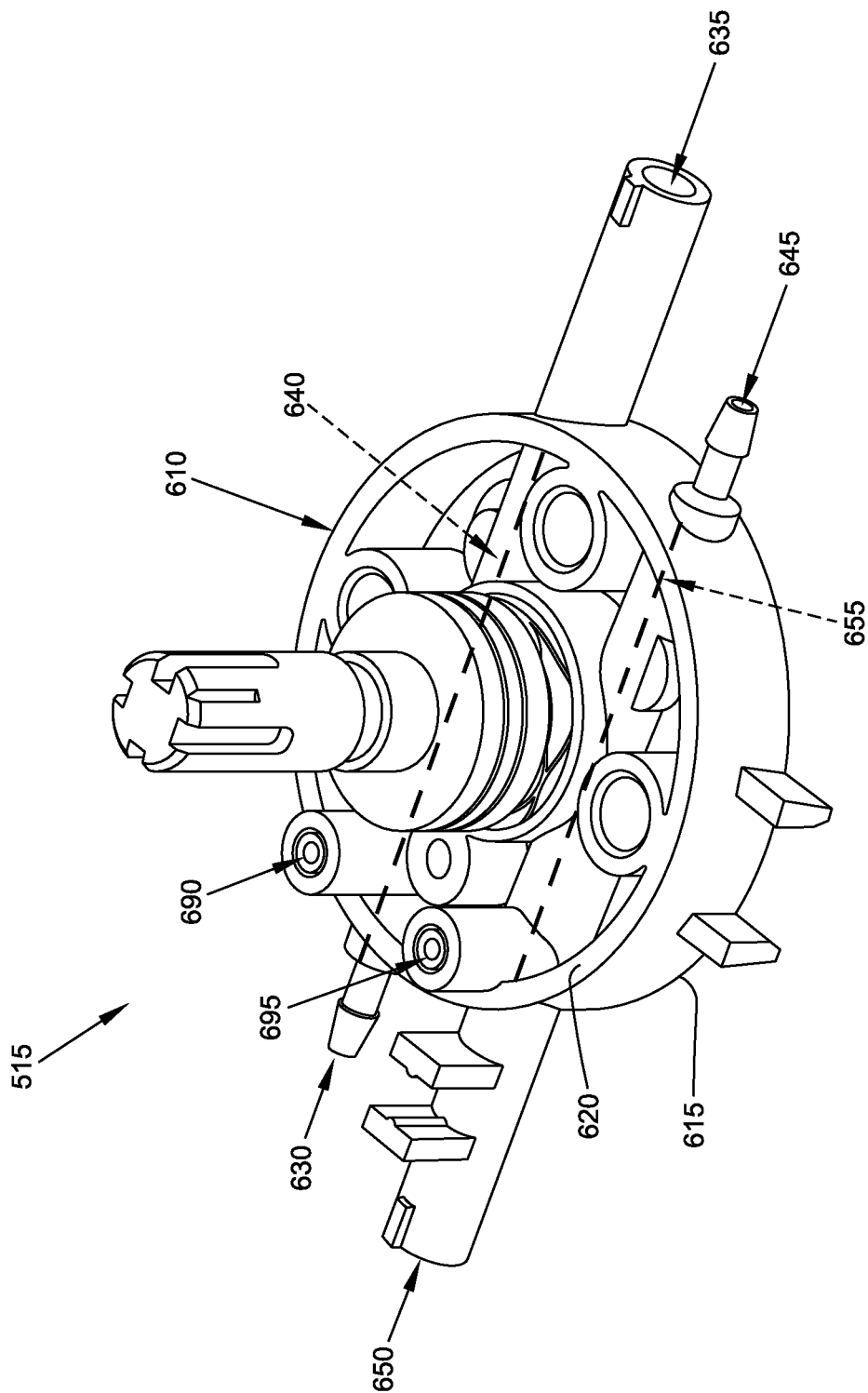
Figure 66:
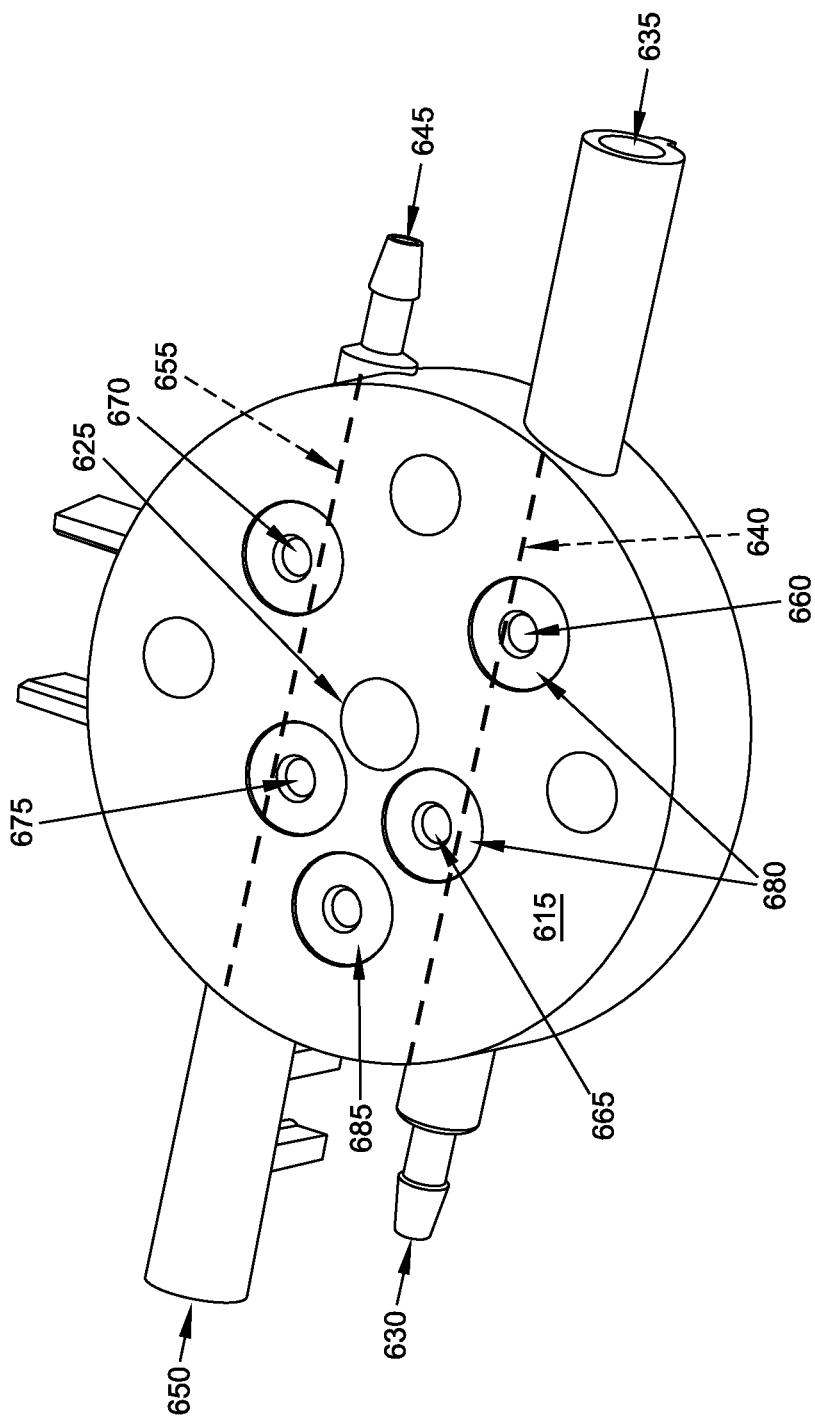
Figure 67:
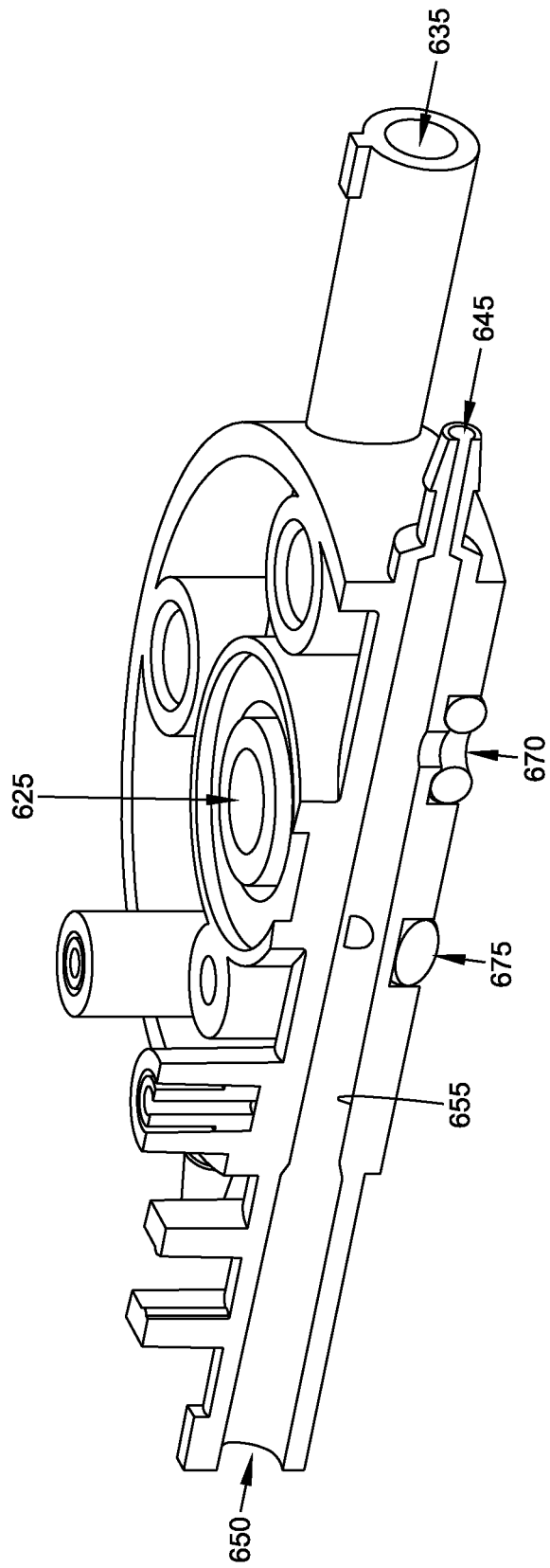

Looking next at FIGS. 65-67, top plate 515 comprises a body 610 having a bottom surface 615, a top surface 620 and a central opening 625 passing through body 610 for rotatably receiving shaft 520. Top plate 515 also comprises an aft balloon connection port 630 for fluidically connecting aft balloon 20 to manifold 500, an aft balloon indicator port 635 for fluidically connecting aft balloon indicator 355 to manifold 500, an aft balloon channel 640 extending between aft balloon connection port 630 and aft balloon indicator port 635, a fore balloon connection port 645 for fluidically connecting fore balloon 35 to manifold 500, a fore balloon indicator port 650 for fluidically connecting fore balloon indicator 350 to manifold 500 and a fore balloon channel 655 extending between fore balloon connection port 645 and fore balloon indicator port 650.

Bottom surface 615 of body 610 comprises an aft balloon inflation port 660 and an aft balloon deflation port 665 which open on bottom surface 615 and which are fluidically connected to aft balloon channel 640. Bottom surface 615 of body 610 also comprises a fore balloon inflation port 670 and a fore balloon deflation port 675 which open on bottom surface 615 and which are fluidically connected to fore balloon channel 655. A plurality of O-rings 680 are disposed about ports 660, 665, 670, 675 for effecting sealing engagement of ports 660, 665, 670, 675 with top surface 590 of middle plate 510 as will hereinafter be discussed in further detail. In one preferred form of the present invention, bottom surface 615 of body 610 also comprises a balance O-ring 685 for helping to maintain sealing engagement of O-rings 680 with top surface 590 of middle plate 510, as will hereinafter be discussed in further detail.

In one preferred form of the invention, top plate 515 also comprises an aft balloon channel check valve 690 disposed in top plate 515 (it will be appreciated that check valve 690 is functionally equivalent to the check valve 365 shown in FIG. 65). Aft balloon check valve 690 is in fluid communication with aft balloon channel 640 and prevents over-inflation of aft balloon 20 by releasing air to atmosphere when the air pressure within aft balloon channel 640 (which is the same as the air pressure within aft balloon 20) exceeds a predetermined threshold. In one preferred form of the invention, top plate 515 also comprises a fore balloon channel check valve 695 disposed in top plate 515 (it will be appreciated that check valve 695 is functionally equivalent to the check valve 360 shown in FIG. 43). Fore balloon check channel valve 695 is in fluid communication with fore balloon channel 655 and prevents over-inflation of fore balloon 35 by releasing air to atmosphere when the air pressure within fore balloon channel 655 (which is the same as the air pressure within fore balloon 35) exceeds a predetermined threshold.

Assembly of the Novel Manifold

Figure 68:
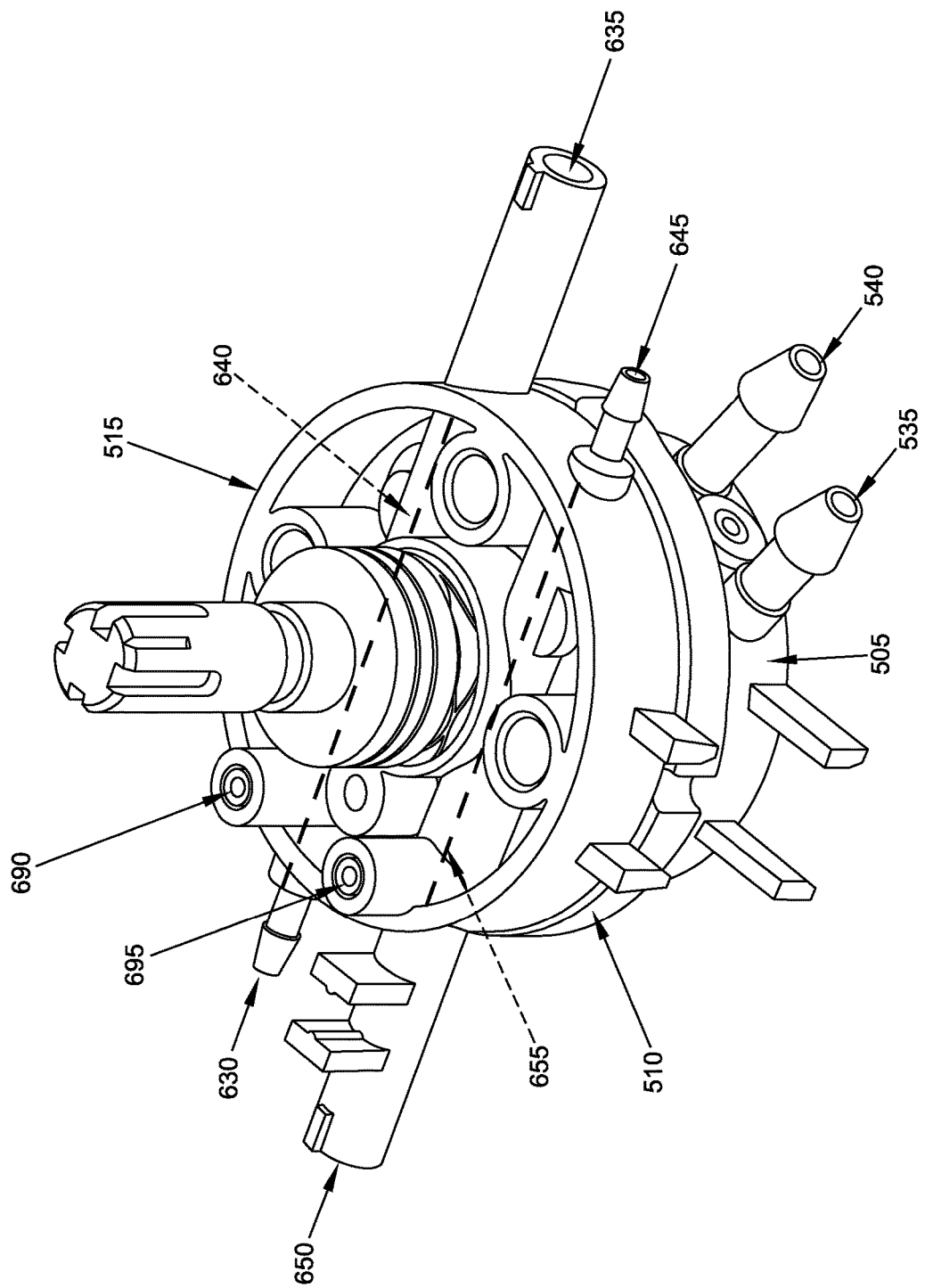
Figure 69:
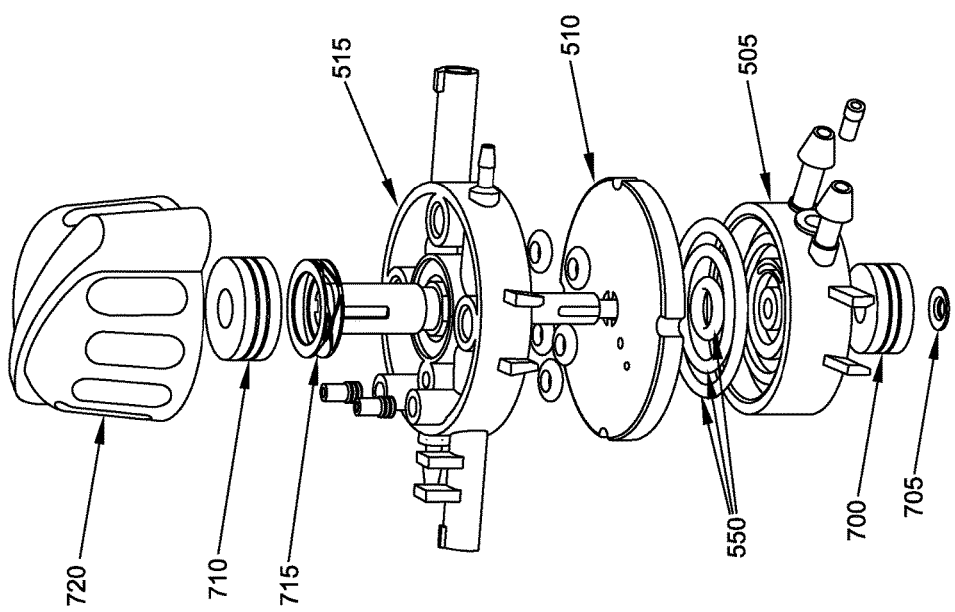

Looking next at FIGS. 68 and 69, manifold 500 is assembled such that middle plate 510 is rotatably disposed between bottom plate 505 and top plate 515, with shaft 520 passing through central opening 625 of top plate 515, through central opening 595 of middle plate 510 and through central opening 545 of bottom plate 505. More particularly, the distal end of shaft 520 comprises a distal bearing 700 which is secured to shaft 520 by a retainer clip 705. The proximal end of shaft 520 comprises a proximal bearing 710 which is secured to the proximal end of shaft 520, with a spring 715 being disposed between proximal bearing 710 and top surface 620 of top plate 515. A selector knob 720 is fixedly mounted to the proximal end of shaft 520 such that rotation of selector knob 720 causes corresponding rotation of shaft 520 (and hence corresponding rotation of middle plate 510). Shaft 520 is able to rotate freely within central opening 625 of top plate 515 and central opening 545 of bottom plate 505, and to also rotate freely within proximal bearing 710 and distal bearing 700. However, shaft 520 engages central opening 595 of middle plate 510 such that rotation of shaft 520 causes corresponding rotation of middle plate 510, whereby to permit a user to selectively rotate middle plate 510 (i.e., by rotating selector knob 720, which, in turn, rotates middle plate 510).

It will be appreciated that when the various components are assembled on shaft 520, bottom plate 505, middle plate 510 and top plate 515 are "sandwiched" between distal bearing 700 and proximal bearing 710 under compression provided by spring 715, whereby to maintain constant contact (i) between bottom surface 585 of middle plate 510 and O-rings 550 of bottom plate 505, (ii) between top surface 590 of middle plate 510 and O-rings 680 of top plate 515 (i.e., between top surface 590 of middle plate 510 and aft balloon inflation port 660, aft balloon deflation port 665, fore balloon inflation port 670 and fore balloon deflation port 675), and (iii) between top surface 590 of middle plate 510 and balance O-ring 685 of top plate 515.

As a result, an air-tight air pathway is maintained through manifold 500 between a selected one of (i) inflation port 535 or deflation port 540, and (ii) a selected one of fore balloon 35 or aft balloon 20, such that bulb 310 may be used to selectively inflate or deflate a selected one of fore balloon 35 or aft balloon 20, as will hereinafter be discussed in further detail.

More particularly, it will be appreciated that rotating selector knob 720 causes shaft 520 to rotate, thereby causing middle plate 510 to rotate. When this occurs, inner hole 600 and outer hole 605 of middle plate 510 also rotate relative to bottom plate 505 and top plate 515. Since inner hole 600 of middle plate 510 is aligned in common orbit with inner deflation zone 555 of bottom plate 505, inner hole 600 is always aligned with inner deflation zone 555, regardless of the rotational position of middle plate 510 (and hence, inner hole 600 is always fluidically connected to deflation port 540, i.e., vis-à-vis opening 565 in inner deflation zone 555). Similarly, since outer hole 605 of middle plate 510 is aligned in common orbit with outer inflation zone 560 of bottom plate 505, outer hole 605 is always aligned with outer inflation zone 560 (and hence, outer hole 605 is always fluidically connected to inflation port 535 vis-à-vis opening 570 in outer inflation zone 560).

It will also be appreciated that when middle plate 510 is rotated (i.e., by rotating selector knob 720), inner hole 600 of middle plate 510 may be positioned so that it is (i) aligned with aft balloon deflation port 665, or (ii) aligned with fore balloon deflation port 675, or (iii) unaligned with a port 665, 675 (and hence open to atmosphere). Similarly, outer hole 605 of middle plate 510 may be positioned so that it is (i) aligned with aft balloon inflation port 660, or (ii) aligned with fore balloon inflation port 670, or (iii) unaligned with a port 660, 670 (and hence open to atmosphere). In this respect it will be appreciated that the provision of O-rings 680 and balance O-ring 685 creates a small gap between bottom surface 615 of top plate 515 and top surface 590 of middle plate 510, such that when either (or both) of inner hole 600 and/or outer hole 605 of middle plate 510 are unaligned with a port 665, 675, 660, 670, inner hole 600 and/or outer hole 605 are connected with atmosphere.

As a result of this construction, it will be appreciated that middle plate 510 can be selectively rotated so as to occupy one of five states: (1) an aft balloon inflation state, wherein outer hole 605 of middle plate 510 is aligned with aft balloon inflation port 660 of top plate 515 and inner hole 600 of middle plate 510 is open to atmosphere ("State 1"); (2) an aft balloon deflation state wherein outer hole 605 of middle plate 510 is open to atmosphere and inner hole 600 of middle plate 510 is aligned with aft balloon deflation port 665 of top plate 515 ("State 2"); (3) a fore balloon inflation state wherein outer hole 605 of middle plate 510 is aligned with fore balloon inflation port 670 of top plate 515 and inner hole 600 of middle plate 510 is open to atmosphere ("State 3"); (4) a fore balloon deflation state wherein outer hole 605 of middle plate 510 is open to atmosphere and inner hole 600 of middle plate 510 is aligned with fore balloon deflation port 675 ("State 4"); or (5) an inactive state wherein neither outer hole 605 nor inner hole 600 of middle plate 510 is aligned with a port 660, 665, 670, 675 in top plate 515, i.e., wherein both outer hole 605 and inner hole 600 are open to atmosphere and with ports 660, 665, 670, 675 of top plate 515 being fluidically sealed against top surface 590 of middle plate 510 ("State 5").

Thus it will be seen that the relative positions of aft balloon inflation port 660, aft balloon deflation port 665, fore balloon inflation port 670 and fore balloon deflation port 675 within bottom surface 615 of top plate 515 can be arranged such that rotation of middle plate 510 causes selective switching between the States 1, 2, 3, 4 and 5 discussed above.

By way of example but not limitation, in one preferred form of the present invention, State 1 is effected when knob 720 is in the "8 o'clock" position, State 2 is effected when knob 720 is in the "4 o'clock" position, State 3 is effected when knob 720 is in the "10 o'clock" position, and State 4 is effected when knob 720 is in the "2 o'clock" position. In this form of the invention, State 5 is effected whenever knob 720 is rotated to a position intermediate the aforementioned positions.

Figure 70:
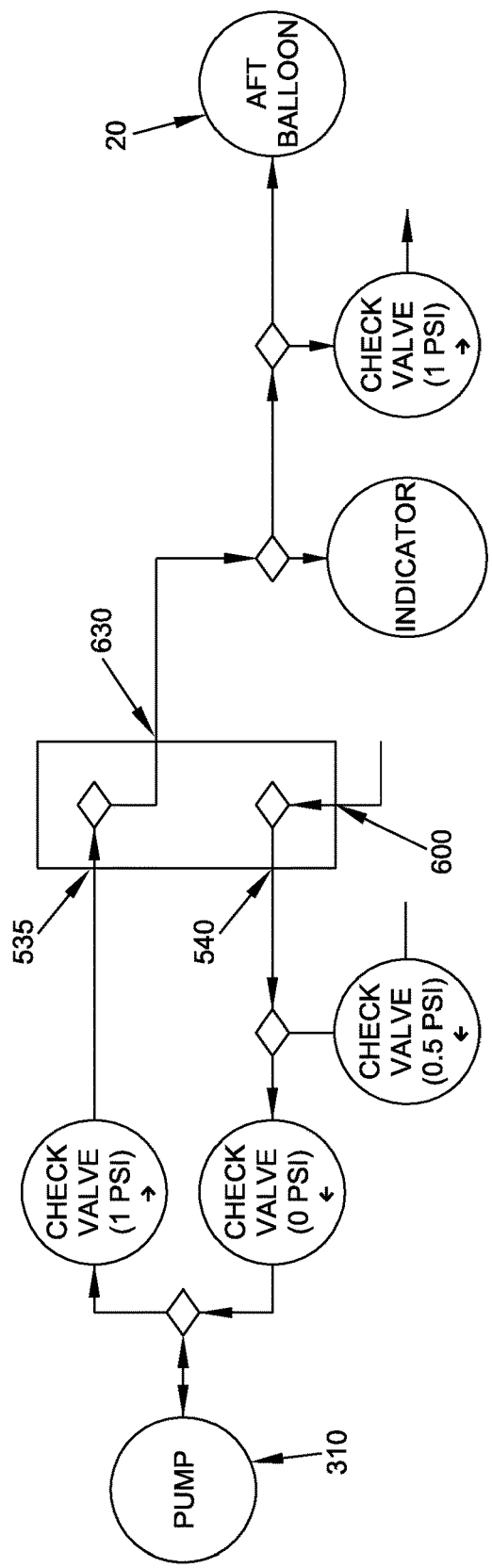
Figure 71:
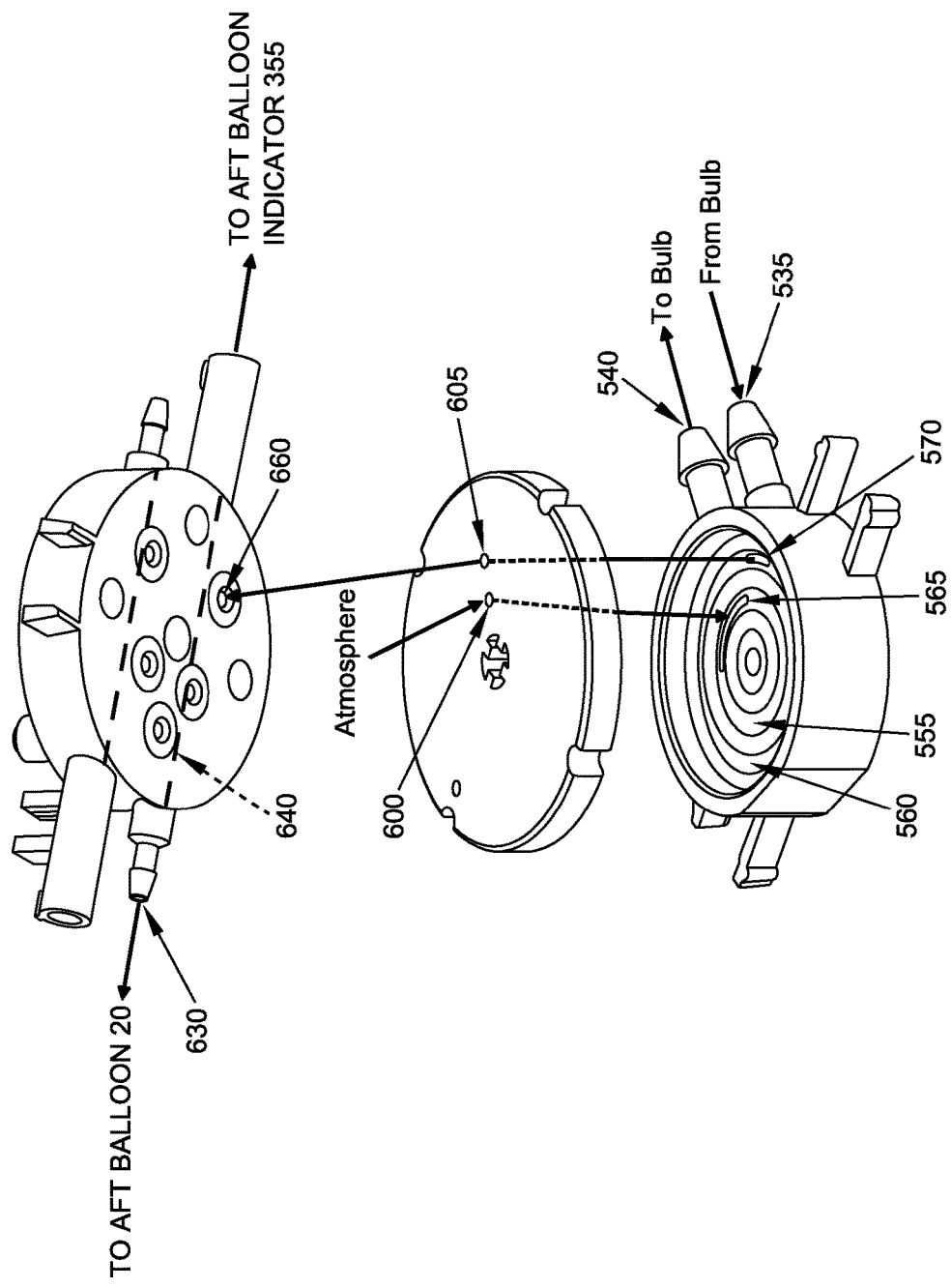
Figure 72:
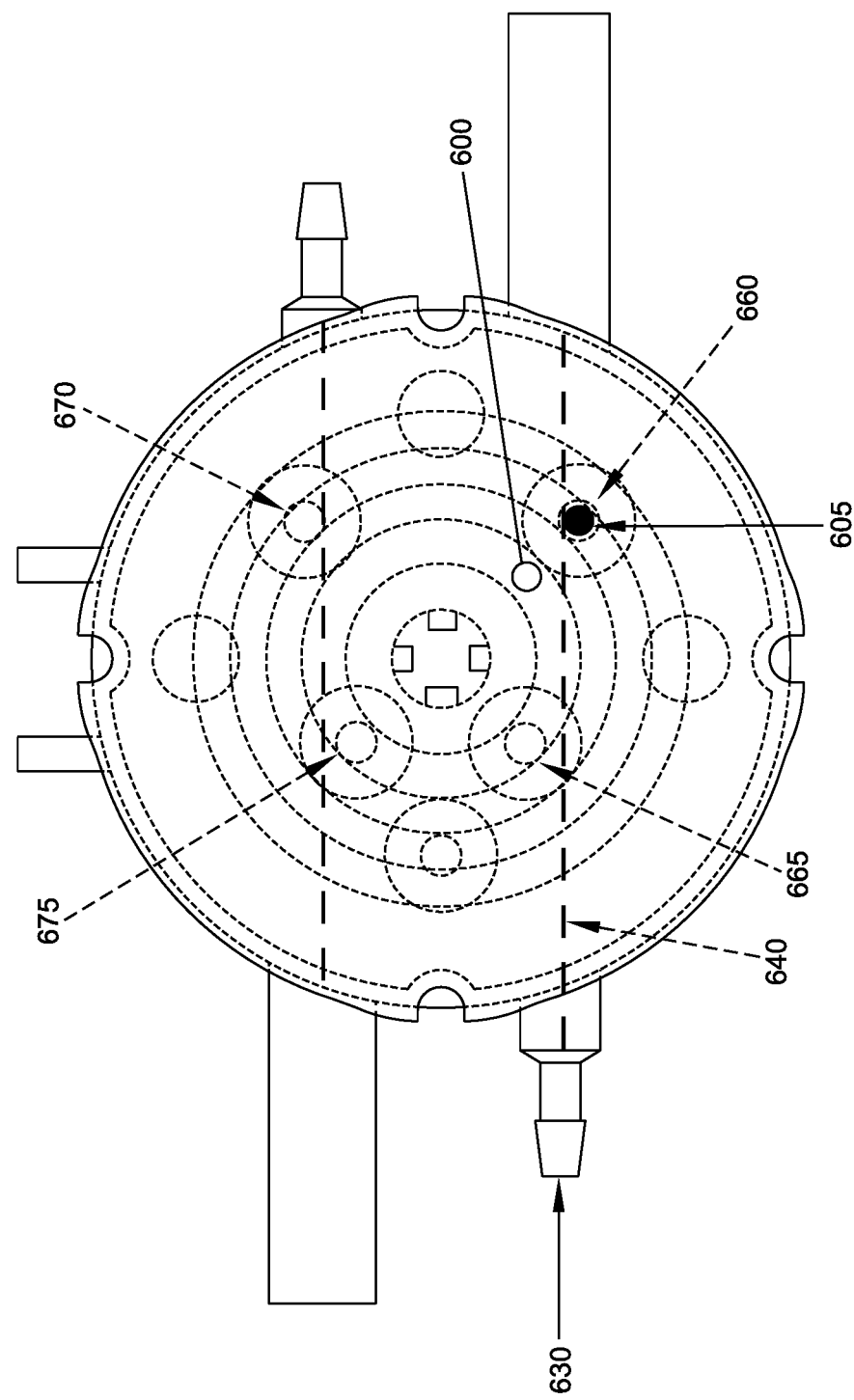

1. Aft Balloon Inflation. Looking now at FIGS. 70-72, there is shown the path that air travels through manifold 500 when middle plate 510 is in State 1 discussed above for effecting aft balloon inflation (i.e., when middle plate 510 is rotated such that outer hole 605 of middle plate 510 is aligned with aft balloon inflation port 660 of top plate 515 and inner hole 600 of middle plate 510 is open to atmosphere). In State 1, when bulb 310 is squeezed and released, free air from atmosphere is drawn into inner hole 600 of middle plate 510, passes into inner deflation zone 555 of bottom plate 505, through opening 565 in inner deflation zone 565, through deflation port 540, into bulb 310 and then back out of bulb 310, into inflation port 535, through opening 570, into outer inflation zone 560, through outer hole 605 of middle plate 510, into aft balloon inflation port 660, through aft balloon channel 640, out of aft balloon connection port 630 and into aft balloon 20. It should be appreciated that as this occurs, and looking now at FIG. 72, aft balloon deflation port 665, fore balloon inflation port 670 and fore balloon deflation port 675 are all fluidically sealed against top surface 590 of middle plate 510 so that air cannot enter or leave via ports 665, 670, 675, and hence, when manifold 500 is in State 1, inflation of aft balloon 20 does not have any effect on fore balloon 35.

Figure 73:
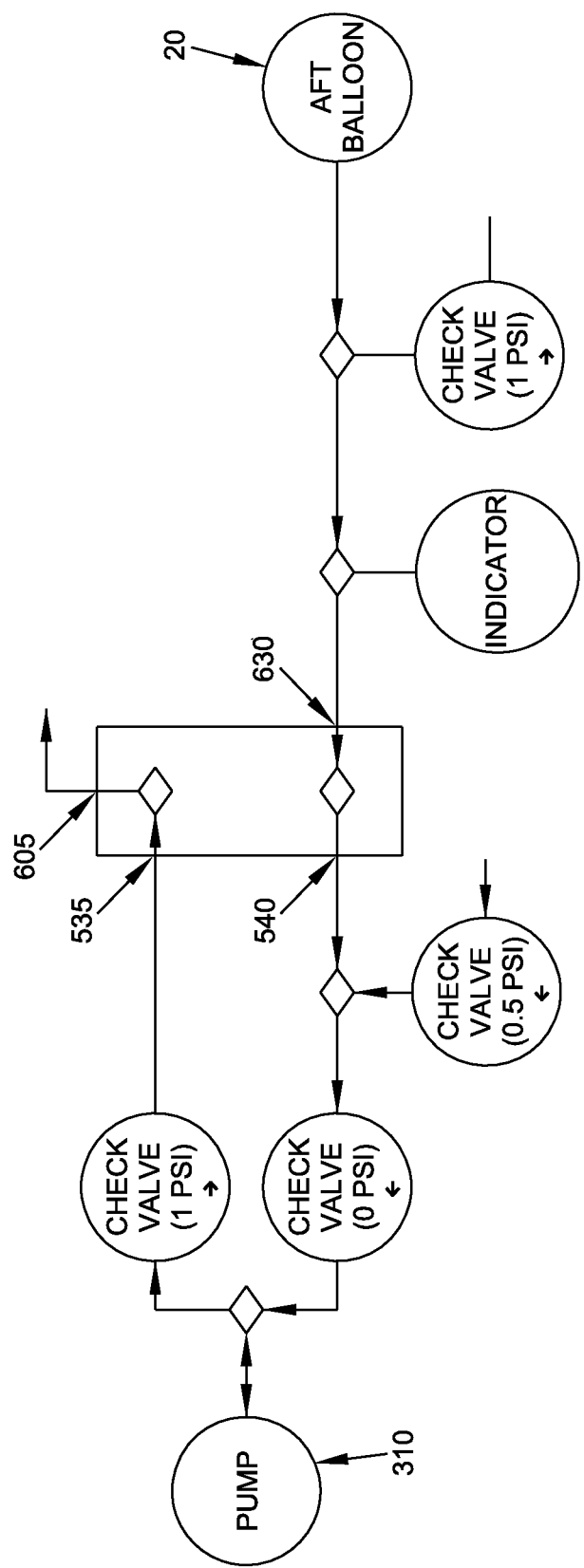
Figure 74:
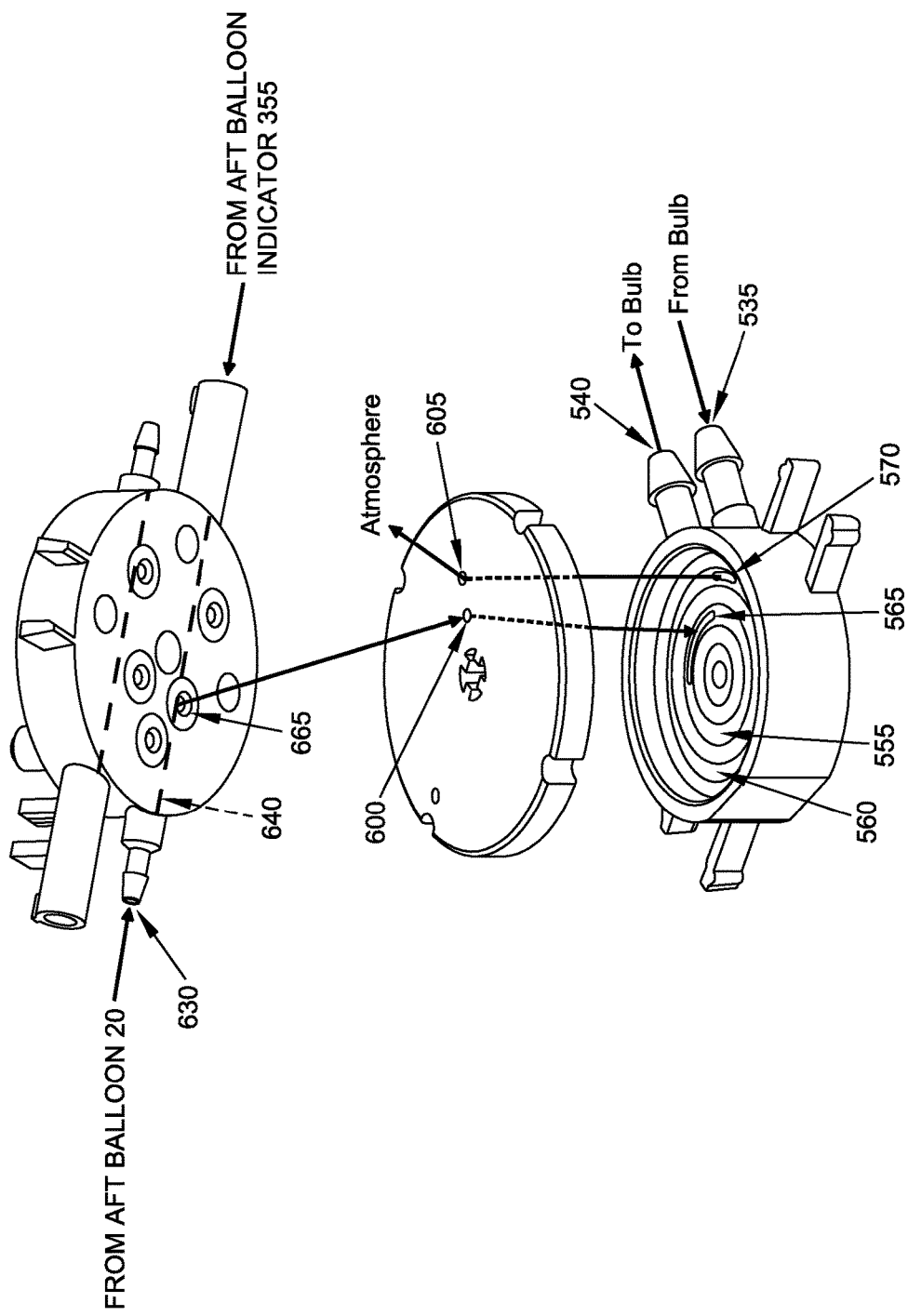

2. Aft Balloon Deflation. Looking next at FIGS. 73 and 74, there is shown the path that air travels through manifold 500 when middle plate 510 is in State 2 discussed above for effecting aft balloon deflation (i.e., when middle plate 510 is rotated such that outer hole 605 of middle plate 510 is open to atmosphere and inner hole 600 of middle plate 510 is aligned with aft balloon deflation port 665). In State 2, when bulb 310 is squeezed and released, air from aft balloon 20 is drawn into aft balloon connection port 630, through aft balloon channel 640, out aft balloon deflation port 665, through inner hole 600 of middle plate 510, into inner deflation zone 555, through opening 565, out deflation port 540, into bulb 310, back out of bulb 310, into inflation port 535, through opening 570 in outer inflation zone 560, into outer inflation zone 560, through outer hole 605 of middle plate 510 and out to atmosphere. It should be appreciated that as this occurs, aft balloon inflation port 660, fore balloon inflation port 670 and fore balloon deflation port 675 are all fluidically sealed against top surface 620 of middle plate 510 so that air cannot enter or leave via ports 660, 670, 675, and hence, when manifold 500 is in State 2, deflation of aft balloon 20 does not have any effect on fore balloon 35.

Figure 75:
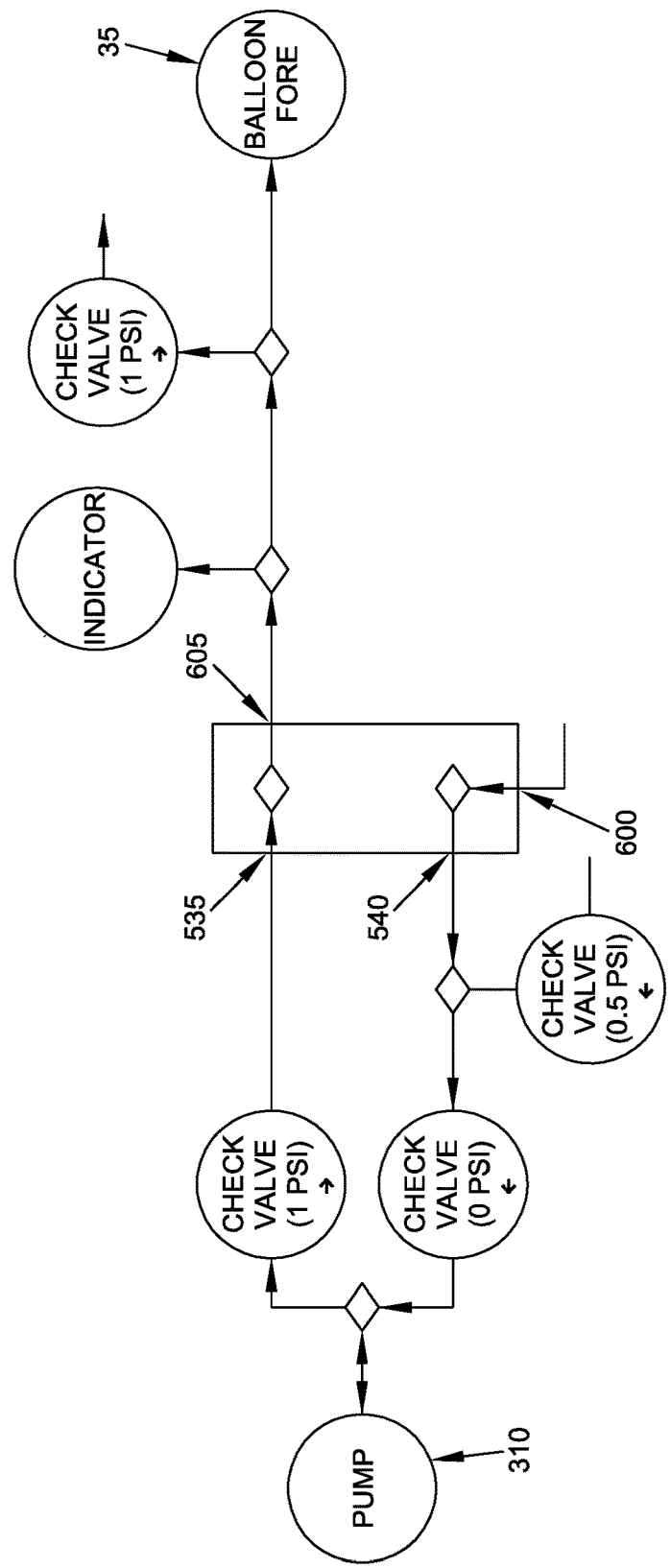
Figure 76:
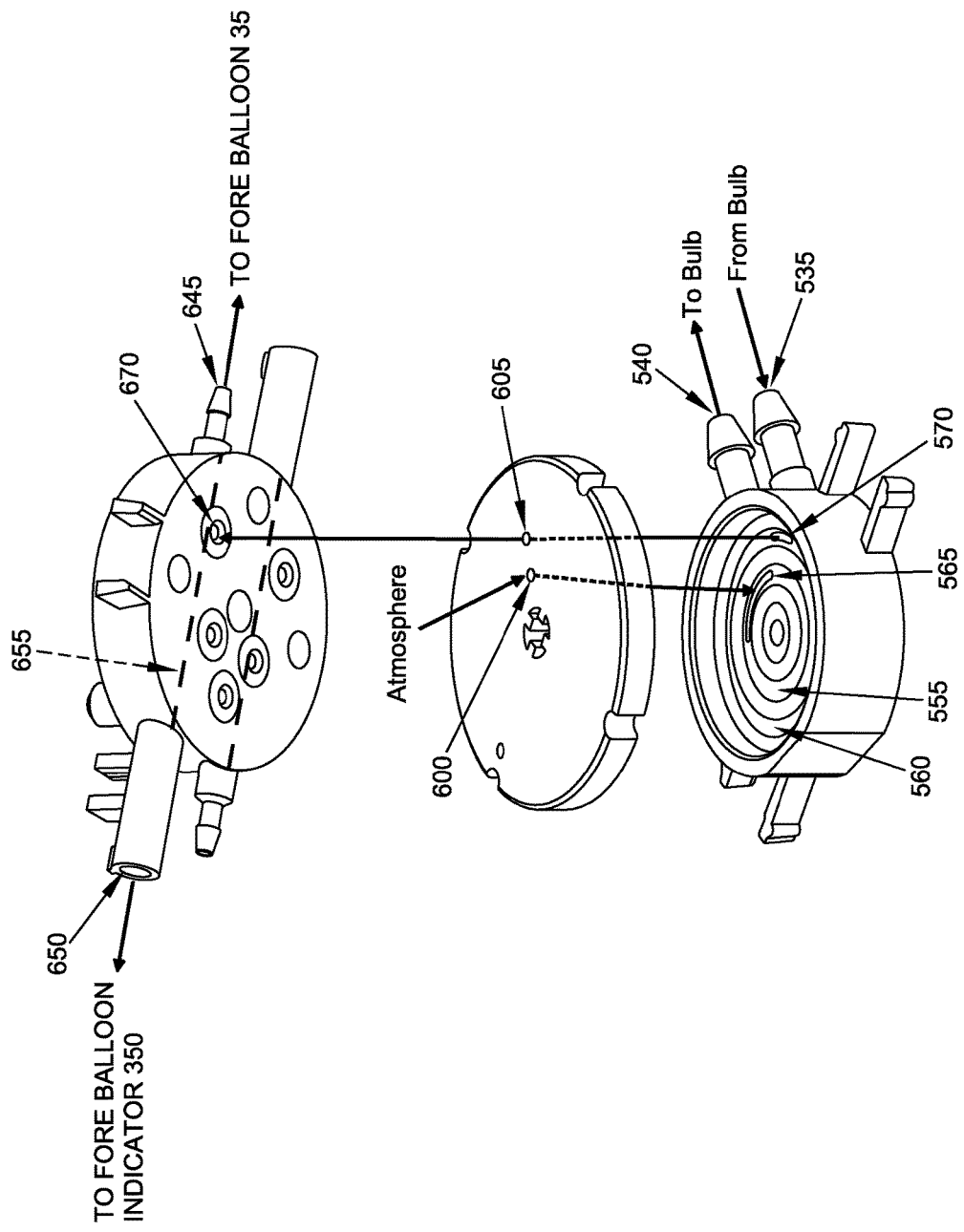

3. Fore Balloon Inflation. Looking next at FIGS. 75 and 76, there is shown the path that air travels through manifold 500 when middle plate 510 is in State 3 discussed above for effecting fore balloon inflation (i.e., when middle plate 510 is rotated such that outer hole 605 of middle plate 510 is aligned with fore balloon inflation port 670 of top plate 515 and inner hole 600 of middle plate 510 is open to atmosphere). In State 3, when bulb 310 is squeezed and released, free air from atmosphere is drawn into inner hole 600 of middle plate 510, passes into inner deflation zone 555 of bottom plate 505, through opening 565 in inner deflation zone 565, through deflation port 540, into bulb 310 and then back out of bulb 310, into inflation port 535, through opening 570, into outer inflation zone 560, through outer hole 605 of middle plate 510, into fore balloon inflation port 670, through fore balloon channel 655, out of fore balloon connection port 645 and into fore balloon 35. It should be appreciated that as this occurs, aft balloon deflation port 665, aft balloon inflation port 660 and fore balloon deflation port 675 are all fluidically sealed against top surface 590 of middle plate 510 so that air cannot enter or leave via ports 665, 660, 675, and hence, when manifold 500 is in State 3, inflation of fore balloon 35 does not have any effect on aft balloon 20.

Figure 77:
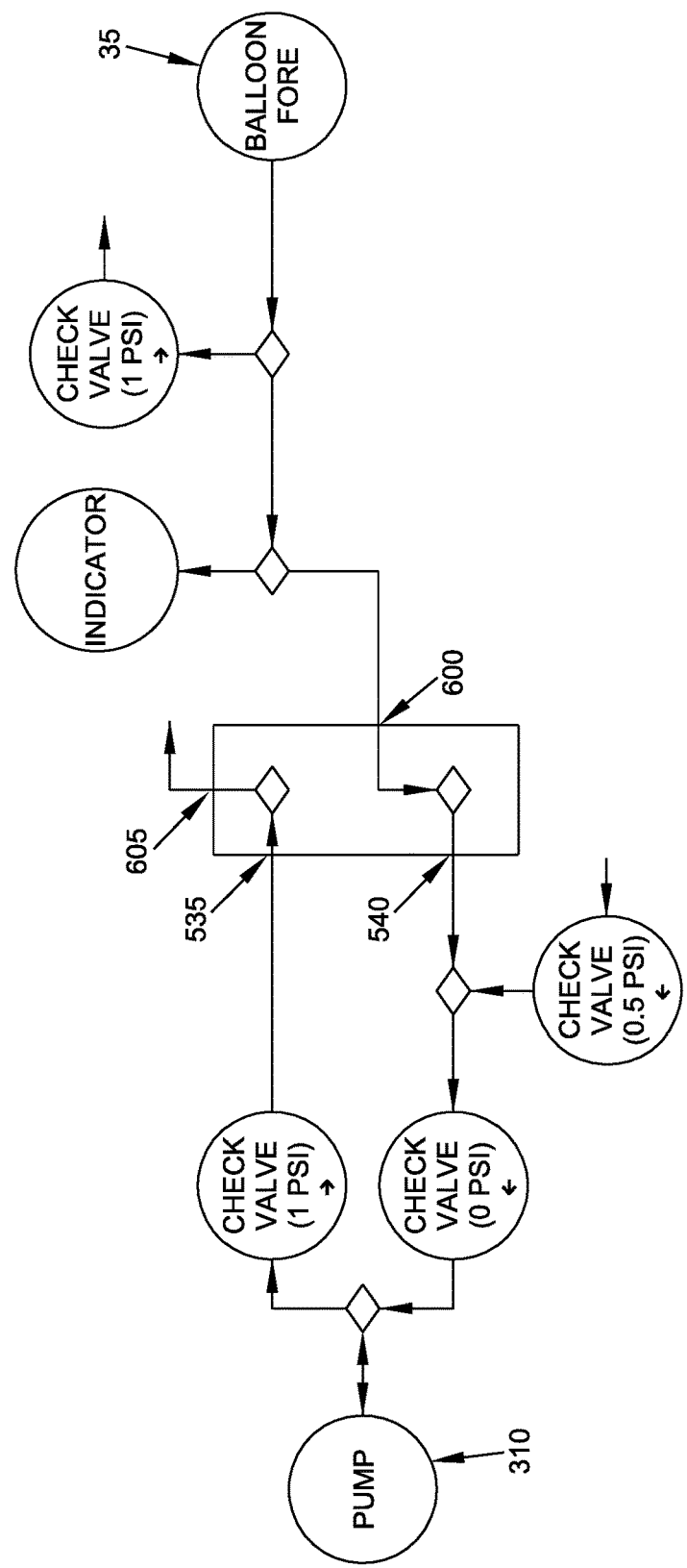
Figure 78:
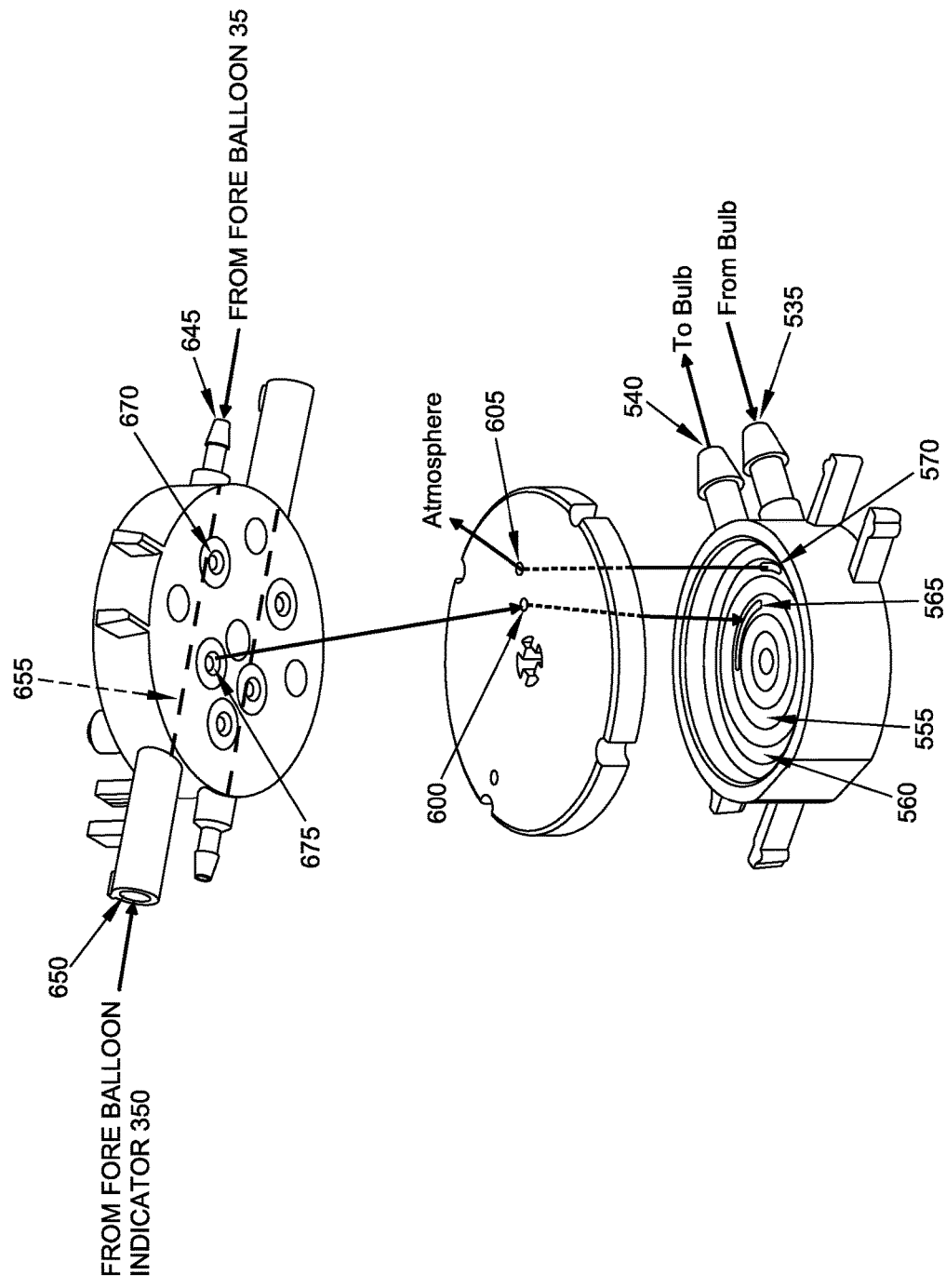

4. Fore Balloon Deflation. Looking next at FIGS. 77 and 78, there is shown the path that air travels through manifold 500 when middle plate 510 is in State 4 discussed above for effecting fore balloon deflation (i.e., when middle plate 510 is rotated such that outer hole 605 of middle plate 510 is open to atmosphere and inner hole 600 of middle plate 510 is aligned with fore balloon deflation port 675). In State 4, when bulb 310 is squeezed and released, air from fore balloon 35 is drawn into fore balloon connection port 645, through fore balloon channel 655, through fore balloon deflation port 675, through inner hole 600 of middle plate 510, into inner deflation zone 555, through opening 565, through deflation port 540, into bulb 310, back out of bulb 310 into inflation port 535, through opening 570 in outer inflation zone 560, into outer inflation zone 560, and through outer hole 605 of middle plate 510 and into atmosphere. It should be appreciated that as this occurs, aft balloon inflation port 660, aft balloon deflation port 665 and fore balloon inflation port 670 are all fluidically sealed against top surface 590 of middle plate 510 so that air cannot enter or leave ports 660, 665, 670, and hence, when manifold 500 is in State 4, deflation of fore balloon 35 does not have any effect on aft balloon 20.

5. Fore Balloon And Aft Balloon Sealed Against Inflation/Deflation. When middle plate 510 is disposed in State 5 discussed above (i.e., when middle plate 510 is rotated such that inner hole 600 and outer hole 605 are both open to atmosphere), aft balloon inflation port 660, aft balloon deflation port 665, fore balloon inflation port 670 and fore balloon deflation port 675 are all sealed against top surface 590 of middle plate 510. In State 5, squeezing and releasing of bulb 310 has no effect on either fore balloon 35 or aft balloon 20 (inasmuch as air is drawn into inner hole 600 of middle plate 510, enters inner deflation zone 555, passes through opening 565, passes out deflation port 540 and into bulb 310, and is then passed from bulb 310, into inflation port 535, through opening 570 and into outer inflation zone 560, and then out through outer hole 605 to atmosphere).

Alternative Novel Manifold

It should be appreciated that other manifolds may be utilized in inflation mechanism 40 in place of the novel manifold 500 discussed above.

Figure 79:
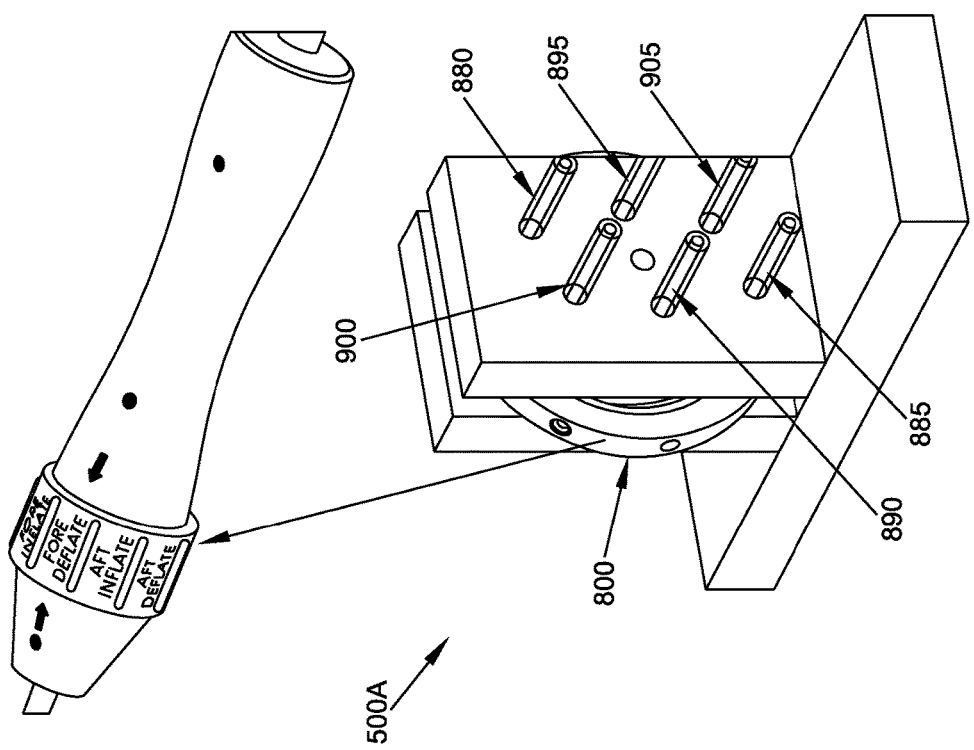

By way of example but not limitation, and looking now at FIG. 79, there is shown another novel manifold 500A for selectively inflating or deflating a selected one of aft balloon 20 and fore balloon 35. Manifold 500A serves the same function as manifold 500 discussed above (i.e., manifold 500A selectively controls a plurality of airway paths in order to permit a user to selectively inflate or deflate a selected one of aft balloon 20 and fore balloon 35 using a single user interface), however, manifold 500A employs a somewhat different construction than manifold 500.

Figure 80:
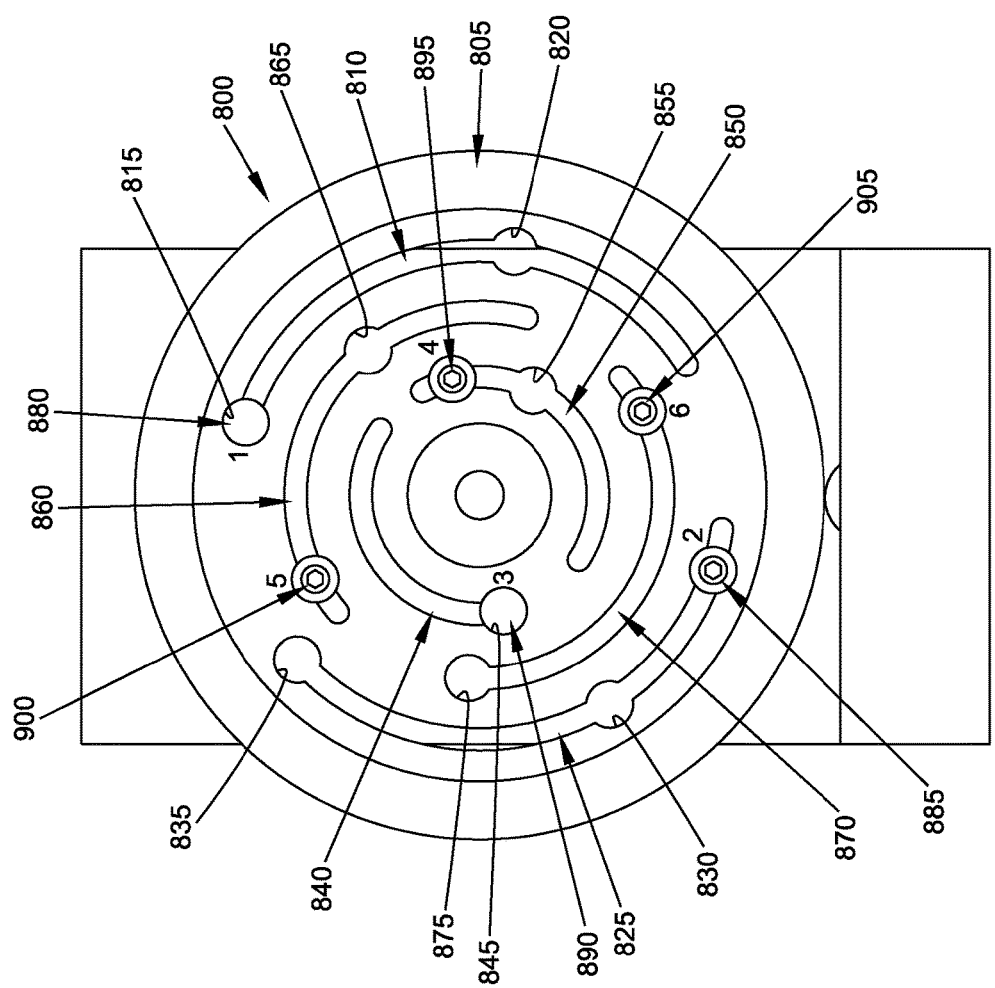

Looking now at FIG. 80, manifold 500A generally comprises a rotatable control dial and a plurality of tubes (labelled 1-6 in FIG. 80), with the control dial being configured to selectively close-off one or more of the plurality of tubes and to selectively open one or more of the plurality of tubes as the rotatable control dial is rotated. More particularly, and still looking at FIG. 80, there is shown a rotatable control dial 800 comprising a body 805. Body 805 comprises a first groove 810 having a first cutout section 815 and a second cutout section 820, a second groove 825 having a first cutout section 830 and a second cutout section 835, a third groove 840 having a cutout section 845, a fourth groove 850 having a cutout section 855, a fifth groove 860 having a cutout section 865 and a sixth groove 870 having a cutout section 875.

The plurality of tubes discussed above are fixed in place relative to rotatable control dial 800 and each of the plurality of tubes passes through one of first groove 810, second groove 825, third groove 840, fourth groove 850, fifth groove 860 and sixth groove 870. More particularly, a first tube 880 in fluid connection with bulb 310 and atmosphere passes through first groove 810, a second tube 885 in fluid connection with bulb 310 and atmosphere passes through second groove 825, a third tube 890 in fluid connection with aft balloon 20 and bulb 310 passes through third groove 840, a fourth tube 895 in fluid connection with aft balloon 20 and bulb 310 passes through fourth groove 850, a fifth tube 900 in fluid connection with fore balloon 35 and bulb 310 passes through fifth groove 860, and a sixth tube 905 in fluid connection with fore balloon 35 and bulb 310 passes through sixth groove 870.

First groove 810, second groove 825, third groove 840, fourth groove 850, fifth groove 860 and sixth groove 870 are sized such that first tube 880, second tube 885, third tube 890, fourth tube 895, fifth tube 900 and sixth tube 905 are "pinched off" such that air cannot flow throw the tube whenever the tube is disposed in a section of its respective groove 810, 825, 840, 860, 870 which is not a cutout section. As a result, air can only flow through a given tube 880, 885, 890, 895, 900, 905 when the tube is disposed in a cutout section formed in the groove that the tube is disposed in.

Figure 81:
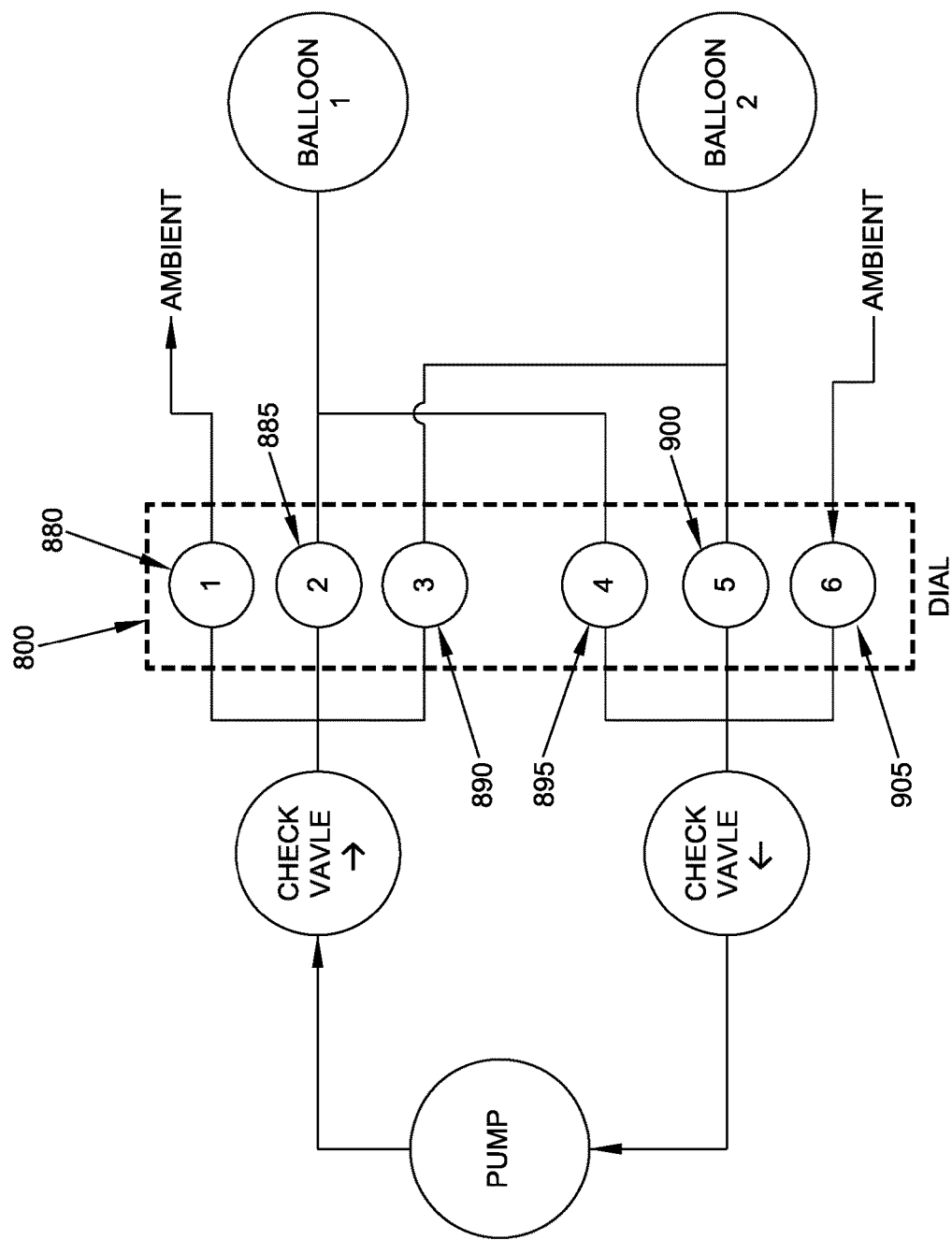

More particularly, first tube 880 only permits passage of air through the tube when it is disposed in either cutout section 815 or cutout section 820 of first groove 810, second tube 885 only permits passage of air through the tube when it is disposed in either cutout section 830 or cutout section 835, third tube 890 only permits passage of air through the tube when it is disposed in cutout section 845, etc. Since tubes 880, 885, 890, 895, 900 and 905 are fixed in location relative to control dial 800, when control dial 800 is selectively rotated by a user, cutout sections 815, 820, 830, 835, 845, 855, 865 and 875 move relative to tubes 880, 885, 890, 895, 900 and 905. By controlling where the cutout sections 815, 820, 830, 835, 845, 855, 865 and 875 are formed in body 805 of control dial 800, it is possible to control which of the tubes 880, 885, 890, 895, 900 and 905 will be "pinched off" and which will reside in a cutout section 815, 820, 830, 835, 845, 855, 865 and 875 when control dial 800 is rotated to a given position. Thus it is possible to control the flow of air to and from bulb 310, and to simultaneously control the flow of air to and from a selected one of aft balloon 20 and fore balloon 35, by selectively moving control dial 800 to a specific position. Further details regarding the flow of air through manifold 500A are provided in FIGS. 81 and 82.

Venting of Balloons through Packaging Design

Figure 83:
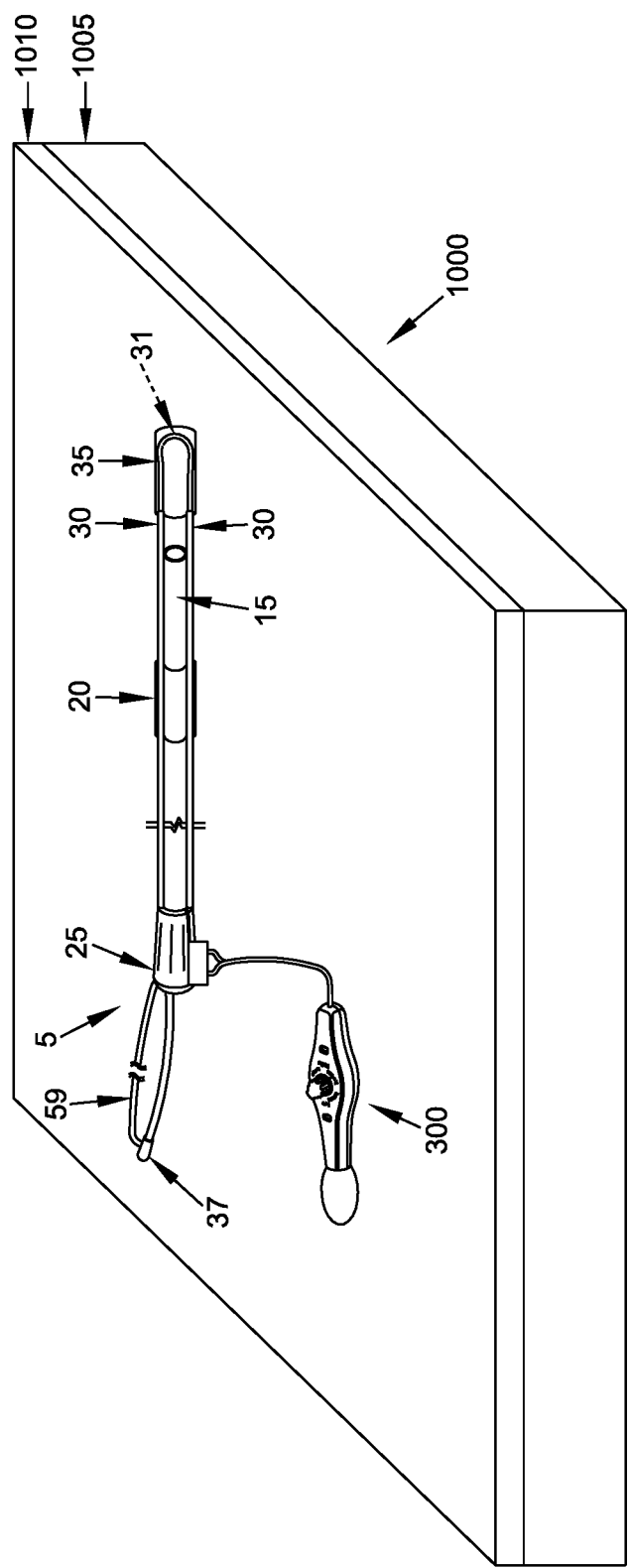
FIG. 83 is a schematic view showing the novel apparatus of the present invention sealed within a novel package formed in accordance with the present invention.

In one preferred form of the present invention, and looking now at FIG. 83, novel apparatus 5 is sealed within a sterile package 1000 until novel apparatus 5 is to be used. Package 1000 is typically provided in the form of a bottom tray 1005 which is sized to hold novel apparatus 5, and a cover 1010 for mating to, and sealing off, bottom tray 1005. Fore balloon 35 and aft balloon 20 are in their deflated condition when novel apparatus 5 is sealed within sterile package 1000.

While fore balloon 35 and aft balloon 20 are stored within package 1000 in their deflated condition, it has been found that it is sometimes possible for a small amount of residual air to remain within fore balloon 35 and/or aft balloon 20 and/or the various fluid pathways leading to fore balloon 35 and/or aft balloon 20 (e.g., hollow push tubes 30, push tube bridge 31, proximal inflation/deflation tube 45, etc.). As a result, when novel apparatus 5 (sealed within package 1000) is thereafter shipped to a recipient via a means of transportation where package 1000 is exposed to a substantial change in air pressure (e.g., when novel apparatus 5 is shipped to a recipient via an airplane), the change in air pressure can cause the residual air remaining within fore balloon 35 and/or aft balloon 20 (and/or the various fluid pathways leading to fore balloon 35 and/or aft balloon 20)

to expand. Such expansion while novel apparatus 5 is sealed within package 1000 can cause damage to fore balloon 35, aft balloon 20 and/or other components of novel apparatus 5.

One possible solution to the foregoing problem is to fully evacuate all of the air from fore balloon 35, aft balloon 20 and all of the pathways, leading to fore balloon 35 and aft balloon 20 before novel apparatus 5 is sealed within package 1000. However, it has been found that it can be challenging to evacuate all of the air from fore balloon 35, aft balloon 20 and the pathways leading to fore balloon 35 and aft balloon 20. In addition, it has also been found that it can be challenging to ensure that no air is thereafter able to leak back into any of the evacuated components of novel apparatus 5.

Another possible solution is to allow the air within the interior of package 1000 to freely enter and exit the components of novel apparatus 5, e.g., by leaving one or both of fittings 46, 56 open to airflow, etc. However, with such an "open valve" configuration, the recipient (e.g., the surgeon) would need to be diligent in closing any open valves prior to using novel apparatus 5. It is possible that a recipient may inadvertently leave a valve open that should be closed prior to using novel apparatus 5, thereby causing malfunction of novel apparatus 5.

Thus there is a need for a new and improved way to maintain a free exchange of air between the interior of package 1000 and fore balloon 35 and aft balloon 20, while automatically sealing off that free exchange of air when the user removes novel apparatus 5 from package 1000.

Figure 84:
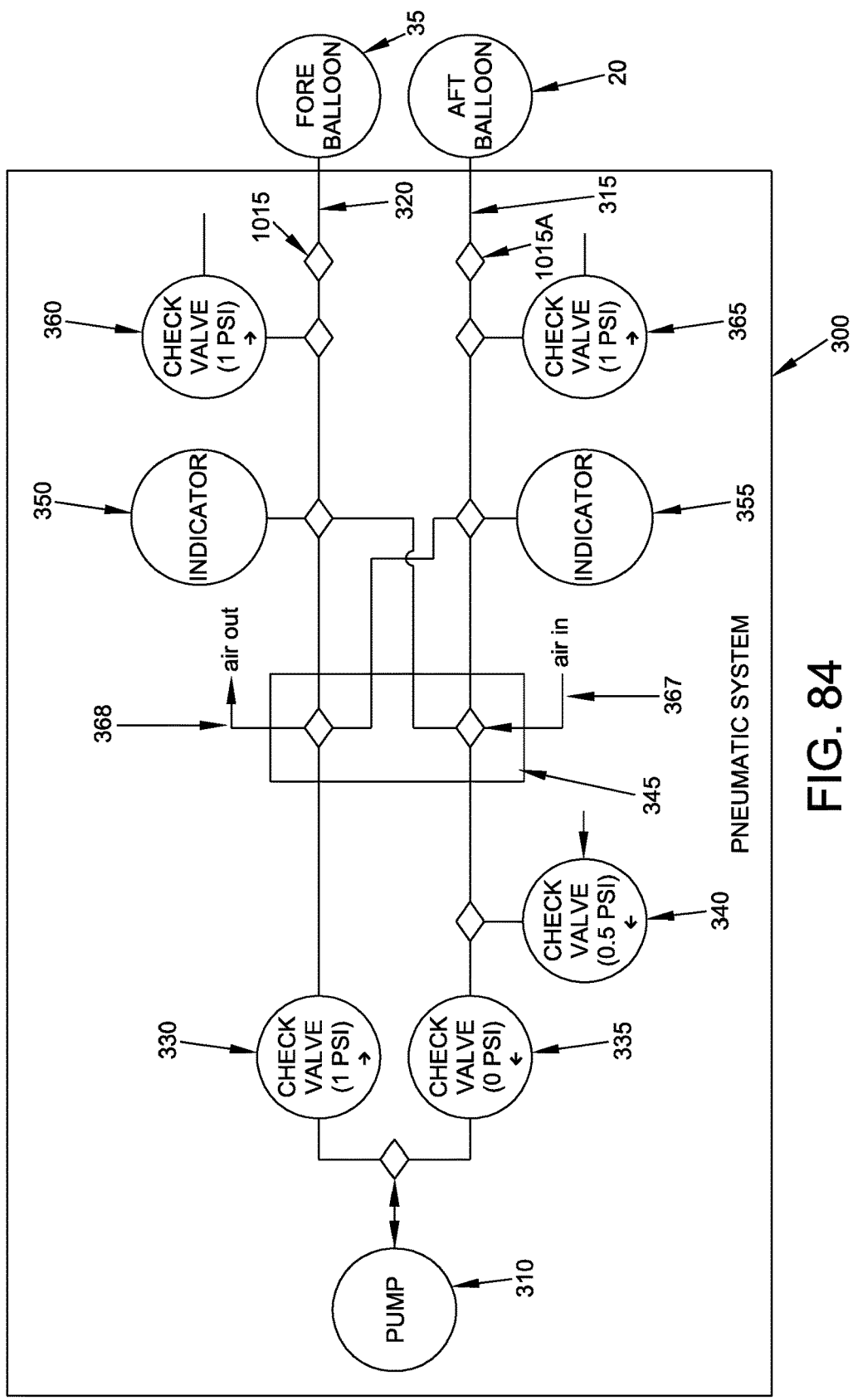
FIG. 84 is a schematic view showing details of a novel inflation mechanism formed in accordance with the present invention.
Figure 85:
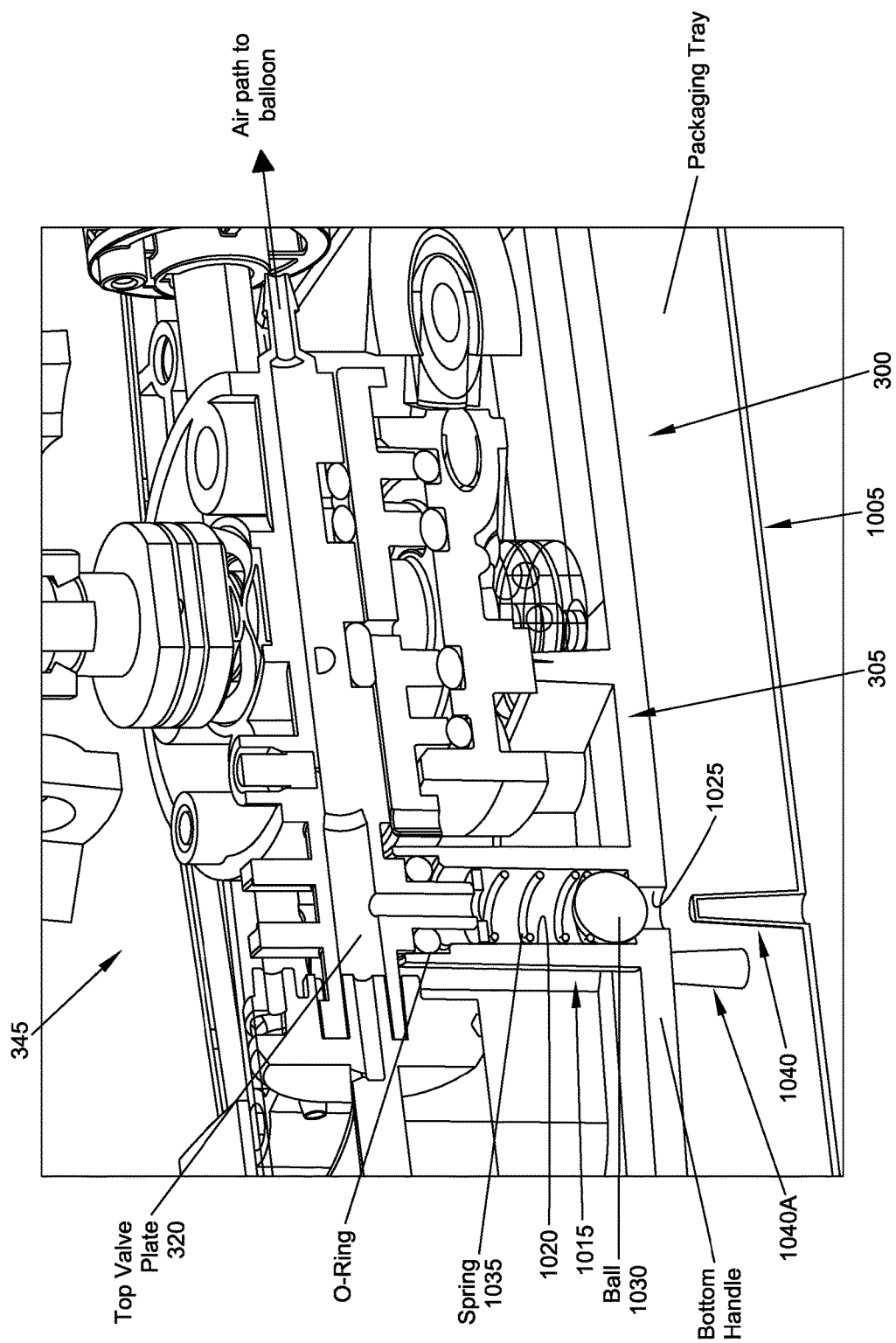
FIG. 85-88 are schematic views showing further details of the novel package of FIG. 83 and further details of the novel inflation mechanism of FIG. 84.
Figure 86:
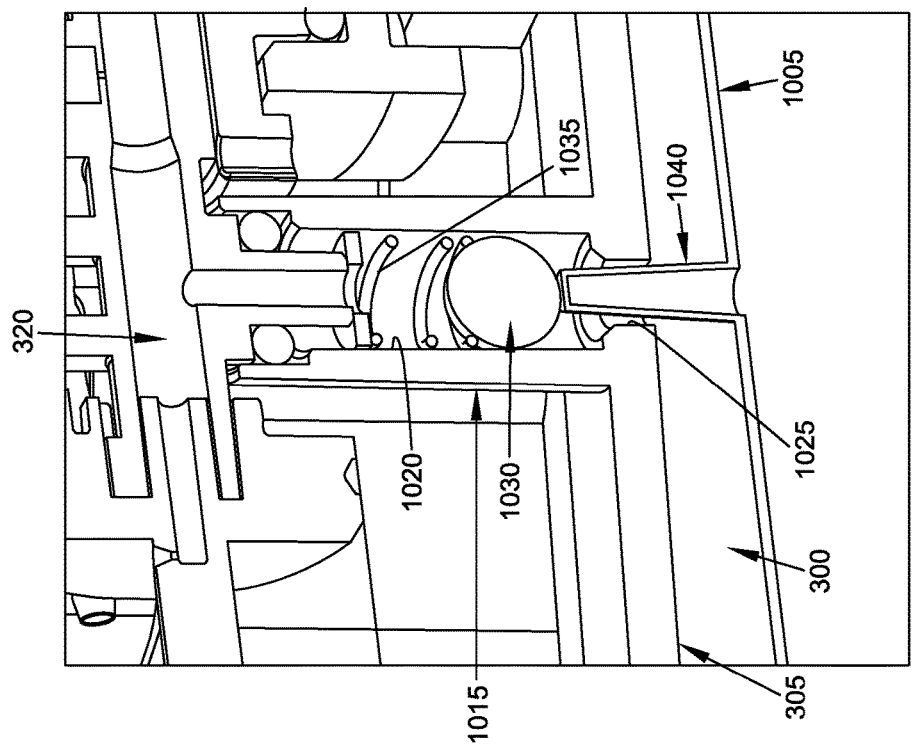

To this end, and looking now at FIG. 84, a fore balloon venting check valve 1015 and an aft balloon venting check valve 1015A are provided in hand inflator 300, with fore balloon venting check valve 1015 being disposed in fore balloon inflation line 320 and with aft balloon venting check valve 1015A being disposed in aft balloon inflation line 315. For clarity of illustration, only fore balloon venting check valve 1015 is shown in FIGS. 85-88 and discussed in detail hereinbelow, however, it should be appreciated that aft balloon venting check valve 1015A is identical in construction and function to fore balloon venting check valve 1015 (although aft balloon venting check valve 1015A is disposed in aft balloon inflation line 315 rather than in fore balloon inflation line 320).

Looking now at FIGS. 85-88, fore balloon venting check valve 1015 and aft balloon venting check valve 1015A are disposed in the bottom surface of housing 305 of hand inflator 300, such that they are in fluid communication with fore balloon inflation line 320 and aft balloon inflation line 315, respectively, and hence in fluid communication with fore balloon 35 and aft balloon 20, respectively. More particularly, fore balloon venting check valve 1015 comprises a lumen 1020 having a first end in fluid communication with fore balloon inflation line 320 and a second end having an opening 1025 formed in the outer surface of housing 305. A ball (e.g., a rubber ball) 1030 is movably disposed within lumen 1020 and is biased against opening 1025 by a spring 1035. When ball 1030 is biased against opening 1025, air cannot pass through opening 1025 and into (or out of) fore balloon inflation line 320, i.e., fore balloon 35 is sealed off against the free passage of air into (or out of) fore balloon 35.

Figure 87:
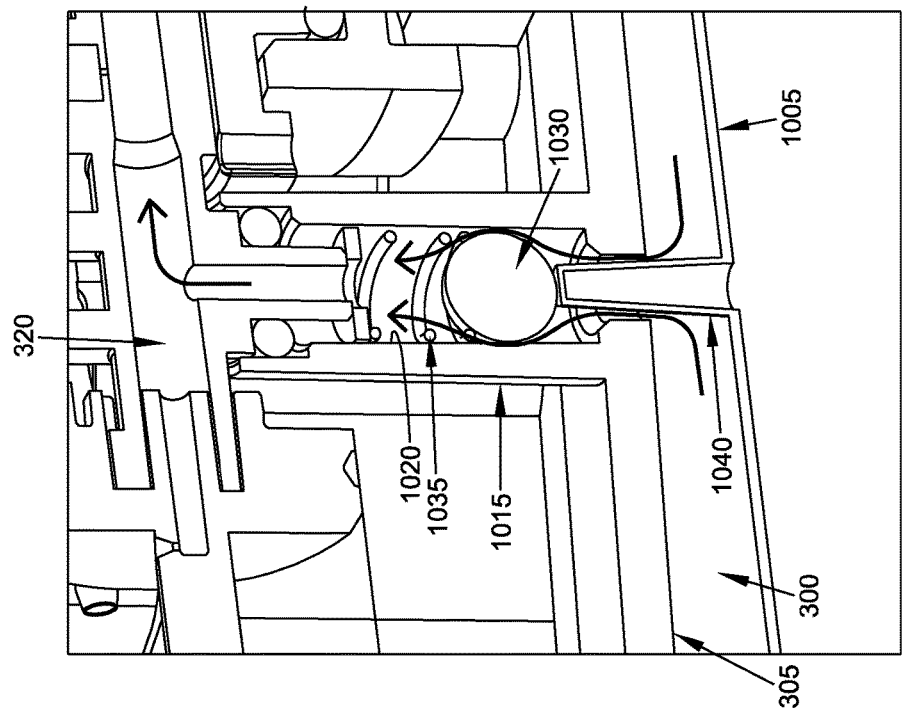
Figure 88:
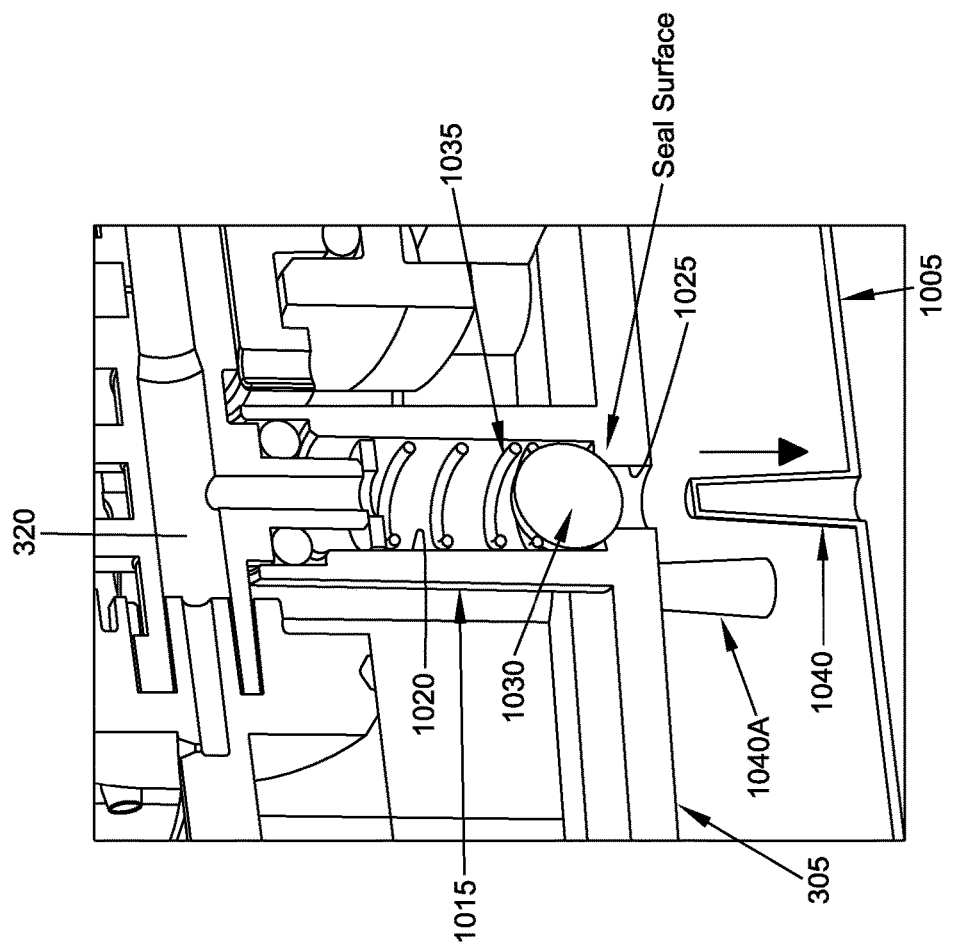

Bottom tray 505 comprises an upwardly-extending finger 1040 which is sized and positioned such that finger 1040 is received within opening 1025 of housing 305 when novel apparatus 5 (and, more specifically, hand inflator 300) is disposed within bottom tray 1005 of package 1000. Finger 1040 is sized such that when it is received within opening 1025, a finger 1040 engages ball 1030 and drives ball 1030 against the power of spring 1035, whereby to unseat ball 1030 from opening 1025. At the same time, a gap remains between finger 1040 and the sides of opening 1025, whereby to allow air to pass from the interior of package 1000 through fore balloon venting check valve 1015, through fore balloon inflation line 320 and into fore balloon 35, and vice versa (FIG. 87).

Bottom tray 1005 comprises a similar finger 1040A for forcing check valve 1015A open when hand inflator 300 is seated in bottom tray 1005 of package 1000.

If desired, an upwardly-extending stop (not shown) may also be provided on bottom tray 1005 of package 1000 for engaging the bottom surface of housing 305 of hand inflator 300 when hand inflator 300 is disposed within bottom tray 1005 of package 1000, whereby to ensure that an air gap is maintained between the bottom surface of hand inflator 300 and the bottom surface of bottom tray 1005, and hence ensure that air is free to flow through check valves 1015, 1015A when hand inflator 300 is seated in bottom tray 1005 of package 1000.

As a result of this construction, when novel apparatus 5 is disposed in bottom tray 1005, fingers 1040, 1040A open fore balloon venting check valve 1015 and aft balloon venting check valve 1015A, respectively, so that air is permitted to freely enter into, and exit out of, fore balloon 35 and aft balloon 20 via fore balloon venting check valve 1015 and aft balloon venting check valve 1015A, respectively. This eliminates the aforementioned problems associated with exposing package 1000 to substantial changes in air pressure (e.g., during shipping) and prevents damage to apparatus 5 during shipping.

When apparatus 5 is to be used, cover 1010 is removed from package 1000 and novel apparatus 5 is removed from bottom tray 1005. When this occurs, fingers 1040, 1040A are withdrawn from fore balloon venting check valve 1015 and aft balloon venting check valve 1015A, respectively, thereby allowing these check valves to return to their "closed" positions.

Thus it will be seen that fore balloon venting check valve 1015 and aft balloon venting check valve 1015A act to protect novel apparatus 5 from exposure to air pressure differentials during shipping/storage and does so in a passive fashion that does not require the recipient to close any valves.

Preferred Method of Using the Novel Apparatus

Apparatus 5 may be used to manipulate, (e.g., stabilize, straighten, expand and/or flatten, etc.) the side wall of a body lumen and/or body cavity so as to better present the side wall tissue (including visualization of areas which may be initially hidden from view or outside the field of view) for examination and/or treatment during an endoscopic procedure using endoscope 10, and/or to stabilize the distal tips and/or working ends of instruments (e.g., graspers, cutters or dissectors, cauterizing tools, ultrasound probes, etc.), e.g., advanced into the therapeutic zone.

More particularly, in use, sleeve 15 is first mounted to endoscope 10 (FIG. 1). This may be accomplished by pulling base 25 proximally over the distal end of endoscope 10 and then pulling proximally along the length of endoscope 10 until the distal end of sleeve 15 is substantially aligned with the distal tip of endoscope 10. At this point, aft balloon 20 is deflated, fore balloon 35 is deflated, and fore balloon 35 is docked over the distal end of endoscope 10, with endoscope 10 nesting in the area beneath raised push tube bridge 31. Endoscope 10 and apparatus 5 are ready to be inserted as a unit into the patient.

Figure 89:
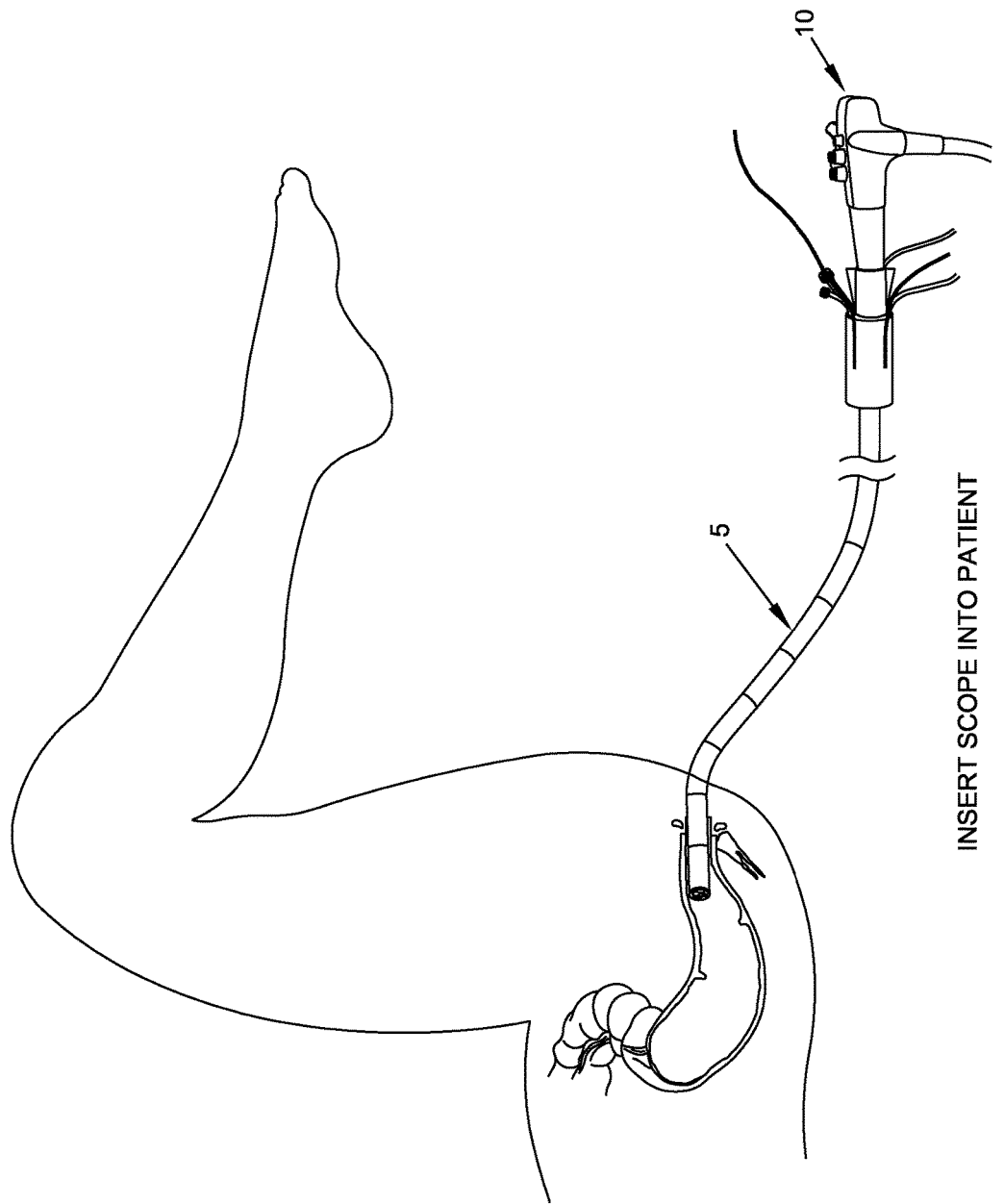
Figure 90:
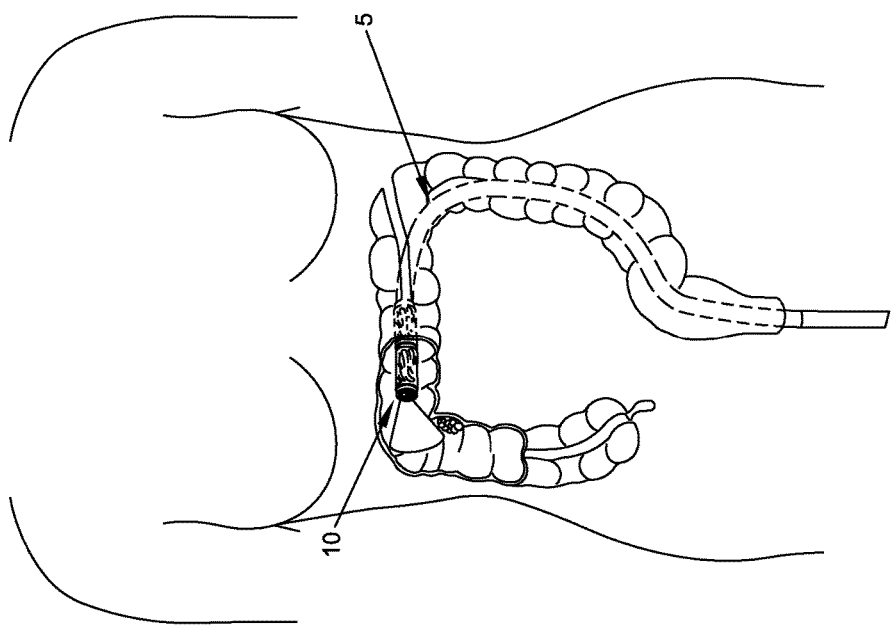
Figure 91:
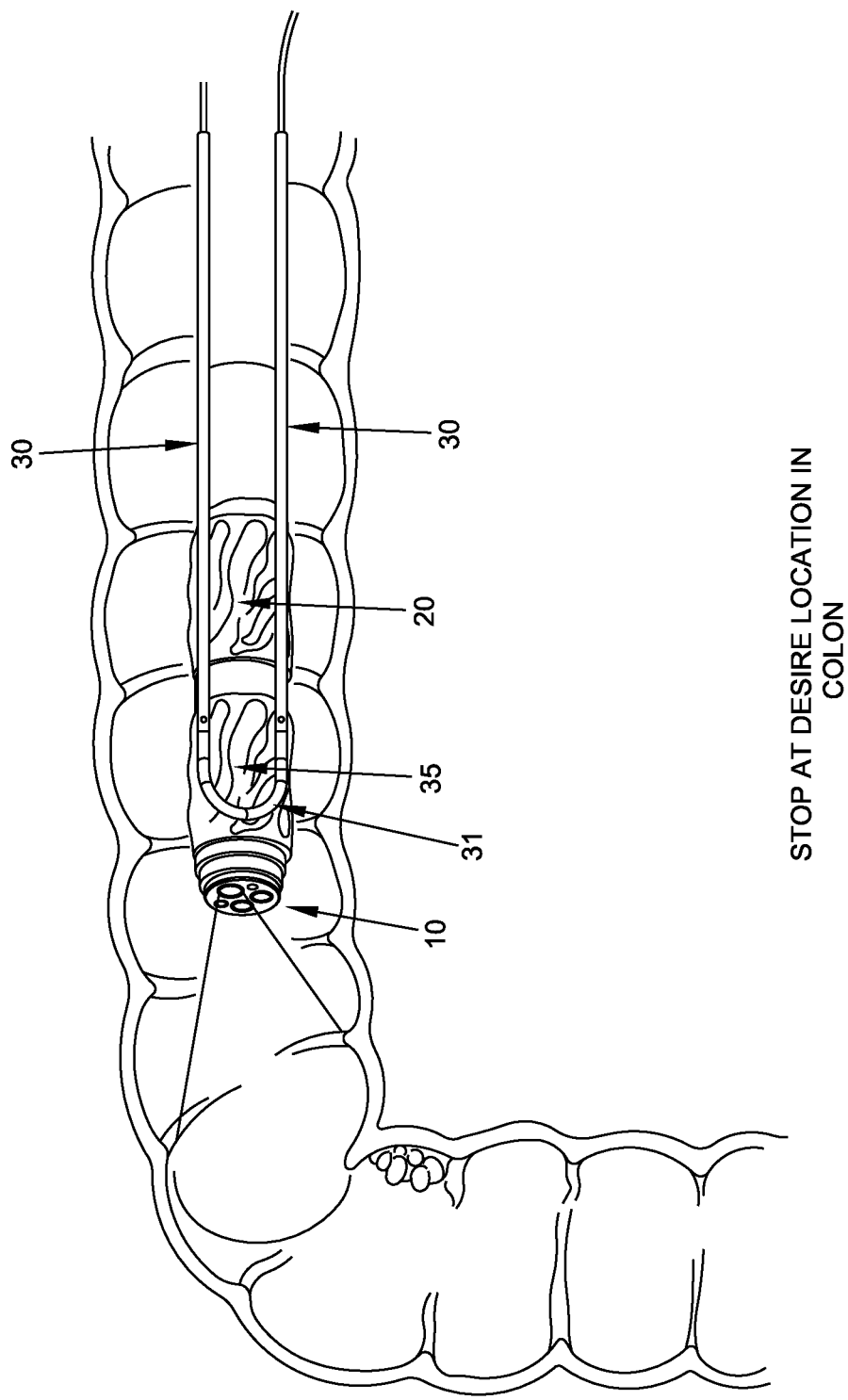

Looking next at FIG. 89, endoscope 10 and apparatus 5 are inserted as a unit into a body lumen and/or body cavity of the patient. By way of example but not limitation, endoscope 10 and apparatus 5 are inserted as a unit into the gastrointestinal (GI) tract of the patient. Endoscope 10 and apparatus 5 are advanced along the body lumen and/or body cavity to a desired location within the patient (FIGS. 90 and 91).

Figure 92:
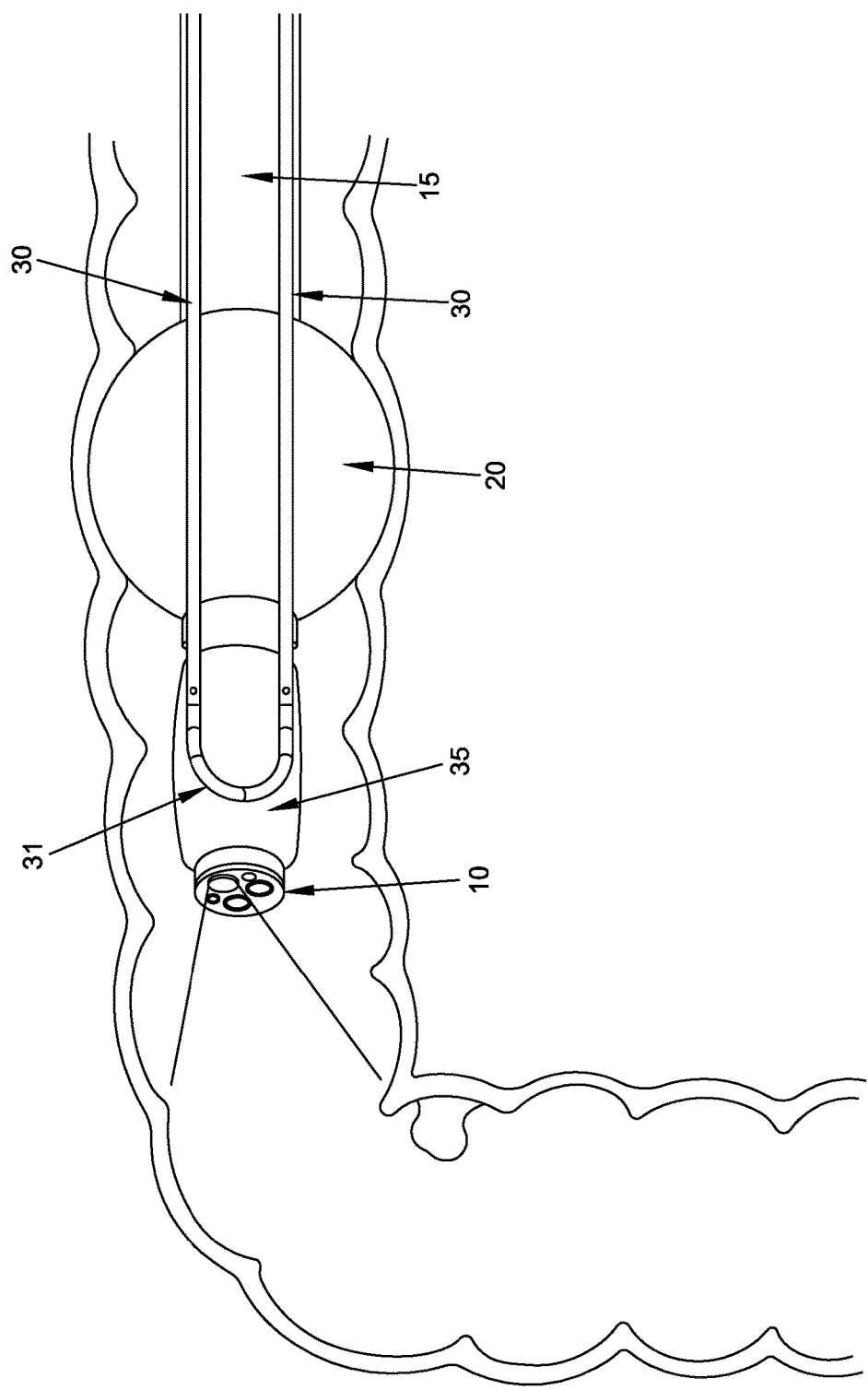

When apparatus 5 is to be used (e.g., to manipulate the side wall of the gastrointestinal tract so as to provide increased visualization of the same and/or increase access to the same, and/or for stabilizing instruments relative to the same), aft balloon 20 is inflated so as to stabilize apparatus 5 (and hence endoscope 10) within the body lumen and/or body cavity. See FIG. 92. This may be done using the aforementioned associated inflation mechanism 40.

In this respect it will be appreciated that inasmuch as the articulating portion of the endoscope resides distal to aft balloon 20, the endoscope will be able to articulate distal to aft balloon 20 so as to facilitate visualization of the anatomy even after aft balloon 20 is inflated. Significantly, such visualization is enhanced, inasmuch as aft balloon 20 stabilizes endoscope 10 within the gastrointestinal tract and distends the colon and increases the colon to a fixed diameter directly adjacent to aft balloon 20.

Next, hollow push tubes 30 are advanced distally in the body lumen and/or body cavity (i.e., so as to move fore balloon 35 further ahead of aft balloon 20) by pushing distally on push tube handle 37. Thus, hollow push tubes 30, and hence fore balloon 35, move distally relative to endoscope 10 (which is stabilized in position within the gastrointestinal tract by the inflated aft balloon 20). Note that raised push tube bridge 31 provides an atraumatic tip for the distal ends of hollow push tubes 30, thereby ensuring atraumatic advancement of fore balloon 35. Note that the deflated fore balloon 35 covers the distal ends of hollow push tubes 30 and raised push tube bridge 31 during such distal advancement of fore balloon 35, thereby ensuring atraumatic advancement of fore balloon 35. Note that atraumatic advancement of fore balloon 35 may be further enhanced by forming the distal ends of hollow push tubes 30 and raised push tube bridge 31 out of a more resilient material.

When hollow push tubes 30 have advanced fore balloon 35 to the desired position distal to endoscope 10, fore balloon 35 is inflated (FIG. 93) so as to secure fore balloon 35 to the anatomy. Again, this may be done using the aforementioned associated inflation mechanism 40. As fore balloon 35 is inflated, the inflated fore balloon 35, the inflated aft balloon 20, and hollow push tubes 30 will all complement one another so as to stabilize, straighten, expand and/or flatten the side wall of the body lumen and/or body cavity so as to better present the side wall tissue (including visualization of areas which may be initially hidden from view or outside the field of view) for examination and/or treatment during an endoscopic procedure using endoscope 10. In this respect it will be appreciated that the inflated fore balloon 35 and the inflated aft balloon 20 will together expand and tension the side wall of the body lumen and/or body cavity, and hollow push tubes 30 will tend to straighten the anatomy between the two inflated balloons when the fore balloon is extended distally from the aft balloon. In this respect it will also be appreciated that once aft balloon 20 and fore balloon 35 have both been inflated, fore balloon 35 will create a substantially full-diameter seal across the body lumen and/or body cavity (because the inflated fore balloon closes down the axial opening 63 extending through the fore balloon when the fore balloon is in its deflated state), and aft balloon 20 will cooperate with sleeve 15 and endoscope 10 to create another substantially full-diameter barrier across the body lumen and/or body cavity. Thus, the inflated fore balloon 35 and the inflated aft balloon 20 will together define a substantially closed region along the body lumen and/or body cavity (i.e., an isolated therapeutic zone which prevents the passage of fluid and/or other liquids by virtue of the air-tight seals established by the inflated fore balloon 35 and aft balloon 20). The side wall of the body lumen and/or body cavity will be tensioned by inflation of fore balloon 35 and aft balloon 20, whereby to better present the side wall of the body lumen and/or body cavity for viewing through endoscope 10.

It should be appreciated that the expansion and tensioning of the side wall of the body lumen and/or body cavity effected by the inflated fore balloon 35, the inflated aft balloon 20, and hollow push tubes 30, can be further enhanced by advancing the fore balloon when it is inflated and gripping the side wall of the body lumen and/or body cavity, whereby to further tension the side wall of the body lumen and/or body cavity.

Significantly, inasmuch as the inflated fore balloon 35 and the inflated aft balloon 20 together define a substantially closed region along the body lumen and/or body cavity (i.e., an isolated therapeutic zone), this region can then be inflated (FIG. 24) with a fluid (e.g., air, $CO_2$, etc.) so as to further tension the side wall of the body lumen and/or body cavity, whereby to better present the side wall of the body lumen and/or body cavity for viewing through endoscope 10 and stabilize the side wall so as to facilitate more precise therapeutic interventions.

If desired, fore balloon 35 can be retracted toward aft balloon 20 (i.e., by pulling push tube handle 37 proximally), while remaining inflated (and hence maintaining a grip on the side wall of the body lumen and/or body cavity), so as to move the visible mucosa and further improve visualization and access (see FIG. 95), e.g., so as to position a particular target area on the side wall of the body lumen and/or body cavity at a convenient angle relative to the endoscope and endoscopic tools.

Alternatively, if desired, once aft balloon 35 has been inflated, hollow push tubes 30 may be advanced distally a portion—but only a portion—of their full distal stroke, then fore balloon 35 may be inflated so as to grip the side wall of the body lumen and/or body cavity, and then hollow push tubes 30 may be further advanced distally. This action will cause flexible hollow push tubes 30 to bow outwardly (see FIGS. 96-99), contacting the side wall of the body lumen and/or body cavity and pushing the side wall of the body lumen and/or body cavity outwardly, e.g., in a "tenting" fashion, whereby to further enhance visualization of the side wall of the body lumen and/or body cavity by endoscope 10.

If desired, instruments 190 (FIG. 100) may be advanced through working channels of endoscope 10 so as to biopsy and/or treat pathologic conditions (e.g., excise pathological anatomy). It will be appreciated that such instruments will extend through the distal end of the endoscope, which is effectively stabilized relative to the anatomy via aft balloon 20, so that the working ends of instruments 190 will also be highly stabilized relative to the anatomy. This is a significant advantage over the prior art practice of advancing instruments out of the non-stabilized end of an endo scope.

Preferably instruments 190 include articulating instruments having a full range of motion, whereby to better access target anatomy.

Figure 101:
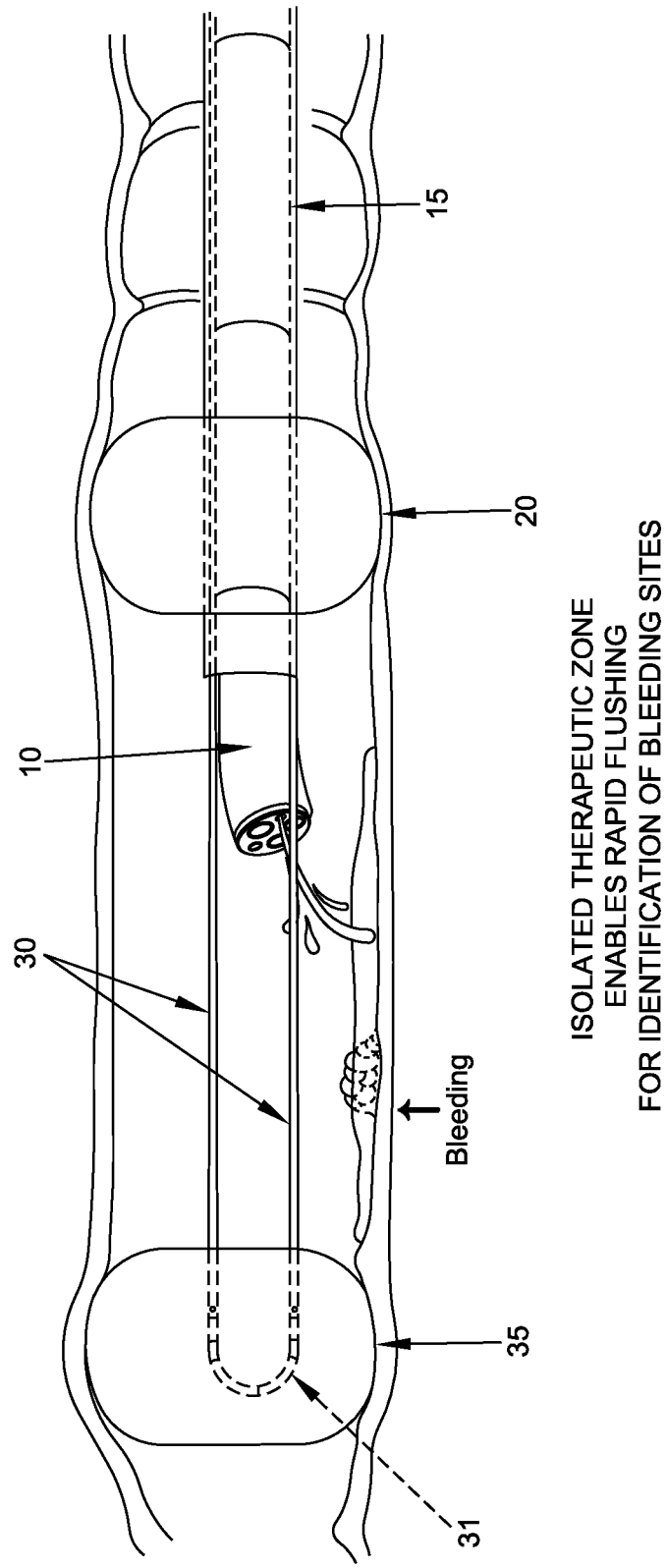
Figure 102:
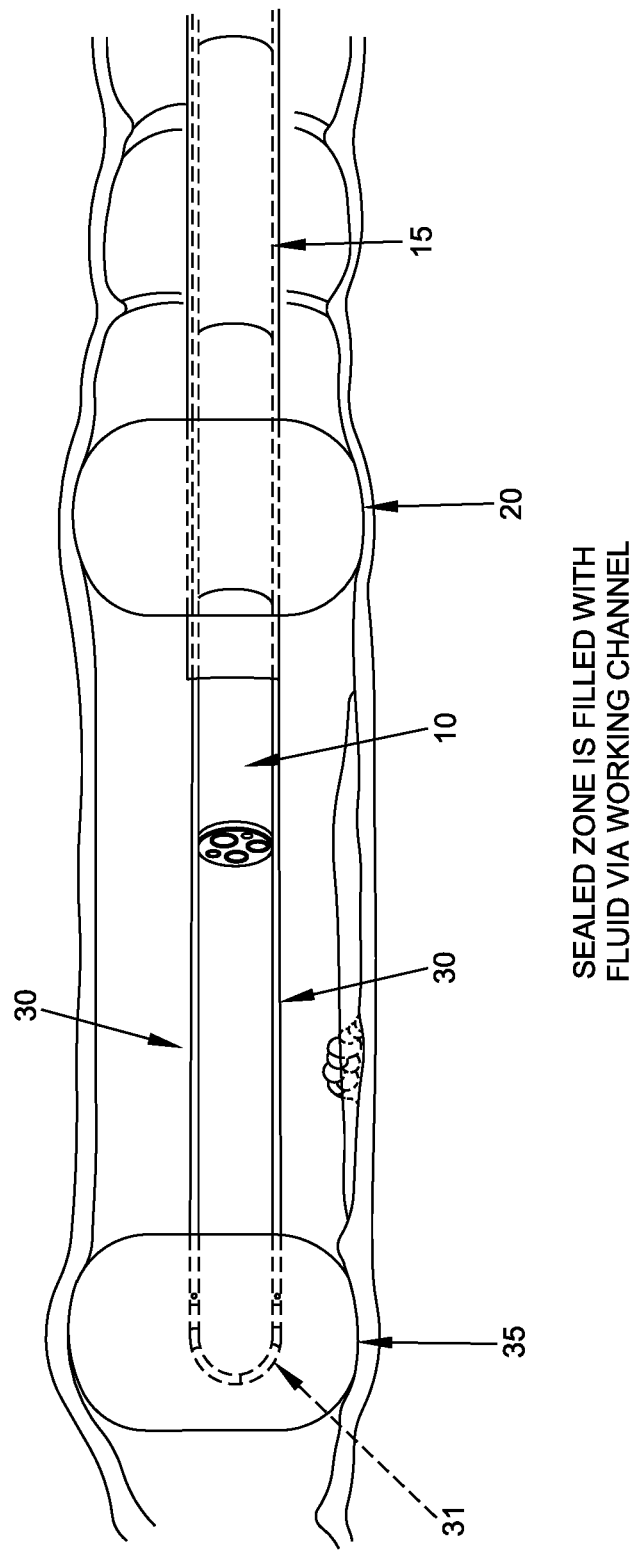
Figure 103:
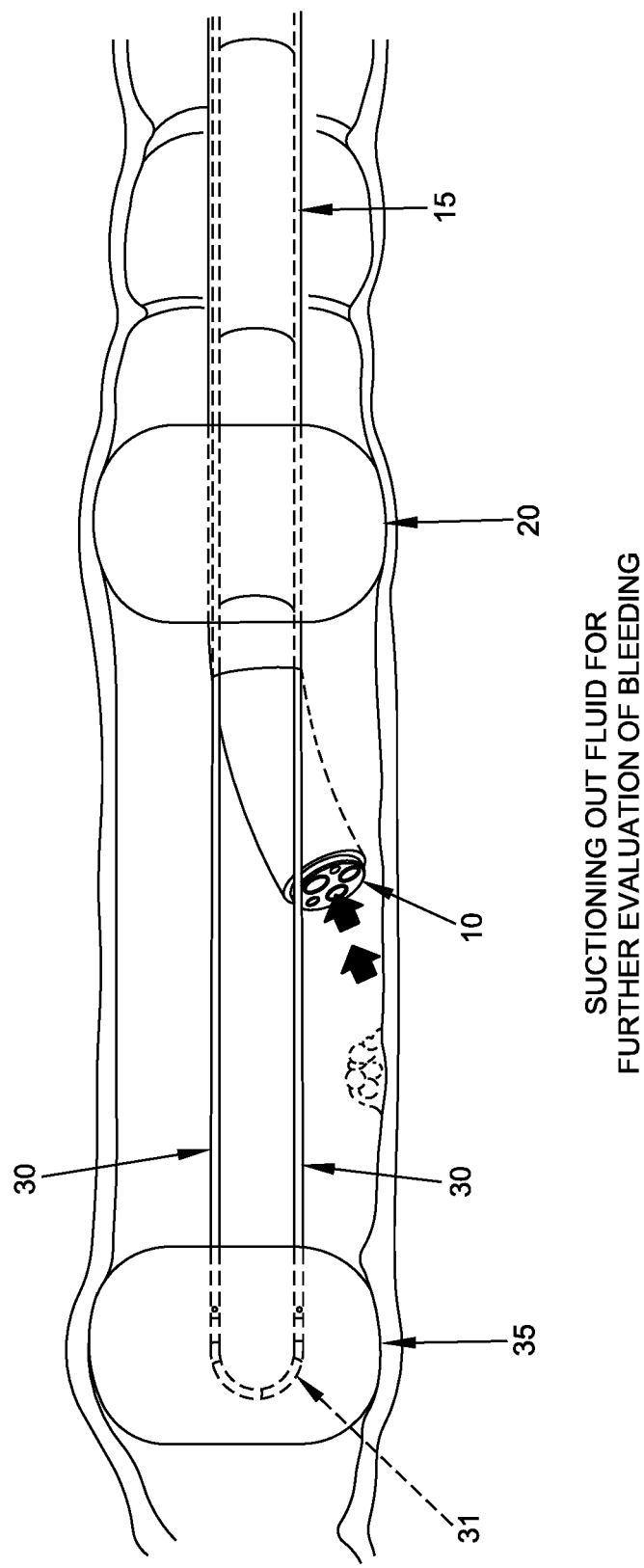

Furthermore, if bleeding were to obscure a tissue site, or if bleeding were to occur and the surgeon is unable to identify the source of the bleeding, the isolated therapeutic zone permits rapid flushing of the anatomic segment in which the therapeutic zone lies (e.g., with a liquid such as saline) with rapid subsequent removal of the flushing liquid (see FIGS. 101-103).

Figure 104:
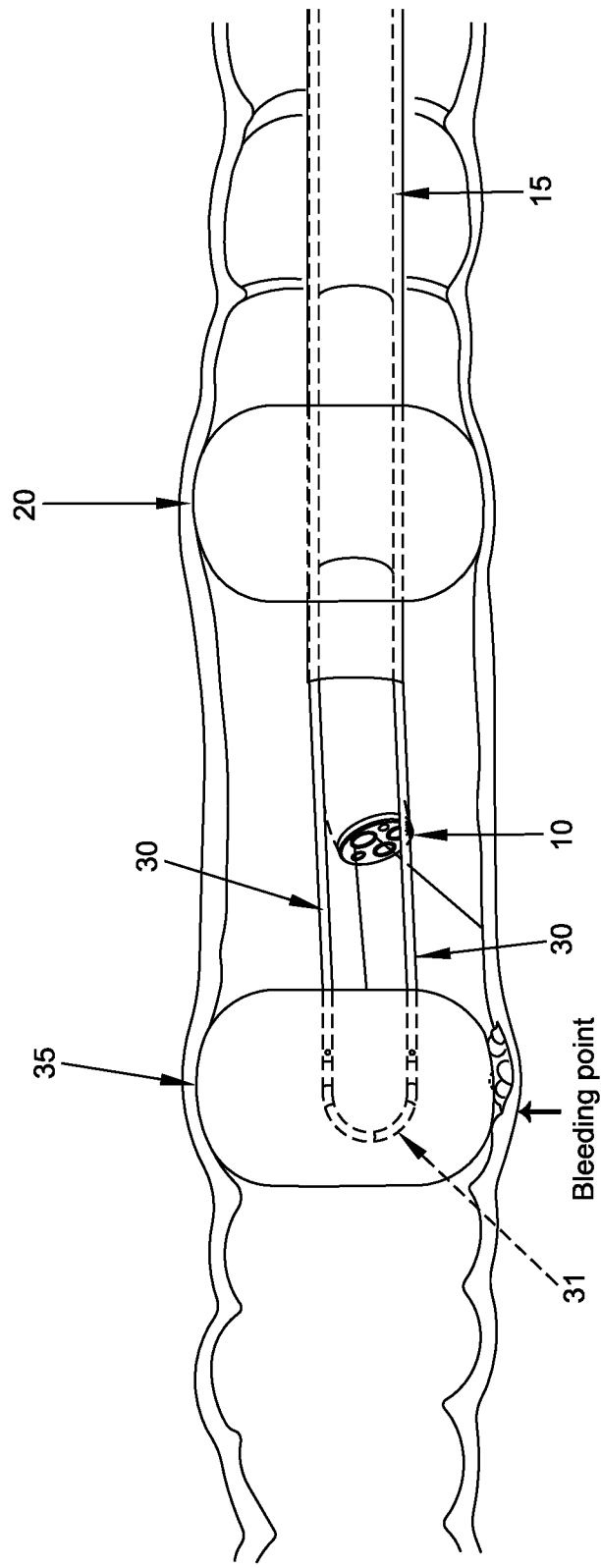

Also, if desired, fore balloon 35 can be directed with high precision to a bleeding site, whereupon fore balloon 35 may be used (e.g., inflated) to apply local pressure to the bleeding site in order to enhance bleeding control (see FIG. 104). This can be done under the visualization provided by endoscope 10.

If it is desired to reposition endoscope 10 within the anatomy with minimal interference from apparatus 5, fore balloon 35 is returned to its torus configuration (i.e., partially deflated), the fore balloon is retracted proximally and "re-docked" on the distal end of endoscope 10 (with endoscope 10 nesting in the area beneath raised push tube bridge 31), aft balloon 20 is deflated, and then endoscope 10 (with apparatus 5 carried thereon) is repositioned within the anatomy. Note that where fore balloon 35 is to be re-docked on the distal end of endoscope 10, fore balloon 35 is preferably only partially deflated until fore balloon 35 is re-docked on the distal end of the endoscope, since partial inflation of fore balloon 35 can leave fore balloon 35 with enough "body" to facilitate the re-docking process. Thereafter, fore balloon 35 may be fully deflated if desired, e.g., so as to positively grip the distal end of endoscope 10.

Figure 105:
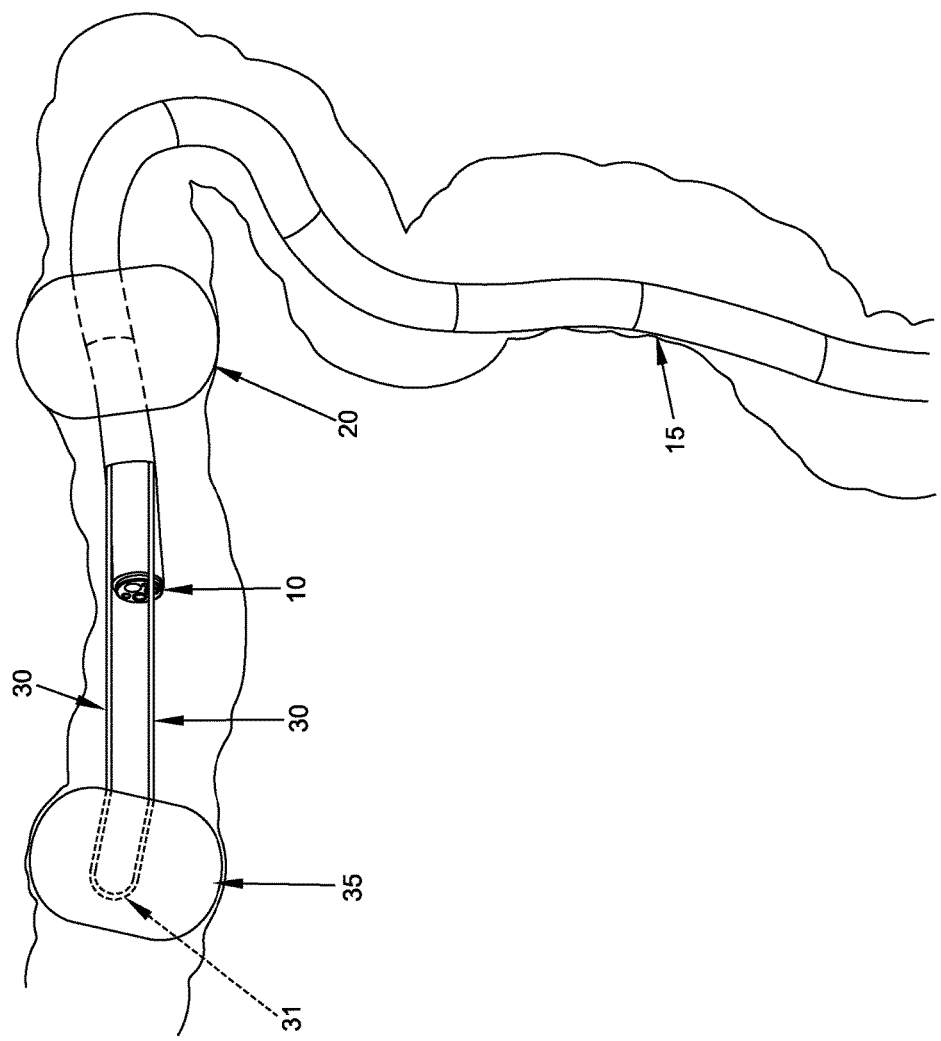
Figure 106:
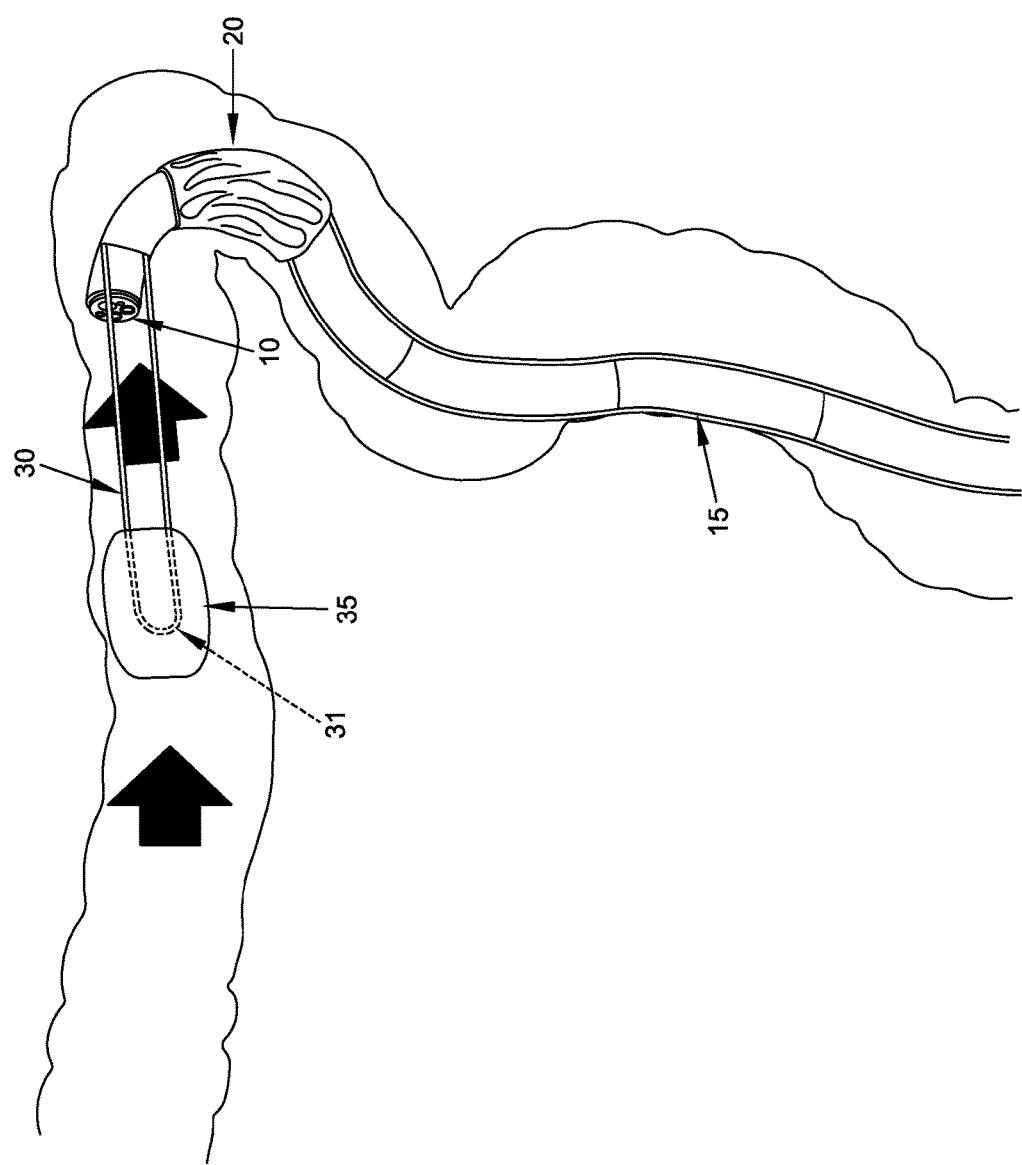
Figure 107:
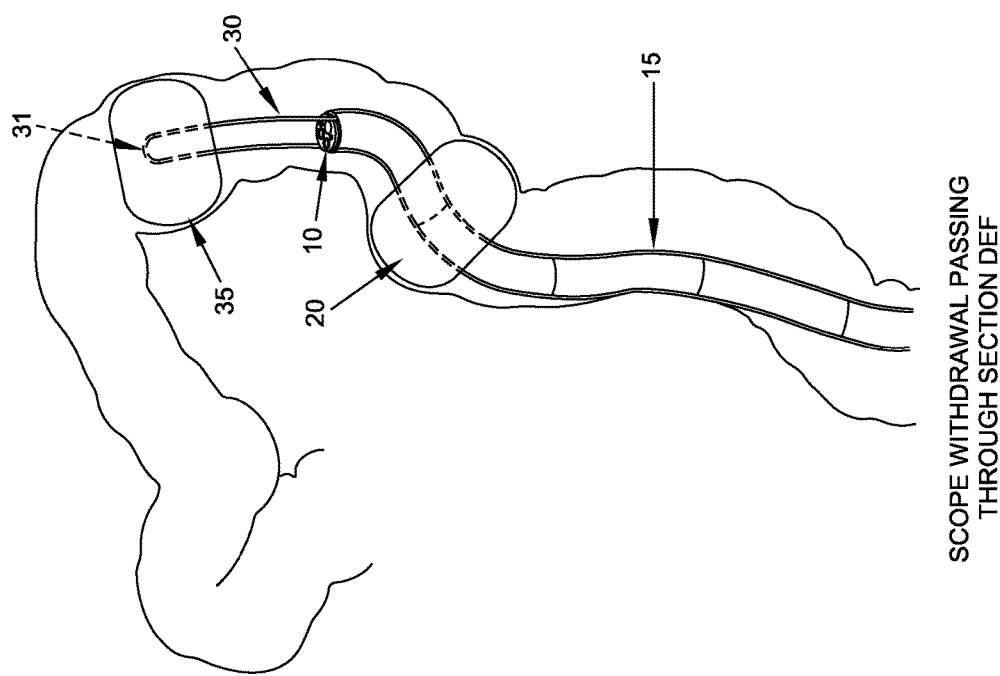

Alternatively, if desired, fore balloon 35 may be used as a drag brake to control retrograde motion of the endoscope. More particularly, in this form of the invention, endoscope 10 and apparatus 5 are first advanced as a unit into the body lumen and/or body cavity until the tip of the endo scope is at the proper location. Next, aft balloon 20 is inflated, hollow push tubes 30 are advanced distally, and then fore balloon 35 is inflated (FIG. 105). Visualization and, optionally, therapeutic treatment may then be effected at that location. When the apparatus is to be moved retrograde, aft balloon 20 is deflated, fore balloon 35 is partially deflated, and then the endoscope is withdrawn proximally, dragging the semi-inflated fore balloon 35 along the body lumen and/or body cavity (FIG. 106), with fore balloon 35 acting as something of a brake as the endoscope is pulled proximally, thereby enabling more controlled retrograde movement of the endoscope and hence better visualization of the anatomy. If at some point it is desired, aft balloon 20 and fore balloon 35 can be re-inflated, as shown in FIG. 107, with or without introduction of a fluid into the "isolated therapeutic zone" established between the two balloons, so as to stabilize, straighten, expand and/or flatten the anatomy.

It is also possible to use aft balloon 20 as a brake when withdrawing the endoscope (and hence apparatus 5) from the anatomy, either alone or in combination with the aforementioned braking action from fore balloon 35.

At the conclusion of the procedure, endoscope 10 and apparatus 5 are withdrawn from the anatomy. Preferably this is done by deflating (or partially deflating) fore balloon 35, retracting hollow push tubes 30 so that fore balloon 35 is "re-docked" onto the distal end of endoscope 10 (with endoscope 10 nesting in the area beneath raised push tube bridge 31), fully deflating fore balloon 35 so that it grips the distal end of the endoscope, deflating aft balloon 20 (if it is not yet deflated), and then withdrawing endoscope 10 and apparatus 5 as a unit from the anatomy.

It should be appreciated that apparatus 5 may also be used advantageously in various ways other than those disclosed above. By way of example but not limitation, when endoscope 10 (and apparatus 5) is to be advanced within the colon, it may be desirable to first project fore balloon 35 distally under visual guidance of the endoscope so that fore balloon 35 leads the distal end of the endoscope. As a result, when the endoscope is advanced distally, with fore balloon 35 being deflated (or partially deflated), the fore balloon and flexible hollow push tubes 30 (and raised push tube bridge 31) may act as an atraumatic lead (guiding structure) for the endoscope as the endoscope advances through the colon. Significantly, inasmuch as the distal ends of hollow push tubes 30 are preferably highly flexible, as the advancing fore balloon 35 encounters the colon wall (e.g., at a turn of the colon), the flexible hollow push tubes can deflect so that the fore balloon tracks the path of the colon, thereby aiding atraumatic advancement of the endo scope along the colon. It should also be appreciated that apparatus 5 may also be used advantageously in other ways to facilitate further examinations of the luminal surface otherwise difficult to be performed currently. Such an example is endoscopic ultrasound examination of the lumen which would be facilitated by the fluid-filled inflated fore balloon and ultrasound probe examination.

Improved Aft Balloon Thermal

Bonding Using Insert Material

Aft balloon 20 is bonded to sleeve 15 along at least the distal edge of aft balloon 20 and the proximal edge of aft balloon 20 (i.e., the distal and proximal edges where aft balloon 20 meets sleeve 15), such that an airtight seal is created between aft balloon 20 and sleeve 15. Pushrod lumens 52 and aft balloon inflation lumen 47 are disposed in contact with, and parallel to, sleeve 15, with pushrod lumens 52 passing entirely through aft balloon 20 (i.e., through both the proximal and distal edges of aft balloon 20 where aft balloon 20 meets sleeve 15) and with aft balloon inflation lumen 47 passing through the proximal edge of aft balloon 20 and extending into the interior of aft balloon 20. As a result, aft balloon 20 must be sealingly bonded to sleeve 15 about a series of components (i.e., pushrod lumens 52 and aft balloon inflation lumen 47) which collectively present a non-circular cross-sectional profile at the bonding sites.

In practice, it has been found that it is challenging to effect airtight thermal bonding of aft balloon 20 to sleeve 15, inasmuch as the presence of pushrod lumens 52 and aft balloon inflation lumen 47 create open wedges (or corners) which the material of aft balloon 20 must fill in order to ensure airtight bonding of aft balloon 20 to sleeve 15.

Figure 108:
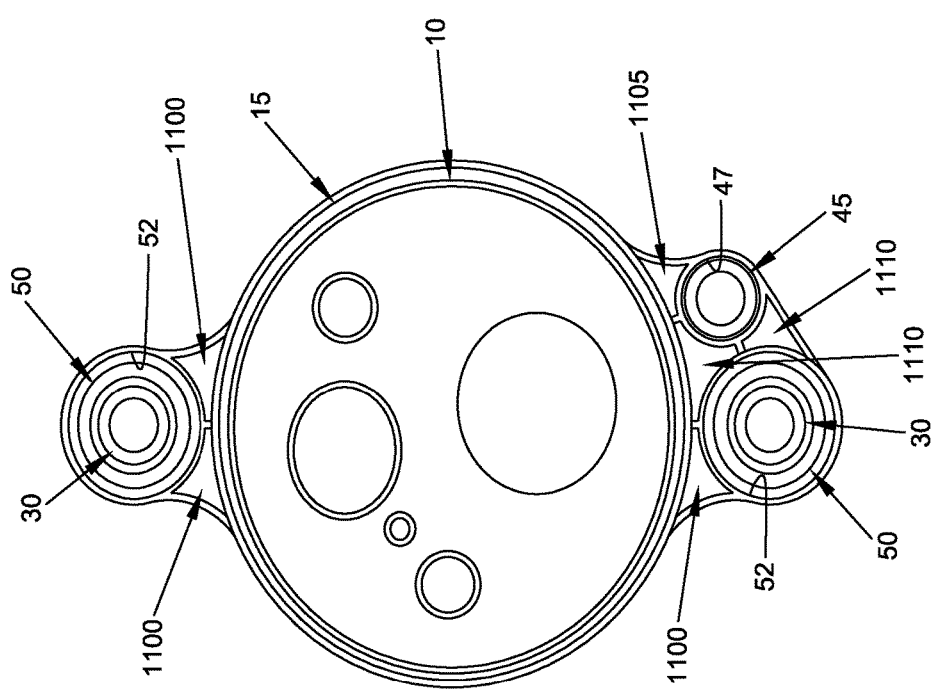
FIG. 108 is a cross-sectional schematic view showing how gaps are created between (i) the sleeve, (ii) the push rod lumens, and (iii) the aft balloon inflation lumen of the apparatus of FIGS. 1-106.
Figure 109:
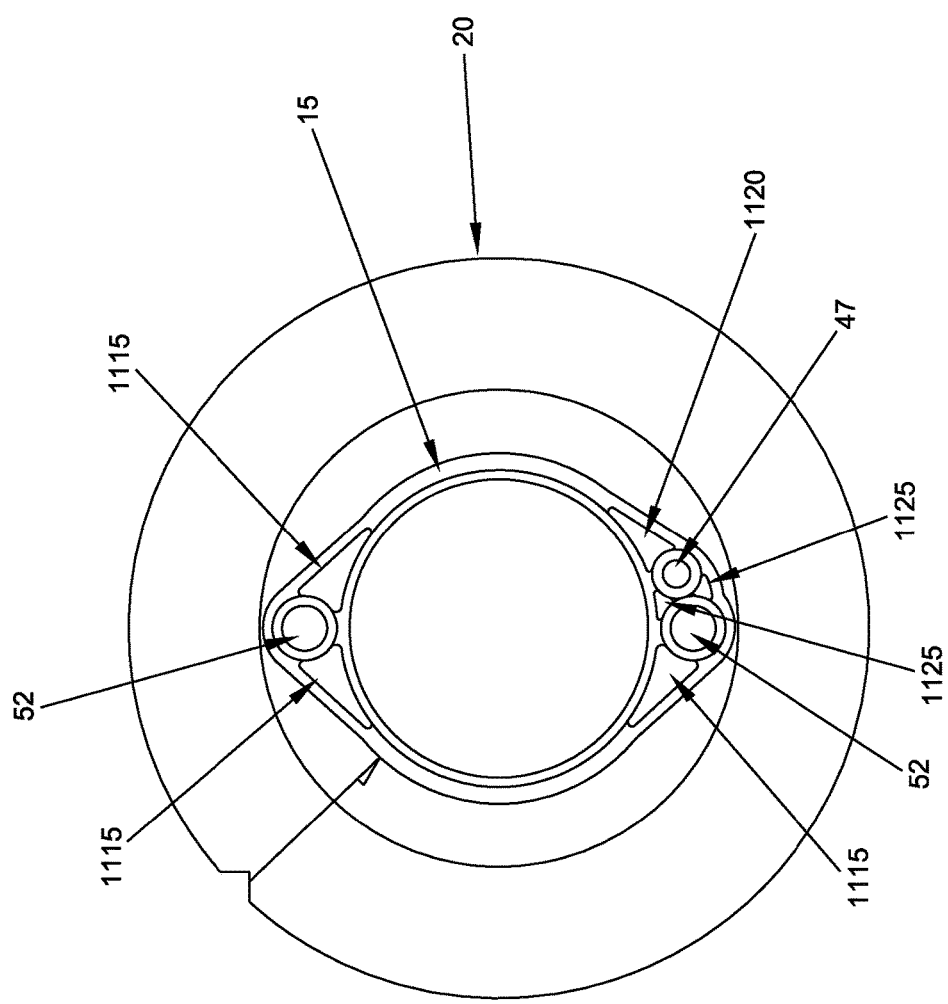
FIG. 109 is a cross-sectional schematic view similar to FIG. 108, showing a plurality of novel extruded inserts filling the aforementioned gaps between the sleeve, the push rod lumens and the aft balloon inflation lumen, whereby to facilitate airtight bonding of the aft balloon to the assembly.
Figure 112:
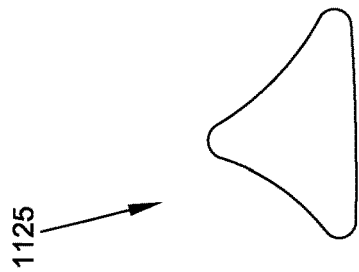
FIGS. 110, 111 and 112 are schematic views showing novel extruded inserts formed in accordance with the present invention.
Figure 111:
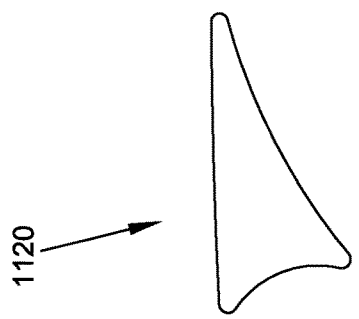
Figure 110:
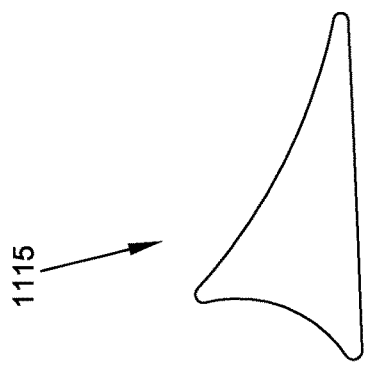
Figure 113:
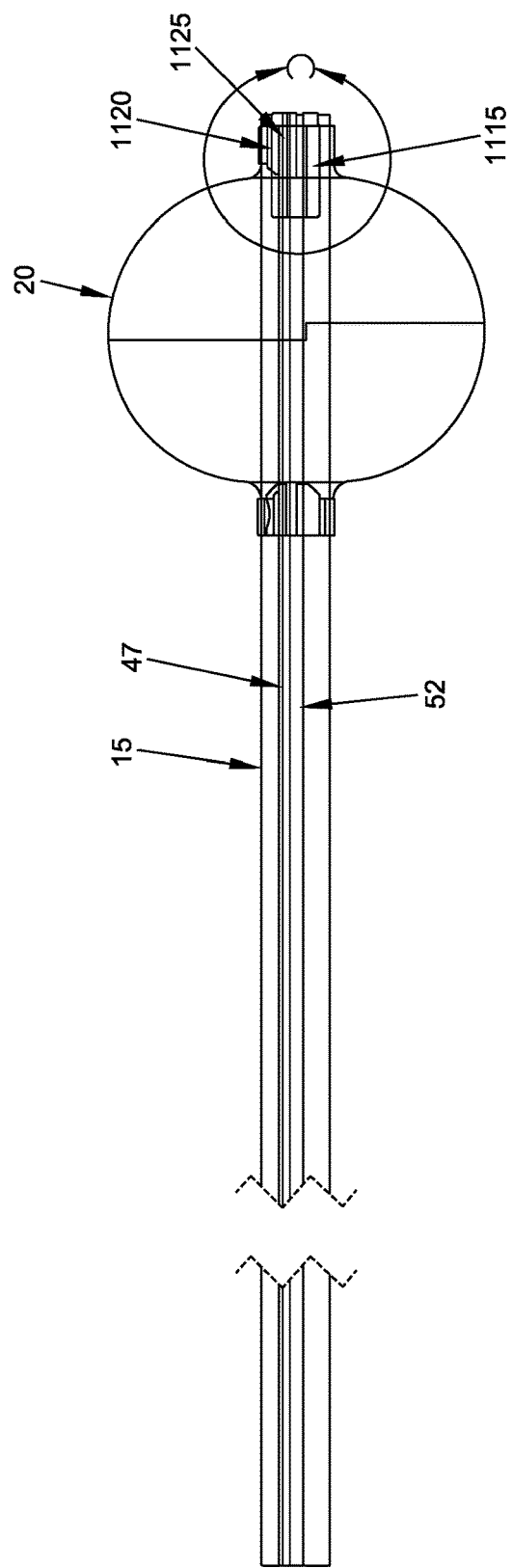
FIGS. 113 and 114 are schematic views showing the novel extruded inserts of FIGS. 110, 111 and 112 disposed along the sheath of the apparatus of FIGS. 1-106 so as to fill the gaps between the sleeve, the push rod lumens and aft balloon inflation lumen.
Figure 114:
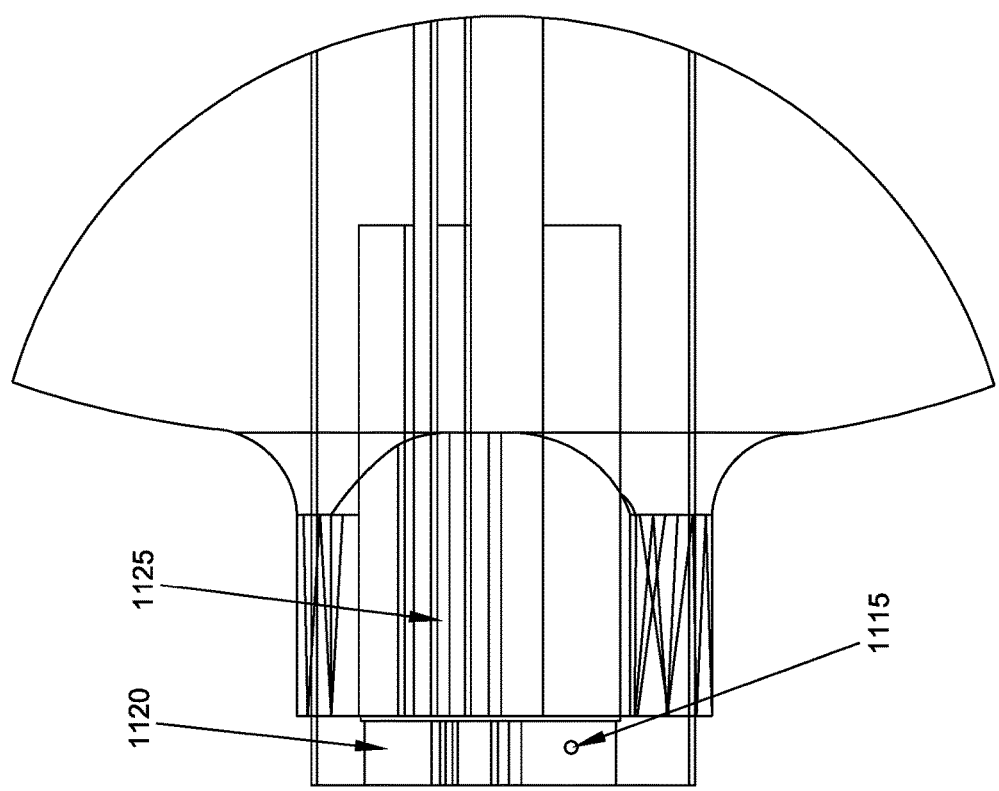
Figure 115:
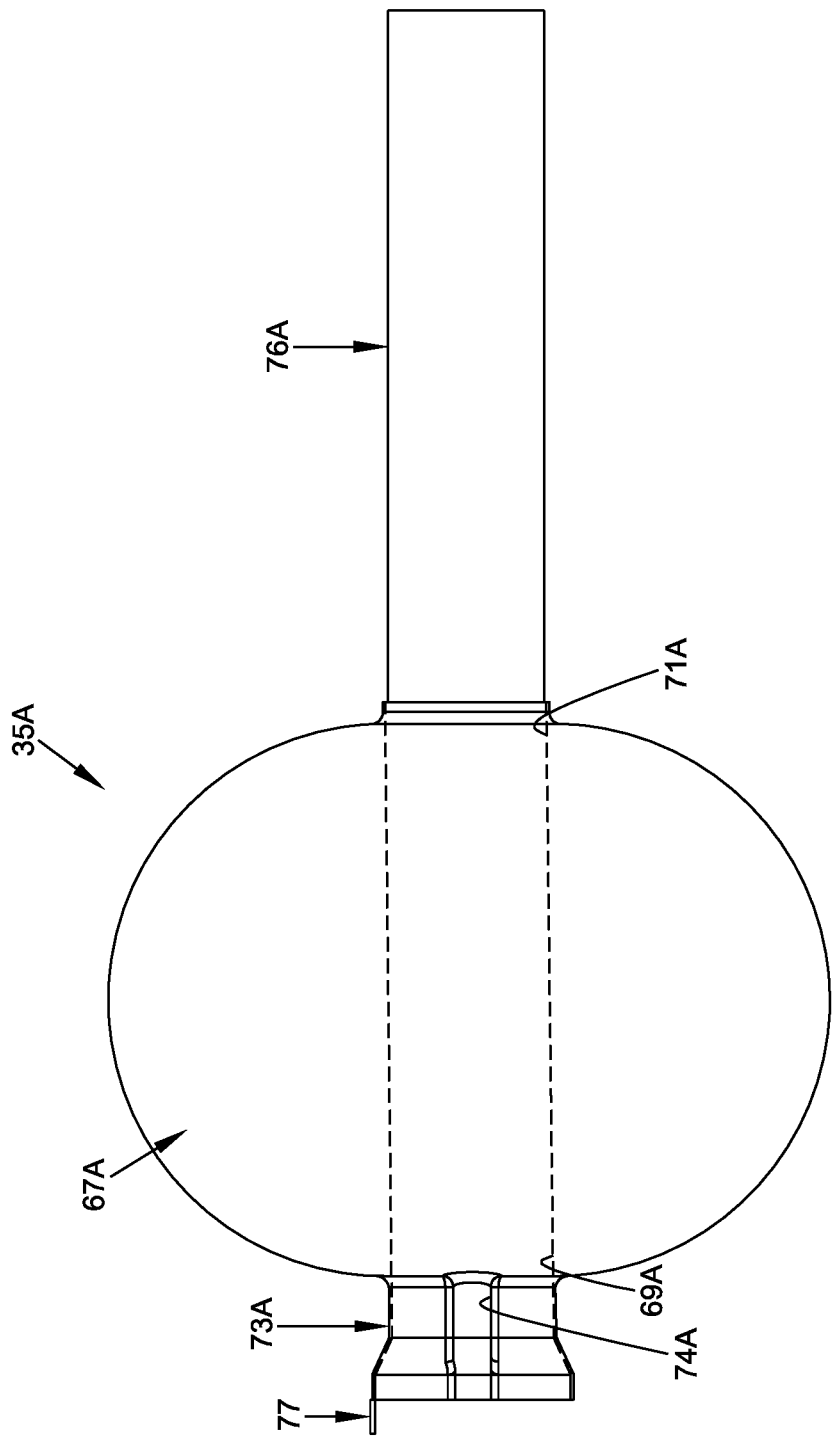
FIGS. 115-122 are schematic views showing an alternative construction for the fore balloon.
Figure 116:
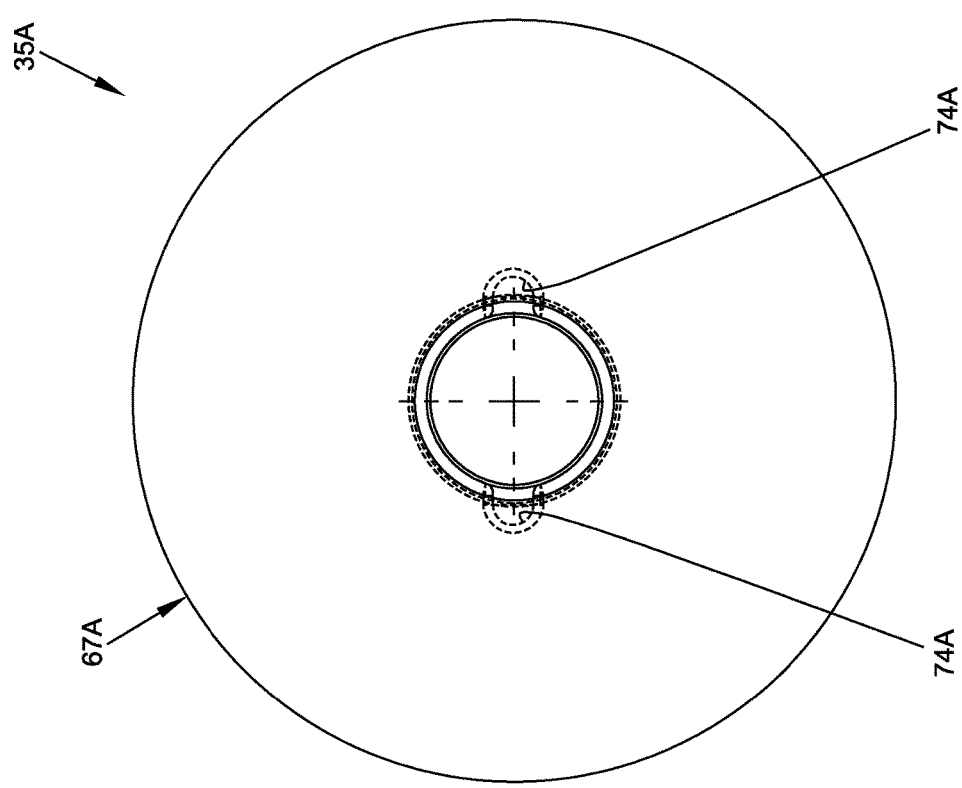
Figure 117:
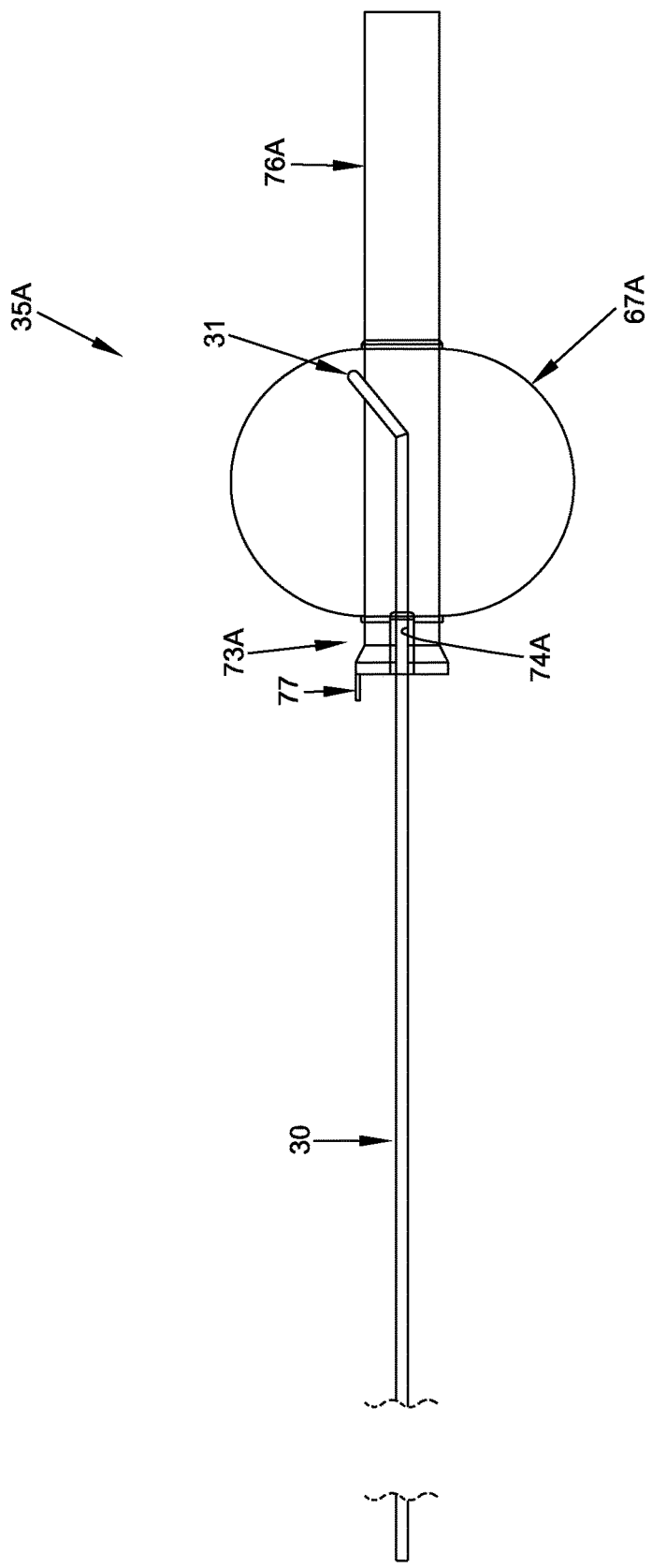
Figure 118:
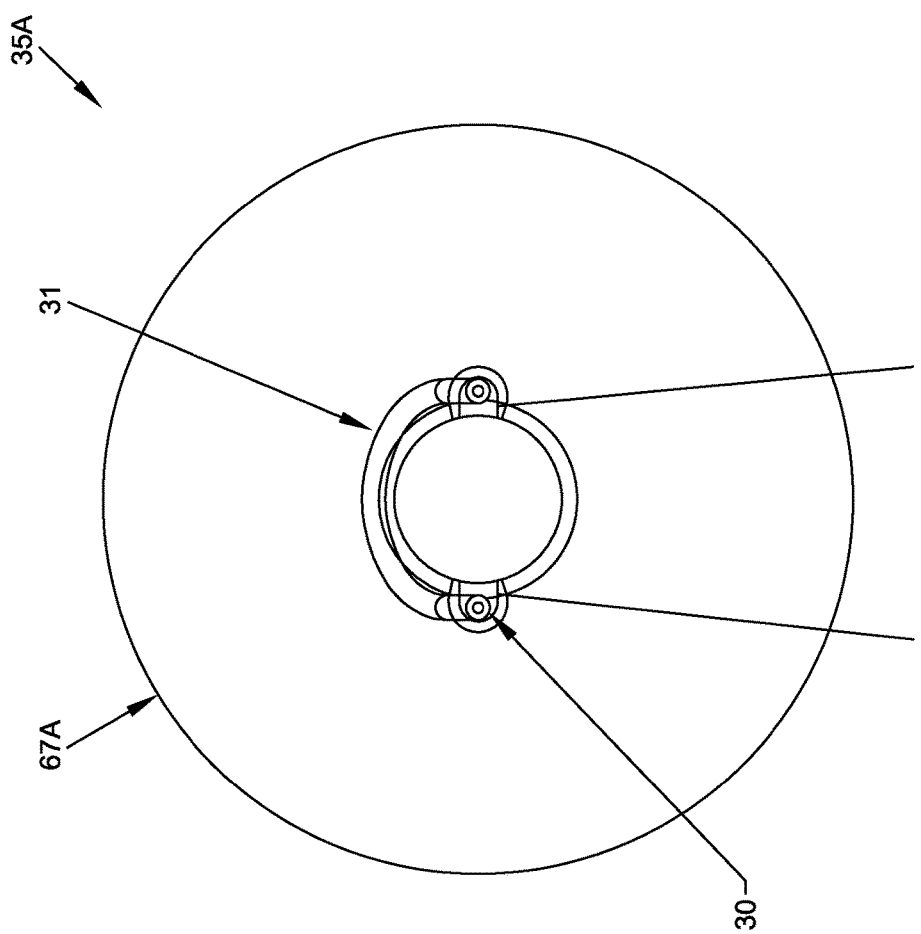
Figure 119:
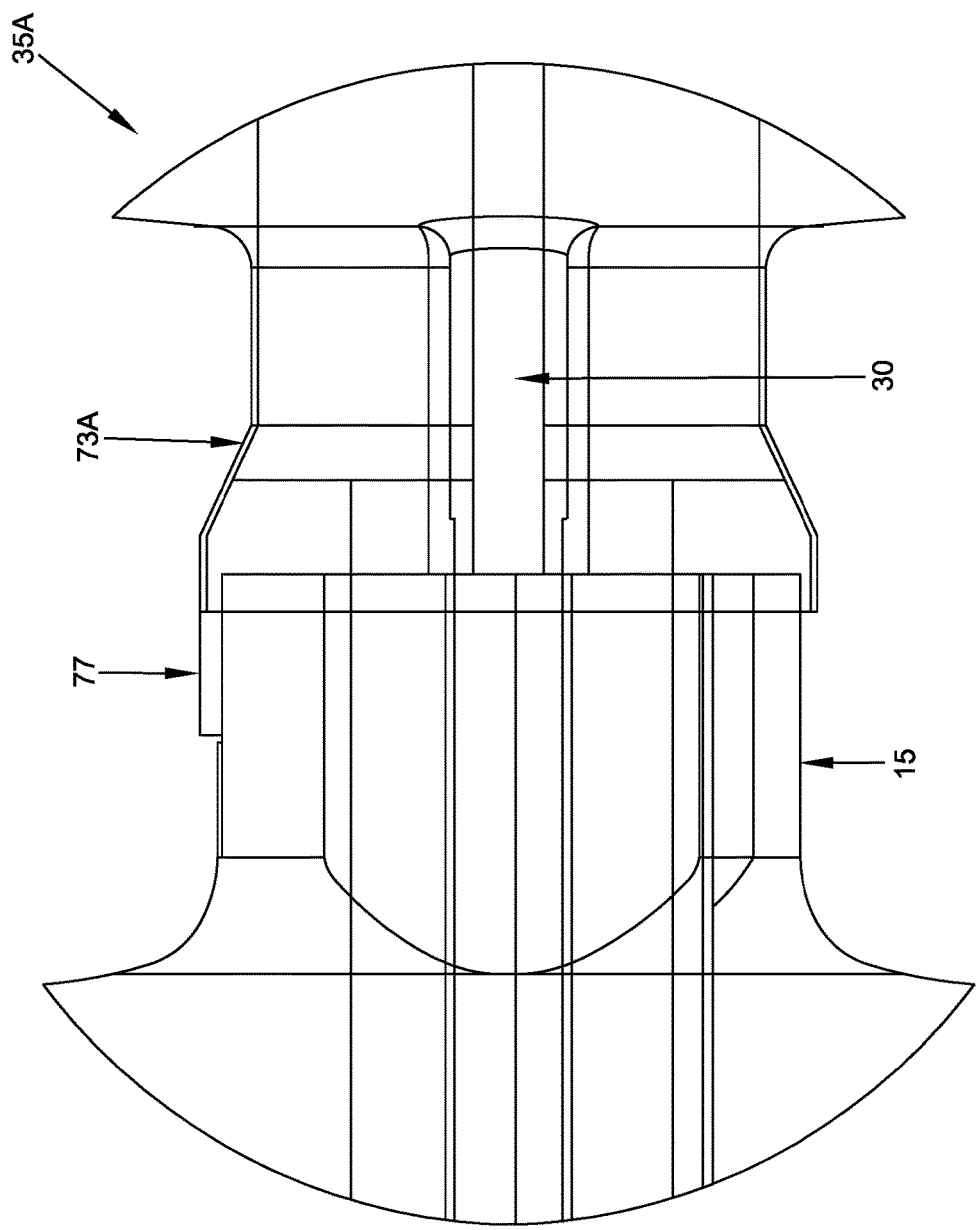

More particularly, and looking now at FIG. 108, gaps 1100 exist in the space between pushrod lumens 52 and sleeve 15, gap 1105 exists in the space between aft balloon inflation lumen 47 and sleeve 15, and gaps 1110 exist in the space between a pushrod lumen 52 and aft balloon inflation lumen 47. The presence of gaps 1100, 1105 and 1110 at the proximal edge of aft balloon 20, and the presence of gaps 1100 at the distal edge of aft balloon 20, compromise the airtight sealing of aft balloon 20 to sleeve 15, since it is difficult to make the material of aft balloon 20 adhere to the irregular perimeter defined by pushrod lumens 52 and aft balloon inflation lumen 47. Stated another way, it can be challenging to make the material of aft balloon 20 enter into gaps 1100, 1105 and 1110.

Thus it would be desirable to provide a new and improved means to fill gaps 1100, 1105 and 1110 so that aft balloon 20 can be thermally bonded to sleeve 15 in an airtight sealing engagement.

To that end, and looking now at FIGS. 109, 110, 111, 112, 113 and 114, there are provided novel extruded inserts 1115 which have a cross-sectional profile matching the aforementioned gaps 1100. Extruded inserts 1115 are sized to fill gaps 1100 at the location where the proximal edge of aft balloon 20 and the distal edge of aft balloon 20 are bonded to sleeve 15 around pushrod lumens 52. Extruded inserts 1110 are preferably flexible and may be of any desired length (e.g., extruded inserts 1115 may extend along substantially the entire length of sleeve 15, or extruded inserts 1115 may extend only along a portion of sleeve 15 where aft balloon 20 is bonded to sleeve 15, or a plurality of extruded inserts 1115 may extend along a plurality of interrupted sections of sleeve 15, etc.). In one preferred form of the invention, extruded inserts 1115 extend from a location just distal to aft balloon 20 to a location just proximal to aft balloon 20.

There is also provided a novel extruded insert 1120 having a cross-sectional profile matching the aforementioned gap 1105. Extruded insert 1120 is sized to fill gap 1105 at the location where the proximal edge of aft balloon 20 and the distal edge of aft balloon 20 are bonded to sleeve 15 around aft balloon inflation lumen 47. Extruded insert 1120 is preferably flexible and may be of any desired length (e.g., extruded inserts 1120 may extend along substantially the entire length of sleeve 15, or extruded inserts 1120 may extend only along a portion of sleeve 15 where aft balloon 20 is bonded to sleeve 15, or a plurality of extruded inserts 1120 may extend along a plurality of interrupted sections of sleeve 15, etc.). In one preferred form of the invention, extruded insert 1120 extends from a location at the distal end of aft balloon inflation lumen 47 to a location just proximal to aft balloon 20.

There are also provided novel extruded inserts 1125 having a cross-sectional profile matching the aforementioned gaps 1110. Extruded inserts 1125 are sized to fill gaps 1110 at the location where the proximal edge of aft balloon and the distal edge of aft balloon 20 are bonded to sleeve 15 around aft balloon inflation lumen 47 and a pushrod lumen 52. Extruded inserts 1125 are preferably flexible and may be of any desired length (e.g., extruded inserts 1125 may extend along substantially the entire length of sleeve 15, or extruded inserts 1125 may extend only along a portion of sleeve 15 where aft balloon 20 is bonded to sleeve 15, or a plurality of extruded inserts 1125 may extend along a plurality of interrupted sections of sleeve 15, etc.). In one preferred form of the invention, extruded insert 1125 extends from a location at the distal end of aft balloon inflation lumen 47 to a location just proximal to aft balloon 20.

Inserts 1115, 1120 and 1125 are preferably formed out of a material which will thermally bond with the material(s) of (i) sleeve 15, (ii) pushrod lumens 52, (iii) aft balloon inflation lumen 47, and (iv) aft balloon 20, whereby to facilitate the airtight bonding of aft balloon 20 to sleeve 15, pushrod lumen 52 and aft balloon inflation lumen 47.

It should be appreciated that where additional components/lumens (e.g., working channels) are disposed coaxially about sleeve 15, additional extruded inserts 1115, 1120, 1125, etc. may be provided, and/or other extruded inserts of different sizes and/or cross-sectional profiles may be provided, without departing from the scope of the present invention.

Improved Fore Balloon Construction

With the "double eversion" fore balloon construction discussed above, fore balloon 35 is formed as a hollow balloon body 67 having two extensions (i.e., proximal extension 73 and distal extension 76) which are both everted inwardly (i.e., the proximal extension is everted first, the distal extension is everted second) into the interior of body 67 and thermally bonded together to form fore balloon 35. With this approach, fore balloon 35 comprises a torus, whereby to facilitate docking of fore balloon 35 over the distal end of sleeve 15 (i.e., the distal end of endoscope 10) when fore balloon 35 is in its deflated condition. At the same time, fore balloon 35 can provide a full-diameter barrier across an anatomical passageway when fore balloon 35 is in its inflated condition.

However, it has been found that it can be challenging to effect good thermal bonding between inwardly-everted proximal extension 73 and inwardly-everted distal extension 76, inasmuch as both proximal extension 73 and distal extension 76 are located within the interior body 67 of fore balloon 35 during bonding, and therefore can be difficult to access during component bonding.

One solution to this problem, and looking now at FIGS. 115-119, is the provision of an alternative fore balloon 35A. Fore balloon 35A is manufactured as a single construct comprising a body 67A having a proximal opening 69A and a distal opening 71A, a proximal extension 73A having a "key-shaped" cross-section comprising lobes 74A, and a distal extension 76A having a circular cross-section. Note that lobes 74A of proximal extension 73A have a configuration that matches the configuration of hollow push tubes 30 (i.e., where apparatus 5 comprises two hollow push tubes 30 diametrically opposed to one another, proximal extension 73A comprises two lobes 74A diametrically opposed to one another—for the purposes of the present invention, proximal extension 73A and lobe(s) 74A may be collectively referred to as having a "key-shaped" cross-section). Proximal extension 73A is relatively short and is preferably flared outwardly at its proximal end, whereby to facilitate docking of fore balloon 35A over sleeve 15 and/or endoscope 10 as will hereinafter be discussed in greater detail. Furthermore, proximal extension 73A preferably comprises a proximally-extending tongue 77 for facilitating docking of fore balloon 35A over the proximal end of sleeve 15 (and/or the proximal end of endoscope 10).

Thus it will be appreciated that fore balloon 35A is formed in a manner generally similar to the aforementioned fore balloon 35, except that proximal extension 73A of fore balloon 35A differs from the aforementioned proximal extension 73 of fore balloon 73 (i.e., by being formed with a shorter length, a flared proximal end and a tongue 77).

Figure 120:
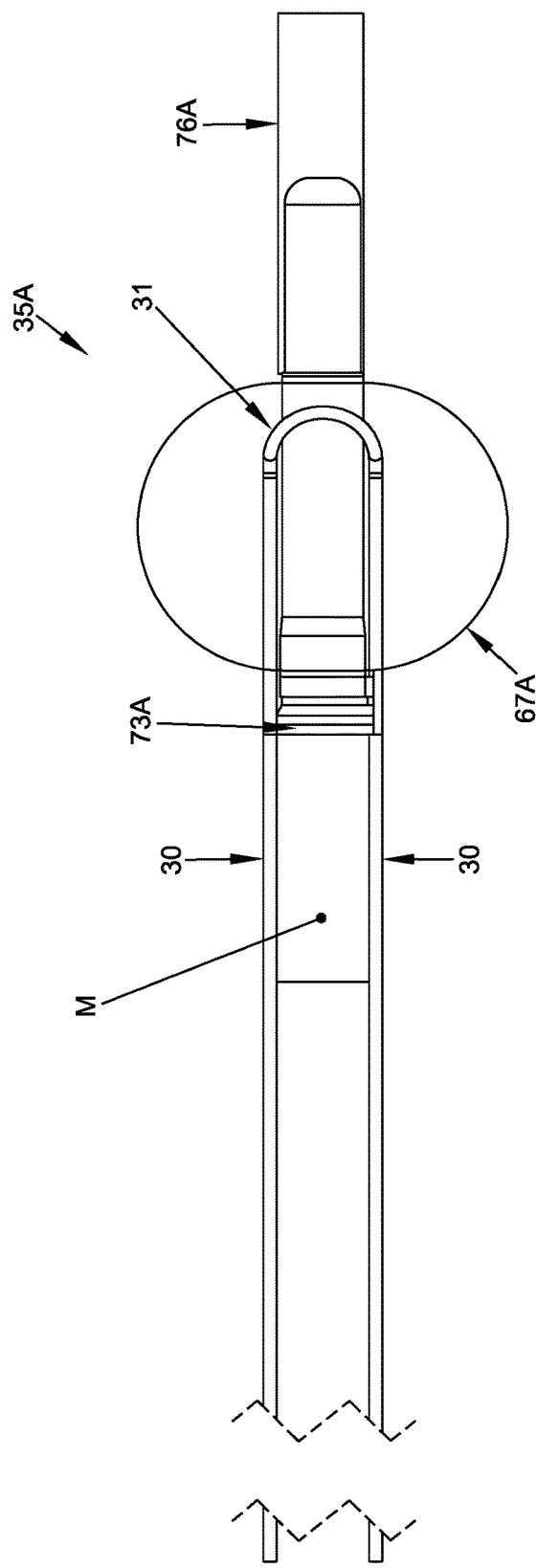
Figure 121:
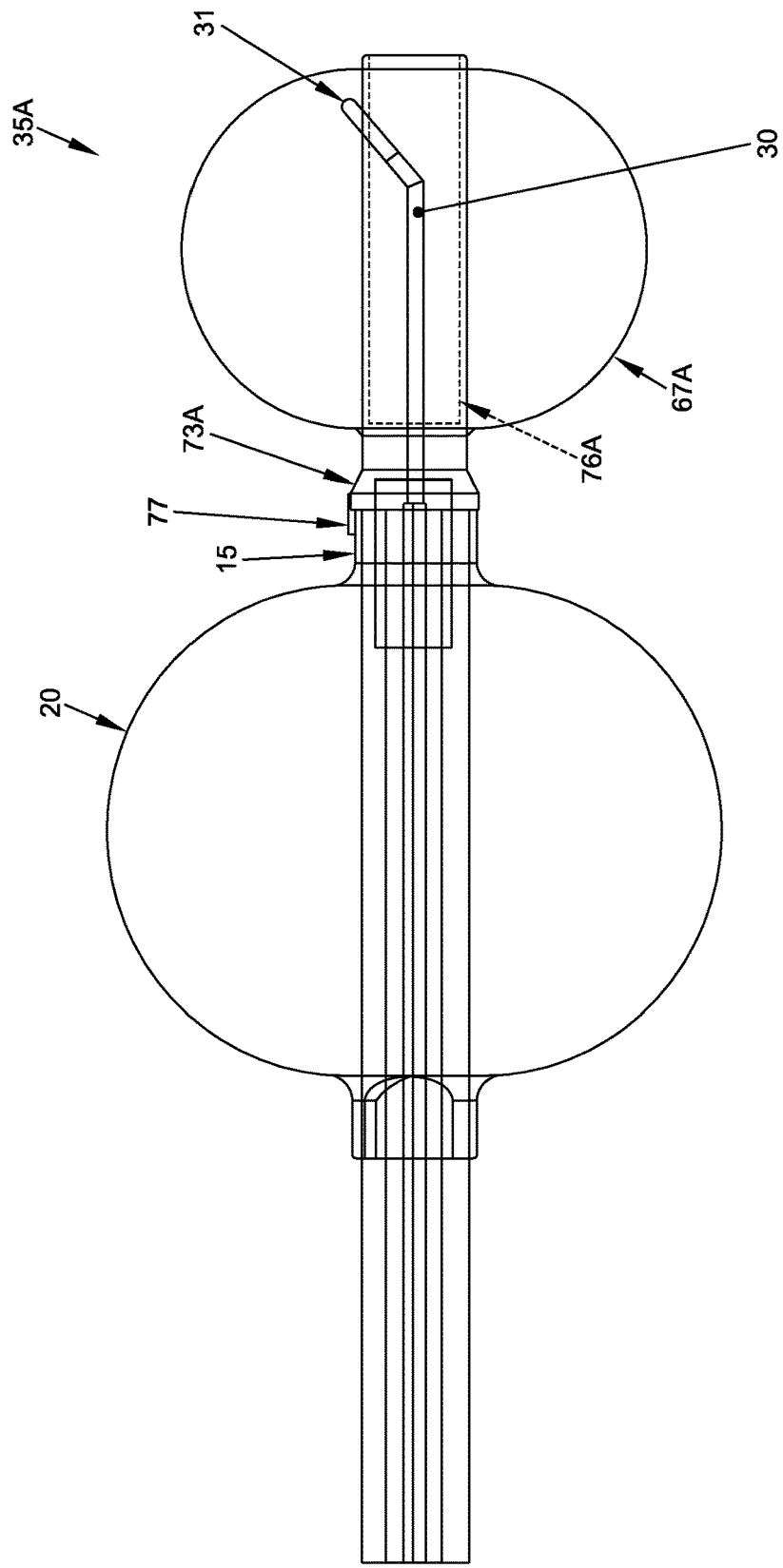
Figure 122:
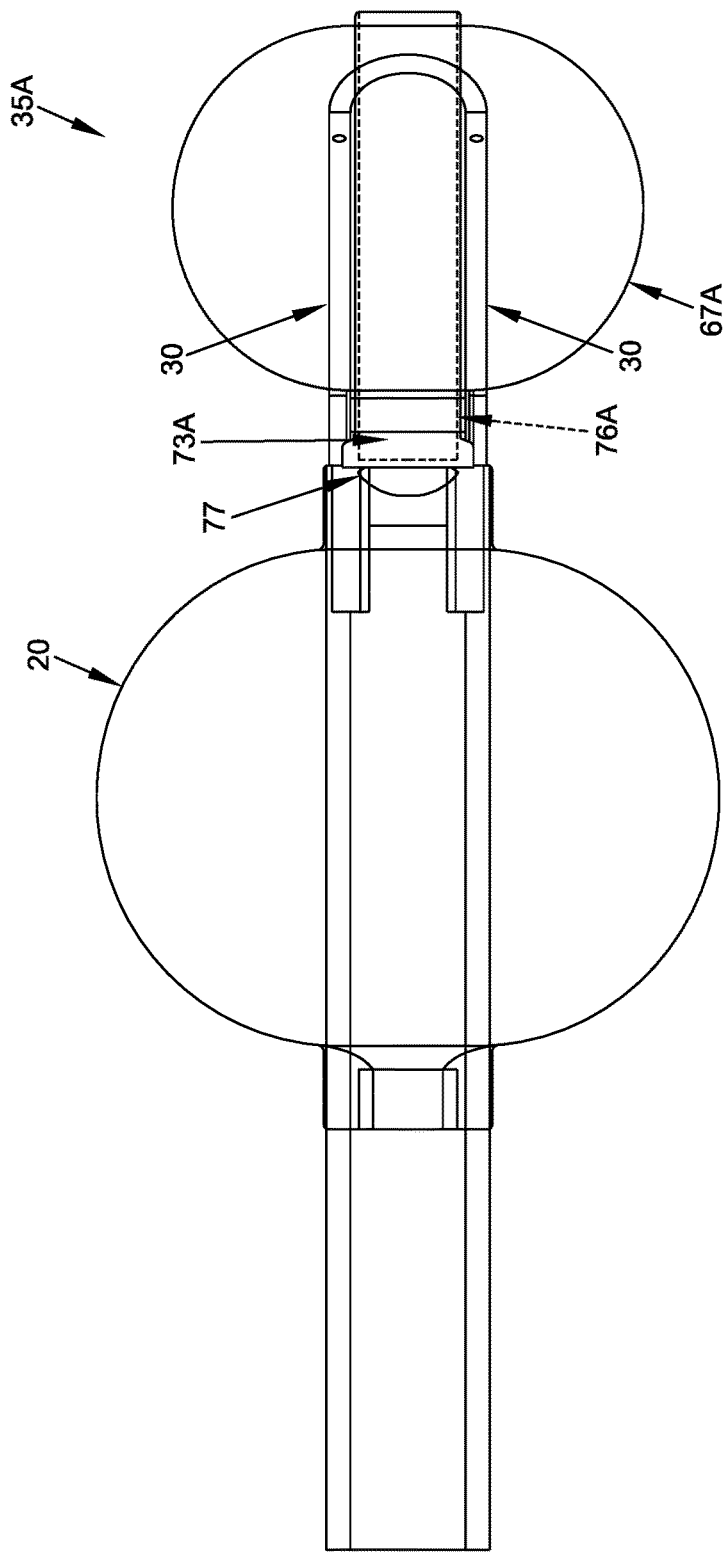

Fore balloon 35A is also assembled in a somewhat different manner than the aforementioned fore balloon 35, as will hereinafter be discussed in greater detail. More particularly, and looking now at FIGS. 120-122, hollow push tubes 30 are seated in lobes 74A of proximal extension 73A, with proximal extension 73A extending proximally away from fore balloon 35A and with distal extension 76 extending distally away from fore balloon 35A. Hollow push tubes 30 are advanced distally into the interior of body 67A of fore balloon 35A such that the interiors of hollow push tubes 30 are in fluid communication with the interior of body 67A and with raised push tube bridge 31 disposed within the interior of body 67A. If desired, an assembly mandrel M may be used during assembly in order to provide support for the components during insertion of hollow push tubes 30 into fore balloon 35A of fore balloon 35A (see FIG. 120).

Next, processing mandrel M is removed (if one is used), and distal extension 76A is everted into the interior of body 67A of fore balloon 35A and passed proximally through body 67A, and through the interior of proximal extension 73A, until distal extension 76A extends to the proximal opening of proximal extension 73A. As a result of this construction, proximal extension 76A extends through body 67A, and both proximal extension 73A and distal extension 76A extend proximally away from body 67A of fore balloon 35A, and push tubes 30 are disposed between proximal extension 73A and distal extension 76A proximal to body 67A of fore balloon 35A. Thus, in this form of the invention, proximal extension 73A is not everted into the interior of fore balloon 35A, rather, proximal extension 73A remains extending proximally away from fore balloon 35.

Proximal extension 73A and distal extension 76A are then bonded together at their proximal ends, with push tubes 30 being sealed therebetween, such that airtight thermal bonding is effected.

As a result of the foregoing, fore balloon 35A has a toroidal configuration, comprising a boy 67 having a center opening formed by (i) proximal extension 73A/everted distal extension 76A on the proximal side of body 67A, and (ii) everted distal extension 76A within the interior of body 67A.

Significantly, this form of the invention results in fore balloon 35A having a toroidal shape which does not require thermal bonding to be carried out within the interior of body 67A of fore balloon 35A, thereby simplifying assembly. Furthermore, by forming proximal extension 73A as a relatively short structure having an outwardly flared proximal end, and by providing tongue 77 on the proximal edge of proximal extension 73A, proximal extension 73A can facilitate docking of fore balloon 35A over sleeve 15 and/or endoscope 10.

Figure 123:
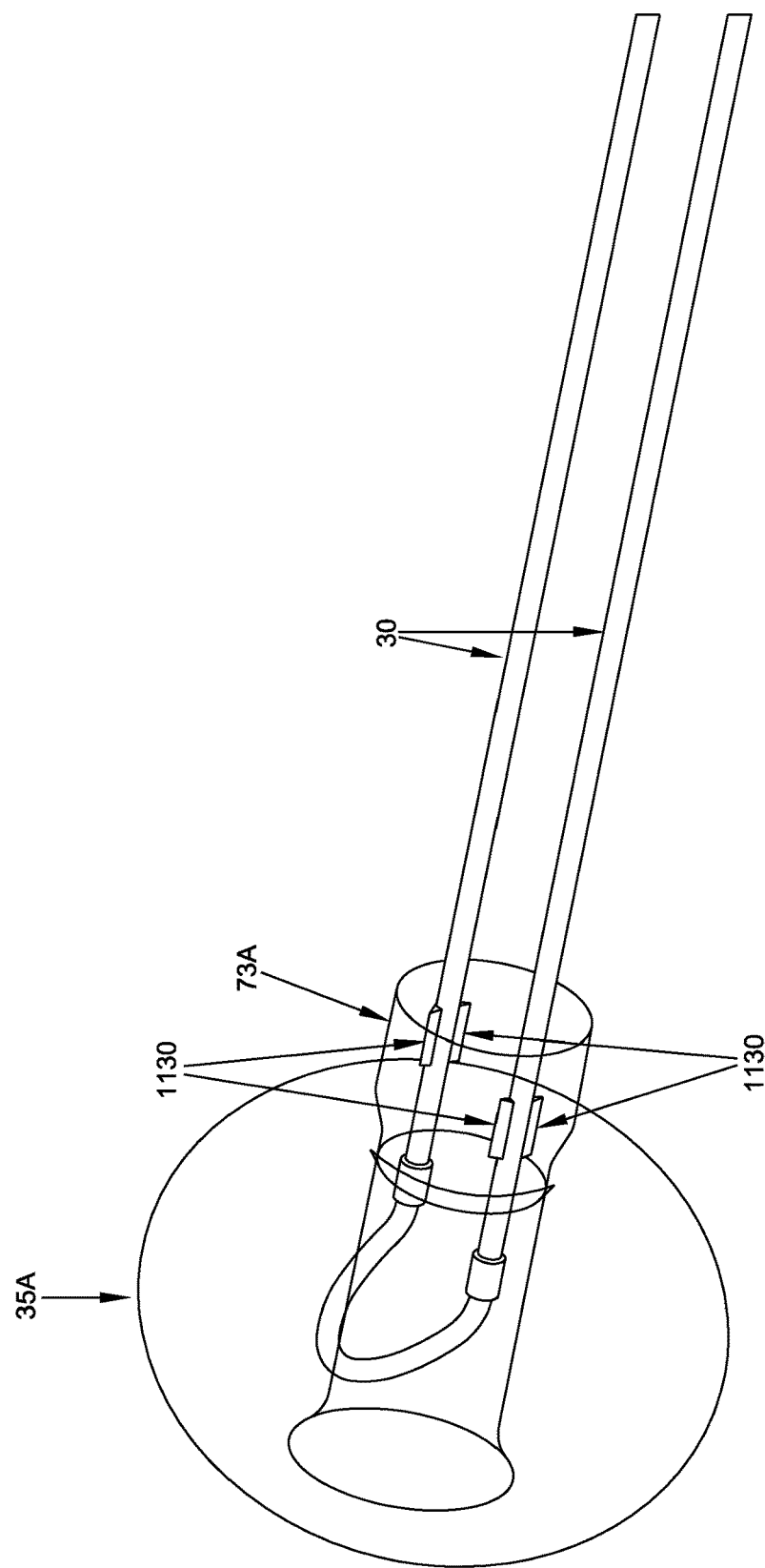
FIG. 123 is a schematic view showing another alternative construction for the fore balloon.

If desired, and looking now at FIG. 123, novel extruded inserts 1130 may be provided alongside hollow push tubes 30 so as to facilitate bonding hollow push tubes 30 to proximal extension 73A and to the everted distal extension 76A.

Furthermore, if desired, additional material and/or extrusions may be provided along either (or both of) proximal extension 73A and distal extension 76A, and/or around the proximal opening of proximal extension 73A, so as to provide increased rigidity to those portions of fore balloon 35A.

Forming the Aft Balloon with an Everted Construction

Figure 124:
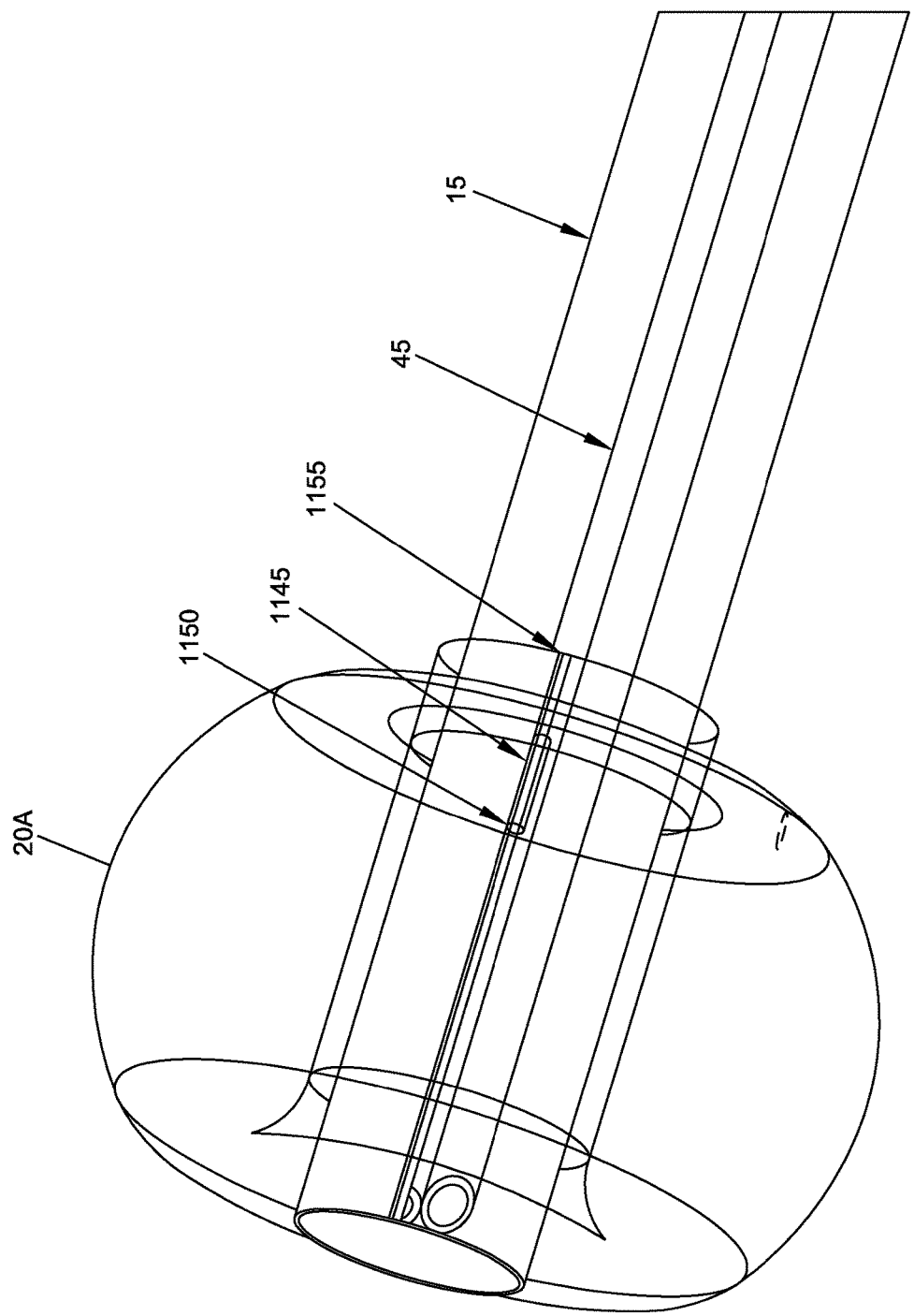
FIGS. 124 and 125 are schematic views showing an alternative construction for the aft balloon.
Figure 125:
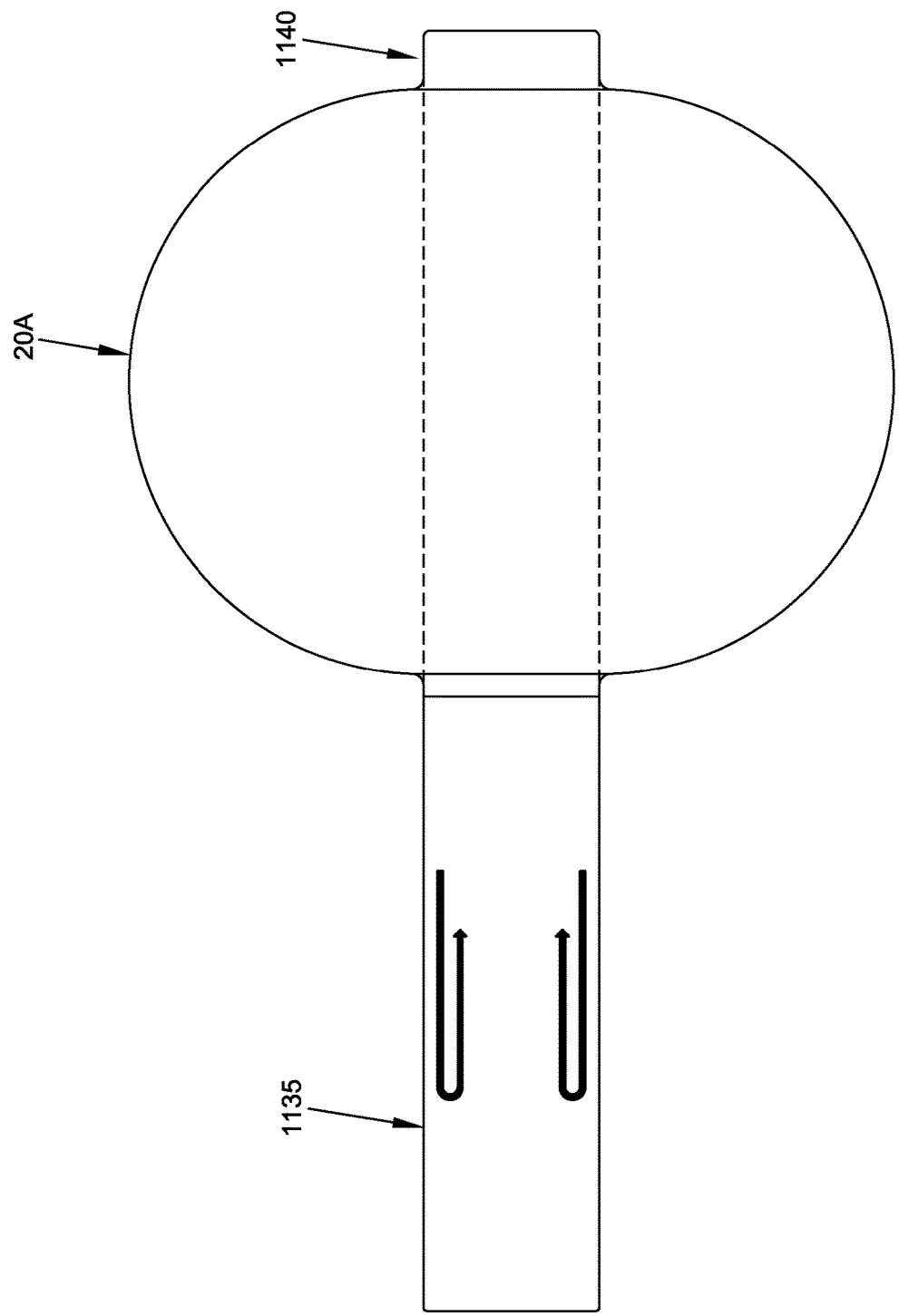

If desired, aft balloon 20 may be formed with an everted construction. More particularly, and looking now at FIGS. 124 and 125, there is shown an aft balloon 20A which generally comprises a distal extension 1135 and a proximal extension 1140. During construction, distal extension 1135 is everted back through the center of aft balloon 20A so as to form a generally toroidal balloon structure which is secured to sleeve 15. In this form of the invention, a tube 1145 has its distal end 1150 disposed exterior to the everted distal extension 1135, and interior to the outside wall of aft balloon 20A, and its proximal end 1155 connected to the aforementioned proximal inflation/deflation tube 45, so that air (or another fluid) can be introduced into aft balloon 20A and removed from aft balloon 20A.

Additional Constructions

If desired, apparatus 5 may be constructed so that hollow push tubes 30 may be advanced or retracted, to a limited extent, independently of one another, as well as in conjunction with one another—such limited independent advancement or retraction of hollow push tubes 30 can aid in steering the partially- or fully-deflated fore balloon 35 through the body lumen and/or body cavity, whereby to facilitate advancement or retraction of endoscope 10 through the body lumen and/or body cavity, and/or such independent advancement or retraction of hollow push tubes 30 can facilitate applying a "turning force" to the anatomy with an inflated fore balloon 35, whereby to better present the anatomy for visualization and/or treatment.

Figure 60:
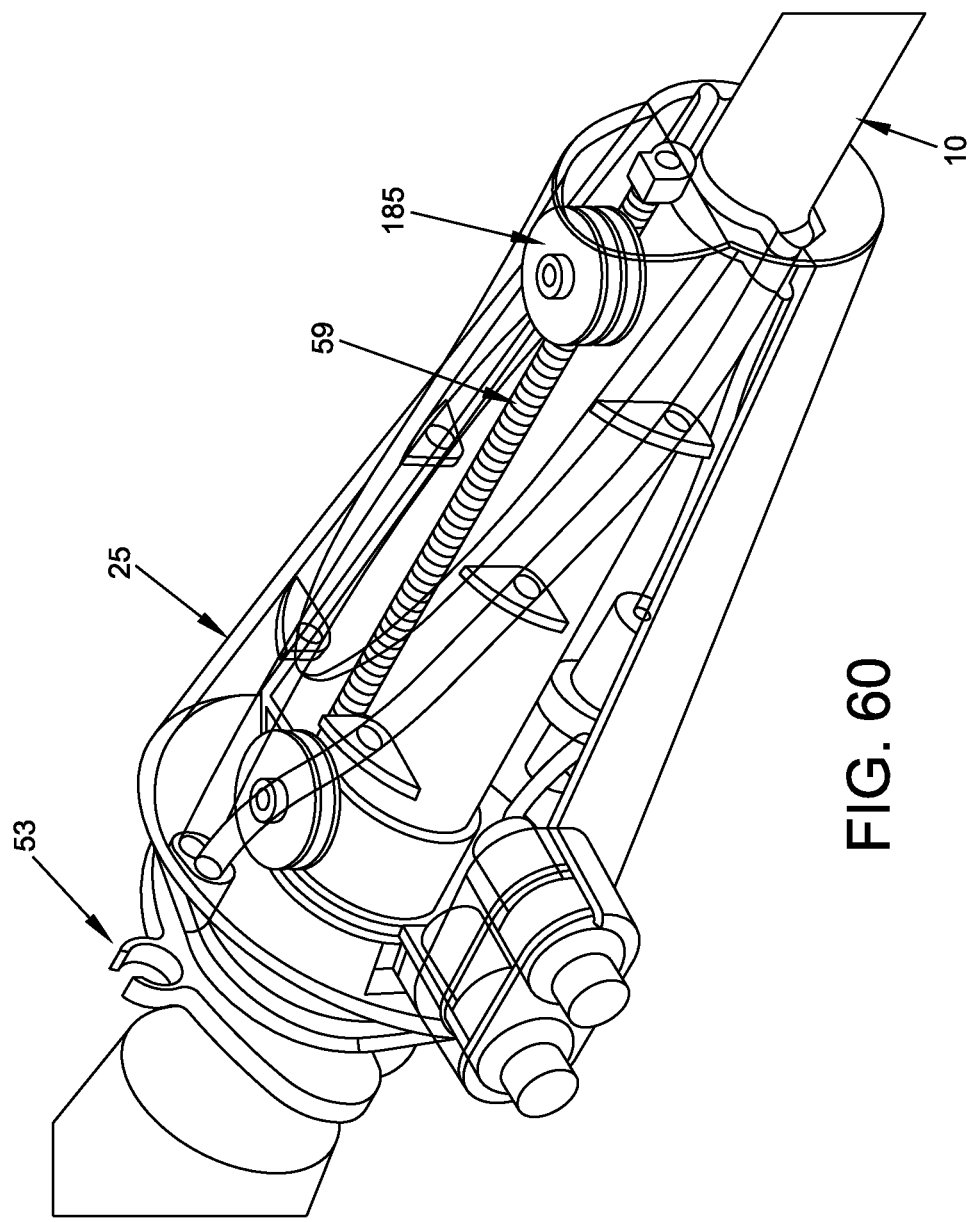
FIG. 60 is a schematic view showing a retraction system which may be used to take up slack in a flexible tube of the apparatus shown in FIG. 1.
Figure 126:
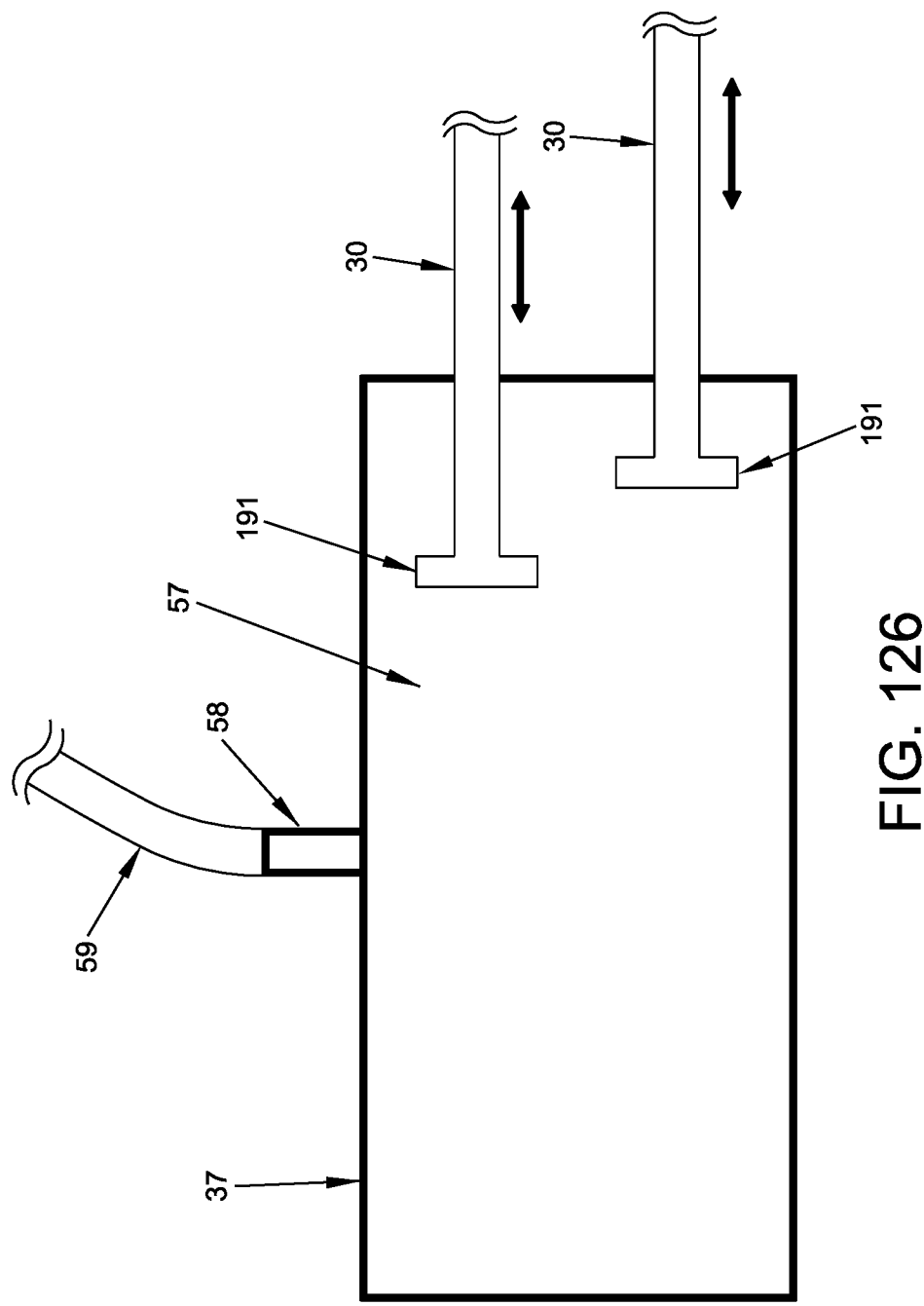
FIG. 126 is a schematic view showing an alternative construction for the hollow push tubes and push tube handle of the present invention.

By way of example but not limitation, in this form of the invention, and looking now at FIG. 126, hollow push tubes 30 are each independently slidably mounted to push tube handle 37 so that hollow push tubes 30 can move, to some extent, independently of push tube handle 37 and each other. Stops 191 limit distal movement of hollow push tubes 30 relative to push tube handle 37 so that a hollow push tube cannot be moved completely out of push tube handle 37. As a result of this construction, when fore balloon 35 is to be moved distally, hollow push tubes 30 are moved distally, either together or, to the extent allowed by raised push tube bridge 31, independently of one another. And when fore balloon 35 is to be moved proximally, hollow push tubes 30 are moved proximally, either together or independently of one another, to the extent allowed by raised push tube bridge 31. At any point in a procedure, hollow push tubes 30 can be moved, to the extent allowed by raised push tube bridge 31, independently of one another so as to "turn" the fore balloon, e.g., such as when fore balloon 35 is inflated and engaging the anatomy, whereby to apply a "turning force" to the anatomy, or where fore balloon 35 is partially inflated and is being used as an atraumatic tip for the advancing assembly, whereby to help "steer" the assembly through the anatomy. Note that raised push tube bridge 31 at the distal ends of hollow push tubes 30 provides a limiting mechanism to limit the extent to which hollow push tubes 30 may be moved, longitudinally, independently of one another, in order to prevent excessive turning of fore balloon 35, and/or hollow push tube cross-over, and/or hollow push tube entanglement, and/or hollow push tube misalignment, etc. Note also that hollow push tubes 30 may be held in a particular disposition by mounting hollow push tubes 30 in the aforementioned clamp 53 (FIGS. 37 and 60).

It should also be appreciated that it is possible to modify the construction of sleeve 15 so as to support instruments (or hollow instrument guide tubes) external to endoscope 10. More particularly, looking again at FIGS. 5 and 6, it will be seen that in the construction shown in FIGS. 5 and 6, sleeve 15 comprises a lumen 47 for receiving inflation/deflation tube 45 for inflating/deflating aft balloon 20, and a pair of lumens 52 for receiving support tubes 50 which receive push tubes 30 for manipulating and inflating/deflating fore balloon 35. However, if desired, sleeve 15 may include additional lumens for supporting instruments (or hollow instrument guide tubes) external to endoscope 10.

Figure 127:
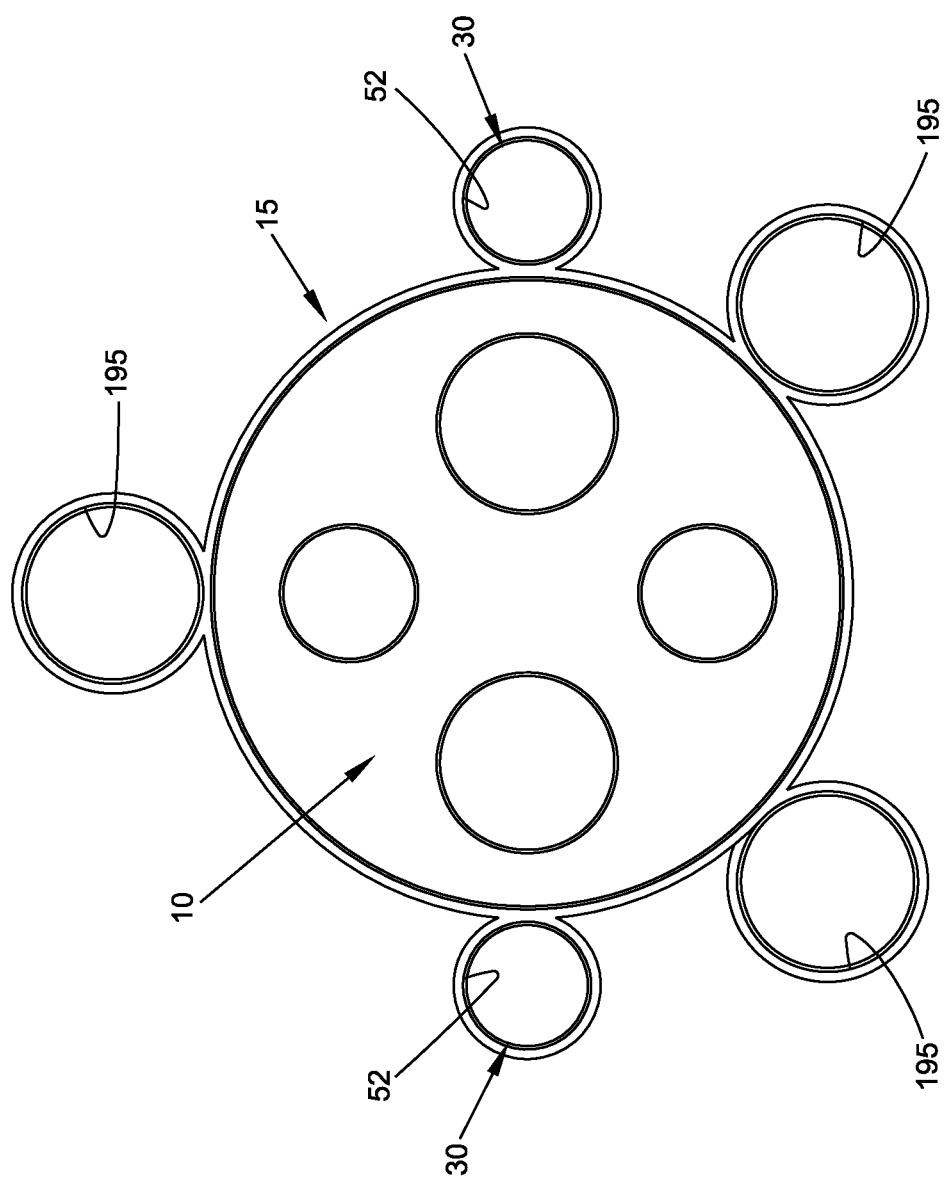
FIG. 127 is a schematic view showing another form of the sleeve, wherein the sleeve comprises additional lumens for receiving instruments.
Figure 128:
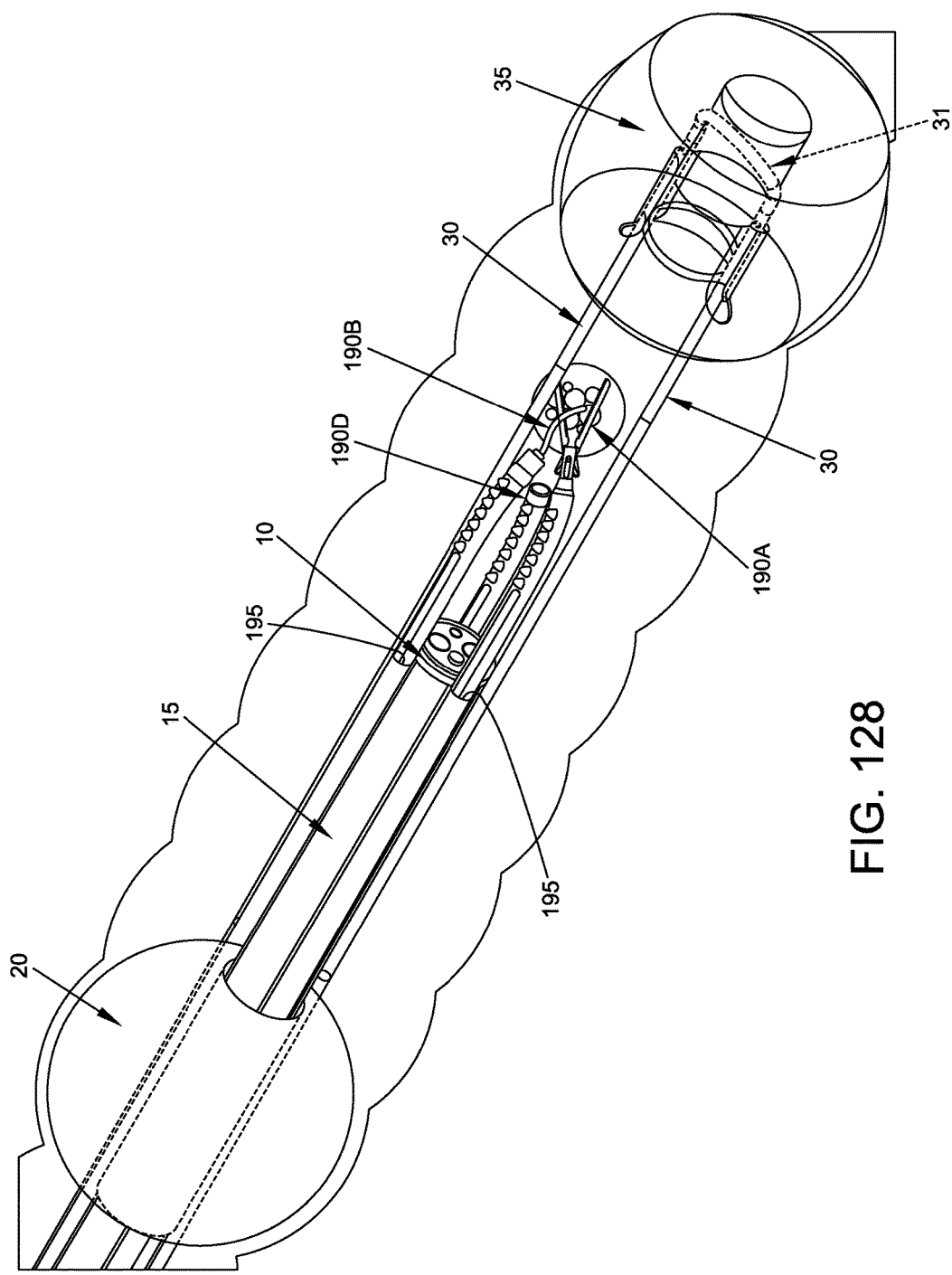
FIGS. 128-131 are schematic views showing how instruments may be advanced through the additional lumens of the sleeve.
Figure 129:
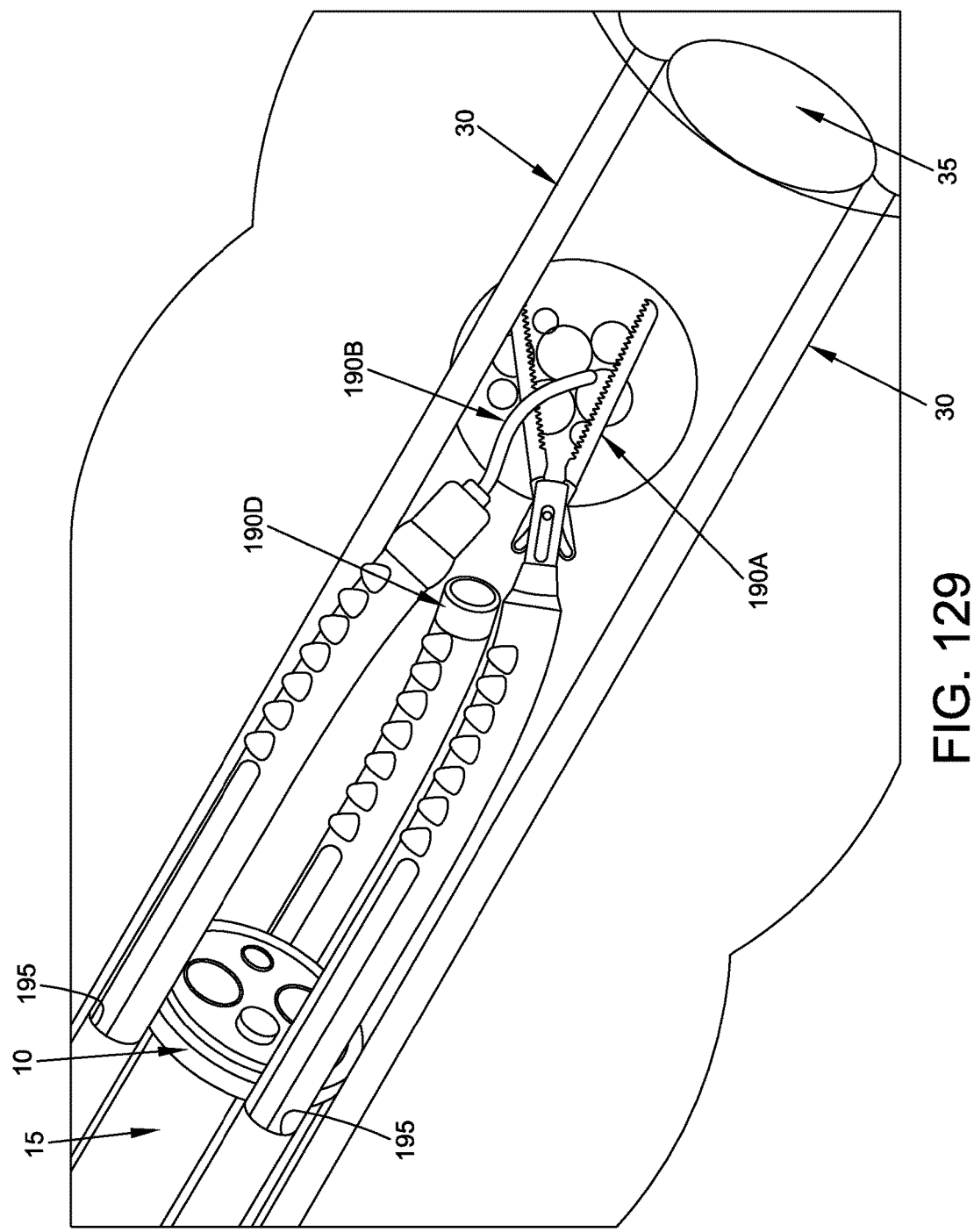
Figure 130:
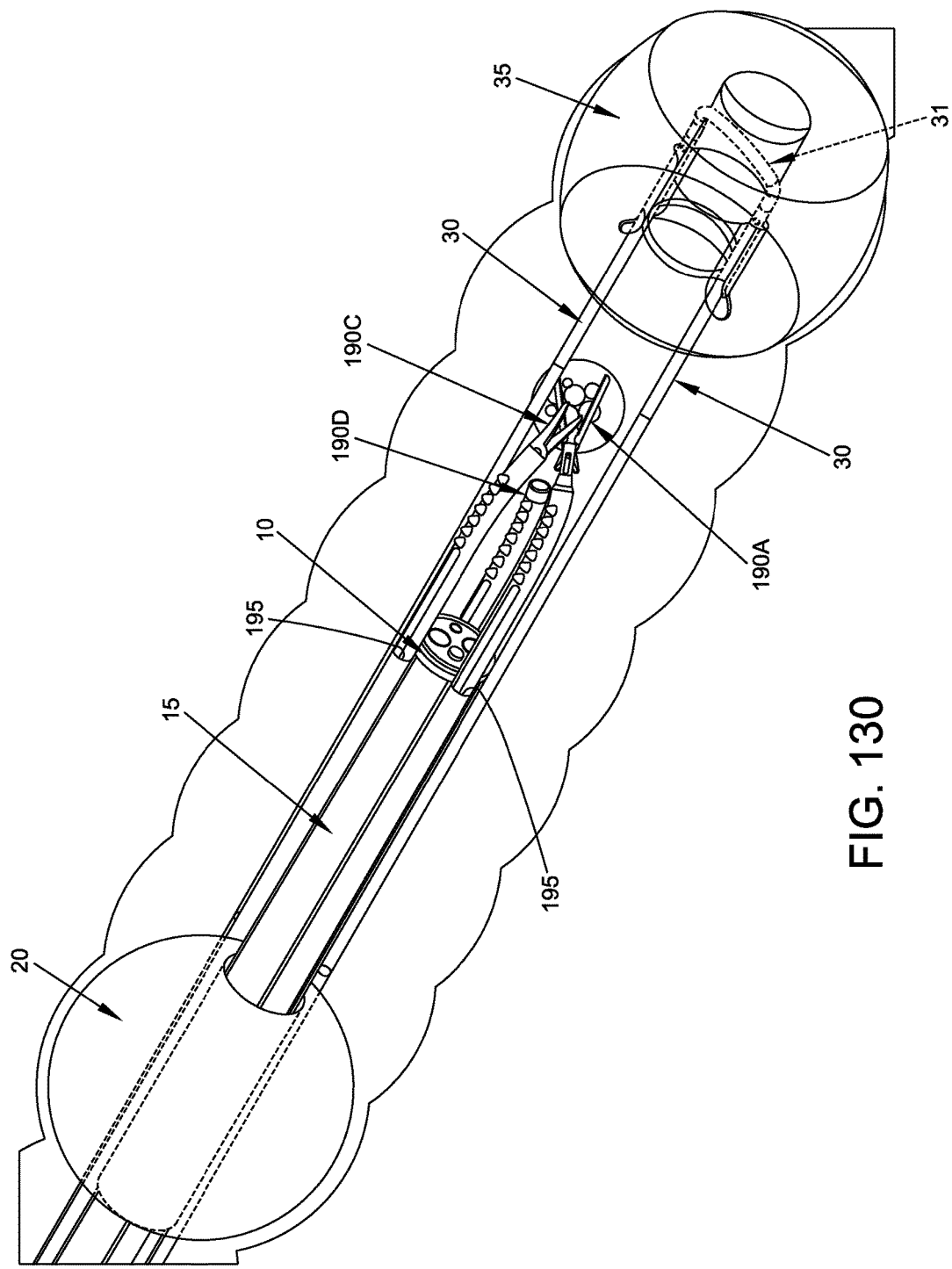
Figure 131:
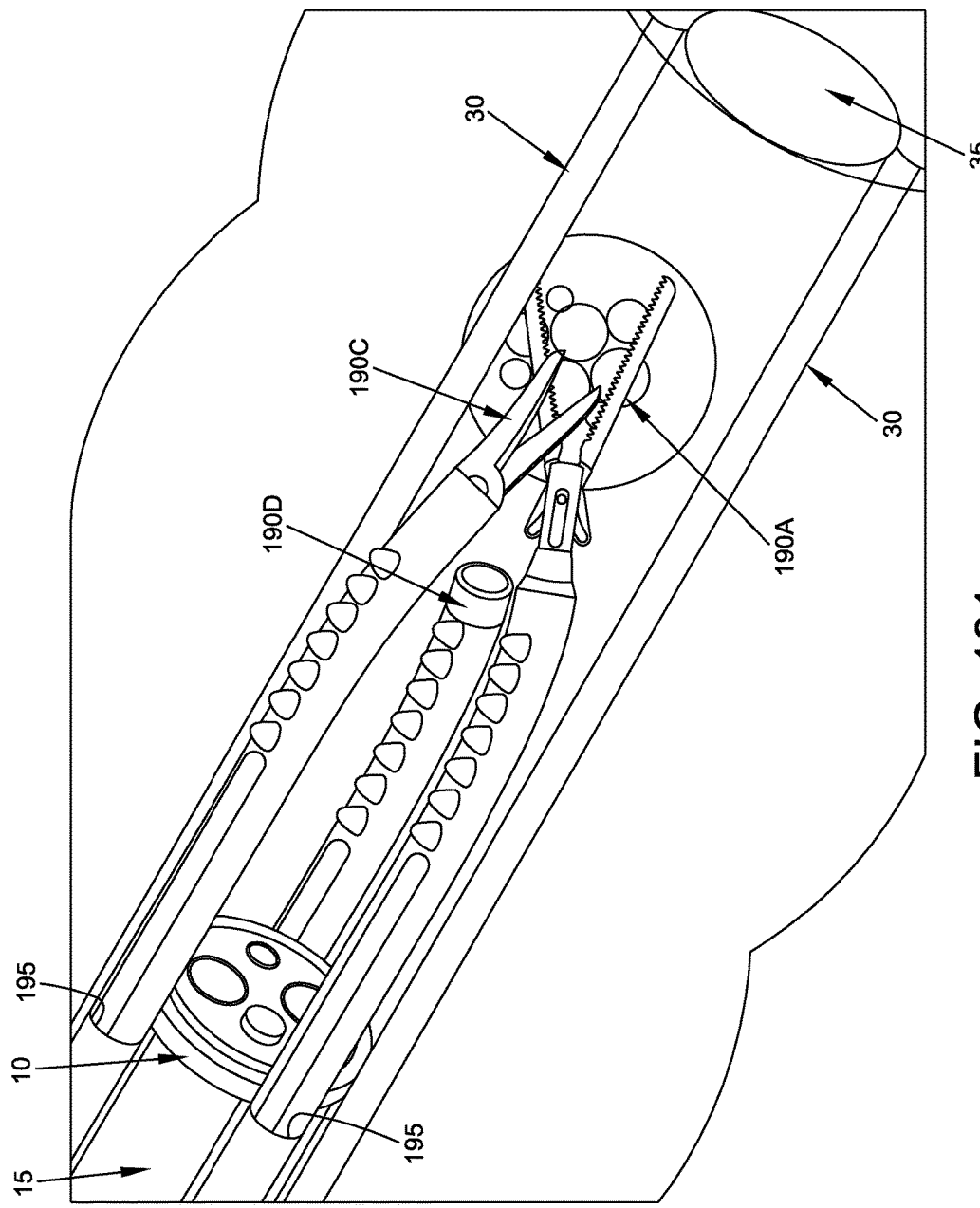

More particularly, and looking now at FIG. 127, there is shown an end view of another form of sleeve 15 which includes a plurality of lumens 195 for slidably receiving instruments 190 therein. Note that, when inflated, aft balloon 20 provides a secure platform for maintaining endoscope 10 and sleeve 15 within a body lumen or body cavity, with endoscope 10 and sleeve 15 centered within the body lumen or body cavity. As a result, the distal ends of lumens 195 of sleeve 15 will also be securely maintained within the body lumen or body cavity so as to provide a secure support for instruments advanced through lumens 195 of sleeve 15.

The proximal ends of lumens 195 may extend to, and through, base 25, in which case instruments may be inserted into lumens 195 at base 25, or the proximal ends of lumens 195 may terminate proximal to base 25 (but still outside the body of the patient), in which case instruments may be inserted into lumens 195 intermediate sleeve 15. By way of example but not limitation, where endoscope 10 is 180 cm in length and instruments 190 are 60 cm in length, it can be advantageous to insert instruments 190 into lumens 195 at a point closer to balloons 20, 35 (rather than at base 25). Note that in FIG. 127, the lumen 47 for receiving inflation/deflation tube 45 and inflation/deflation tube 45 for inflating/deflating aft balloon 20 are not visible, since the view is distal-facing and is taken at a location distal to where lumen 47 and inflation/deflation tube 45 terminate on sleeve 15.

FIGS. 128-131 show various instruments 190 extending out of lumens 195. Note that instruments 190 preferably comprise articulating instruments, e.g., graspers 190A in FIGS. 128-131, a cauterizing device 190B in FIGS. 128-129, scissors 190C in FIGS. 130 and 131, and a suction device 190D in FIGS. 128-131.

It should be appreciated that where sleeve 15 comprises its central passageway for receiving endoscope 10, lumen 47 for receiving inflation/deflation tube 45, lumens 52 for receiving support tubes 50 which receive hollow push tubes 30, and/or lumens 195 for slidably receiving instruments 190 therein, sleeve 15 is preferably formed by an extrusion process.

In one preferred form of the invention, lumen 47 for receiving inflation/deflation tube 45, lumens 52 for receiving support tubes 50 which receive hollow push tubes 30, and/or lumens 195 for slidably receiving instruments 190 may have a fixed configuration (i.e., a fixed diameter), so that sleeve 15 has a fixed outer profile.

In another preferred form of the invention, lumen 47 for receiving inflation/deflation tube 45, lumens 52 for receiving support tubes 50 which receive hollow push tubes 30, and/or lumens 195 for slidably receiving instruments 190 may have an expandable configuration (i.e., they may have a minimal profile when empty and expand diametrically as needed when filled), so that the overall profile of sleeve 15 is minimized.

It should also be appreciated that where sleeve 15 comprises a plurality of lumens 195 for slidably receiving instruments 190 therein, it can be desirable to provide greater structural integrity to the distal ends of lumens 195 so as to provide improved support for the instruments 190 received within lumens 195. To this end, a support ring may be provided at the distal end of sleeve 15, wherein the support ring provides openings for the passage of hollow push tubes 30 and openings for the passage of instruments 190. Note that the openings in such a support ring for the passage of instruments 190 preferably make a close fit with the instruments so as to provide excellent instrument support at the distal end of sleeve 15.

Alternatively and/or additionally, lumens 195 may accommodate hollow instrument guide tubes which themselves accommodate instruments therein. Such hollow instrument guide tubes can provide greater structural integrity to the distal ends of lumens 195 so as to provide improved support for the instruments 190 received within lumens 195.

Figure 132:
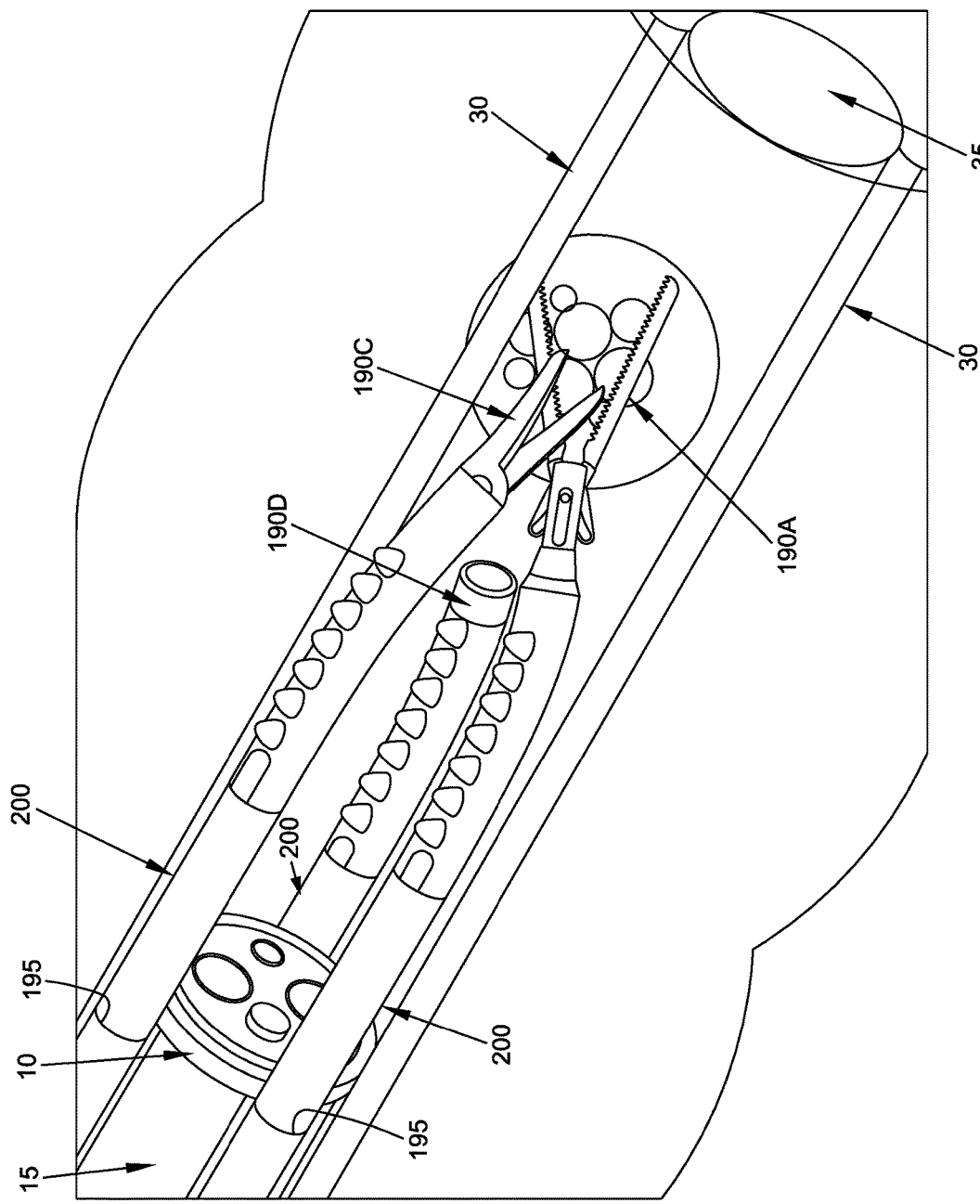
FIG. 132 is a schematic view showing instrument guide tubes which may be disposed in the additional lumens of the sleeve, wherein instruments may be advanced through the instrument guide tubes.

And such hollow instrument guide tubes may be of fixed geometry or of bendable or articulating geometry. See, for example, FIG. 132, which shows hollow instrument guide tubes 200 extending out of lumens 195 and receiving instruments 190 therein. Note that hollow instrument guide tubes 200 may be independently movable relative to one another (and independently movable relative to sleeve 15). Note also that instruments 190 preferably make a close fit with hollow instrument guide tubes 200 so as to provide excellent instrument support at the distal end of sleeve 15.

In another form of the present invention, the toroidal construction of fore balloon 35 may be replaced by a "conventional" balloon construction, i.e., by a balloon having a substantially uniform, full-diameter cross-section. In this form of the invention, the deflated fore balloon is not "docked" over the endoscope during insertion—instead, the deflated fore balloon resides alongside the endoscope during insertion; and in this form of the invention, the fore balloon is not "re-docked" back over the endoscope during withdrawal—instead, the balloon resides distal to the endoscope (or alongside the endoscope) during withdrawal. It will be appreciated that, in this form of the invention, the raised push tube bridge 31 can help retain the deflated fore balloon alongside the endoscope.

Distal Locking Assembly for Releasably Locking the Sleeve to the Endoscope

As discussed above, in one preferred form of the invention, apparatus 5 generally comprises a sleeve 15 adapted to be slid over the exterior of the shaft of endoscope 10, a proximal (or "aft") balloon 20 secured to sleeve 15 near the distal end of the sleeve, and a base 25 secured to sleeve 15 at the proximal end of the sleeve. In one preferred form of the invention, apparatus 5 also comprises a pair of hollow push tubes 30 slidably mounted to sleeve 15, the pair of hollow push tubes being connected to one another at their distal ends with a raised push tube bridge 31, the raised push tube bridge 31 being configured to nest an endoscope therein, and a distal (or "fore") balloon 35 being secured to the distal ends of hollow push tubes 30, such that the spacing between distal (or "fore") balloon 35 and proximal (or "aft") balloon 20 can be adjusted by the physician (or other operator or user) by moving hollow push tubes 30 relative to sleeve 15 (e.g., by distally advancing the two hollow push tubes simultaneously at push tube handle 37).

In one preferred form of the invention, sleeve 15 comprises a plurality of lumens 52 for slidably receiving hollow push tubes 30, and a plurality of lumens 195 for slidably receiving instruments 190.

Where sleeve 15 is configured to include a plurality of lumens 195 (for slidably receiving instruments 190 therein), it is generally desirable to keep lumens 195 circumferentially stationary (i.e., to keep lumens 195 from rotating) relative to endoscope 10, so that instruments 190 always have the same frame of reference with respect to the view provided by endoscope 10. By way of example but not limitation, where apparatus 5 has been advanced through a tortuous path (e.g., the colon of a patient), and where the physician is using endoscope 10 to view a surgical field while also using lumens 195 to manipulate one or more instruments 190 at the surgical field, it is generally desirable to maintain the positions of lumens 195 relative to endoscope 10 so as to also maintain the positions of instruments

190 relative to the endoscope. To this end, it can be undesirable if the distal end of sleeve 15 inadvertently moves (i.e., rotates) about endoscope 10 (particularly when apparatus 5 is advanced through a tortuous path), thereby causing lumens 195 to also move (i.e., rotate) relative to endoscope 10.

Figure 133:
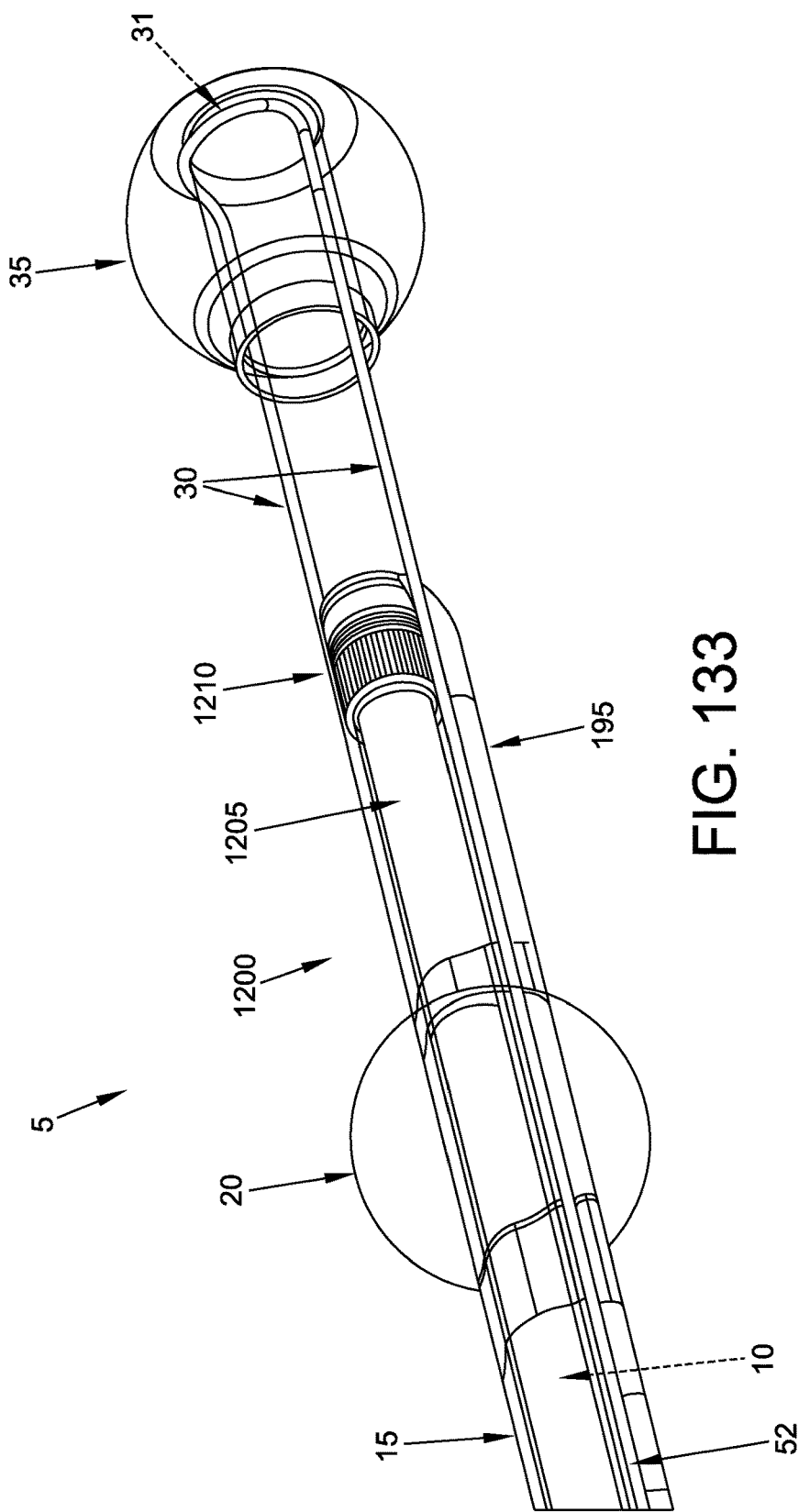
FIGS. 133 and 134 are schematic views showing a novel distal locking assembly for releasably locking the sleeve to the endoscope.
Figure 134:
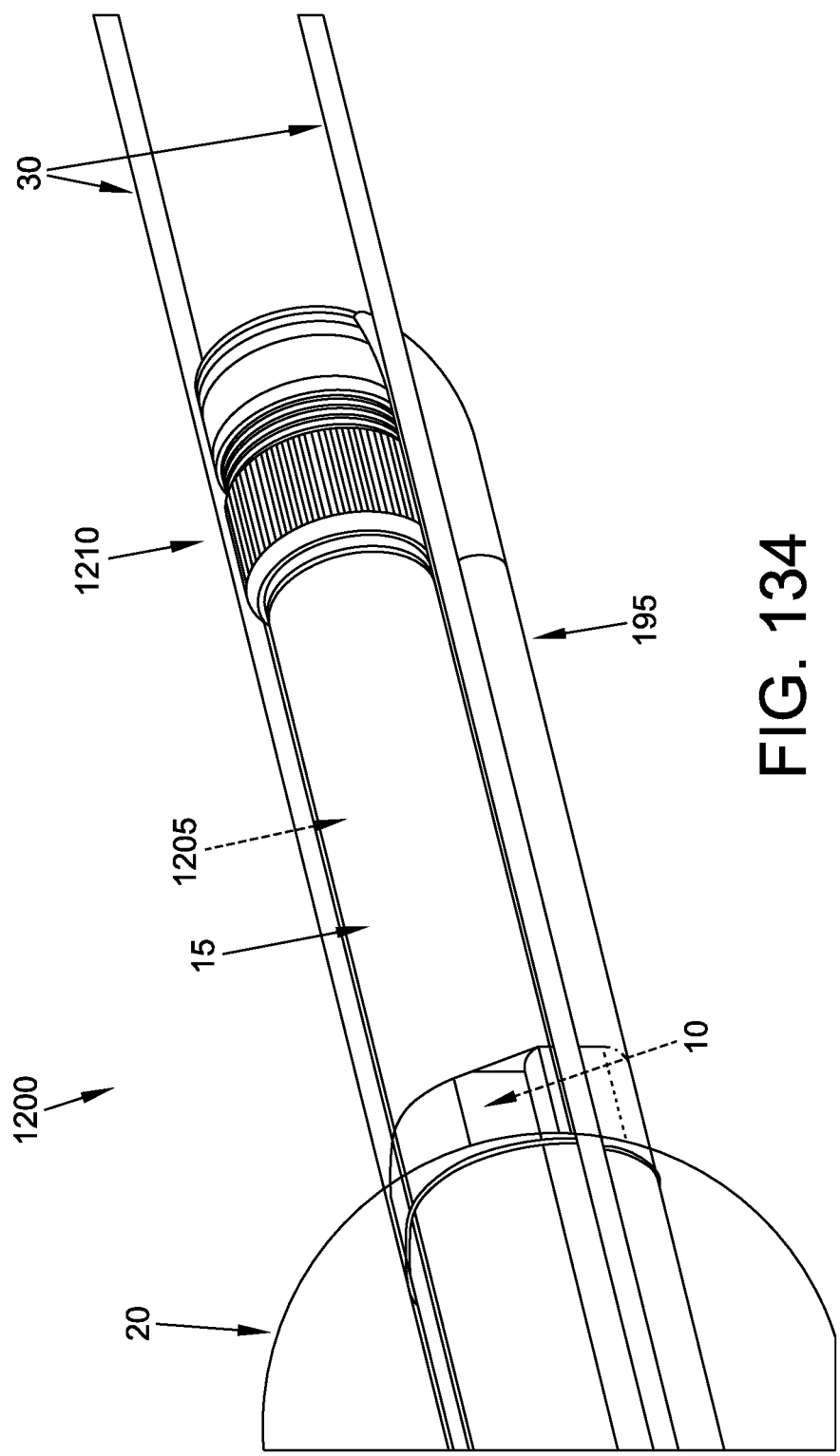

In order to address this issue, and looking now at FIGS. 133 and 134, in one form of the present invention there is provided a novel distal locking assembly 1200 which is disposed at the distal end of sleeve 15. Distal locking assembly 1200 generally comprises a tapered tube 1205 and a collet mechanism 1210 for selectively locking distal locking assembly 1200 (and hence the distal end of sleeve 15) to endoscope 10, as will hereinafter be discussed in further detail. Lumens 195 extend along sleeve 15 to the distal end of distal locking assembly 1200, as will hereinafter be discussed in further detail.

Tapered tube 1205 is mounted to (or formed integral with) the distal end of sleeve 15, with tapered tube 1205 being disposed internal to sleeve 15 (and with tapered tube 1205 being disposed external to endoscope 10). More particularly, tapered tube 1205 is radially compressible, and in the preferred form of the invention, the diameter of the tube is tapered from the proximal end to the distal end so as to act as a funnel for the insertion of the endosope into the tube.

Collet mechanism 1210 is mounted to the distal end of tapered tube 1205, with collet mechanism 1210 being disposed external to tapered tube 1205 (and external to sleeve 15). Collet mechanism 1210 can be selectively tightened in order to compress tapered tube 1205 inwardly and thereby bind tapered tube 1205 (and hence sleeve 15) to endoscope 10. More particularly, and looking now at FIGS. 135 and 136, collet mechanism 1210 generally comprises a collet base 1215 disposed circumferentially about the distal end of tapered tube 1205 (and disposed circumferentially about sleeve 15) and a collet cap 1220 adapted to threadingly engage collet base 1215.

Collet base 1215 comprises a threaded proximal portion 1225 for engagement by collet cap 1220, a plurality of flexible fingers 1230 extending proximally from threaded proximal portion 1225 for selectively binding collet mechanism 1210 (and hence tapered tube 1205 and sleeve 15) to endoscope 10, and one or more seats 1235 formed in the distal end portion of collet base 1215 for receiving one or more lumens 195. Each of the flexible fingers 1230 preferably comprises a tapered surface 1237.

Collet cap 1220 comprises a threaded distal portion 1240 for engaging threaded proximal portion 1225 of collet base 1215, and an inwardly-tapered proximal portion 1245 for engaging tapered surfaces 1237 of the plurality of flexible fingers 1230 of collet base 1215. As a result of this construction, when collet cap 1220 is advanced relative to collet base 1215 (i.e., when collet cap 1220 is rotated so as to be advanced distally relative to collet base 1215), inwardly-tapered proximal portion 1245 of collet cap 1220 engages tapered surfaces 1237 of flexible fingers 1230 of collet base 1215 and flexes the flexible fingers 1230 radially inwardly, whereby to compress tapered tube 1205 inwardly and thereby bind tapered tube 1205 (and hence sleeve 15) to endoscope 10.

It will be appreciated that when apparatus 5 is to be mounted to endoscope 10 (i.e., prior to a procedure), distal locking assembly 1200 is initially in its unlocked condition (i.e., with collet cap 1220 not screwed onto collet base 1215) as apparatus 5 is mounted to the endoscope. Thereafter, distal locking assembly 1200 is placed into its locked condition (i.e., collet cap 1220 is screwed onto collet base 1215) so that collet mechanism 1210 compresses tapered tube 1205 inwardly and thereby binds tapered tube 1205 (and hence sleeve 15) to endoscope 10. Then endoscope 10 and apparatus 5 may be used for a procedure. At the conclusion of the procedure, apparatus 5 can be dismounted from endoscope 10 by placing distal locking assembly 1200 into its unlocked condition (i.e., by unscrewing collet cap 1220 from collet base 1215) so that collet mechanism 1210 is no longer compressing tapered tube 1205 inwardly and binding tapered tube 1205 (and hence sleeve 15) to endoscope 10, and then apparatus 5 may be dismounted from the endoscope.

Figure 135:
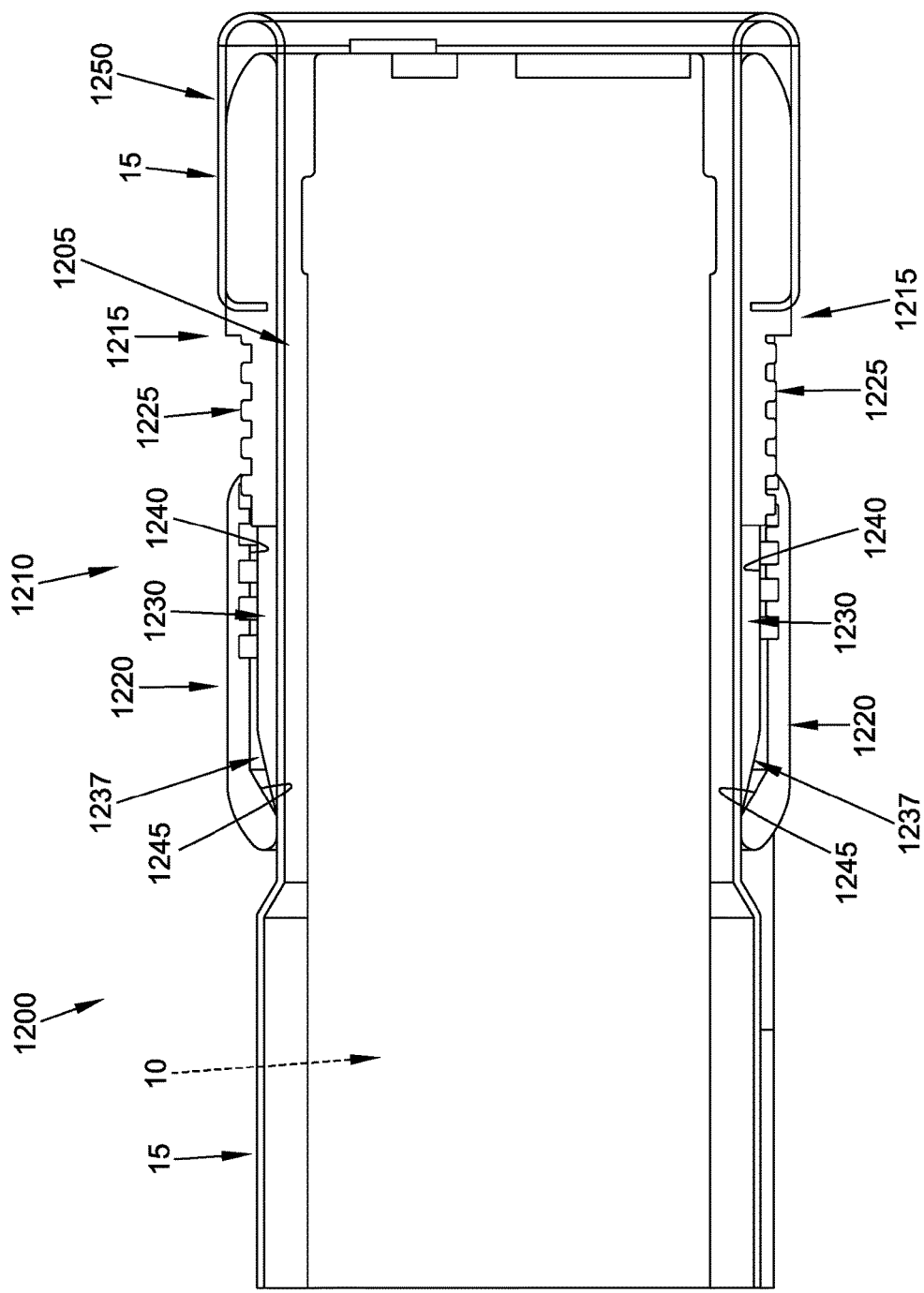
FIGS. 135 and 136 are schematic views showing further details of a collet mechanism of the distal locking assembly of FIGS. 133 and 134.
Figure 136:
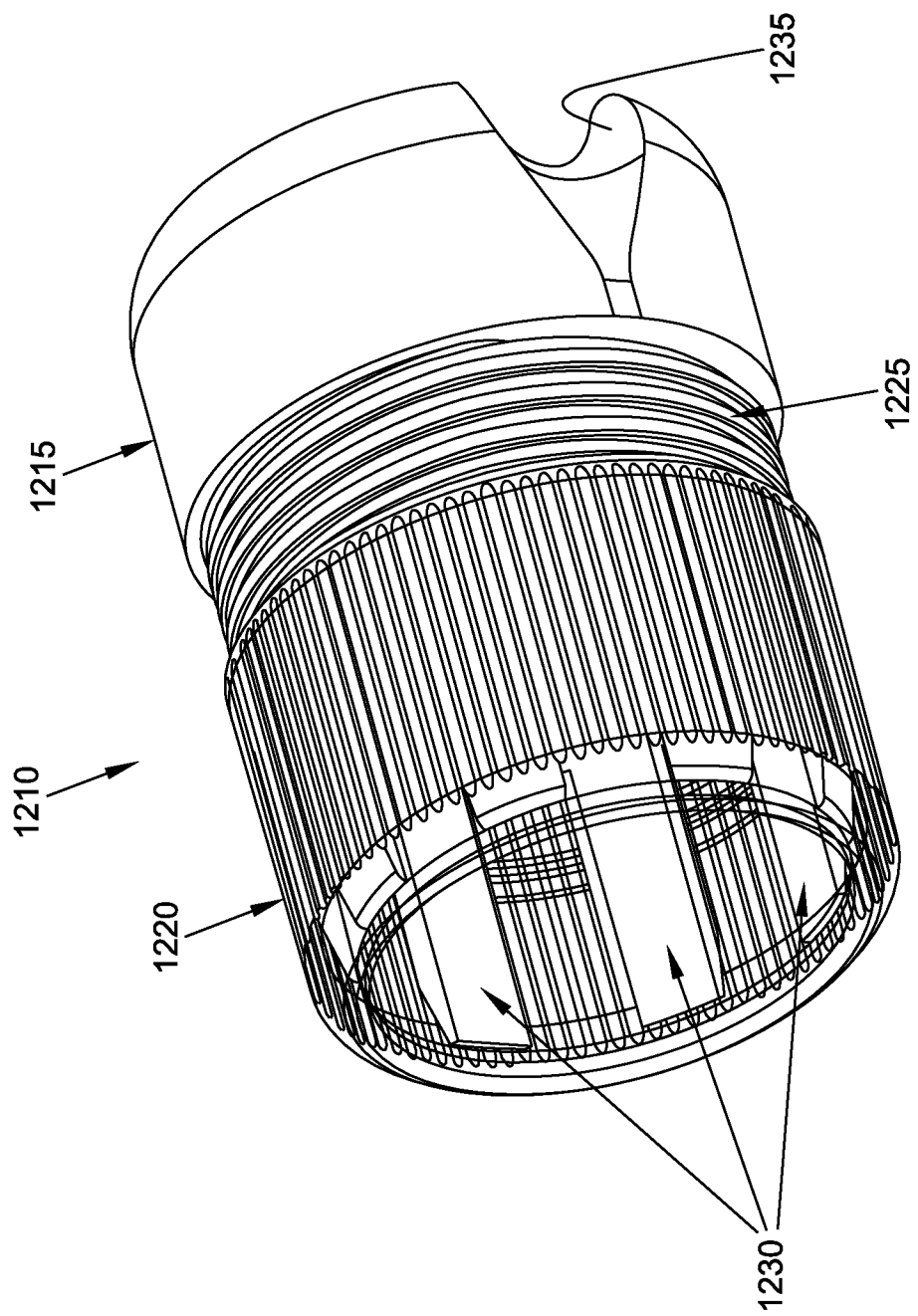
Figure 137:
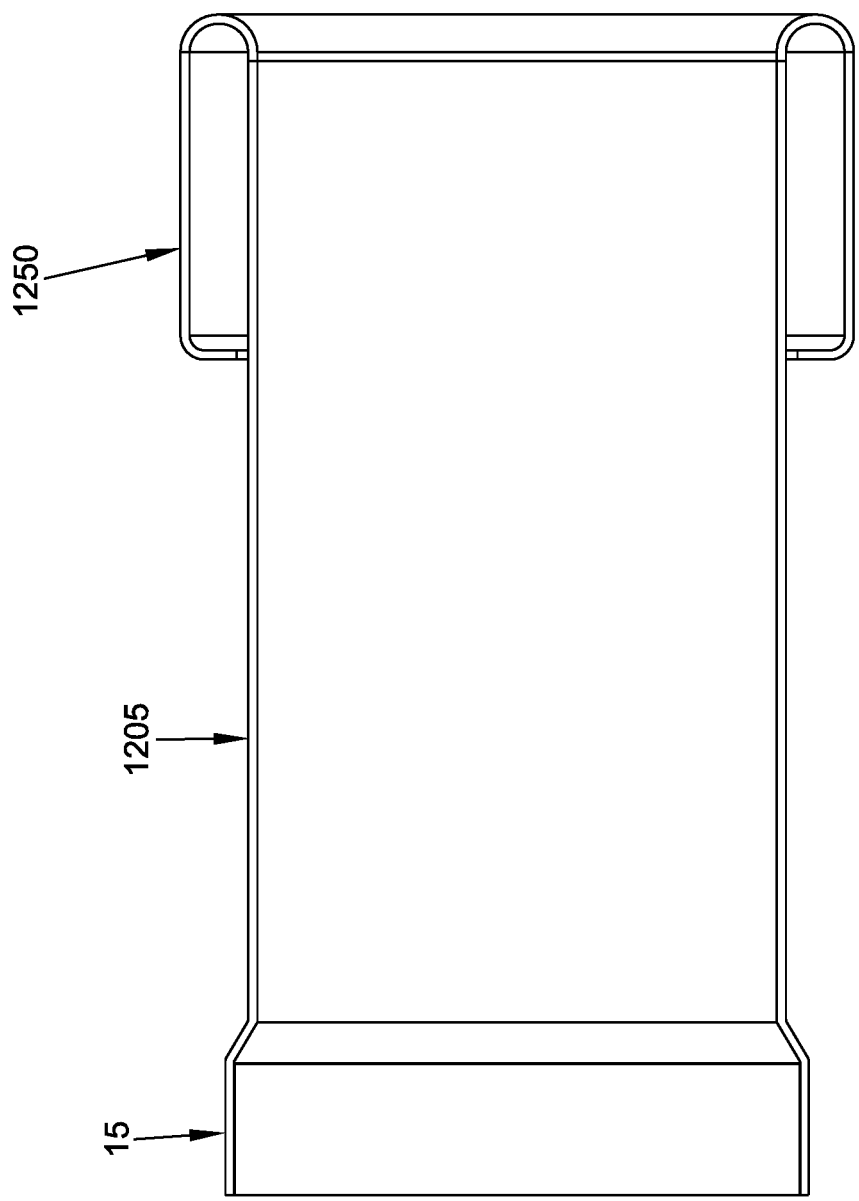
FIG. 137 is a schematic view showing, in conjunction with FIG. 135, how the distal end of the sleeve can be everted over the distal end of the collet mechanism so as to form an elastomeric distal boot (note that in FIG. 137, only the tapered tube and sleeve are shown, and the collet mechanism is omitted, for clarity of illustration)

In one preferred form of the invention, the distal end of sleeve 15 is everted back over the distal end of collet base 1215 so as to form an elastomeric distal boot 1250 (FIGS. 135 and 137). Note that elastomeric distal boot 1250 is also disposed circumferentially about the one or more lumens 195 seated in the one or more seats 1235 of collet base 1215. Also note that the distal end of sleeve 15 comprises one or more slits aligned with the one or more lumens 195 so that an instrument emerging from a lumen 195 can pass by the everted distal end of sleeve 15. Elastomeric distal boot 1250 provides an atraumatic distal end to distal locking assembly 1200 and keeps lumens 195 in position within seats 1235 of collet base 1215. Elastomeric distal boot 1250 also provides a smaller atraumatic distal end for distal locking assembly 1200 by keeping lumens 195 folded into position within seats 1235 of collet base 1215 when instruments 190 are absent from lumens 195, which can facilitate insertion of apparatus 5 into a patient. In a preferred form of the present invention, elastomeric distal boot 1250 exerts sufficient inwardly-directed force so as to capture lumens 195 in seats 1235 of collet base 1215 and so as to close-off the distal end(s) of lumen(s) 195 when instrument(s) 190 are not disposed within lumen(s) 195. At the same time, elastomeric distal boot 1250 is preferably sufficiently elastic such that an instrument 190 can easily force the distal end of a given lumen 195 radially outwardly, out of seats 1235 of collet base 1215, and force the distal end of a given lumen 195 open when an instrument 190 is advanced distally out of the distal end of a given lumen 195 (and out of a corresponding slit in sleeve 15). As a result of this construction, lumen(s) 195 are effectively folded into seats 1235 of collet base 1215, and are effectively self-sealing, when instrument(s) 190 are absent from lumen(s) 195, thereby providing a reduced distal profile for apparatus 5 and also preventing ingress of material (e.g., blood, bodily fluids, etc.) into lumen(s) 195 when lumen(s) 195 are not in use. In addition, when instrument(s) 190 are disposed within lumen(s) 195, elastomeric distal boot 1250 also causes lumen(s) 195 to seal around instrument(s) 190.

Figure 140:
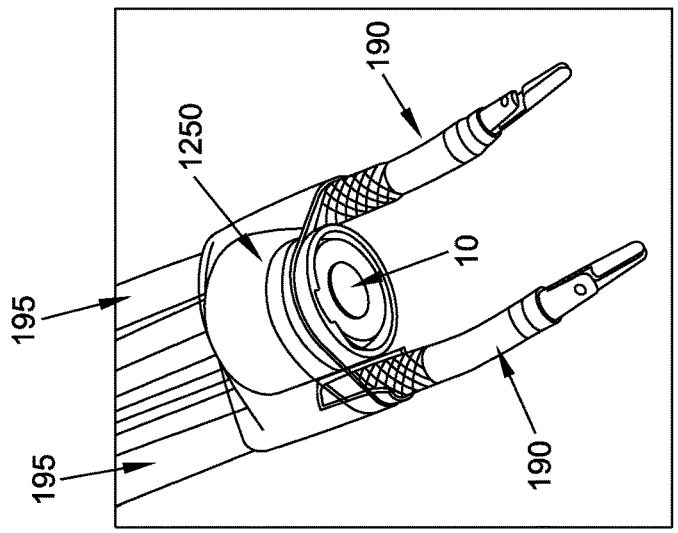
FIGS. 138-140 are schematic views showing another way of forming an elastomeric distal boot.
Figure 139:
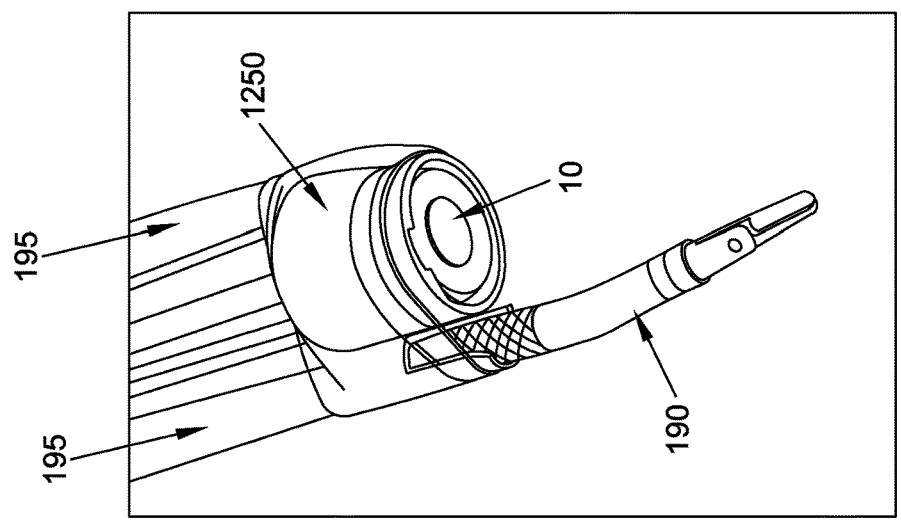
Figure 138:
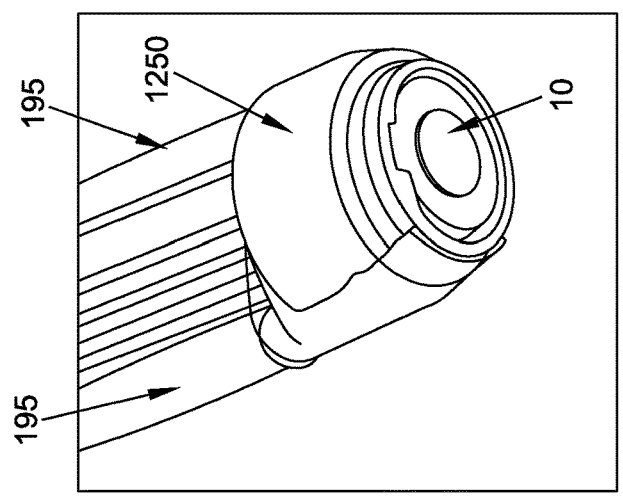

In another preferred form of the invention, and looking now at FIGS. 138-140, the distal end of sleeve 15 is not everted back over the distal end of collet base 1215. Instead, in this form of the invention, elastomeric distal boot 1250 comprises an elastomeric ring which is fit over the distal end of collet base 1215 (and over the one or more lumens 195 seated in the one or more seats 1235 of collet base 1215) so as to form the elastomeric distal boot 1250 (FIG. 138). Again, elastomeric distal boot 1250 provides an atraumatic distal end to distal locking assembly 1200 and keeps lumens 195 in position within seats 1235 of collet base 1215. Elastomeric distal boot 1250 also provides a smaller atraumatic distal end for distal locking assembly 1200 by keeping lumens 195 folded into position within seats 1235 of collet base 1215 (FIG. 138) when instruments 190 are absent from lumens 195, which can facilitate insertion of apparatus 5 into a patient. In a preferred form of the present invention, elastomeric distal boot 1250 exerts sufficient inwardly-directed force so as to capture lumens 195 in seats 1235 of collet base 1215 and so as to close-off the distal end(s) of lumen(s) 195 when instrument(s) 190 are not disposed within lumen(s) 195. At the same time, elastomeric distal boot 1250 is preferably sufficiently elastic such that an instrument 190 can easily force the distal end of a given lumen 195 radially outwardly, out of seats 1235 of collet base 1215, and force the distal end of a given lumen 195 open when an instrument 190 is advanced distally out of the distal end of a given lumen 195 (FIGS. 138 and 139). As a result of this construction, lumen(s) 195 are effectively folded into seats 1235 of collet base 1215, and are effectively self-sealing, when instrument(s) 190 are absent from lumen(s) 195, thereby providing a reduced distal profile for apparatus 5 and also preventing ingress of material (e.g., blood, bodily fluids, etc.) into lumen(s) 195 when lumen(s) 195 are not in use. In addition, when instrument(s) 190 are disposed within lumen(s) 195, elastomeric distal boot 1250 also causes lumen(s) 195 to seal around instrument(s) 190.

It should be appreciated that, in a preferred form of the invention, push tubes 30 are not mounted to distal locking assembly 1200, and are free to move longitudinally relative to distal locking assembly 1200.

Figure 141:
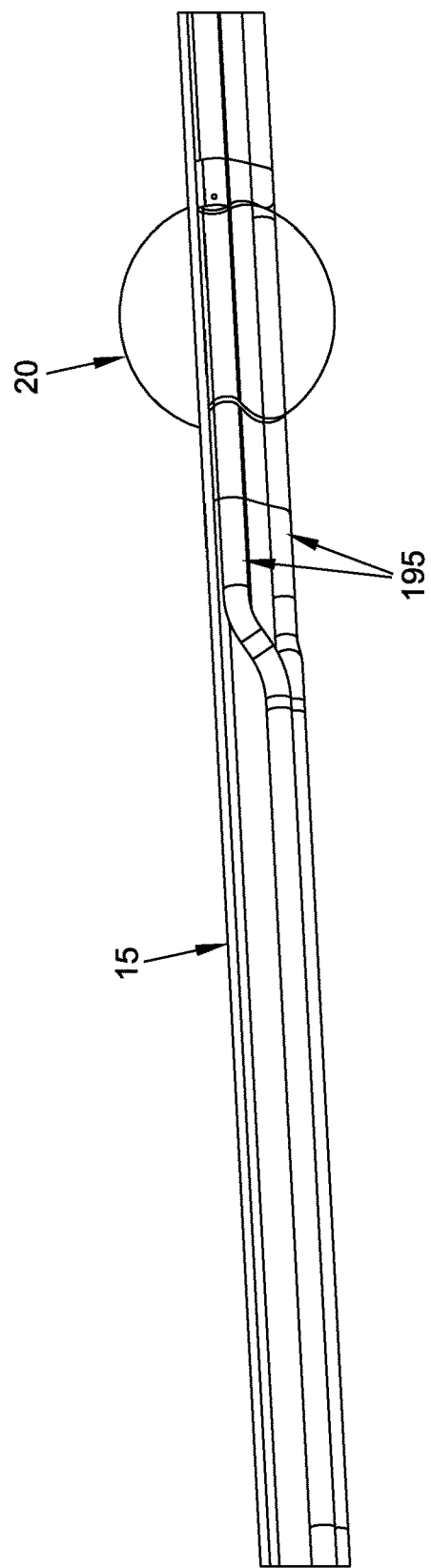
FIG. 141 is a schematic view showing one configuration for how multiple instrument lumens may be mounted to the sleeve.

In addition, and looking now at FIG. 141, it should be appreciated that lumen(s) 195 (for receiving instruments 190) can be carried by sleeve 15 along most of the length of sleeve 15 (or from a location intermediate the distal and proximal ends of sleeve 15) in close relation to one another, and then diverge from one another so that the distal ends of lumen(s) 195 are disposed about the distal end of distal locking assembly 1200 (and hence, the distal end of endoscope 10) in a preferred orientation, e.g., at the "3 o'clock" position and the "9 o'clock" position, etc.

In another preferred form of the invention, and looking now at FIGS. 142-145, there is shown another distal locking assembly 1200A for binding the distal end of sleeve 15 to an endoscope. More particularly, in this form of the invention, distal locking assembly 1200A comprises tapered tube 1205A, a collet mechanism 1210A and an elastomeric distal boot 1250A.

Sheath 15 is secured to the proximal end of tapered tube 1205A, with sheath 15 overlying tapered tube 1205A. Tapered tube 1205A is radially compressible, and in the preferred form of the invention, the diameter of the tube is tapered from the proximal end to the distal end so as to act as a funnel for the insertion of the endosope into the tube. Collet mechanism 1210A is mounted to the distal end of tapered tube 1205A, with the collet mechanism being disposed external to tapered tube 1205A, and collet mechanism 1210A can be selectively tightened in order to compress tapered tube 1205A inwardly and thereby bind tapered tube 1205A (and hence sleeve 15) to endoscope 10.

Figure 142:
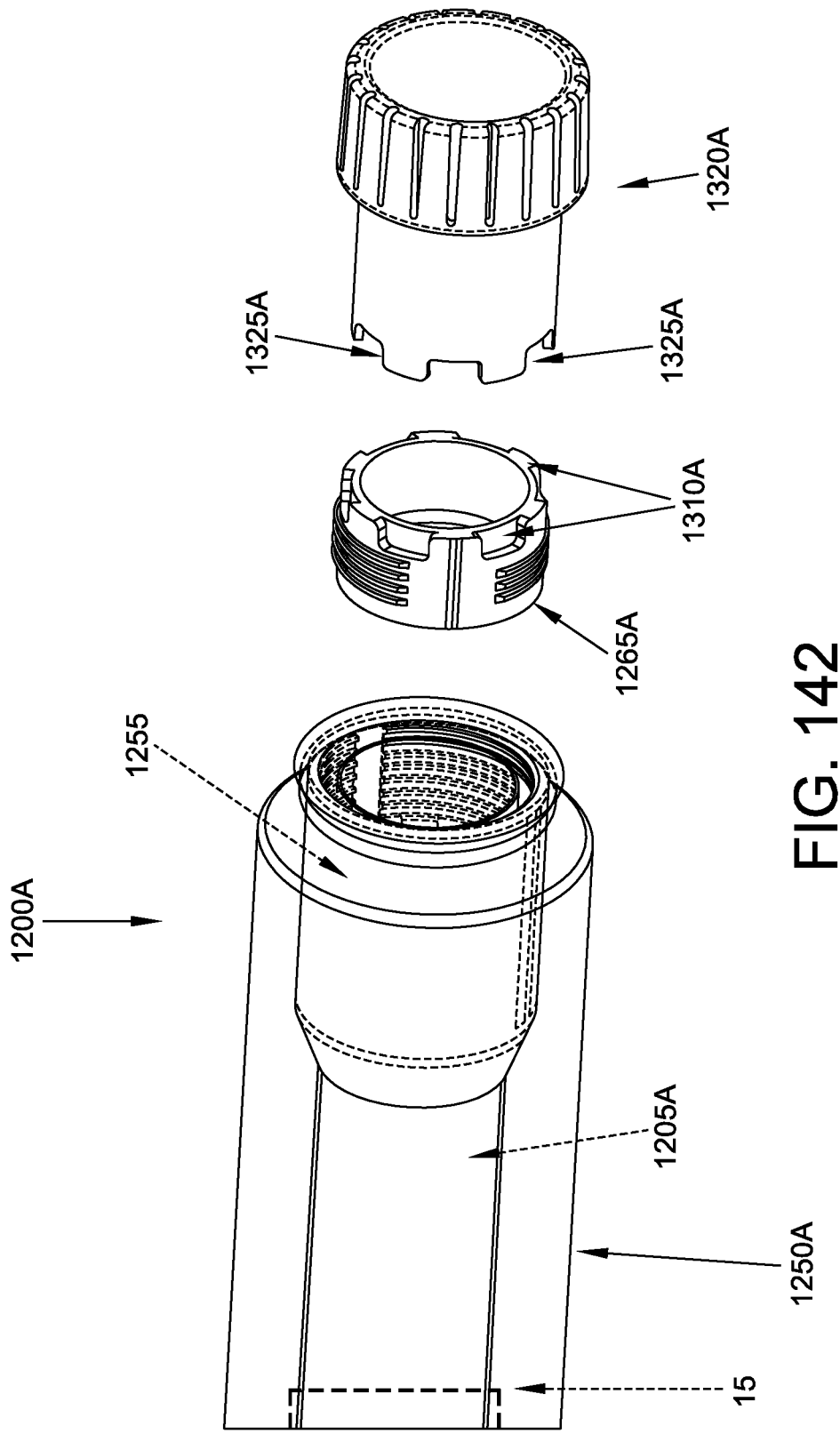
FIGS. 142-145 are schematic views showing another distal locking assembly for releasably locking the sleeve to the endoscope.
Figure 143:
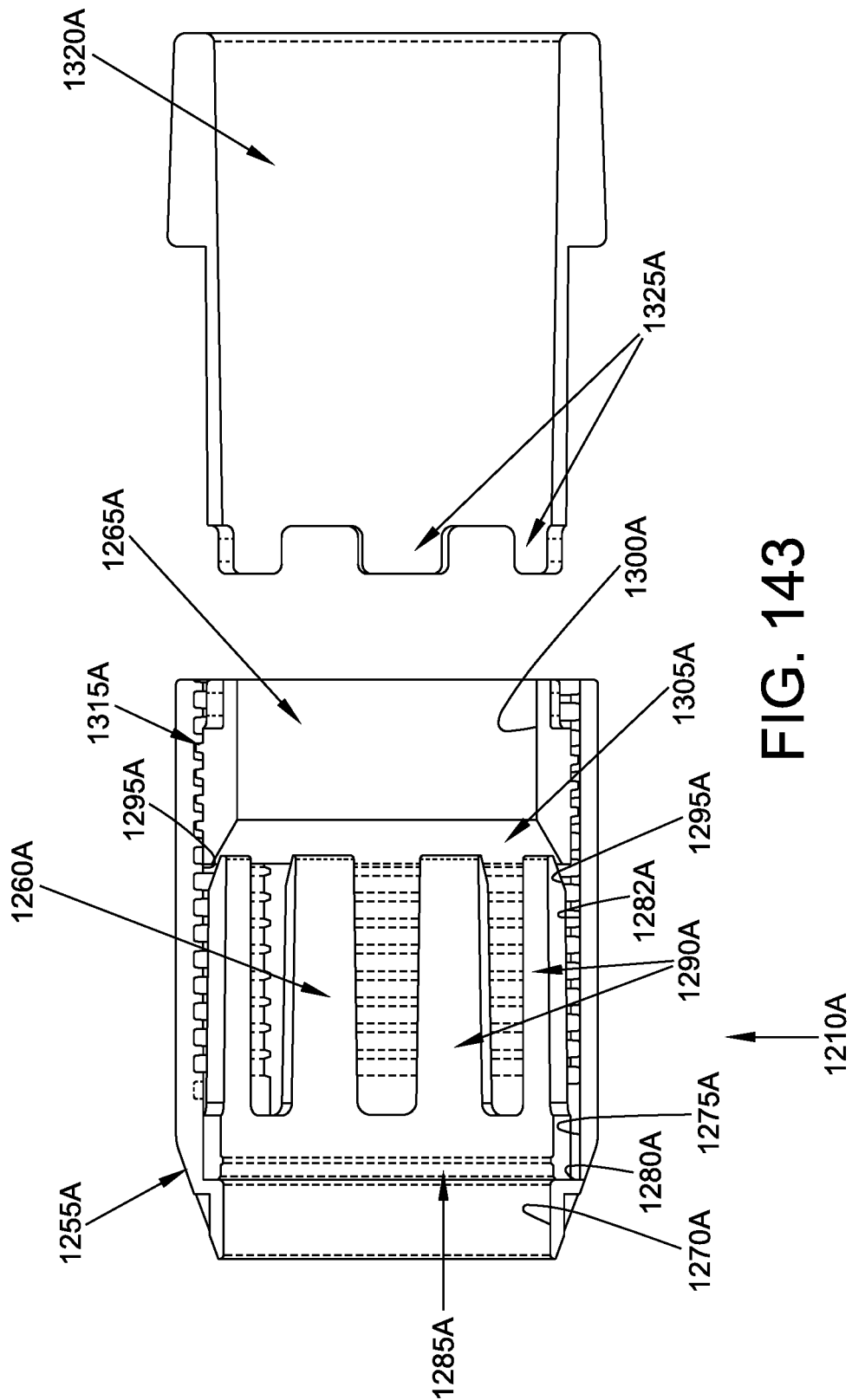
Figure 144:
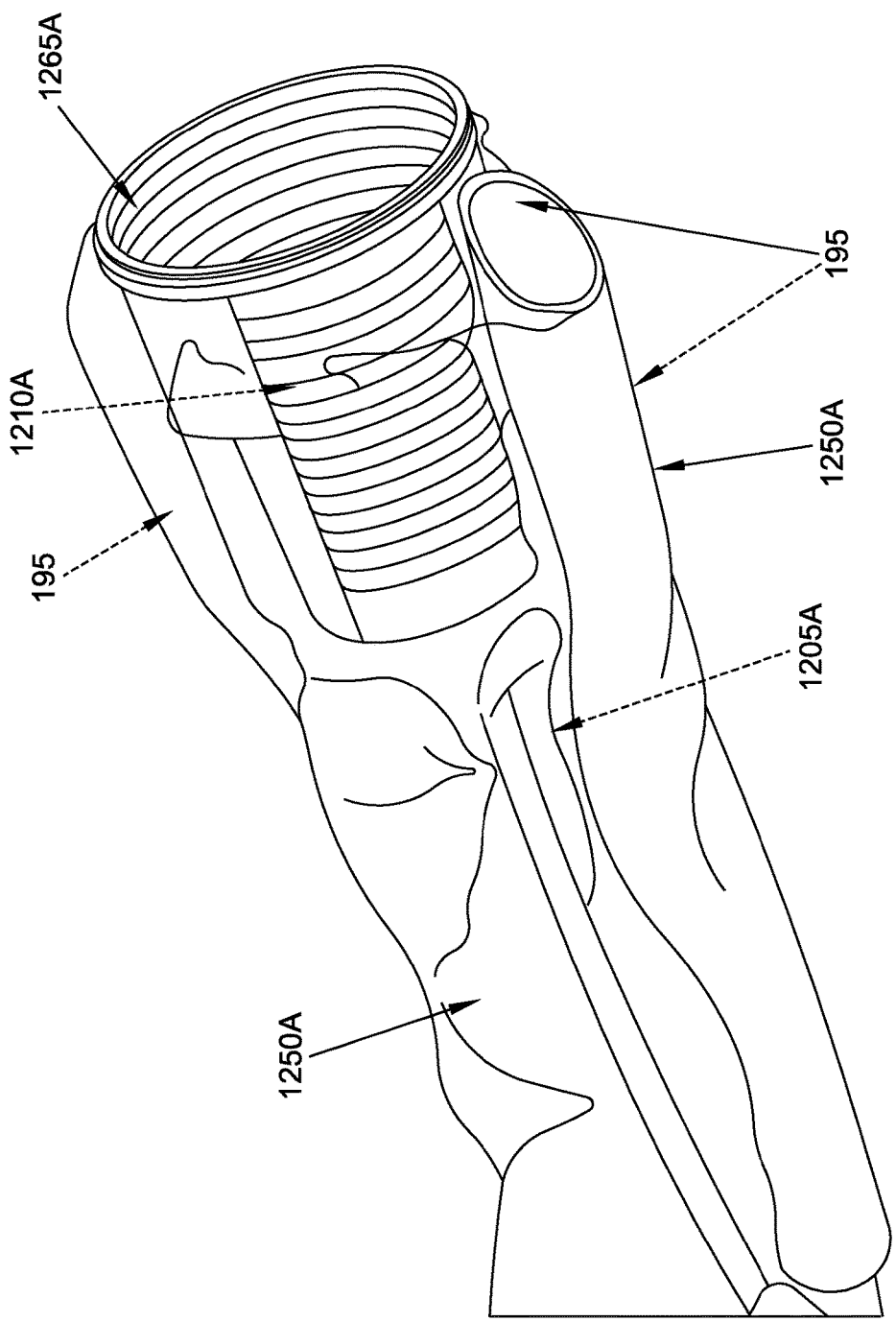
Figure 145:
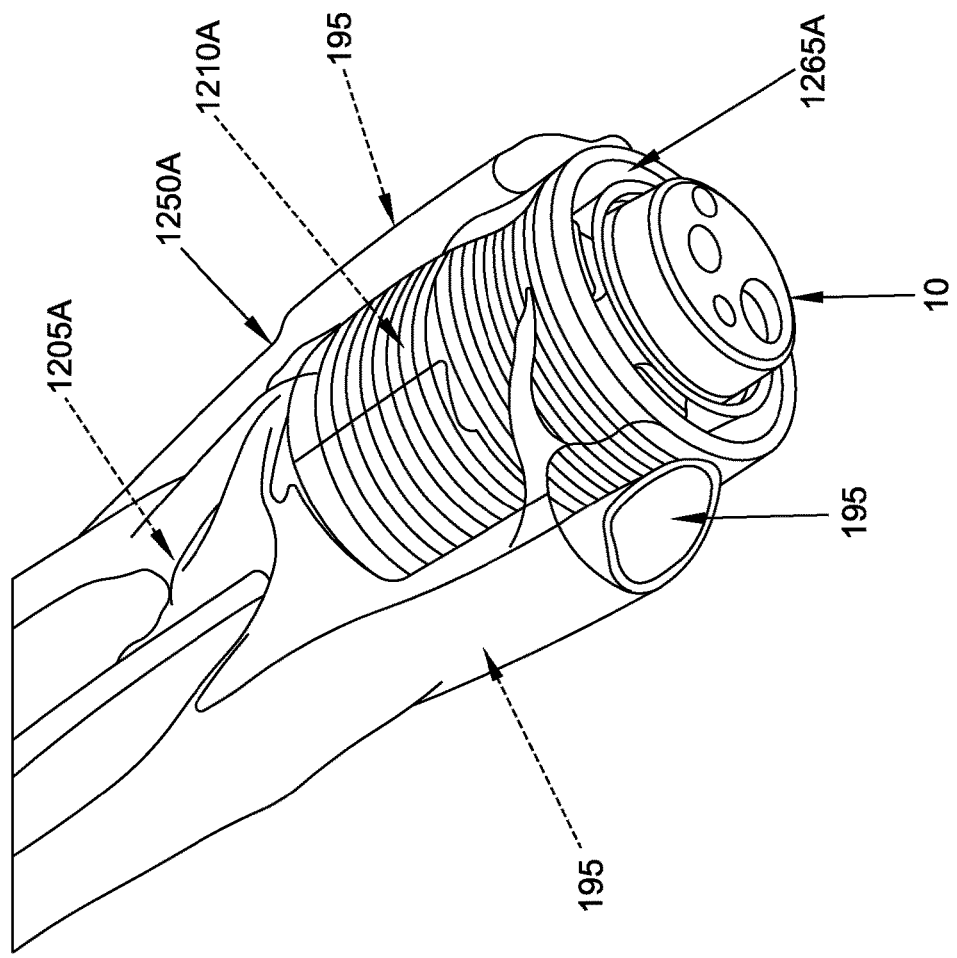

More particularly, collet mechanism 1210A generally comprises a proximal collet 1255A, a middle collet 1260A and a distal collet 1265A. Proximal collet 1255A comprises a bore 1270A, a counterbore 1275A and an annular shoulder 1280A. Counterbore 1275A comprises threads 1282A. Middle collet 1260A comprises an annular body 1285A and a plurality of flexible fingers 1290A extending distally from annular body 1285A. Flexible fingers 1290A terminate in tapered surfaces 1295A. Distal collet 1265A comprises a tubular body comprising a lumen 1300A terminating in a tapered annulus 1305A on its proximal end and a plurality of ears 1310A on its distal end (FIG. 142). Distal collet 1265A comprises threads 1315A on its exterior surface. Proximal collet 1255A is secured to the distal end of tapered tube 1205A, middle collet 1260A is disposed within counterbore 1275A of proximal collet 1255A so that its annular body 1285A abuts annular shoulder 1280A and is secured in place, and distal collet 1265A is disposed within middle collet 1260A with threads 1315A of distal collet 1265A engaging threads 1282A of proximal collet 1255A. As a result of this construction, when distal collet 1265A is moved proximally relative to proximal collet 1255A, tapered annulus 1305A engages tapered surfaces 1295A of flexible fingers 1290A and flexes the flexible fingers 1290A radially inwardly, whereby to compress tapered tube 1205 onto endoscope 10 and hence bind sleeve 15 to endoscope 10.

A collet tool 1320A, comprising fingers 1325A, is provided for turning distal collet 1265A relative to proximal collet 1255A.

Elastomeric distal boot 1250A is disposed over the exterior of tapered tube 1205A and collet mechanism 1210A so as to provide an atraumatic distal tip and so as to secure lumens 195 to tapered tube 1205A. In the embodiment shown in FIGS. 144 and 145, elastomeric distal boot 1250A is disposed over lumens 195, but does not compress lumens 195 inboard against tapered tube 1205A and collet mechanism 1210A. Furthermore, elastomeric distal boot 1250A does not cover the distal openings of lumens 195. However, if desired, elastomeric distal boot 1250A could yieldably compress lumens 195 inboard against tapered tube 1205A and collet mechanism 1210A and/or elastomeric distal boot 1250A could cover the distal openings of lumens 195 so as to seal the lumens and prevent ingress of material (e.g., blood, bodily fluids, etc.) into lumen(s) 195 when lumen(s) 195 are not in use.

It will be appreciated that when apparatus 5 is to be mounted to endoscope 10 (i.e., prior to a procedure), distal locking assembly 1200A is initially in its unlocked condition (i.e., with distal collet 1265A not flexing flexible fingers 1290A of middle collet 1260A) as apparatus 5 is mounted to the endoscope. Thereafter, distal locking assembly 1200A is placed into its locked condition (i.e., distal collet 1265A is moved proximally (via collet tool 1320A) so as to cam flexible fingers 1290A of middle collet 1260A inwardly, whereby to compress tapered tube 1205A inwardly and thereby bind tapered tube 1205A (and hence sleeve 15) to endoscope 10. Then endoscope 10 and apparatus 5 may be used for a procedure. At the conclusion of the procedure, apparatus 5 can be dismounted from endoscope 10 by placing distal locking assembly 1200A into its unlocked condition (i.e., by unscrewing distal collet 1265A away from flexible fingers 1290A of middle collet 1260A) so that sleeve 15 is no longer bound to endoscope 10, and then apparatus 5 may be dismounted from the endoscope.

It will also be appreciated that sleeve 15 and distal locking mechanisms 1200 and 1200A can be provided in different sizes so as to accommodate different sizes of endoscopes. By way of example but not limitation, a small distal collet 1265A having a lumen 1300A with a small inner diameter can be provided for accommodating endoscopes having a small diameter, and a large distal collet 1265A having a lumen 1300A with a large inner diameter can be provided for accommodating endoscopes having a large diameter. Thus, if the user has a large diameter endoscope that does not fit inside the small lumen 1300A of a small distal collet 1265A, the user can replace the small lumen distal collet with a large lumen distal collet so as to accommodate the larger diameter endoscope. Preferably, the remaining components of distal locking assembly 1200A (i.e., tapered tube 1205A, proximal collet 1255A, middle collet 1260A and elastomeric distal boot 1250A) are provided in a single size.

Applications

Thus it will be seen that the present invention comprises the provision and use of novel apparatus for manipulating the side wall of a body lumen and/or body cavity so as to better present the side wall tissue (including visualization of areas which may be initially hidden from view or outside the field of view) for examination and/or treatment during an endoscopic procedure, e.g., to straighten bends, "iron out" inner luminal surface folds and create a substantially static or stable side wall of the body lumen and/or body cavity which enables more precise visual examination (including visualization of areas which may be initially hidden from view or outside the field of view) and/or therapeutic intervention. By way of example but not limitation, the novel apparatus can be used to stabilize, straighten, expand and/or flatten bends and/or curves and/or folds in the side wall of the intestine so as to better present the side wall tissue (including visualization of areas which may be initially hidden from view or outside the field of view) for examination and/or treatment during an endoscopic procedure.

The present invention also comprises the provision and use of novel apparatus capable of steadying and/or stabilizing the distal tips and/or working ends of instruments (e.g., endoscopes, articulating and/or non-articulating devices such as graspers, cutters or dissectors, cauterizing tools, ultrasound probes, etc.) inserted into a body lumen and/or body cavity during an endoscopic procedure with respect to the side wall of the body lumen and/or body cavity, whereby to facilitate the precision use of those instruments.

By way of example but not limitation, the present apparatus can provide a stable platform (i.e., a stable endoscope, stable therapeutic tools and a stable colon wall, all stable with respect to one another) for the performance of numerous minimally-invasive procedures within a body lumen and/or body cavity, including the stabilization of an endoscope and/or other surgical instruments (e.g., graspers, cutters or dissectors, cauterizing tools, ultrasound probes, etc.) within the body lumen and/or body cavity, e.g., during a lesion biopsy and/or lesion removal procedure, an organ resection procedure, endoscopic submucosal dissection (ESD), endoscopic mucosal resection (EMR), etc., while at the same time stabilizing the colon (including decreasing deformation of the colon wall) so as to enable more precise visualization, intervention and/or surgery.

Significantly, the present invention provides novel apparatus capable of steadying and/or stabilizing the distal tips and/or working ends of endoscopes (and hence also steadying and/or stabilizing the distal tips and/or working ends of other instruments inserted through the working channels of those endoscopes, such as graspers, cutters or dissectors, cauterizing tools, ultrasound probes, etc.) with respect to the side wall of the body lumen and/or body cavity, and stabilizing the side wall of the body lumen and/or body cavity relative to these instruments.

And the present invention provides novel apparatus capable of steadying and/or stabilizing the distal tips and/or working ends of instruments (such as graspers, cutters or dissectors, cauterizing tools, ultrasound probes, etc.) advanced to the surgical site by means other than through the working channels of endoscopes.

The novel apparatus of the present invention can be used in substantially any endoscopic procedure to facilitate the alignment and presentation of tissue during an endoscopic procedure and/or to stabilize the working end of an endoscope (and/or other instruments advanced through the endoscope) relative to tissue or to assist in the advancement of the endoscope during such a procedure.

The present invention is believed to have widest applications with respect to the gastrointestinal (GI) tract (e.g., large and small intestines, esophagus, stomach, etc.), which is generally characterized by frequent turns and which has a side wall characterized by numerous folds and disease processes located on and between these folds. However, the methods and apparatus of the present invention may also be used inside other body lumens (e.g., blood vessels, lymphatic vessels, the urinary tract, fallopian tubes, bronchi, bile ducts, etc.) and/or inside other body cavities (e.g., the head, chest, abdomen, nasal sinuses, bladder, cavities within organs, etc.).

Modifications

While the present invention has been described in terms of certain exemplary preferred embodiments, it will be readily understood and appreciated by those skilled in the art that it is not so limited, and that many additions, deletions and modifications may be made to the preferred embodiments discussed above while remaining within the scope of the present invention.

What is claimed is:

1. Apparatus comprising:
   a sleeve adapted to be slid over the exterior of an endoscope, the sleeve having a distal end and a proximal end;
   an aft balloon secured to the sleeve;
   a fore balloon movably mounted to the sleeve so that the fore balloon may be advanced relative to the sleeve; and
   a locking assembly for releasably securing the distal end of the sleeve to the endoscope, wherein the locking assembly comprises:
      a tapered tube mounted to the distal end of the sleeve; and
      a collet mechanism for selectively compressing the tapered tube against the endoscope, wherein the collet mechanism comprises a proximal collet, a middle collet, and a distal collet, and further wherein the proximal collet is secured to the tapered tube and comprises threads, the middle collet is secured to the proximal collet and comprises a plurality of flexible fingers, and the distal collet comprises threads for engaging the threads of the proximal collet, such that when the distal collet is advanced towards the proximal end of the proximal collet, the flexible fingers of the middle collet are compressed onto the tapered tube.

2. Apparatus according to claim 1 wherein the tapered tube is formed separately from the distal end of the sleeve and secured thereto during manufacture.

3. Apparatus according to claim 1 wherein the tapered tube is formed integral with the distal end of the sleeve.

4. Apparatus according to claim 1 wherein the plurality of flexible fingers of the middle collet comprise tapered portions, and wherein the distal collet comprises a tapered portion, and further wherein the tapered portion of the distal collet engages the tapered portions of the plurality of flexible fingers of the middle collet when the threaded portion of the distal collet is screwed onto the threaded portion of the proximal collet.

5. Apparatus according to claim 4 wherein the plurality of flexible fingers extend distally from the middle collet.

6. Apparatus according to claim 4 wherein the distal collet moves proximally when the threaded portion of the distal collet is screwed onto the threaded portion of the proximal collet.

7. Apparatus according to claim 1 wherein the sleeve comprises at least one instrument lumen, and further wherein the proximal collet comprises at least one seat for receiving the at least one instrument lumen of the sleeve.

8. Apparatus according to claim 7 wherein the at least one instrument lumen comprises at least one tube mounted to the exterior of the sleeve.

9. Apparatus according to claim 8 wherein the at least one tube is formed integral with the sleeve.

10. Apparatus according to claim 8 wherein the apparatus comprises an elastomeric boot for yieldably maintaining the at least one instrument lumen in the at least one seat of the proximal collet.

11. Apparatus according to claim 10 wherein the elastomeric boot is formed by everting the sleeve around the distal end of the proximal collet.

12. Apparatus according to claim 10 wherein the elastomeric boot comprises an elastomeric ring disposed around the distal end of the proximal collet.

13. Apparatus according to claim 1 wherein the fore balloon is movably mounted to the sleeve by a pair of hollow push tubes slidably mounted to the sleeve.

14. Apparatus according to claim 13 wherein the pair of hollow push tubes comprise distal ends, and further wherein the distal ends of the pair of hollow push tubes are connected to one another with a raised push tube bridge, the raised push tube bridge being configured to nest the endoscope therein.

15. Apparatus according to claim 13 wherein the pair of hollow push tubes comprise distal ends, wherein the fore balloon is secured to the distal ends of the pair of hollow push tubes, wherein the interior of the fore balloon is in fluid communication with the interiors of the pair of hollow push tubes, and wherein the fore balloon is capable of assuming a deflated condition and an inflated condition.

16. Apparatus according to claim 15 wherein (i) when the fore balloon is in its deflated condition, an axial opening extends therethrough, the axial opening being sized to receive the endoscope therein, and (ii) when the fore balloon is in its inflated condition, the axial opening is closed down.

17. Apparatus according to claim 1 wherein the endoscope is steerable, and further wherein the aft balloon is secured to the sleeve proximal to the articulating portion of the steerable endoscope.

18. Apparatus according to claim 1 further comprising an elastomeric distal boot disposed about the distal end of the proximal collet.

19. Apparatus according to 18 wherein the elastomeric distal boot covers the entire proximal collet.

20. A method for performing a procedure in a body lumen and/or body cavity, said method comprising:
  providing apparatus comprising:
    a sleeve adapted to be slid over the exterior of an endoscope, the sleeve having a distal end and a proximal end;
    an aft balloon secured to the sleeve;
    a fore balloon movably mounted to the sleeve so that the fore balloon may be advanced relative to the sleeve; and
    a locking assembly for releasably securing the distal end of the sleeve to the endoscope, wherein the locking assembly comprises:
      a tapered tube mounted to the distal end of the sleeve; and
      a collet mechanism for selectively compressing the tapered tube against the endoscope, wherein the collet mechanism comprises a proximal collet, a middle collet, and a distal collet, and further wherein the proximal collet is secured to the tapered tube and comprises threads, the middle collet is secured to the proximal collet and comprises a plurality of flexible fingers, and the distal collet comprises threads for engaging the threads of the proximal collet, such that when the distal collet is advanced towards the proximal end of the proximal collet, the flexible fingers of the middle collet are compressed onto the tapered tube;
  positioning the apparatus in the body lumen and/or body cavity;
  inflating the aft balloon;
  advancing the fore balloon distally;
  inflating the fore balloon; and
  performing the procedure.

21. A method according to claim 20 wherein the tapered tube is formed separately from the distal end of the sleeve and secured thereto during manufacture.

22. A method according to claim 20 wherein the tapered tube is formed integral with the distal end of the sleeve.

23. method according to claim 20 wherein the plurality of flexible fingers of the middle collet comprise tapered portions, and wherein the distal collet comprises a tapered portion, and further wherein the tapered portion of the distal collet engages the tapered portions of the plurality of flexible fingers of the middle collet when the threaded portion of the distal collet is screwed onto the threaded portion of the proximal collet.

24. A method according to claim 23 wherein the plurality of flexible fingers extend distally from the middle collet.

25. A method according to claim 23 wherein the distal collet moves proximally when the threaded portion of the distal collet is screwed onto the threaded portion of the proximal collet.

26. A method according to claim 20 wherein the sleeve comprises at least one instrument lumen, and further wherein the proximal collet comprises at least one seat for receiving the at least one instrument lumen of the sleeve.

27. A method according to claim 26 wherein the at least one instrument lumen comprises at least one tube mounted to the exterior of the sleeve.

28. A method according to claim 27 wherein the at least one tube is formed integral with the sleeve.

29. A method according to claim 27 wherein the collet mechanism comprises an elastomeric boot for yieldably maintaining the at least one instrument lumen in the at least one seat of the proximal collet.

30. A method according to claim 29 wherein the elastomeric boot is formed by everting the sleeve around the distal end of the proximal collet.

31. A method according to claim 29 wherein the elastomeric boot comprises an elastomeric ring disposed around the distal end of the proximal collet.

32. A method according to claim 20 wherein the fore balloon is movably mounted to the sleeve by a pair of hollow push tubes slidably mounted to the sleeve.

33. A method according to claim 32 wherein the pair of hollow push tubes comprise distal ends, and further wherein the distal ends of the pair of hollow push tubes are connected to one another with a raised push tube bridge, the raised push tube bridge being configured to nest the endoscope therein.

34. A method according to claim 32 wherein the pair of hollow push tubes comprise distal ends, wherein the fore balloon is secured to the distal ends of the pair of hollow push tubes, wherein the interior of the fore balloon is in fluid communication with the interiors of the pair of hollow push tubes, and wherein the fore balloon is capable of assuming a deflated condition and an inflated condition.

35. A method according to claim 34 wherein (i) when the fore balloon is in its deflated condition, an axial opening extends therethrough, the axial opening being sized to receive the endoscope therein, and (ii) when the fore balloon is in its inflated condition, the axial opening is closed down.

36. A method according to claim 20 wherein the endoscope is steerable, and further wherein the aft balloon is secured to the sleeve proximal to the articulating portion of the steerable endoscope.

37. A method according to claim 20 further comprising an elastomeric distal boot disposed about the distal end of the proximal collet.

38. A method according to 37 wherein the elastomeric distal boot covers the entire proximal collet.

39. Apparatus comprising:
   a sleeve adapted to be slid over the exterior of an endoscope, the sleeve having a distal end and a proximal end, wherein the sleeve comprises at least one instrument lumen, and further wherein the at least one instrument lumen comprises at least one tube mounted to the exterior of the sleeve;
   an aft balloon secured to the sleeve;
   a fore balloon movably mounted to the sleeve so that the fore balloon may be advanced relative to the sleeve;
   a locking assembly for releasably securing the distal end of the sleeve to the endoscope, wherein the locking assembly comprises:
      a tapered tube mounted to the distal end of the sleeve; and
      a collet mechanism for selectively compressing the tapered tube against the endoscope, the collet mechanism comprising a collet base for disposition around the tapered tube, and a collet cap configured to selectively engage the collet base and compress the collet base against the tapered tube, wherein the collet base comprises at least one seat for receiving the at least one instrument lumen of the sleeve; and
   an elastomeric boot for yieldably maintaining the at least one instrument lumen in the at least one seat of the collet base.

40. Apparatus according to claim 39 wherein the tapered tube is formed separately from the distal end of the sleeve and secured thereto during manufacture.

41. Apparatus according to claim 39 wherein the tapered tube is formed integral with the distal end of the sleeve.

42. Apparatus according to claim 39 wherein the collet base is mounted to the tapered tube.

43. Apparatus according to claim 39 wherein the collet base comprises a plurality of flexible fingers, and further wherein the collet cap is configured to selectively engage the plurality of flexible fingers and compress the plurality of flexible fingers against the tapered tube.

44. Apparatus according to claim 43 wherein the collet base comprises a threaded portion, wherein the collet cap comprises a threaded portion, and further wherein screwing the threaded portion of the collet cap onto the threaded portion of the collet base causes the collet cap to selectively engage the plurality of flexible fingers and compress the plurality of flexible fingers against the tapered tube.

45. Apparatus according to claim 44 wherein the plurality of flexible fingers of the collet base comprise tapered portions, and wherein the collet cap comprises a tapered portion, and further wherein the tapered portion of the collet cap engages the tapered portions of the plurality of flexible fingers of the collet base when the threaded portion of the collet cap is screwed onto the threaded portion of the collet base.

46. Apparatus according to claim 45 wherein the plurality of flexible fingers extend proximally from the collet base.

47. Apparatus according to claim 45 wherein the collet cap moves distally when the threaded portion of the collet cap is screwed onto the threaded portion of the collet base.

48. Apparatus according to claim 39 wherein the at least one tube is formed integral with the sleeve.

49. Apparatus according to claim 39 wherein the elastomeric boot is formed by everting the sleeve around the distal end of the collet base.

50. Apparatus according to claim 39 wherein the elastomeric boot comprises an elastomeric ring disposed around the distal end of the collet base.

51. Apparatus according to claim 39 wherein the fore balloon is movably mounted to the sleeve by a pair of hollow push tubes slidably mounted to the sleeve.

52. Apparatus according to claim 51 wherein the pair of hollow push tubes comprise distal ends, and further wherein the distal ends of the pair of hollow push tubes are connected to one another with a raised push tube bridge, the raised push tube bridge being configured to nest the endoscope therein.

53. Apparatus according to claim 51 wherein the pair of hollow push tubes comprise distal ends, wherein the fore balloon is secured to the distal ends of the pair of hollow push tubes, wherein the interior of the fore balloon is in fluid communication with the interiors of the pair of hollow push tubes, and wherein the fore balloon is capable of assuming a deflated condition and an inflated condition.

54. Apparatus according to claim 53 wherein (i) when the fore balloon is in its deflated condition, an axial opening extends therethrough, the axial opening being sized to receive the endoscope therein, and (ii) when the fore balloon is in its inflated condition, the axial opening is closed down.

55. Apparatus according to claim 39 wherein the endoscope is steerable, and further wherein the aft balloon is secured to the sleeve proximal to the articulating portion of the steerable endoscope.

56. Apparatus according to claim 39 wherein the elastomeric distal boot is disposed about the distal end of the collet base.

57. Apparatus according to 56 wherein the elastomeric distal boot covers the entire collet base.

58. A method for performing a procedure in a body lumen and/or body cavity, said method comprising:
   providing apparatus comprising:
      a sleeve adapted to be slid over the exterior of an endoscope, the sleeve having a distal end and a proximal end, wherein the sleeve comprises at least one instrument lumen, and further wherein the at least one instrument lumen comprises at least one tube mounted to the exterior of the sleeve;
      an aft balloon secured to the sleeve;
      a fore balloon movably mounted to the sleeve so that the fore balloon may be advanced relative to the sleeve;
      a locking assembly for releasably securing the distal end of the sleeve to the endoscope, wherein the locking assembly comprises:

a tapered tube mounted to the distal end of the sleeve; and a collet mechanism for selectively compressing the tapered tube against the endoscope, the collet mechanism comprising a collet base for disposition around the tapered tube, and a collet cap configured to selectively engage the collet base and compress the collet base against the tapered tube, wherein the collet base comprises at least one seat for receiving the at least one instrument lumen of the sleeve; and an elastomeric boot for yieldably maintaining the at least one instrument lumen in the at least one seat of the collet base;

positioning the apparatus in the body lumen and/or body cavity;

inflating the aft balloon;

advancing the fore balloon distally;

inflating the fore balloon; and performing the procedure.

59. A method according to claim 58 wherein the tapered tube is formed separately from the distal end of the sleeve and secured thereto during manufacture.

60. A method according to claim 58 wherein the tapered tube is formed integral with the distal end of the sleeve.

61. A method according to claim 58 wherein the collet base is mounted to the tapered tube.

62. A method according to claim 58 wherein the collet base comprises a plurality of flexible fingers, and further wherein the collet cap is configured to selectively engage the plurality of flexible fingers and compress the plurality of flexible fingers against the tapered tube.

63. A method according to claim 62 wherein the collet base comprises a threaded portion, wherein the collet cap comprises a threaded portion, and further wherein screwing the threaded portion of the collet cap onto the threaded portion of the collet base causes the collet cap to selectively engage the plurality of flexible fingers and compress the plurality of flexible fingers against the tapered tube.

64. A method according to claim 63 wherein the plurality of flexible fingers of the collet base comprise tapered portions, and wherein the collet cap comprises a tapered portion, and further wherein the tapered portion of the collet cap engages the tapered portions of the plurality of flexible fingers of the collet base when the threaded portion of the collet cap is screwed onto the threaded portion of the collet base.

65. A method according to claim 64 wherein the plurality of flexible fingers extend proximally from the collet base.

66. A method according to claim 64 wherein the collet cap moves distally when the threaded portion of the collet cap is screwed onto the threaded portion of the collet base.

67. A method according to claim 58 wherein the at least one tube is formed integral with the sleeve.

68. A method according to claim 58 wherein the elastomeric boot is formed by everting the sleeve around the distal end of the collet base.

69. A method according to claim 58 wherein the elastomeric boot comprises an elastomeric ring disposed around the distal end of the collet base.

70. A method according to claim 58 wherein the fore balloon is movably mounted to the sleeve by a pair of hollow push tubes slidably mounted to the sleeve.

71. A method according to claim 70 wherein the pair of hollow push tubes comprise distal ends, and further wherein the distal ends of the pair of hollow push tubes are connected to one another with a raised push tube bridge, the raised push tube bridge being configured to nest the endoscope therein.

72. A method according to claim 70 wherein the pair of hollow push tubes comprise distal ends, wherein the fore balloon is secured to the distal ends of the pair of hollow push tubes, wherein the interior of the fore balloon is in fluid communication with the interiors of the pair of hollow push tubes, and wherein the fore balloon is capable of assuming a deflated condition and an inflated condition.

73. A method according to claim 72 wherein (i) when the fore balloon is in its deflated condition, an axial opening extends therethrough, the axial opening being sized to receive the endoscope therein, and (ii) when the fore balloon is in its inflated condition, the axial opening is closed down.

74. A method according to claim 58 wherein the endoscope is steerable, and further wherein the aft balloon is secured to the sleeve proximal to the articulating portion of the steerable endoscope.

75. A method according to claim 58 wherein the elastomeric distal boot is disposed about the distal end of the collet base.

76. A method according to 75 wherein the elastomeric distal boot covers the entire collet base.

77. Apparatus comprising:

a sleeve adapted to be slid over the exterior of an endoscope, the sleeve having a distal end and a proximal end;

an aft balloon secured to the sleeve;

a fore balloon movably mounted to the sleeve so that the fore balloon may be advanced relative to the sleeve, wherein the fore balloon is movably mounted to the sleeve by a pair of hollow push tubes slidably mounted to the sleeve, wherein the pair of hollow push tubes comprise distal ends, wherein the fore balloon is secured to the distal ends of the pair of hollow push tubes, wherein the interior of the fore balloon is in fluid communication with the interiors of the pair of hollow push tubes, and wherein the fore balloon is capable of assuming a deflated condition and an inflated condition; and a locking assembly for releasably securing the distal end of the sleeve to the endoscope.

78. Apparatus according to claim 77 wherein the locking assembly comprises a tapered tube mounted to the distal end of the sleeve.

79. Apparatus according to claim 78 wherein the tapered tube is formed separately from the distal end of the sleeve and secured thereto during manufacture.

80. Apparatus according to claim 78 wherein the tapered tube is formed integral with the distal end of the sleeve.

81. Apparatus according to claim 78 wherein the locking assembly further comprises a collet mechanism for selectively compressing the tapered tube against the endoscope.

82. Apparatus according to claim 81 wherein the collet mechanism comprises a collet base for disposition around the tapered tube, and a collet cap configured to selectively engage the collet base and compress the collet base against the tapered tube.

83. Apparatus according to claim 82 wherein the collet base is mounted to the tapered tube.

84. Apparatus according to claim 82 wherein the collet base comprises a plurality of flexible fingers, and further wherein the collet cap is configured to selectively engage the plurality of flexible fingers and compress the plurality of flexible fingers against the tapered tube.

85. Apparatus according to claim 84 wherein the collet base comprises a threaded portion, wherein the collet cap comprises a threaded portion, and further wherein screwing the threaded portion of the collet cap onto the threaded portion of the collet base causes the collet cap to selectively engage the plurality of flexible fingers and compress the plurality of flexible fingers against the tapered tube.

86. Apparatus according to claim 85 wherein the plurality of flexible fingers of the collet base comprise tapered portions, and wherein the collet cap comprises a tapered portion, and further wherein the tapered portion of the collet cap engages the tapered portions of the plurality of flexible fingers of the collet base when the threaded portion of the collet cap is screwed onto the threaded portion of the collet base.

87. Apparatus according to claim 86 wherein the plurality of flexible fingers extend proximally from the collet base.

88. Apparatus according to claim 86 wherein the collet cap moves distally when the threaded portion of the collet cap is screwed onto the threaded portion of the collet base.

89. Apparatus according to claim 82 wherein the sleeve comprises at least one instrument lumen, and further wherein the collet base comprises at least one seat for receiving the at least one instrument lumen of the sleeve.

90. Apparatus according to claim 89 wherein the at least one instrument lumen comprises at least one tube mounted to the exterior of the sleeve.

91. Apparatus according to claim 90 wherein the at least one tube is formed integral with the sleeve.

92. Apparatus according to claim 90 wherein the apparatus comprises an elastomeric boot for yieldably maintaining the at least one instrument lumen in the at least one seat of the collet base.

93. Apparatus according to claim 92 wherein the elastomeric boot is formed by everting the sleeve around the distal end of the collet base.

94. Apparatus according to claim 92 wherein the elastomeric boot comprises an elastomeric ring disposed around the distal end of the collet base.

95. Apparatus according to claim 77 wherein the pair of hollow push tubes comprise distal ends, and further wherein the distal ends of the pair of hollow push tubes are connected to one another with a raised push tube bridge, the raised push tube bridge being configured to nest the endoscope therein.

96. Apparatus according to claim 77 wherein (i) when the fore balloon is in its deflated condition, an axial opening extends therethrough, the axial opening being sized to receive the endoscope therein, and (ii) when the fore balloon is in its inflated condition, the axial opening is closed down.

97. Apparatus according to claim 77 wherein the endoscope is steerable, and further wherein the aft balloon is secured to the sleeve proximal to the articulating portion of the steerable endoscope.

98. Apparatus according to claim 81 wherein the collet mechanism comprises a proximal collet, a middle collet, and a distal collet, and further wherein the proximal collet is secured to the tapered tube and comprises threads, the middle collet is secured to the proximal collet and comprises a plurality of flexible fingers, and the distal collet comprises threads for engaging the threads of the proximal collet, such that when the distal collet is advanced towards the proximal end of the proximal collet, the flexible fingers of the middle collet are compressed onto the tapered tube.

99. Apparatus according to claim 98 further comprising an elastomeric distal boot disposed about the distal end of the proximal collet.

100. Apparatus according to 99 wherein the elastomeric distal boot covers the entire proximal collet.

101. A method for performing a procedure in a body lumen and/or body cavity, said method comprising:
providing apparatus comprising:
a sleeve adapted to be slid over the exterior of an endoscope, the sleeve having a distal end and a proximal end;
an aft balloon secured to the sleeve;
a fore balloon movably mounted to the sleeve so that the fore balloon may be advanced relative to the sleeve, wherein the fore balloon is movably mounted to the sleeve by a pair of hollow push tubes slidably mounted to the sleeve, wherein the pair of hollow push tubes comprise distal ends, wherein the fore balloon is secured to the distal ends of the pair of hollow push tubes, wherein the interior of the fore balloon is in fluid communication with the interiors of the pair of hollow push tubes, and wherein the fore balloon is capable of assuming a deflated condition and an inflated condition; and
a locking assembly for releasably securing the distal end of the sleeve to the endoscope;
positioning the apparatus in the body lumen and/or body cavity;
inflating the aft balloon;
advancing the fore balloon distally;
inflating the fore balloon; and
performing the procedure.

102. A method according to claim 101 wherein the locking assembly comprises a tapered tube mounted to the distal end of the sleeve.

103. A method according to claim 102 wherein the tapered tube is formed separately from the distal end of the sleeve and secured thereto during manufacture.

104. A method according to claim 102 wherein the tapered tube is formed integral with the distal end of the sleeve.

105. A method according to claim 102 wherein the locking assembly further comprises a collet mechanism for selectively compressing the tapered tube against the endoscope.

106. A method according to claim 105 wherein the collet mechanism comprises a collet base for disposition around the tapered tube and a collet cap configured to selectively engage the collet base, and compress the collet base against the tapered tube.

107. A method according to claim 106 wherein the collet base is mounted to the tapered tube.

108. A method according to claim 106 wherein the collet base comprises a plurality of flexible fingers, and further wherein the collet cap is configured to selectively engage the plurality of flexible fingers and compress the plurality of flexible fingers against the tapered tube.

109. A method according to claim 108 wherein the collet base comprises a threaded portion, wherein the collet cap comprises a threaded portion, and further wherein screwing the threaded portion of the collet cap onto the threaded portion of the collet base causes the collet cap to selectively engage the plurality of flexible fingers and compress the plurality of flexible fingers against the tapered tube.

110. A method according to claim 109 wherein the plurality of flexible fingers of the collet base comprise tapered portions, and wherein the collet cap comprises a tapered portion, and further wherein the tapered portion of the collet cap engages the tapered portions of the plurality of flexible fingers of the collet base when the threaded portion of the collet cap is screwed onto the threaded portion of the collet base.

111. A method according to claim 110 wherein the plurality of flexible fingers extend proximally from the collet base.

112. A method according to claim 110 wherein the collet cap moves distally when the threaded portion of the collet cap is screwed onto the threaded portion of the collet base.

113. A method according to claim 106 wherein the sleeve comprises at least one instrument lumen, and further wherein the collet base comprises at least one seat for receiving the at least one instrument lumen of the sleeve.

114. A method according to claim 113 wherein the at least one instrument lumen comprises at least one tube mounted to the exterior of the sleeve.

115. A method according to claim 114 wherein the at least one tube is formed integral with the sleeve.

116. A method according to claim 114 wherein the collet mechanism comprises an elastomeric boot for yieldably maintaining the at least one instrument lumen in the at least one seat of the collet base.

117. A method according to claim 116 wherein the elastomeric boot is formed by everting the sleeve around the distal end of the collet base.

118. A method according to claim 116 wherein the elastomeric boot comprises an elastomeric ring disposed around the distal end of the collet base.

119. A method according to claim 101 wherein the pair of hollow push tubes comprise distal ends, and further wherein the distal ends of the pair of hollow push tubes are connected to one another with a raised push tube bridge, the raised push tube bridge being configured to nest the endoscope therein.

120. A method according to claim 101 wherein (i) when the fore balloon is in its deflated condition, an axial opening extends therethrough, the axial opening being sized to receive the endoscope therein, and (ii) when the fore balloon is in its inflated condition, the axial opening is closed down.

121. A method according to claim 101 wherein the endoscope is steerable, and further wherein the aft balloon is secured to the sleeve proximal to the articulating portion of the steerable endoscope.

122. A method according to claim 105 wherein the collet mechanism comprises a proximal collet, a middle collet, and a distal collet, and further wherein the proximal collet is secured to the tapered tube and comprises threads, the middle collet is secured to the proximal collet and comprises a plurality of flexible fingers, and the distal collet comprises threads for engaging the threads of the proximal collet, such that when the distal collet is advanced towards the proximal end of the proximal collet, the flexible fingers of the middle collet are compressed onto the tapered tube.

123. A method according to claim 122 further comprising an elastomeric distal boot disposed about the distal end of the proximal collet.

124. A method according to 123 wherein the elastomeric distal boot covers the entire proximal collet.

125. Apparatus comprising:
a sleeve adapted to be slid over the exterior of an endoscope, the sleeve having a distal end and a proximal end;
an aft balloon secured to the sleeve;
a fore balloon movably mounted to the sleeve so that the fore balloon may be advanced relative to the sleeve, wherein the fore balloon is movably mounted to the sleeve by a pair of hollow push tubes slidably mounted to the sleeve, wherein the pair of hollow push tubes comprise distal ends, and further wherein the distal ends of the pair of hollow push tubes are connected to one another with a raised push tube bridge, the raised push tube bridge being configured to nest the endoscope therein; and
a locking assembly for releasably securing the distal end of the sleeve to the endoscope.

126. Apparatus according to claim 125 wherein the locking assembly comprises a tapered tube mounted to the distal end of the sleeve.

127. Apparatus according to claim 126 wherein the tapered tube is formed separately from the distal end of the sleeve and secured thereto during manufacture.

128. Apparatus according to claim 126 wherein the tapered tube is formed integral with the distal end of the sleeve.

129. Apparatus according to claim 126 wherein the locking assembly further comprises a collet mechanism for selectively compressing the tapered tube against the endoscope.

130. Apparatus according to claim 129 wherein the collet mechanism comprises a collet base for disposition around the tapered tube, and a collet cap configured to selectively engage the collet base and compress the collet base against the tapered tube.

131. Apparatus according to claim 130 wherein the collet base is mounted to the tapered tube.

132. Apparatus according to claim 130 wherein the collet base comprises a plurality of flexible fingers, and further wherein the collet cap is configured to selectively engage the plurality of flexible fingers and compress the plurality of flexible fingers against the tapered tube.

133. Apparatus according to claim 132 wherein the collet base comprises a threaded portion, wherein the collet cap comprises a threaded portion, and further wherein screwing the threaded portion of the collet cap onto the threaded portion of the collet base causes the collet cap to selectively engage the plurality of flexible fingers and compress the plurality of flexible fingers against the tapered tube.

134. Apparatus according to claim 133 wherein the plurality of flexible fingers of the collet base comprise tapered portions, and wherein the collet cap comprises a tapered portion, and further wherein the tapered portion of the collet cap engages the tapered portions of the plurality of flexible fingers of the collet base when the threaded portion of the collet cap is screwed onto the threaded portion of the collet base.

135. Apparatus according to claim 134 wherein the plurality of flexible fingers extend proximally from the collet base.

136. Apparatus according to claim 134 wherein the collet cap moves distally when the threaded portion of the collet cap is screwed onto the threaded portion of the collet base.

137. Apparatus according to claim 130 wherein the sleeve comprises at least one instrument lumen, and further wherein the collet base comprises at least one seat for receiving the at least one instrument lumen of the sleeve.

138. Apparatus according to claim 137 wherein the at least one instrument lumen comprises at least one tube mounted to the exterior of the sleeve.

139. Apparatus according to claim 138 wherein the at least one tube is formed integral with the sleeve.

140. Apparatus according to claim 138 wherein the apparatus comprises an elastomeric boot for yieldably maintaining the at least one instrument lumen in the at least one seat of the collet base.

141. Apparatus according to claim 140 wherein the elastomeric boot is formed by everting the sleeve around the distal end of the collet base.

142. Apparatus according to claim 140 wherein the elastomeric boot comprises an elastomeric ring disposed around the distal end of the collet base.

143. Apparatus according to claim 125 wherein the pair of hollow push tubes comprise distal ends, wherein the fore balloon is secured to the distal ends of the pair of hollow push tubes, wherein the interior of the fore balloon is in fluid communication with the interiors of the pair of hollow push tubes, and wherein the fore balloon is capable of assuming a deflated condition and an inflated condition.

144. Apparatus according to claim 143 wherein (i) when the fore balloon is in its deflated condition, an axial opening extends therethrough, the axial opening being sized to receive the endoscope therein, and (ii) when the fore balloon is in its inflated condition, the axial opening is closed down.

145. Apparatus according to claim 125 wherein the endoscope is steerable, and further wherein the aft balloon is secured to the sleeve proximal to the articulating portion of the steerable endoscope.

146. Apparatus according to claim 129 wherein the collet mechanism comprises a proximal collet, a middle collet, and a distal collet, and further wherein the proximal collet is secured to the tapered tube and comprises threads, the middle collet is secured to the proximal collet and comprises a plurality of flexible fingers, and the distal collet comprises threads for engaging the threads of the proximal collet, such that when the distal collet is advanced towards the proximal end of the proximal collet, the flexible fingers of the middle collet are compressed onto the tapered tube.

147. Apparatus according to claim 146 further comprising an elastomeric distal boot disposed about the distal end of the proximal collet.

148. Apparatus according to 147 wherein the elastomeric distal boot covers the entire proximal collet.

149. A method for performing a procedure in a body lumen and/or body cavity, said method comprising:
providing apparatus comprising:
a sleeve adapted to be slid over the exterior of an endoscope, the sleeve having a distal end and a proximal end;
an aft balloon secured to the sleeve;
a fore balloon movably mounted to the sleeve so that the fore balloon may be advanced relative to the sleeve, wherein the fore balloon is movably mounted to the sleeve by a pair of hollow push tubes slidably mounted to the sleeve, wherein the pair of hollow push tubes comprise distal ends, and further wherein the distal ends of the pair of hollow push tubes are connected to one another with a raised push tube bridge, the raised push tube bridge being configured to nest the endoscope therein; and
a locking assembly for releasably securing the distal end of the sleeve to the endoscope;
positioning the apparatus in the body lumen and/or body cavity;
inflating the aft balloon;
advancing the fore balloon distally;
inflating the fore balloon; and
performing the procedure.

150. A method according to claim 149 wherein the locking assembly comprises a tapered tube mounted to the distal end of the sleeve.

151. A method according to claim 150 wherein the tapered tube is formed separately from the distal end of the sleeve and secured thereto during manufacture.

152. A method according to claim 150 wherein the tapered tube is formed integral with the distal end of the sleeve.

153. A method according to claim 150 wherein the locking assembly further comprises a collet mechanism for selectively compressing the tapered tube against the endoscope.

154. A method according to claim 153 wherein the collet mechanism comprises a collet base for disposition around the tapered tube and a collet cap configured to selectively engage the collet base, and compress the collet base against the tapered tube.

155. A method according to claim 154 wherein the collet base is mounted to the tapered tube.

156. A method according to claim 154 wherein the collet base comprises a plurality of flexible fingers, and further wherein the collet cap is configured to selectively engage the plurality of flexible fingers and compress the plurality of flexible fingers against the tapered tube.

157. A method according to claim 156 wherein the collet base comprises a threaded portion, wherein the collet cap comprises a threaded portion, and further wherein screwing the threaded portion of the collet cap onto the threaded portion of the collet base causes the collet cap to selectively engage the plurality of flexible fingers and compress the plurality of flexible fingers against the tapered tube.

158. A method according to claim 157 wherein the plurality of flexible fingers of the collet base comprise tapered portions, and wherein the collet cap comprises a tapered portion, and further wherein the tapered portion of the collet cap engages the tapered portions of the plurality of flexible fingers of the collet base when the threaded portion of the collet cap is screwed onto the threaded portion of the collet base.

159. A method according to claim 158 wherein the plurality of flexible fingers extend proximally from the collet base.

160. A method according to claim 158 wherein the collet cap moves distally when the threaded portion of the collet cap is screwed onto the threaded portion of the collet base.

161. A method according to claim 154 wherein the sleeve comprises at least one instrument lumen, and further wherein the collet base comprises at least one seat for receiving the at least one instrument lumen of the sleeve.

162. A method according to claim 161 wherein the at least one instrument lumen comprises at least one tube mounted to the exterior of the sleeve.

163. A method according to claim 162 wherein the at least one tube is formed integral with the sleeve.

164. A method according to claim 162 wherein the collet mechanism comprises an elastomeric boot for yieldably maintaining the at least one instrument lumen in the at least one seat of the collet base.

165. A method according to claim 164 wherein the elastomeric boot is formed by everting the sleeve around the distal end of the collet base.

166. A method according to claim 164 wherein the elastomeric boot comprises an elastomeric ring disposed around the distal end of the collet base.

167. A method according to claim 149 wherein the pair of hollow push tubes comprise distal ends, wherein the fore balloon is secured to the distal ends of the pair of hollow push tubes, wherein the interior of the fore balloon is in fluid communication with the interiors of the pair of hollow push tubes, and wherein the fore balloon is capable of assuming a deflated condition and an inflated condition.

168. A method according to claim 167 wherein (i) when the fore balloon is in its deflated condition, an axial opening extends therethrough, the axial opening being sized to receive the endoscope therein, and (ii) when the fore balloon is in its inflated condition, the axial opening is closed down.

169. A method according to claim 149 wherein the endoscope is steerable, and further wherein the aft balloon is secured to the sleeve proximal to the articulating portion of the steerable endoscope.

170. A method according to claim 153 wherein the collet mechanism comprises a proximal collet, a middle collet, and a distal collet, and further wherein the proximal collet is secured to the tapered tube and comprises threads, the middle collet is secured to the proximal collet and comprises a plurality of flexible fingers, and the distal collet comprises threads for engaging the threads of the proximal collet, such that when the distal collet is advanced towards the proximal end of the proximal collet, the flexible fingers of the middle collet are compressed onto the tapered tube.

171. A method according to claim 170 further comprising an elastomeric distal boot disposed about the distal end of the proximal collet.

172. A method according to 171 wherein the elastomeric distal boot covers the entire proximal collet.

\* \* \* \* \*